US011628072B2

(12) United States Patent
van der Merwe et al.

(10) Patent No.: US 11,628,072 B2
(45) Date of Patent: *Apr. 18, 2023

(54) SYSTEM AND APPARATUS FOR ROBOTIC DEVICE AND METHODS OF USING THEREOF

(71) Applicant: DEKA Products Limited Partnership, Manchester, NH (US)

(72) Inventors: Dirk A. van der Merwe, Canterbury, NH (US); Christopher C. Langenfeld, Nashua, NH (US); Stewart M. Coulter, Bedford, NH (US); Christopher M. Werner, San Jose, CA (US); Michael J. Slate, Merrimack, NH (US); Ethan D. Stern, Meredith, NH (US)

(73) Assignee: DEKA Products Limited Partnership, Manchester, NH (US)

( * ) Notice: Subject to any disclaimer, the term of this patent is extended or adjusted under 35 U.S.C. 154(b) by 148 days.

This patent is subject to a terminal disclaimer.

(21) Appl. No.: 17/144,580

(22) Filed: Jan. 8, 2021

(65) Prior Publication Data
US 2021/0128322 A1    May 6, 2021

Related U.S. Application Data

(63) Continuation of application No. 16/871,722, filed on May 11, 2020, now Pat. No. 10,888,439, which is a
(Continued)

(51) Int. Cl.
*G05B 15/00* (2006.01)
*G05B 19/00* (2006.01)
(Continued)

(52) U.S. Cl.
CPC ............... *A61F 2/54* (2013.01); *A61F 2/581* (2013.01); *A61F 2/585* (2013.01); *A61F 2/586* (2013.01);
(Continued)

(58) Field of Classification Search
CPC .. A61F 2/54; A61F 2/581; A61F 2/585; A61F 2/586; A61F 2/588; A61F 2/68;
(Continued)

(56) References Cited

U.S. PATENT DOCUMENTS

| 43,590 A | 7/1864 | Koeller |
| 975,029 A | 11/1910 | Galvin |

(Continued)

FOREIGN PATENT DOCUMENTS

| DE | 357699 | 8/1922 |
| DE | 19624215 | 4/1997 |

(Continued)

OTHER PUBLICATIONS

International Preliminary Report on Patentability and Written Opinion, dated Oct. 9, 2012, received in international patent application No. PCT/US2011/031797, 8 pages.
(Continued)

*Primary Examiner* — Harry Y Oh
(74) *Attorney, Agent, or Firm* — William A. Bonk, III

(57) ABSTRACT

A robotic assembly control system is disclosed. The robotic assembly control system includes an exoskeleton apparatus adapted to be worn by a user, at least one robotic assembly, the at least one robotic assembly controlled by the user by way of the exoskeleton, and at least one mobile platform, the
(Continued)

at least one mobile platform controlled by the user and wherein the at least one robotic assembly is attached to the at least one mobile platform.

20 Claims, 83 Drawing Sheets

Related U.S. Application Data continuation of application No. 16/272,463, filed on Feb. 11, 2019, now Pat. No. 10,646,355, which is a continuation of application No. 15/845,505, filed on Dec. 18, 2017, now Pat. No. 10,201,435, which is a continuation of application No. 13/083,245, filed on Apr. 8, 2011, now Pat. No. 9,844,447.

(60) Provisional application No. 61/322,469, filed on Apr. 9, 2010.

(51) Int. Cl.
| | |
|---|---|
| A61F 2/54 | (2006.01) |
| A61F 2/58 | (2006.01) |
| B25J 3/04 | (2006.01) |
| B25J 9/00 | (2006.01) |
| A61F 2/70 | (2006.01) |
| A61F 2/68 | (2006.01) |
| A61F 2/78 | (2006.01) |
| A61F 2/50 | (2006.01) |
| A61F 2/76 | (2006.01) |
| A61F 2/74 | (2006.01) |

(52) U.S. Cl.
CPC ........... *A61F 2/588* (2013.01); *A61F 2/68* (2013.01); *A61F 2/70* (2013.01); *B25J 3/04* (2013.01); *B25J 9/0006* (2013.01); *A61F 2/74* (2021.08); *A61F 2/78* (2013.01); *A61F 2002/5001* (2013.01); *A61F 2002/5083* (2013.01); *A61F 2002/587* (2013.01); *A61F 2002/6881* (2013.01); *A61F 2002/701* (2013.01); *A61F 2002/704* (2013.01); *A61F 2002/7625* (2013.01); *A61F 2002/7665* (2013.01); *A61F 2250/008* (2013.01); *A61F 2250/0074* (2013.01)

(58) Field of Classification Search
CPC ...... A61F 2/70; A61F 2/74; A61F 2/78; A61F 2002/5001; A61F 2002/5083; A61F 2002/587; A61F 2002/6881; A61F 2002/701; A61F 2002/704; A61F 2002/7625; A61F 2002/7665; A61F 2250/0074; A61F 2250/008; B25J 3/04; B25J 9/0006
See application file for complete search history.

(56) References Cited

U.S. PATENT DOCUMENTS

| | | | |
|---|---|---|---|
| 1,745,959 | A | 2/1930 | Steiner |
| 1,928,368 | A | 9/1933 | Coffey |
| 2,070,960 | A | 2/1937 | Phillips |
| 2,350,339 | A | 6/1944 | Quirno |
| 2,408,880 | A | 10/1946 | Rebers |
| 2,516,791 | A | 7/1950 | Motis et al. |
| 2,535,489 | A | 12/1950 | Edwards |
| 3,654,855 | A | 4/1972 | Longo |
| 3,745,998 | A | 7/1973 | Rose |
| 3,763,773 | A | 10/1973 | Clay |
| 3,802,302 | A | 4/1974 | Bengtson |
| 3,883,900 | A | 5/1975 | Jerard et al. |
| 3,935,795 | A | 2/1976 | Hawley |
| 4,067,070 | A | 1/1978 | Seamone et al. |
| 4,155,169 | A | 5/1979 | Drake et al. |
| 4,155,769 | A | 5/1979 | Almagro |
| 4,258,441 | A | 3/1981 | Bell |
| 4,413,895 | A | 11/1983 | Lee |
| 4,604,098 | A | 8/1986 | Seamone et al. |
| 4,628,765 | A | 12/1986 | Dien et al. |
| 4,657,003 | A | 4/1987 | Wirtz |
| 4,674,351 | A | 6/1987 | Byrd |
| 4,720,923 | A | 1/1988 | Quinton et al. |
| 4,792,338 | A | 12/1988 | Rennerfelt |
| 4,831,897 | A | 5/1989 | Dobbs |
| 4,840,634 | A | 6/1989 | Muller et al. |
| 4,896,239 | A | 1/1990 | Ghose |
| 4,903,536 | A | 2/1990 | Salisbury, Jr. et al. |
| 4,908,037 | A | 3/1990 | Ross |
| 4,946,421 | A | 8/1990 | Kerley, Jr. |
| 5,018,513 | A | 5/1991 | Charles |
| 5,088,171 | A | 2/1992 | Suzuki |
| 5,108,456 | A | 4/1992 | Coonan, III |
| 5,201,772 | A | 4/1993 | Maxwell |
| 5,263,990 | A | 11/1993 | Handal |
| 5,376,128 | A | 12/1994 | Bozeman, Jr. |
| 5,405,405 | A | 4/1995 | Love |
| 5,413,611 | A | 5/1995 | Haslam, II et al. |
| 5,420,489 | A | 5/1995 | Hansen et al. |
| 5,480,454 | A | 1/1996 | Bozeman, Jr. |
| 5,501,498 | A | 3/1996 | Ulrich |
| 5,673,367 | A | 9/1997 | Buckley |
| 5,724,714 | A | 3/1998 | Love |
| 5,796,229 | A | 8/1998 | Akeel |
| 5,825,983 | A | 10/1998 | Park et al. |
| 5,836,083 | A | 11/1998 | Sangwan |
| 5,888,213 | A | 3/1999 | Sears et al. |
| 5,910,720 | A | 6/1999 | Williamson et al. |
| 5,971,091 | A | 10/1999 | Kamen et al. |
| 6,129,476 | A | 10/2000 | Berman et al. |
| 6,163,739 | A | 12/2000 | Park et al. |
| 6,223,104 | B1 | 4/2001 | Kamen et al. |
| 6,244,644 | B1 | 6/2001 | Lovchik et al. |
| 6,276,155 | B2 | 8/2001 | Siman-Tov et al. |
| 6,286,225 | B1 | 9/2001 | Schimmels et al. |
| 6,287,159 | B1 | 9/2001 | Polakowski et al. |
| 6,301,526 | B1 | 10/2001 | Kim et al. |
| 6,301,964 | B1 | 10/2001 | Fyfe et al. |
| 6,344,062 | B1 | 2/2002 | Abboudi et al. |
| 6,379,393 | B1 | 4/2002 | Mavroidis et al. |
| 6,424,886 | B1 | 7/2002 | Iversen et al. |
| 6,454,513 | B1 | 9/2002 | Friederichs et al. |
| 6,494,039 | B2 | 12/2002 | Pratt et al. |
| 6,585,774 | B2 | 7/2003 | Dean, Jr. et al. |
| 6,597,965 | B2 | 7/2003 | Graves et al. |
| 6,806,621 | B2 | 10/2004 | Heim et al. |
| 6,876,213 | B2 | 4/2005 | Beck |
| 6,896,704 | B1 | 5/2005 | Higuchi et al. |
| 6,962,220 | B2 | 11/2005 | Takenaka et al. |
| 6,987,374 | B2 | 1/2006 | Iribe et al. |
| 7,001,434 | B2 | 2/2006 | Iribe et al. |
| 7,086,322 | B2 | 2/2006 | Van De Veen |
| 7,150,762 | B2 | 8/2006 | Schulz |
| 7,744,551 | B2 | 6/2010 | Pick et al. |
| 7,828,857 | B2 | 11/2010 | Farnsworth et al. |
| 8,074,559 | B2 | 12/2011 | Altobelli et al. |
| 8,409,118 | B2 * | 4/2013 | Agrawal ............ B25J 9/0006 601/5 |
| 8,453,340 | B2 | 6/2013 | van der Merwe et al. |
| 8,821,587 | B2 | 9/2014 | Lanier et al. |
| 8,870,970 | B2 | 10/2014 | Altobelli et al. |
| 9,052,710 | B1 * | 6/2015 | Farwell ............ B25J 9/1656 |
| 2002/0054060 | A1 | 5/2002 | Schena |
| 2002/0143405 | A1 | 10/2002 | Davalli et al. |
| 2003/0078674 | A1 | 4/2003 | Phillips |
| 2003/0120183 | A1 | 6/2003 | Simmons |
| 2003/0149384 | A1 | 8/2003 | Davis et al. |
| 2003/0181990 | A1 | 9/2003 | Phillips |
| 2003/0196490 | A1 | 10/2003 | Cardarelli |
| 2003/0223844 | A1 * | 12/2003 | Schiele ............ A63B 23/12 414/5 |

(56) References Cited

U.S. PATENT DOCUMENTS

| | | |
|---|---|---|
| 2004/0030411 A1 | 2/2004 | Caspers |
| 2004/0049290 A1 | 3/2004 | Bedard |
| 2004/0064286 A1 | 4/2004 | Levi et al. |
| 2004/0078091 A1 | 4/2004 | Elkins |
| 2004/0088057 A1 | 5/2004 | Bedard |
| 2005/0119777 A1 | 6/2005 | Arbogast et al. |
| 2005/0156878 A1 | 7/2005 | Logue |
| 2005/0192676 A1 | 9/2005 | Sears et al. |
| 2005/0192677 A1 | 9/2005 | Ragnarsdottir et al. |
| 2005/0197717 A1 | 9/2005 | Ragnarsdottir et al. |
| 2005/0234564 A1 | 10/2005 | Fink et al. |
| 2006/0006280 A1 | 1/2006 | Wood |
| 2006/0083454 A1 | 4/2006 | Ason et al. |
| 2006/0122710 A1 | 6/2006 | Bedard |
| 2006/0150753 A1* | 7/2006 | Massimo .............. G06F 3/016 600/595 |
| 2006/0158146 A1* | 7/2006 | Tadano .............. B25J 15/0009 318/568.21 |
| 2006/0167562 A1 | 7/2006 | Williams, III et al. |
| 2006/0167564 A1 | 7/2006 | Flaherty et al. |
| 2006/0224249 A1 | 10/2006 | Winfrey |
| 2006/0248478 A1* | 11/2006 | Liau .................. G06F 3/014 715/702 |
| 2007/0011919 A1 | 1/2007 | Case, Jr. |
| 2007/0021841 A1 | 1/2007 | Al-Temen et al. |
| 2007/0038311 A1* | 2/2007 | Kuiken .................. A61F 2/72 623/24 |
| 2007/0055383 A1 | 3/2007 | King |
| 2007/0078564 A1* | 4/2007 | Hoshino .............. G06V 40/10 700/245 |
| 2007/0093944 A1* | 4/2007 | Lee .................. G05G 1/01 701/3 |
| 2007/0198098 A1 | 8/2007 | Roston et al. |
| 2007/0282228 A1 | 12/2007 | Einav et al. |
| 2008/0009771 A1* | 1/2008 | Perry .................. A61H 1/0281 600/587 |
| 2008/0045932 A1 | 2/2008 | Beau et al. |
| 2008/0193260 A1* | 8/2008 | Yokokohji .............. G05G 9/04 901/4 |
| 2008/0288088 A1 | 11/2008 | Langenfeld et al. |
| 2008/0312753 A1 | 12/2008 | Puchhammer |
| 2009/0038421 A1 | 2/2009 | Wilson et al. |
| 2009/0067973 A1* | 3/2009 | Eliuk .................. B66C 1/42 700/231 |
| 2009/0132088 A1* | 5/2009 | Taitier .................. G05B 19/42 700/264 |
| 2009/0139359 A1 | 6/2009 | Wagner et al. |
| 2009/0210093 A1* | 8/2009 | Jacobsen .............. A61H 3/00 700/260 |
| 2009/0264799 A1 | 10/2009 | Bonutti et al. |
| 2010/0068024 A1* | 3/2010 | Agens .............. B25J 15/04 901/30 |
| 2010/0113994 A1 | 5/2010 | Ingimundarson et al. |
| 2010/0120404 A1 | 5/2010 | Bernal |
| 2010/0145510 A1* | 6/2010 | Ihrke .................. B25J 17/0241 700/245 |
| 2010/0268351 A1* | 10/2010 | van der Merwe ..... G01C 21/16 600/595 |
| 2010/0274365 A1* | 10/2010 | Evans .................. A61F 2/54 623/57 |
| 2011/0017030 A1* | 1/2011 | Chambers .............. B25J 11/0025 83/13 |
| 2011/0172787 A1* | 7/2011 | Latour .................. A61F 2/78 623/57 |
| 2011/0201978 A1* | 8/2011 | Jeon .................. A61H 3/00 601/35 |
| 2011/0238079 A1* | 9/2011 | Hannaford .............. A61B 34/76 606/130 |
| 2011/0257765 A1 | 10/2011 | Evans et al. |
| 2012/0330198 A1* | 12/2012 | Patoglu .............. A61H 1/0281 601/33 |
| 2016/0284968 A1* | 9/2016 | Miyazawa .............. H02N 2/108 |
| 2017/0231787 A1* | 8/2017 | Noda .................. B25J 9/144 623/26 |
| 2019/0232485 A1* | 8/2019 | Reese .................. A61H 1/0262 |

FOREIGN PATENT DOCUMENTS

| | | |
|---|---|---|
| EP | 1159940 | 12/2001 |
| EP | 1675212 | 6/2006 |
| EP | 2133662 | 12/2009 |
| FR | 2877227 | 5/2006 |
| WO | 2004096502 | 11/2004 |
| WO | 2005087583 | 9/2005 |
| WO | 2006069264 | 6/2006 |
| WO | 2008044207 | 4/2008 |
| WO | 2008098059 | 8/2008 |
| WO | 2010120403 | 10/2010 |
| WO | 2010120404 | 10/2010 |

OTHER PUBLICATIONS

Karoui M S et al., "Study and Design of a Loop Antenna for Application of Medical Telemetry" Industrial Technology, 2004, IEEE ICIT '04, IEEE International Conference on Hammamet, Tunsia, vol. 3, Dec. 8, 2004, pp. 1589-1595.

Merriam Webster Online Dictionary, Definition of "prosthesis" accessed Jul. 5, 2010.

Yekeh K et al., "Wireless Communications for Body Implanted Medical Device" Microwave Conference, 2007, Asia-Pacific, IEEE, Piscataway, NJ Dec. 11, 2007, pp. 1-4.

International Search Report & Written Opinion dated Mar. 5, 2012, received in International patent application No. PCT/US2011/041345, 22 pgs.

International Search Report & Written Opinion dated Mar. 5, 2012, received in International patent application No. PCT/US2011/041343, 23 pgs.

Supplementary European Search Report dated Feb. 6, 2012, received in European patent application No. 08729167.0, 6 pgs.

International Partial Search Report dated Dec. 19, 2011, received in International patent application No. PCT/US2011/041345, 7 pgs.

International Partial Search Report dated Dec. 8, 2011, received in International patent application No. PCT/US2011/031797, 4 pgs.

International Partial Search Report dated Nov. 24, 2011, received in International patent application No. PCT/US2011/041343, 6 pgs.

International Preliminary Report on Patentability & Written Opinion dated Oct. 27, 2011, received in International patent application No. PCT/US2010/024326, 10 pgs.

International Preliminary Report on Patentability & Written Opinion dated Oct. 27, 2011, received in International patent application No. PCT/US2010/024316, 7 pgs.

European Search Report dated Aug. 29, 2011, received in European patent application No. 08729171.2, 7 pgs.

International Search Report & Written Opinion dated Oct. 1, 2008, received in International patent application No. PCT/US2008/053187, 9 pgs.

International Preliminary Report on Patentability & Written Opinion dated Aug. 20, 2009, received in International patent application No. PCT/US2008/053187, 7 pgs.

U.S. Appl. No. 13/323,094 entitled "Dynamic Support Apparatus and System", filed Dec. 12, 2011.

U.S. Appl. No. 13/088,035 on "Dynamic Support Apparatus and System", filed Apr. 15, 2011.

U.S. Appl. No. 13/088,085 on "System, Method and Apparatus for Control of a Prosthetic Device", filed Apr. 15, 2011.

U.S. Appl. No. 13/088,063 on "Arm Prosthetic Device", filed Apr. 15, 2011.

International Search Report & Written Opinion dated May 20, 2010, received in International patent application No. PCT/US2009/069491, 13 pgs.

European Search Report dated Aug. 29, 2011, received in European patent application No. 08729175.3, 5 pgs.

(56) References Cited

OTHER PUBLICATIONS

International Search Report & Written Opinion dated Dec. 13, 2010, received in International patent application No. PCT/US2010/024326, 17 pgs.
International Search Report & Written Opinion dated Dec. 16, 2010, received in International patent application No. PCT/US2010/024334, 16 pgs.
U.S. Appl. No. 12/706,340 on "Dynamic Support Apparatus and System", filed Feb. 16, 2010.
U.S. Appl. No. 12/706,575 on "System, Method and Apparatus for Control of a Prosthetic Device", filed Feb. 16, 2010.
U.S. Appl. No. 12/706,609 on "Arm Prosthetic Device", filed Feb. 16, 2010.
U.S. Appl. No. 12/706,471 on "System, Method and Apparatus for Orientation Control", filed Feb. 16, 2010.
International Search Report & Written Opinion dated Jun. 11, 2010, received in International patent application No. PCT/US2010/024316, 14 pgs.
International Partial Search Report dated Jul. 21, 2010, received in International patent application No. PCT/US2010/024326, 6 pgs.
International Partial Search Report dated Jul. 21, 2010, received in International patent application No. PCT/US2010/024334, 7 pgs.
International Preliminary Report on Patentability dated Aug. 20, 2009, received in International patent application No. PCT/US2008/053183, 6 pgs.
International Preliminary Report on Patentability dated Aug. 20, 2009, received in International patent application No. PCT/US2008/053191, 7 pgs.
International Search Report & Written Opinion dated Jul. 7, 2008, received in International patent application No. PCT/US2008/053183, 7 pgs.
International Search Report & Written Opinion dated Aug. 6, 2008, received in International patent application No. PCT/US2008/53191, 9 pgs.
U.S. Appl. No. 12/026,971 on "Dynamic Support Apparatus", filed Feb. 6, 2008.
U.S. Appl. No. 12/027,116 on "Method and Apparatus for Control of a Prosthetic", filed Feb. 6, 2008.
U.S. Appl. No. 12/027,141 on "Arm Prosthetic Device", filed Feb. 6, 2008.
International Search Report & Written Opinion dated Jun. 15, 2012, received in International patent application No. PCT/US2011/031797, 14 pgs.
U.S. Appl. No. 16/871,722, filed May 11, 2020.
U.S. Appl. No. 16/272,463, filed Feb. 11, 2019.
U.S. Appl. No. 15/845,505, filed Dec. 18, 2017.
U.S. Appl. No. 13/083,245, filed Apr. 8, 2011.

\* cited by examiner

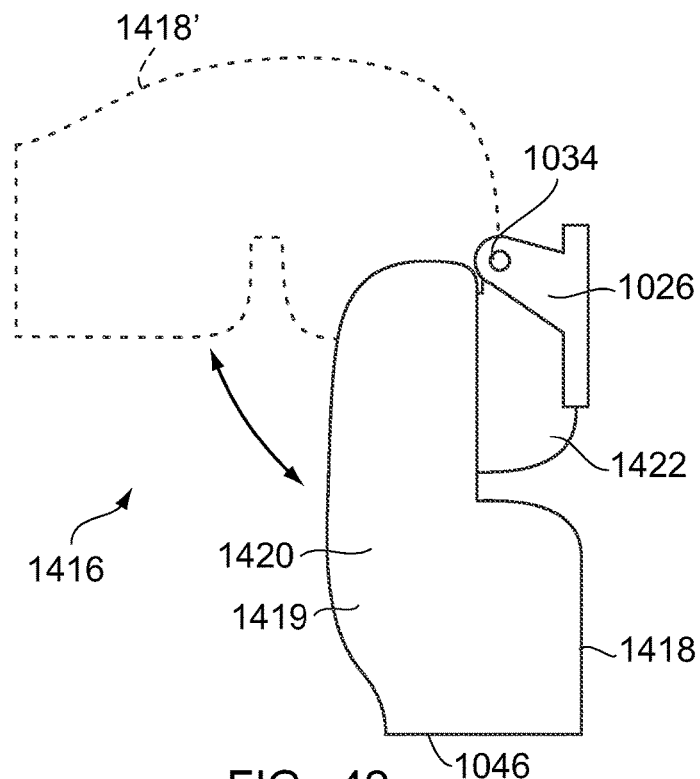
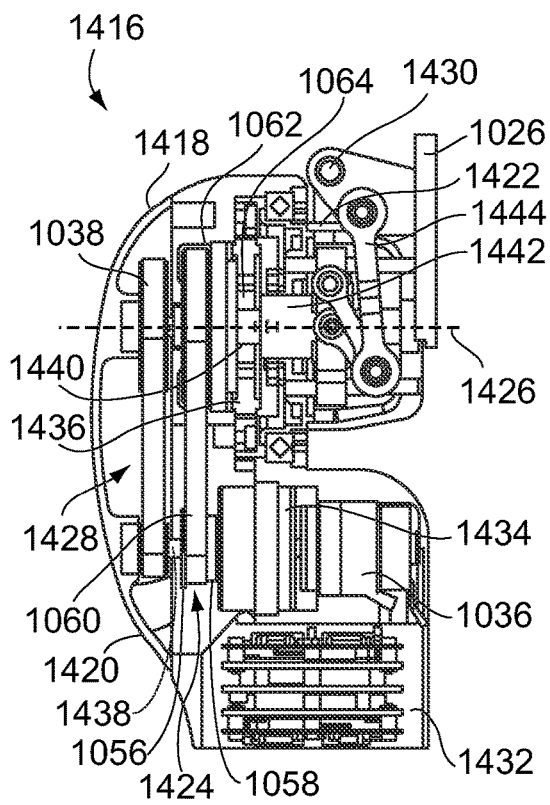
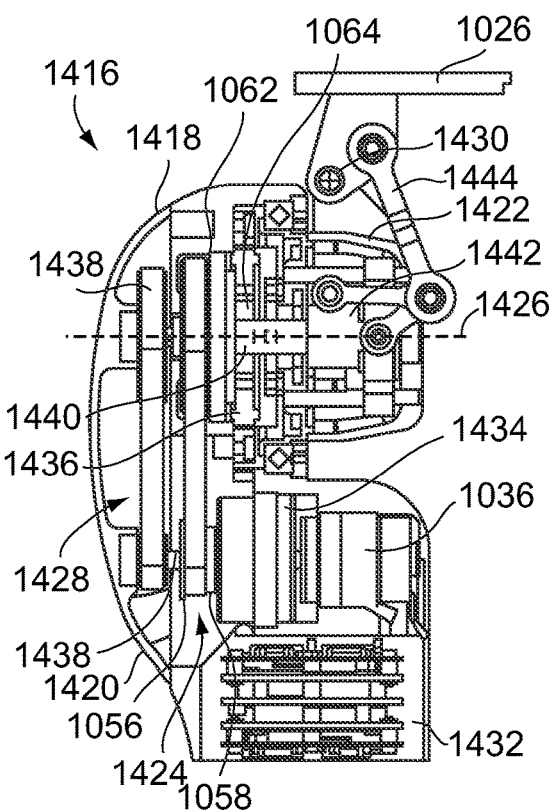
FIG. 42
FIG. 43
FIG. 44

SYSTEM AND APPARATUS FOR ROBOTIC DEVICE AND METHODS OF USING THEREOF

CROSS REFERENCE TO RELATED APPLICATIONS

The present application is a continuation of U.S. patent application Ser. No. 16/871,722, filed May 11, 2020, and entitled System and Apparatus for Robotic Device and Method of Using Thereof, now U.S. Pat. No. 10,888,439, issued Jan. 12, 2021, which is a continuation of U.S. patent application Ser. No. 16/272,463, filed February 11, and entitled System and Apparatus for Robotic Device and Method of Using Thereof, now U.S. Pat. No. 10,646,355, issued May 12, 2020, which is a continuation of U.S. patent application Ser. No. 15/845,505, filed Dec. 18, 2017 and entitled System and Apparatus for Robotic Device and Method of Using Thereof, now U.S. Pat. No. 10,201,435, issued Feb. 12, 2019, which is a continuation of U.S. patent application Ser. No. 13/083,245, filed Apr. 8, 2011 and entitled System and Apparatus for Robotic Device and Method of Using Thereof, now U.S. Pat. No. 9,844,447, issued Dec. 19, 2017, which is a Non-Provisional Application which claims the benefit of U.S. Provisional Patent Application Ser. No. 61/322,469, filed Apr. 9, 2010 and entitled Exoskeleton System and Apparatus for Robotic Device and Methods of Using Thereof, each of which is hereby incorporated herein by reference in its entirety.

TECHNICAL FIELD

The present development relates to mechanical devices and, more particularly, to robotic devices. More particularly, the development relates to a system and apparatus for robotic device and methods of using thereof.

BACKGROUND INFORMATION

For many reasons, there may be a desire for a task to be completed without the direct intervention of a human. For example, but not as a limiting example, there exist methods and tasks that are dangerous, hazardous and/or harmful for a human to perform. Some of these tasks may include those with high risk of bodily injury or death. These include, but are not limited to, the handling of or contact with hazardous materials and working with explosives. Additionally, some environments may be inherently dangerous for humans. However, for many reasons, it may be necessary and/or desirable for a human to handle dangerous materials and/or be in an environment that may be inherently dangerous.

Accordingly, there is a need for a system for performing tasks that may be harmful to a human, under the control of a human, either in the same environment as the task is performed or remotely. Thus, there is a need for a system and apparatus to control a robotic device such that the human is not required to be in the same environment as the robotic device and/or the human is not required to perform the task.

SUMMARY

In accordance with one aspect of the present invention, a robotic assembly control system is disclosed. The robotic assembly control system includes an exoskeleton apparatus adapted to be worn by a user, at least one robotic assembly, the at least one robotic assembly controlled by the user by way of the exoskeleton, and at least one mobile platform, the at least one mobile platform controlled by the user and wherein the at least one robotic assembly is attached to the at least one mobile platform.

In accordance with one aspect to the present invention, a method for mapping movement by a user to a remote robotic assembly is disclosed. The method includes collecting signals from a plurality of sensors reflecting movement of the user, and mapping the signals to control the movement of at least one robotic assembly, wherein the mapping ratio of the user movement to the remote robotic assembly may change at preprogrammed points in the path of the user movement.

In accordance with one aspect to the present invention, a method for mapping movement by a user to a robotic assembly is disclosed. The method includes collecting signals from sensors reflecting movement of the user, and mapping the signals to control the movement of at least one robotic assembly.

Some embodiments of this aspect of the present invention may include one or more of the following. Wherein the method further includes determining the center point of rotation of a shoulder, measuring the shoulder abduction with at least one potentiometer, measuring the shoulder flexion with at least one potentiometer, and mapping the movement of a shoulder and translating the movement of the shoulder to movement of a robotic device.

In accordance with one aspect to the present invention, a robotic assembly control system is disclosed. The system includes an exoskeleton apparatus adapted to be worn by a user, at least one robotic assembly, the at least one robotic assembly controlled by the user by way of the exoskeleton, and at least one mobile platform, the at least one mobile platform controlled by the user and wherein the at least one robotic assembly is attached to the at least one mobile platform.

Some embodiments of this aspect of the present invention may include one or more of the following. Wherein the exoskeleton further includes an attachment system comprising a plurality of straps, the attachment system for attaching to a user, and a frame including a lower portion and an upper portion wherein the upper portion telescopingly connects to the lower portion wherein the frame is adjustable. Wherein the frame further comprising a ball detent mechanism for adjusting the frame. Wherein the system further including at least one potentiometer. Wherein the system further including at least two ball joints. Wherein the system further including a compliance section wherein the compliance section senses sternoclavicular motion by a user. Wherein the compliance section is a torsion spring. Wherein the torsion spring is preloaded with a hard stop, wherein the hard stop is adjustable. Wherein the system further including at least one tactor motor wherein the at least one tactor motor provides feedback from at least one joint on the at least one robotic assembly. Wherein the system further including a tactor strap for each tactor motor wherein the tactor strap attaches to a user. Wherein the at least one tactor motor is a vibration motor. Wherein the exoskeleton further including a hand portion comprising at least one force sensor. Wherein the hand portion comprising a thumb force sensor, an index finger sensor and a middle finger sensor. Wherein the thumb force sensor further comprising at least one potentiometer. Wherein the hand portion further comprising at least one tactor motor wherein the tactor motor provides feedback of the robotic assembly thumb grip to the user.

These aspects of the invention are not meant to be exclusive and other features, aspects, and advantages of the present invention will be readily apparent to those of ordinary skill in the art when read in conjunction with the appended claims and accompanying drawings.

BRIEF DESCRIPTION OF THE DRAWINGS

These and other features and advantages of the present invention will be better understood by reading the following detailed description, taken together with the drawings wherein:

FIG. 42 shows an embodiment of an integrated shoulder unit according to an embodiment of the present invention;

FIG. 43 is a partial cutaway view of the integrated shoulder unit of FIG. 42 in an inactuated state;

FIG. 44 is a partial cutaway view of the integrated shoulder unit of FIG. 42 in an actuated state;

Like reference symbols in the various drawings indicate like elements.

DETAILED DESCRIPTION OF THE PREFERRED EMBODIMENTS

Figure 1:
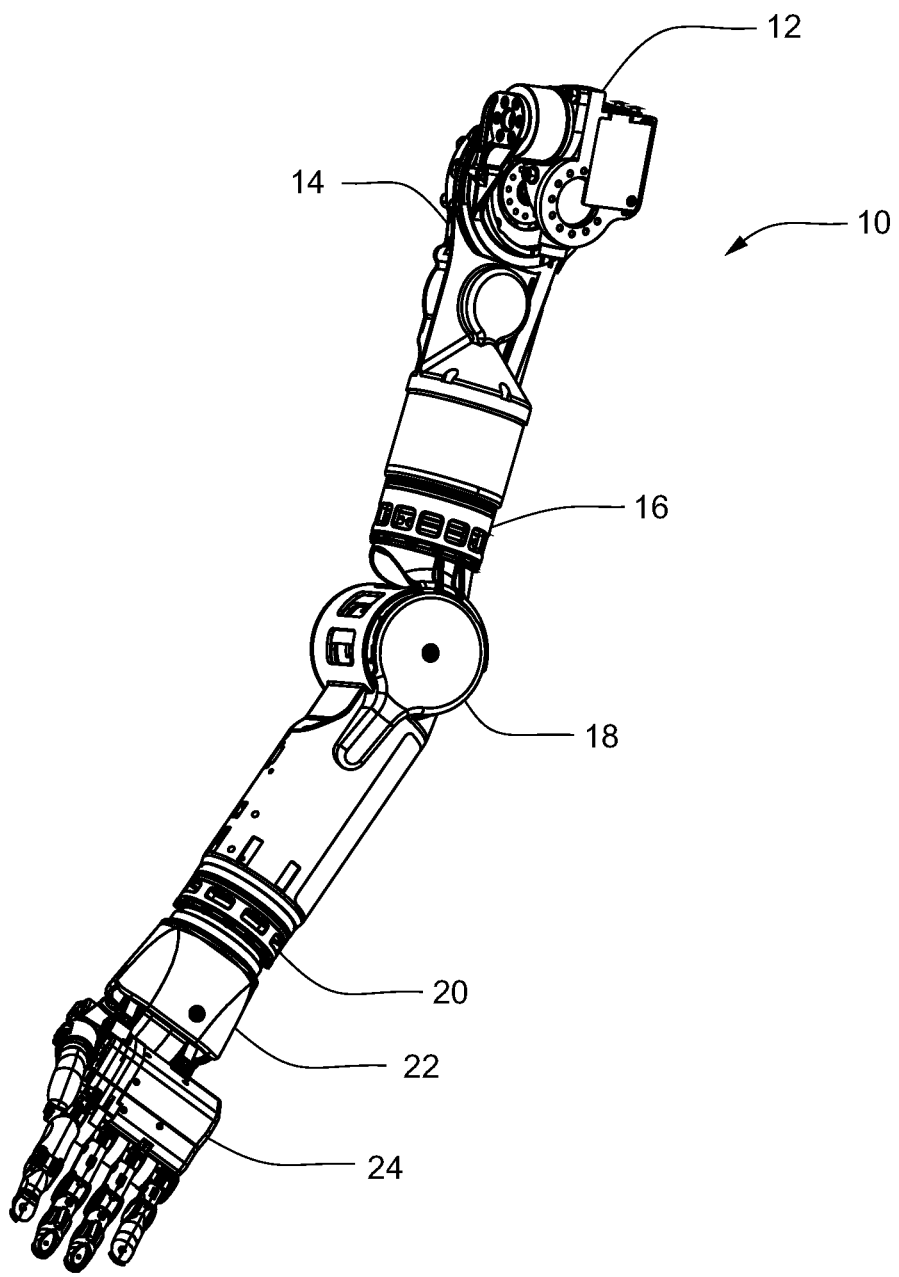
FIG. 1 is a perspective view of one embodiment of a prosthetic arm apparatus according to the present invention.

In some embodiments, the system includes at least one robotic assembly/apparatus and at least one exoskeleton and/or system for control of the at least one robotic assembly. The robotic assembly may include, but is not limited to, a prosthetic and/or robotic arm and/or hand, which, in some embodiments, may be one of the various embodiments of prosthetic/robotic hands/arms described below. However in some embodiments, the system may include at least one robotic apparatus, which, in some embodiments, may be a prosthetic arm, but in other embodiments, may be any robotic apparatus including, but not limited to, a robotic hand, a robotic arm, a robotic leg, a robotic foot and/or a robotic being that may resemble a robotic human or a robotic mammal. In some embodiments, the robotic assembly/apparatus may be any assembly/apparatus with at least one robotic feature.

In some embodiments, the system includes at least two robotic arms, complete with hands. In some embodiments, the at least one robotic arm may be attached to a device which may be a mobile platform. However, in some embodiments, the device may not be attached to a mobile platform, but rather, may be attached to anything, including, but not limited to, a wall, floor or other non-movable structure. In some embodiments, the device may be attached to a structure which may be movable, however, may not be "mobile" in the sense that it may not include one or more wheels. In some embodiments, at least one, and in some embodiments, at least two, prosthetic arms may be attached to a structure, and in some exemplary embodiments, at least two prosthetic arms may be attached to a mobile platform.

In some embodiments, the robotic assembly may not require attachment to any structure but rather, may be a stand alone robotic object.

The system may include at least one exoskeleton apparatus. The exoskeleton apparatus may be adapted to be worn/configured to be worn by a being of any size. In some embodiments, the exoskeleton may be adjustable such that the exoskeleton may be configured to any user. A "user" may be defined as anything, whether human, other mammalian or robotic, that may wear the exoskeleton. In the exemplary embodiments, the exoskeleton is used to at least partially/partly control the at least one robotic assembly. In some embodiments, the exoskeleton may be used to fully control the at least one robotic assembly.

In some embodiments, the exoskeleton may be worn by a human and used to control two robotic arm/hand assemblies. In some embodiments, the exoskeleton may also include at least one component for control of a mobile platform to which the two robotic arm/hand assemblies are mounted by way of at least one compliant feature. In some embodiments, the exoskeleton may control the at least one robotic assembly from a remote location, including, but not limited to, using wireless communication.

In some embodiments, the robotic assembly may be controlled using a camera mapping/camera tracking device which may, using a camera, track the movements of a user, and map the movement of the user onto the robotic assembly. In some embodiments, the cameral mapping/camera tracking device may be one known in the art, for example, the Osprey Digital RealTime Sytem made by Motion Analysis Corporation, Santa Rosa, Calif., U.S.A, however, other system may also be used.

Figure 2:
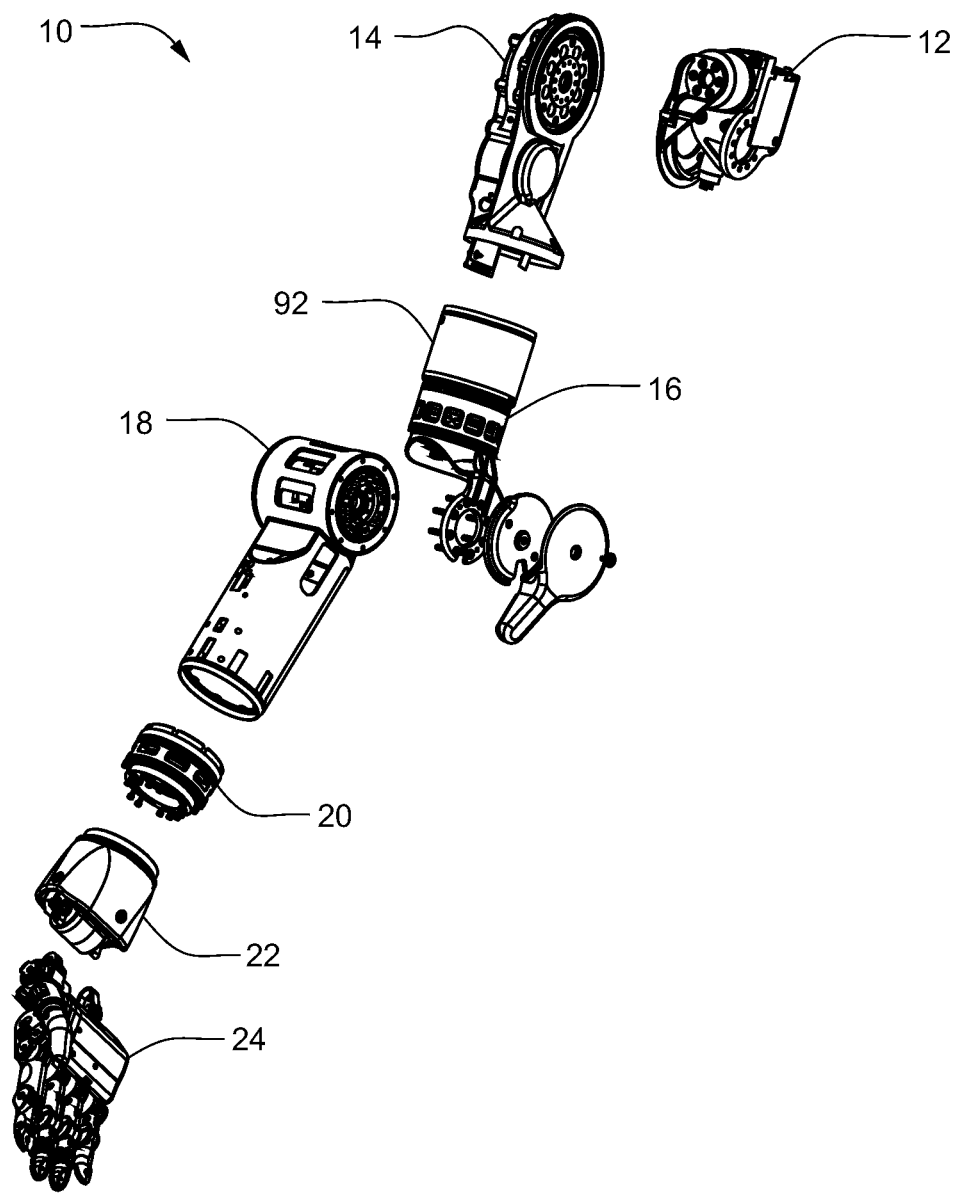
FIG. 2 is an exploded view of the prosthetic arm apparatus of FIG. 1.

As discussed above, in the exemplary embodiment, the robotic assembly is a robotic arm/hand assembly which may be referred to herein, for purposes of description, as a prosthetic arm apparatus. In some embodiments, the prosthetic arm apparatus may be one described below. Referring to FIGS. 1 and 2, a prosthetic arm apparatus 10 for attachment to a shoulder of a shoulder disarticulated amputee includes a plurality of segments, including a shoulder abductor 12, a shoulder flexion assembly 14, a humeral rotator 16, an elbow flexion assembly 18, a wrist rotator 20, a wrist flexion assembly 22, and a hand assembly 24. The prosthetic arm apparatus 10, in the exemplary embodiment, has the dimensions and weight of a female arm of a fiftieth percentile, so that many different users may comfortably use the prosthetic arm apparatus 10. As should be understood by those skilled in the art, the prosthetic arm apparatus 10 may be constructed to larger or smaller dimensions if desired. The prosthetic arm apparatus 10 may be controlled by a control system (not shown), such as the various control systems described in U.S. patent application Ser. No. 12/027,116, filed Feb. 6, 2008, now U.S. Publication No. US-2008-0243265, published Oct. 2, 2008 and entitled METHOD AND APPARATUS FOR CONTROL OF A PROSTHETIC DEVICE; U.S. patent application Ser. No. 12/706,609, filed Feb. 16, 2010, now U.S. Publication No. US-2010-0274365, published Oct. 28, 2010 and entitled ARM PROSTHETIC DEVICE; U.S. patent application Ser. No. 12/706,471, filed Feb. 16, 2010, now U.S. Publication No. US 2010-0211185, published Aug. 19, 2010 and entitled SYSTEM, METHOD AND APPARATUS FOR ORIENTATION CONTROL each of which is hereby incorporated by reference in its entirety.

Figure 3:
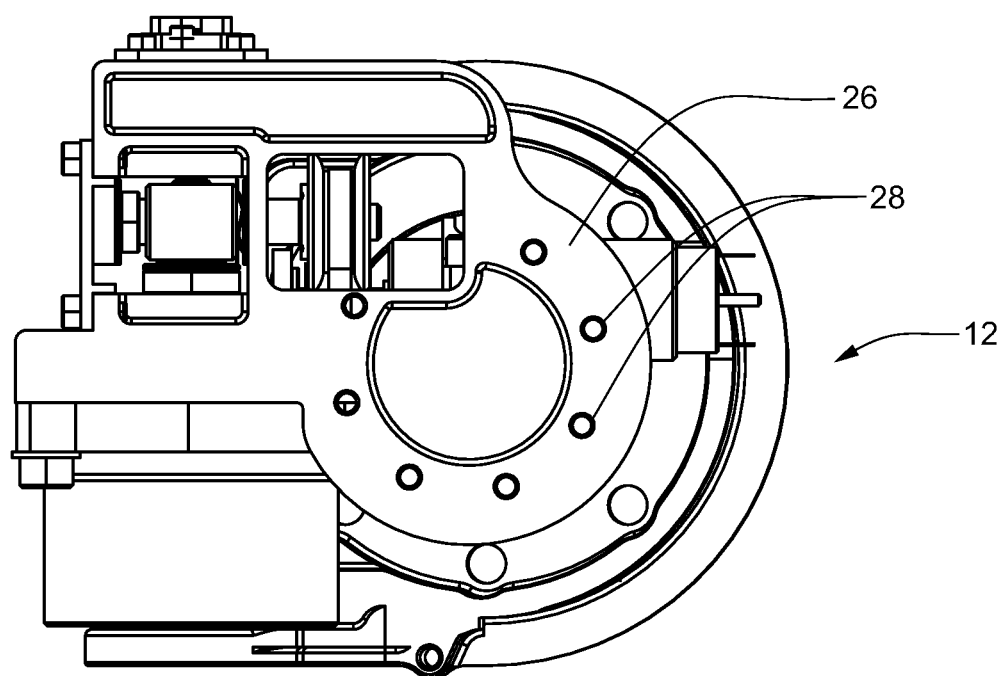
FIG. 3 is a rear view of a shoulder abductor of the prosthetic arm apparatus of FIG. 1 according to the present invention.

Referring to FIG. 3, one embodiment of the shoulder abductor 12 is shown. The shoulder abductor 12 includes a harness mount 26 for connecting the prosthetic arm apparatus 10, shown in FIG. 1, to a support apparatus, as the various prosthetic supports described in U.S. patent application Ser. No. 12/026,971, filed Feb. 6, 2008, now U.S. Publication No. US-2009-0271000, published Oct. 29, 2009 and entitled DYNAMIC SUPPORT APPARATUS; U.S. patent application Ser. No. 12/706,340, filed Feb. 16, 2010, now U.S. Publication No. US-2010-0211189, published Aug. 19, 2010 and entitled DYNAMIC SUPPORT APPARATUS AND SYSTEM, each of which is hereby incorporated by reference in its entirety. The harness mount 26 has harness interface holes 28 that may be used to attach the abductor 12 to a prosthetic harness (not shown) or other system for supporting the prosthetic arm apparatus 10. In the exemplary embodiment, the harness or prosthetic support apparatus may also be one disclosed in co-pending U.S. patent application Ser. No. 12/026,971, filed Feb. 6, 2008, now U.S. Publication No. US-2009-0271000, published Oct. 29, 2009 and entitled DYNAMIC SUPPORT APPARATUS, which is hereby incorporated by reference in its entirety.

Figure 4:
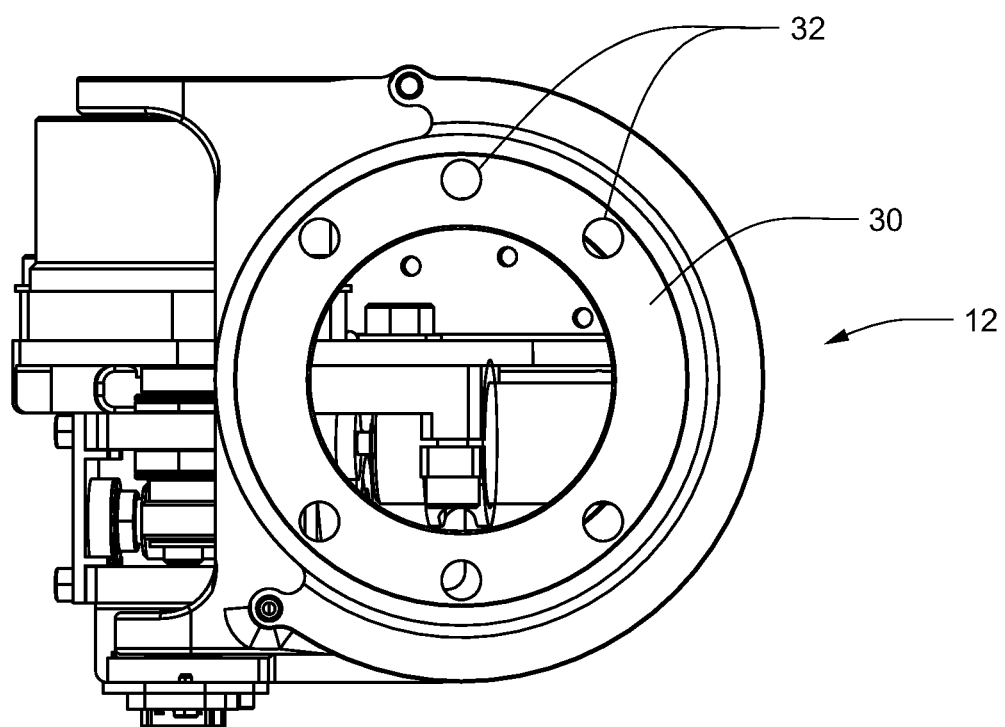
FIG. 4 is a front view of the shoulder abductor of FIG. 3.

Referring to FIG. 4, the shoulder abductor 12 also has a shoulder flexion assembly mount 30, shown according to one embodiment. The shoulder flexion assembly mount 30 interfaces with the shoulder flexion assembly 14 to mount the shoulder flexion assembly 14 onto the shoulder abductor 12. In one embodiment, the flexion assembly mount 30 has interface holes 32 to facilitate connection of the shoulder flexion assembly 14 by attachment means such as bolts.

Figure 5:
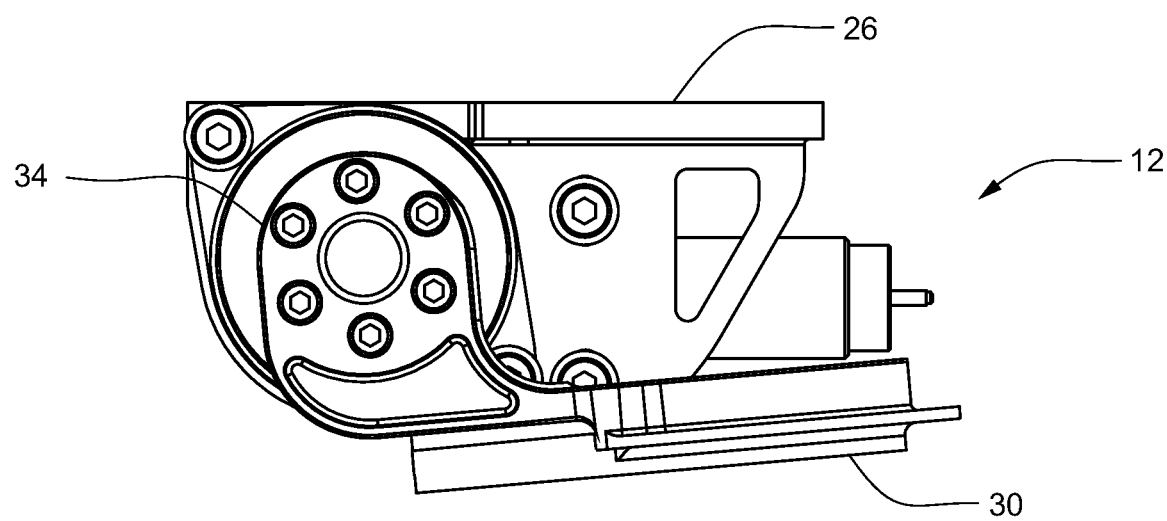
FIG. 5 is a side view of the shoulder abductor of FIG. 3.

Referring to FIG. 5, the shoulder abductor 12 further includes an abductor joint 34, shown according to one embodiment. The abductor joint 34 is used to pivot the shoulder flexion assembly mount 30 away from the harness mount 26 and back toward the harness mount 26.

Figure 6:
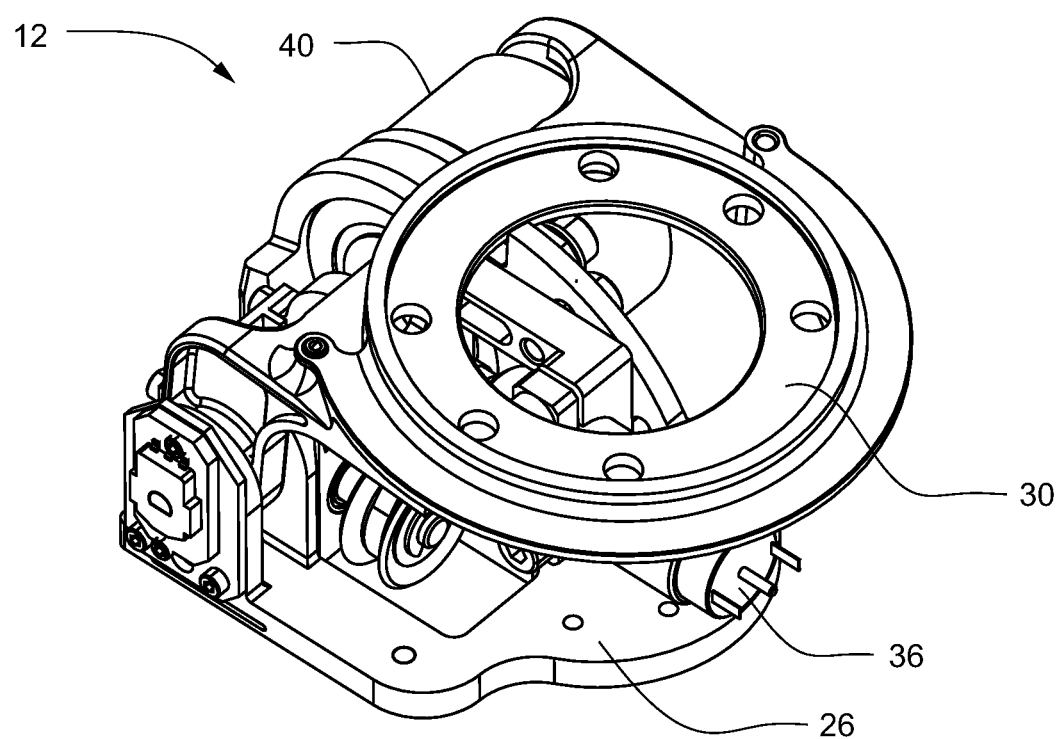
FIG. 6 is a perspective view of the shoulder abductor of FIG. 3.
Figure 7:
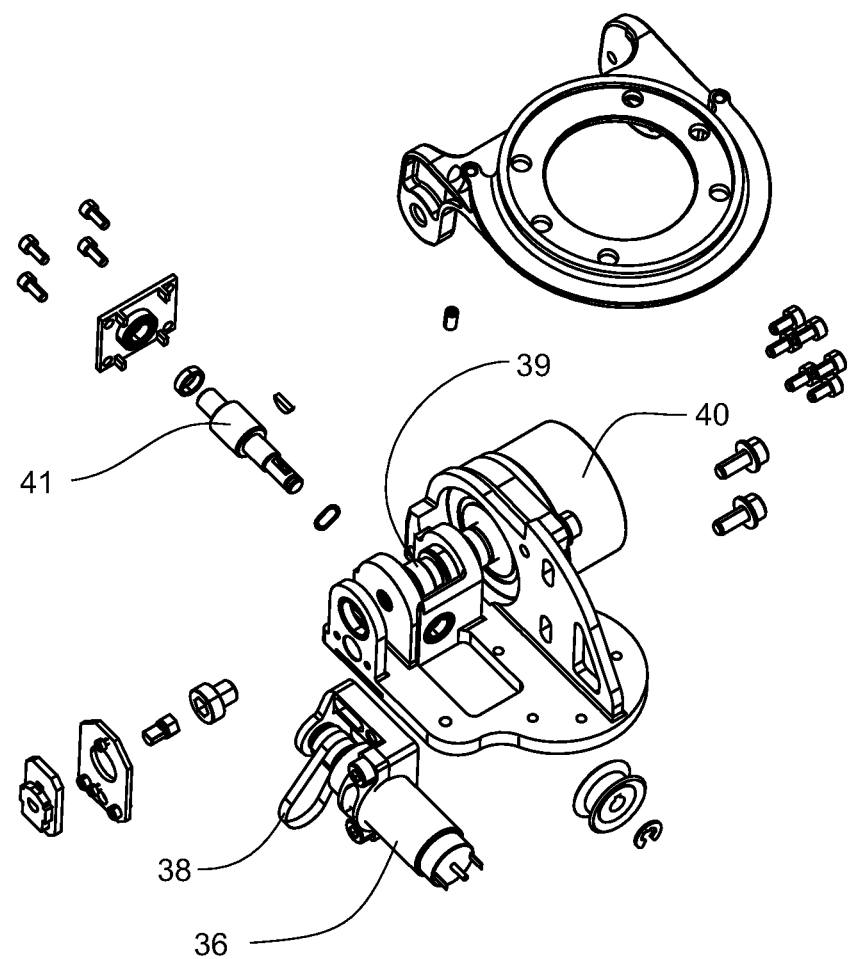
FIG. 7 is an exploded perspective view of the shoulder abductor of FIG. 6.

Referring to FIGS. 6 and 7, the shoulder abductor 12 includes an abductor motor 36 to control the pivotal movement of the abductor joint 34, both the shoulder abductor 12 and abductor motor 36 shown according to one embodiment. In this embodiment, the abductor motor 36 is a brushed DC motor controlling the pivotal movement through an abductor belt 38 connected to a worm drive 41 driving a worm wheel 39 connected to an abductor harmonic drive gearing system 40.

Figure 8:
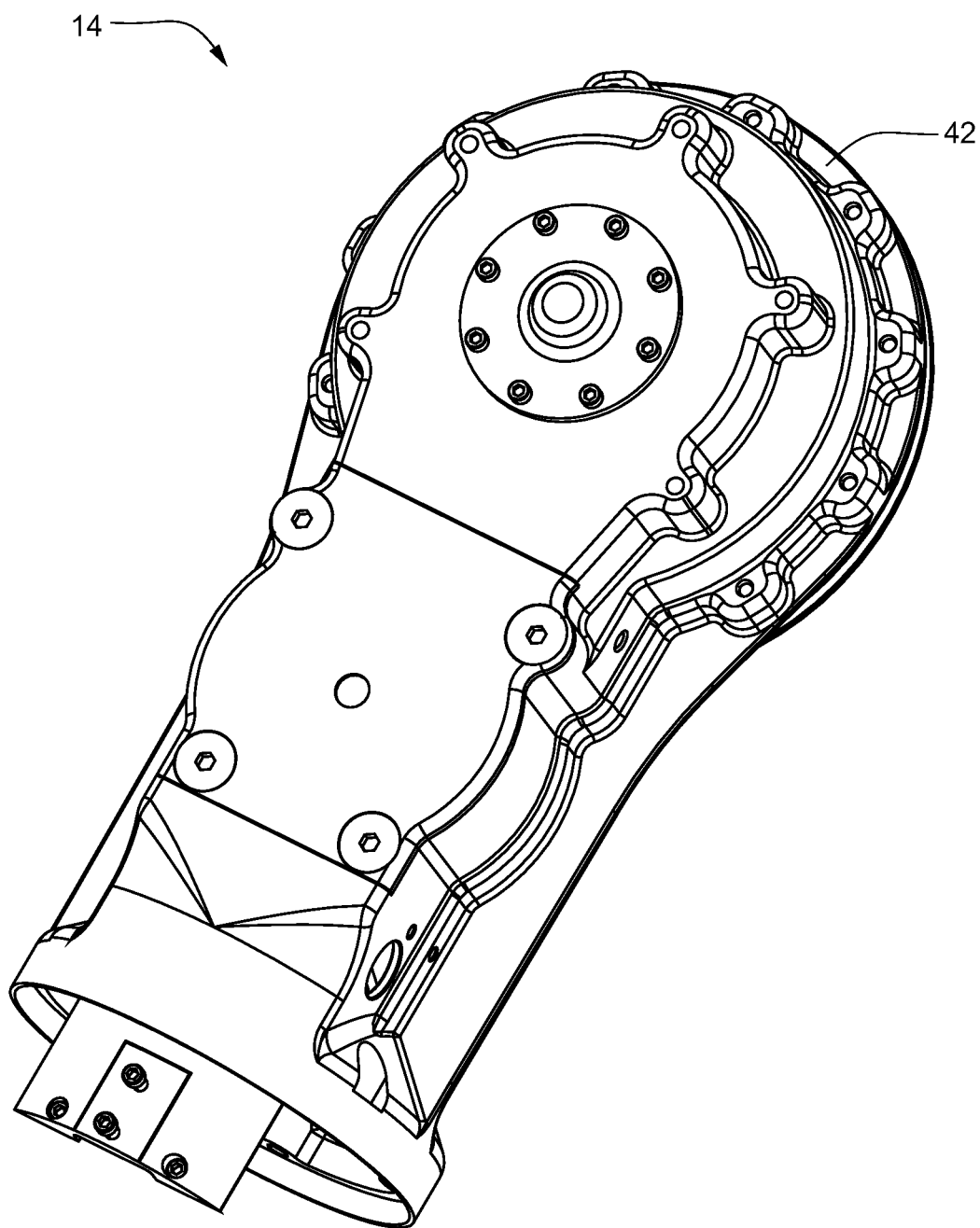
FIG. 8 is a perspective view of a shoulder flexion assembly of the prosthetic arm apparatus of FIG. 1 according to the present invention.
Figure 9:
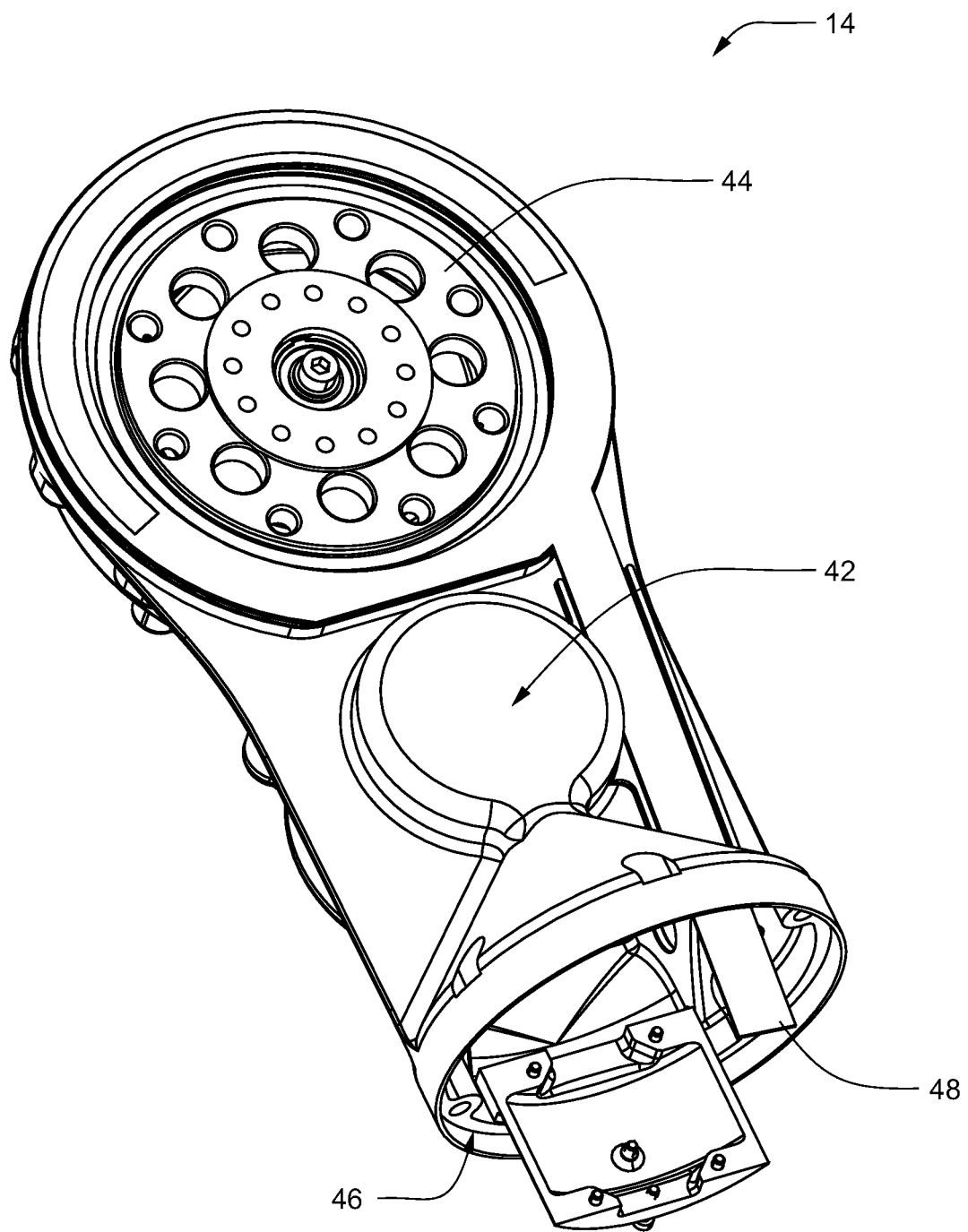
FIG. 9 is a reverse perspective view of the shoulder flexion assembly of FIG. 8.

Referring to FIGS. 8 and 9, the shoulder flexion assembly 14, in one embodiment, has a main shoulder housing 42, with an abductor interface 44 for connecting the shoulder flexion assembly 14 to the shoulder abductor 12. The shoulder flexion assembly 14 also has a humeral interface 46 for connecting the humeral rotator 16 to the shoulder flexion assembly 14.

Figure 10:
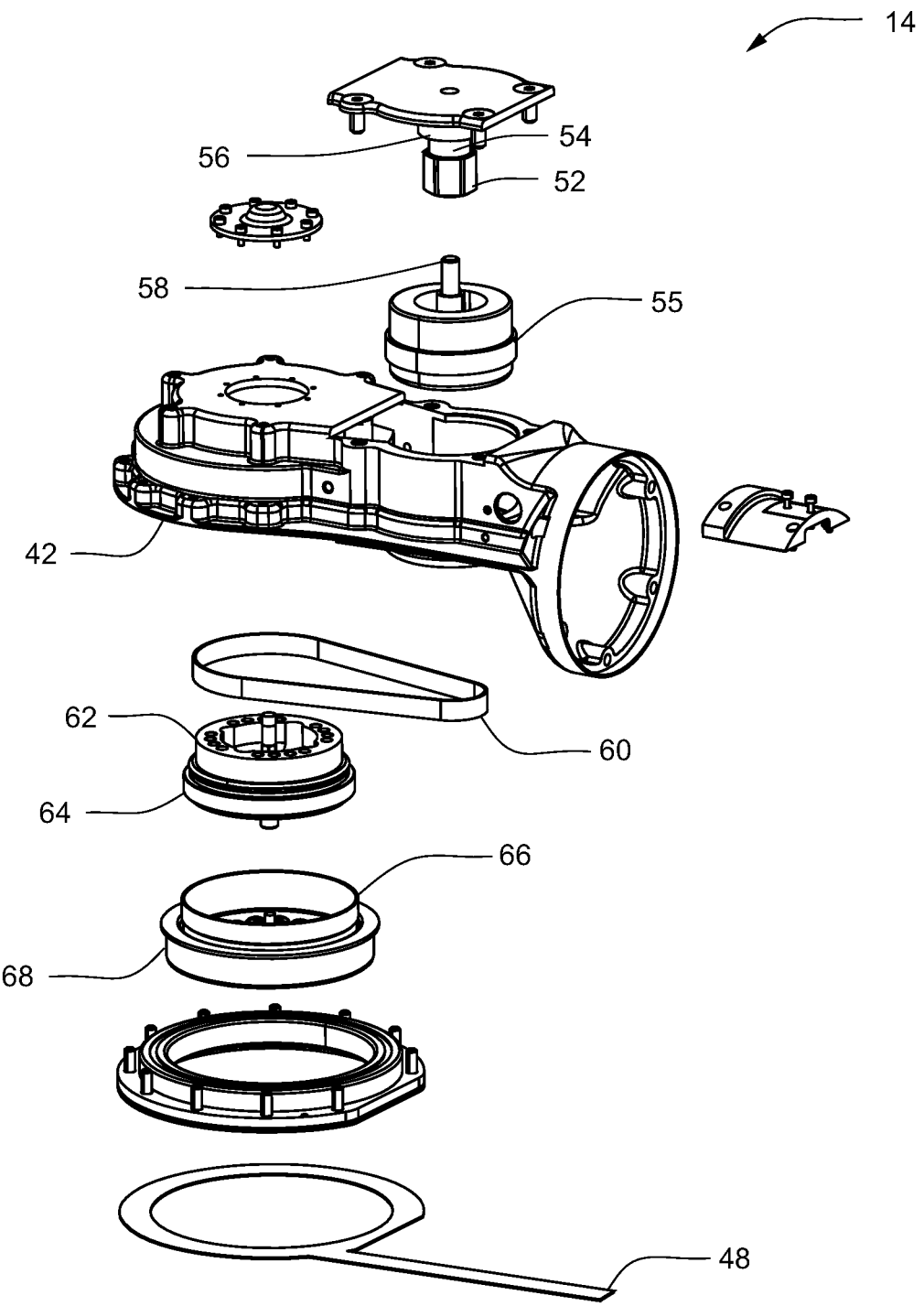
FIG. 10 is an exploded perspective view of the shoulder flexion assembly of FIG. 8.
Figure 11:
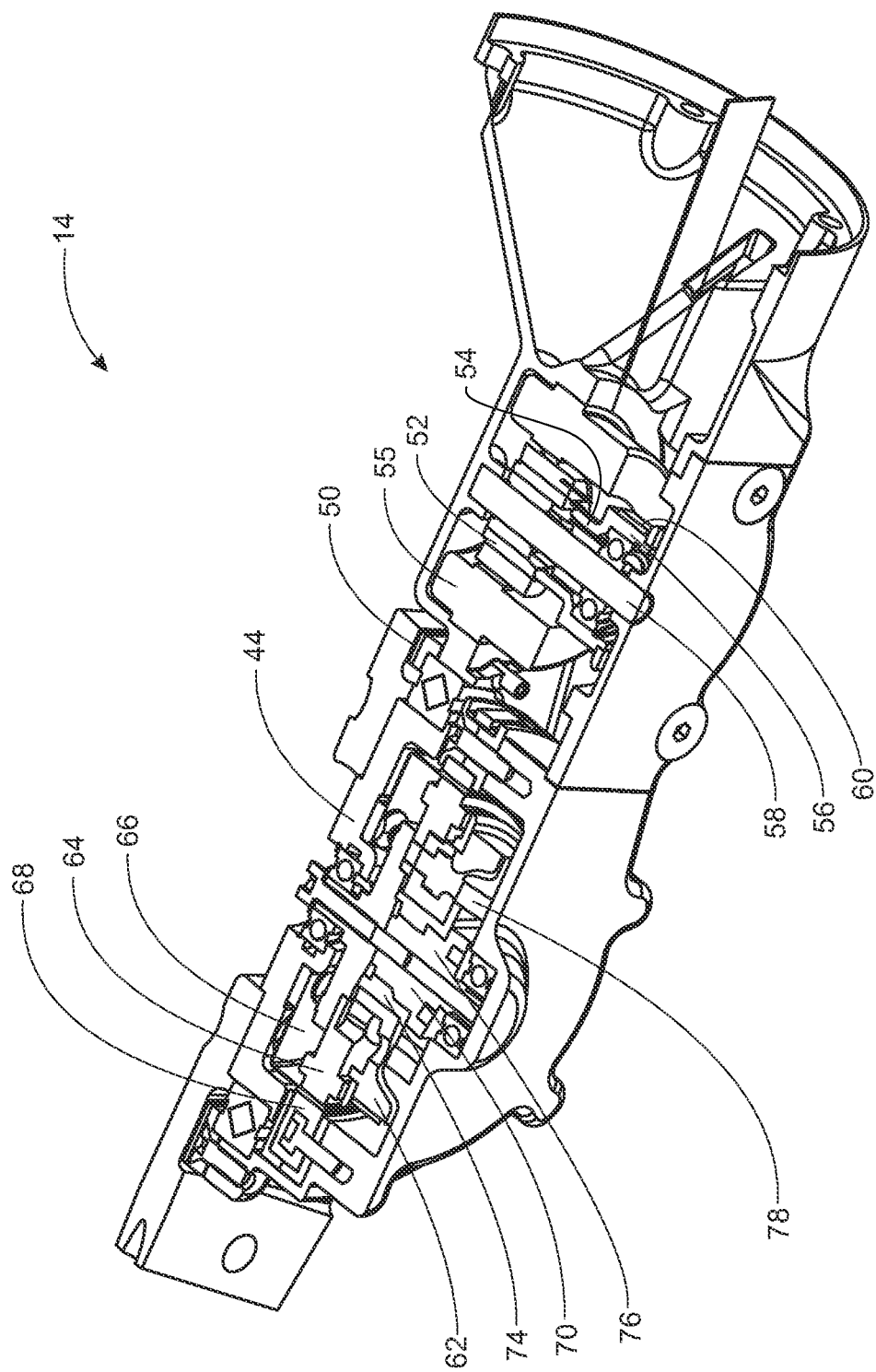
FIG. 11 is a cross-sectional perspective view of the shoulder flexion assembly of FIG. 8.

Referring to FIGS. 10 and 11, in one embodiment, shoulder flexion motor magnets 52 are disposed around a shaft 58 of a shoulder flexion motor rotor 54. In this embodiment, a shoulder flexion motor armature 55 drives the shoulder flexion motor rotor 54, which in turn drives a shoulder flexion motor pulley 56 around a motor shaft 58. The shoulder flexion motor pulley 56 supports a shoulder flexion belt 60, which is linked between the shoulder flexion motor pulley 56 and a shoulder flexion belt-driven pulley 62. The shoulder flexion belt-driven pulley 62 drives a shoulder flexion harmonic drive gearing system wave generator 64. A shoulder flexion harmonic drive gearing system flexspline 66 rotates against the shoulder flexion harmonic drive gearing system wave generator 64 and a shoulder flexion harmonic drive gearing system circular spline 68, resulting in reduced speed for the joint movement. The shoulder flexion harmonic drive gearing system flexspline 66 is connected to the abductor interface 44, and is thus able to rotate the shoulder flexion assembly 14 in reference to the abductor interface.

Referring to FIG. 11, in one embodiment, a non-backdriving clutch 70 is disposed inside the main shoulder housing 42. The non-backdriving clutch 70 allows the prosthetic arm 10 to hold position by locking when the prosthetic arm 10 is not moving.

Figure 12:
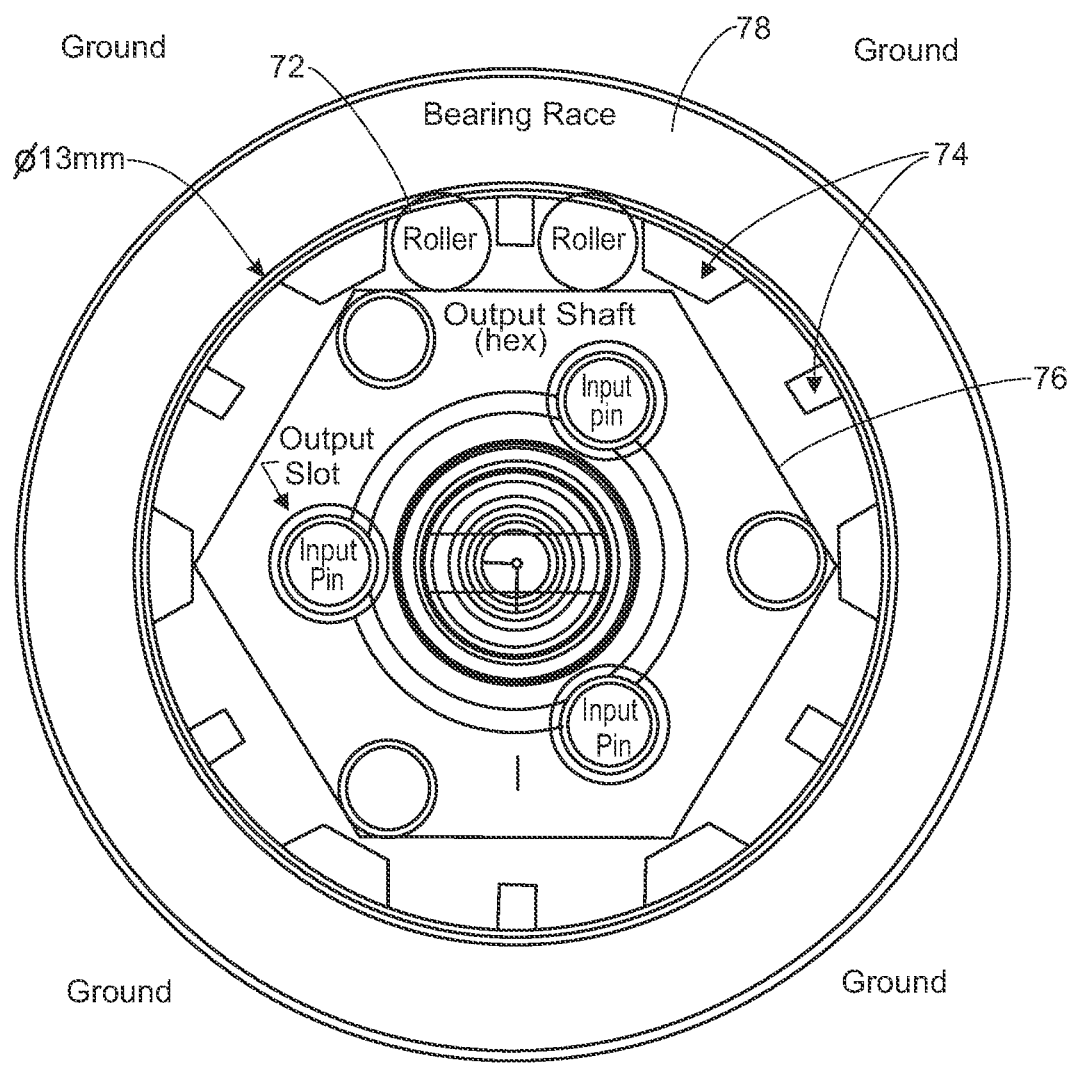
FIG. 12 is a top view of a non-backdriving clutch according to the present invention.

Referring to FIG. 12, in one embodiment, roller bearings 72 line the interface between an input cage 74 and an output hex 76. When a force is applied to the shoulder abductor interface 44, the output hex 76 locks against the bearing race 78 and the roller bearings 72. This prevents the shoulder flexion assembly 14 from moving due to force applied to its output, shoulder abductor interface 44. Upon the exertion of a necessary amount of input force through the clutch input cage 74, the output hex 76 disengages and allows the shoulder flexion assembly 14 to move. The clutch input cage 74 and the output hex 76 are both constrained by a clutch race 78. It should be understood by those skilled in the art, that other mechanisms could be used to prevent backdriving of the prosthetic arm 10, such as a clutch that locks in one direction or a solenoid with brakes that engage when the solenoid is powered. Additionally, although described in connection with the shoulder flexion assembly 14, it should be understood by those skilled in the art that the non-backdriving clutch 70 may be included in other prosthetic joints described herein.

Figure 13:
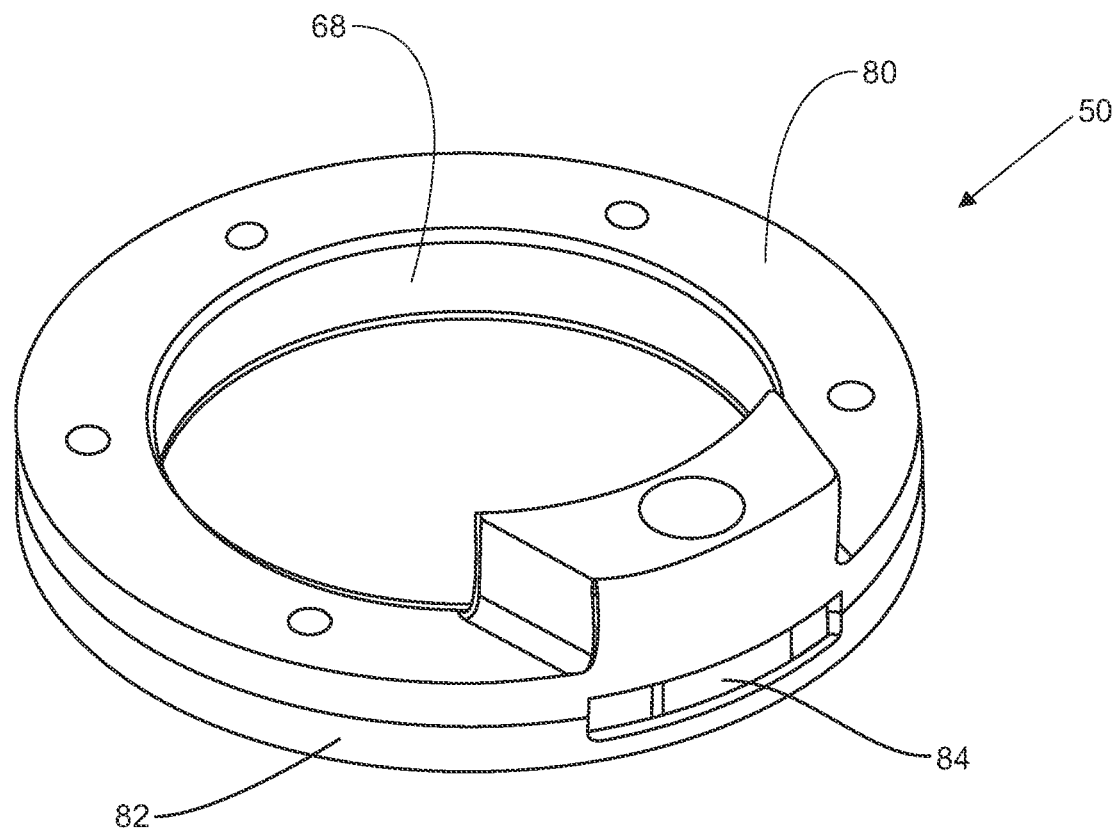
FIG. 13 is a perspective view of a fully assembled compliance subassembly of the shoulder flexion assembly of FIG. 8.

Referring to FIG. 13, in one embodiment, a compliance subassembly 50 includes a compliance reactor 80 positioned on top of the shoulder flexion harmonic drive gearing system circular spline 68 and held in place by the clamp 82. The compliance reactor 80 measures the amount of displacement in the compliance subassembly 50 in relation to the position of a compliance sensor magnet 84.

Figure 14:
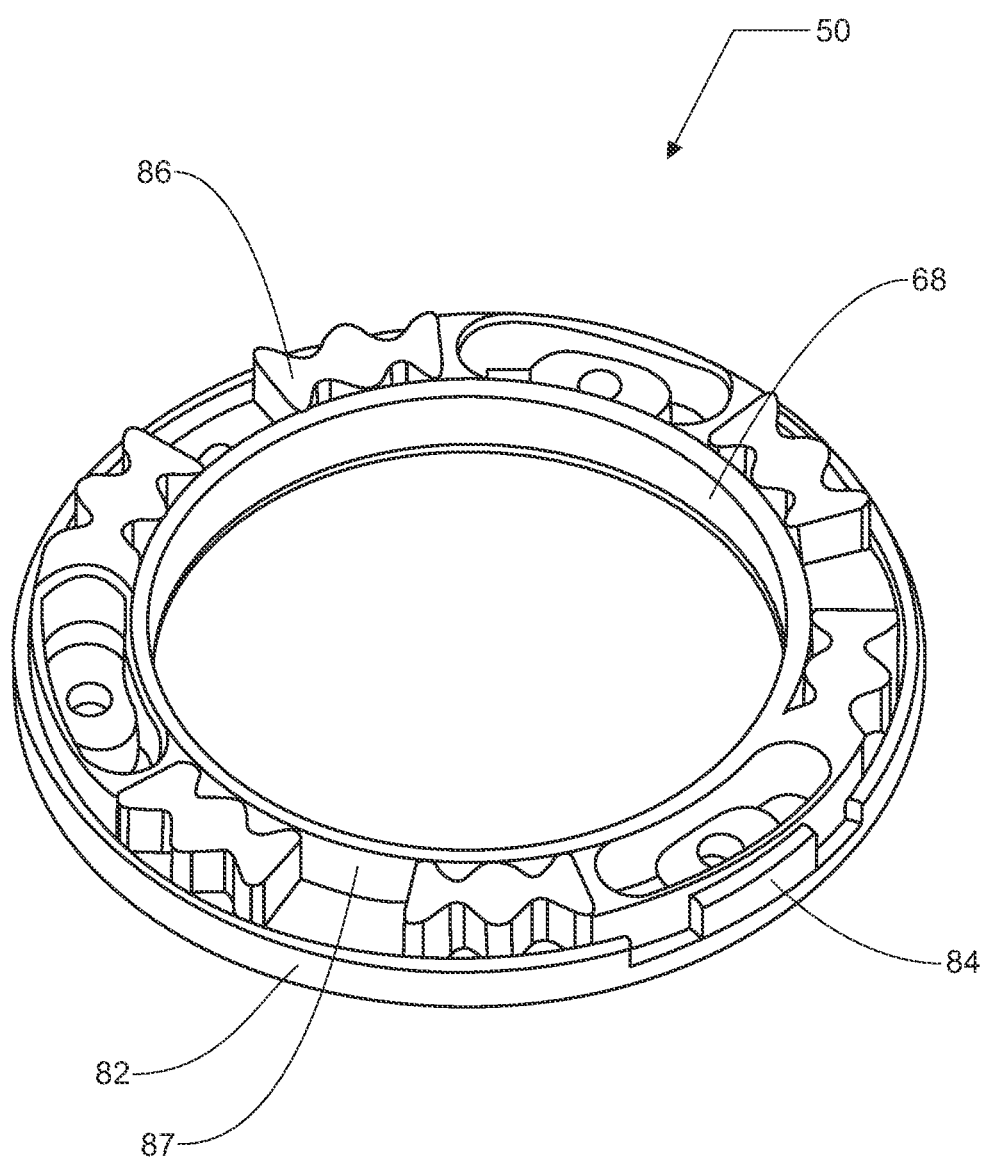
FIG. 14 is a perspective view of the bottom portion of the compliance subassembly of FIG. 13.

Referring to FIG. 14, in one embodiment, the interior of compliance subassembly 50 includes series elastic elements 86. The shoulder flexion harmonic drive gearing system circular spline 68 defines the interior of the compliance subassembly 50 and is formed to accommodate the placement of the series elastic elements 86 around an outer diameter 87 of the shoulder flexion harmonic drive gearing system circular spline 68. The series elastic elements 86 are confined by the shoulder flexion harmonic drive gearing system circular spline 68 and the clamp 82.

Figure 15:
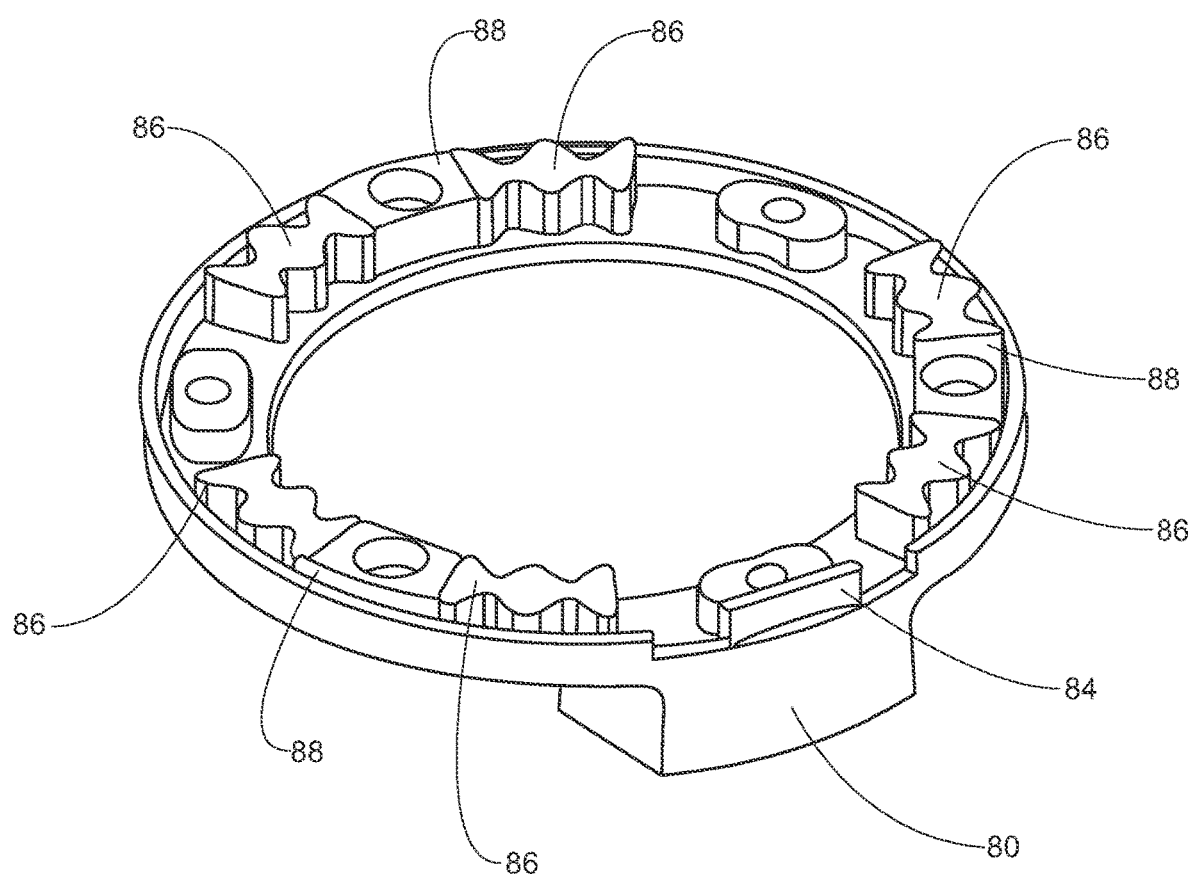
FIG. 15 is a perspective view of the top portion of the compliance subassembly of FIG. 13.

Referring to FIG. 15, the placement of the compliance reactor 80 in relation to the series elastic elements 86 and reactor elements 88 is shown. In this embodiment, three reactor elements 88 are positioned around the compliance reactor 80, equidistant to each other. One series elastic element 86 is placed on either side of each reactor element 88. When the shoulder flexion assembly 14 is subjected to unexpected force, such as a sudden jolt or impact, the compliance reactor 80 and reactor elements 88 displace from their rest positions and compress against the series elastic elements 86. In that way, the compliance subassembly 50 attenuates the shock being transferred to the rest of the shoulder flexion assembly 14. The compliance reactor 80 may also measure the amount of displacement and compliance by measuring the movement of the compliance reactor 80 in relation to the stationary position of the compliance sensor magnet 84.

Figure 16:
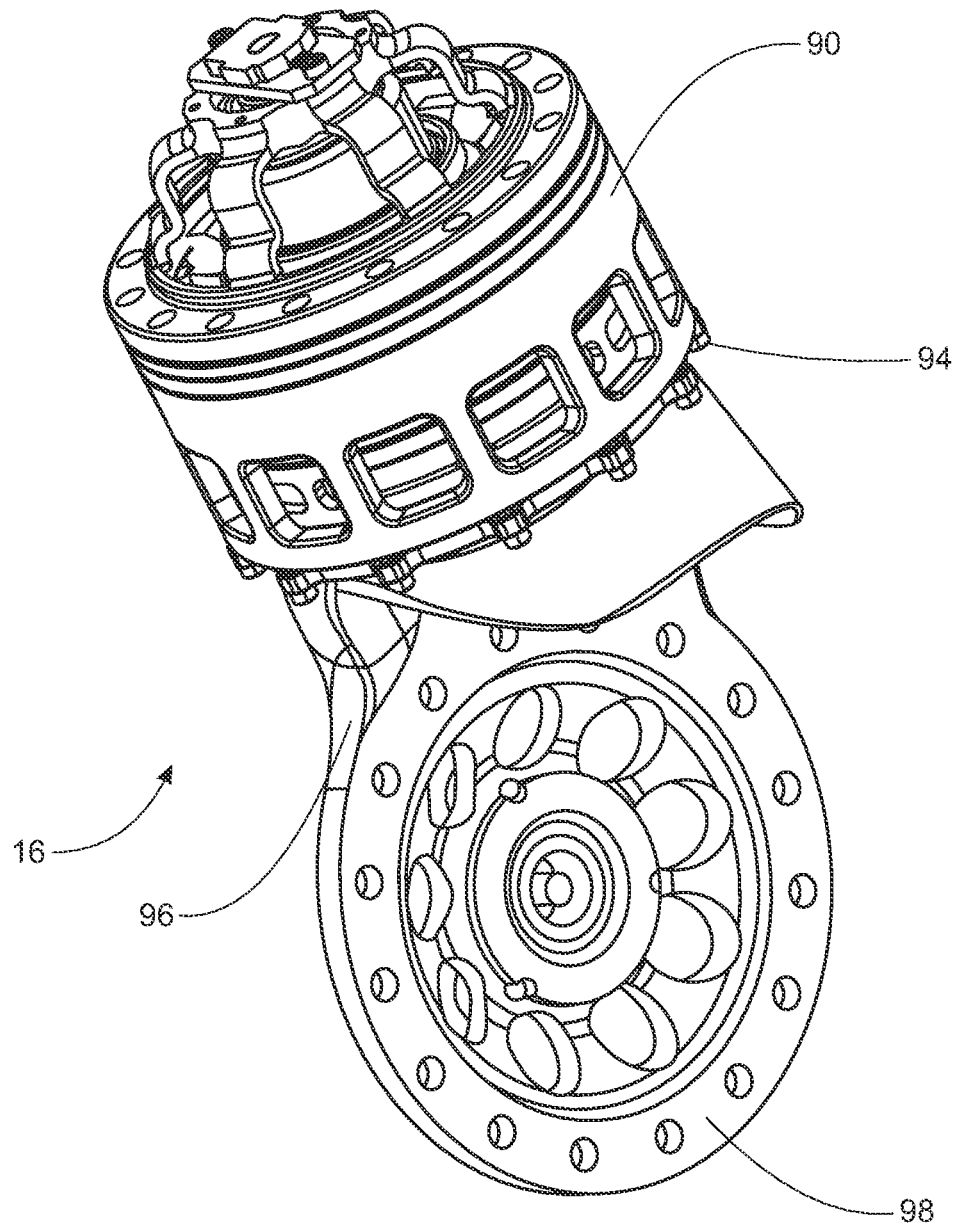
FIG. 16 is a perspective view of a humeral rotator of the prosthetic arm apparatus of FIG. 1 according to the present invention.

Referring to FIG. 16, one embodiment of the humeral rotator 16 is shown. The humeral rotator 16 includes an outer bearing carrier 90 attached to the first control housing 92, shown in FIG. 2. The first control housing 92, shown in FIG. 2, is used to connect the humeral rotator 16 to the shoulder flexion assembly 14. The inner rotational elements of the humeral rotator are held in place by a clamp 94, which is fastened to the outer bearing carrier 90. A humeral mount 96 passes through the clamp 94 and includes an elbow interface 98 for attaching the elbow flexion assembly 18 to the humeral rotator 16.

Figure 17:
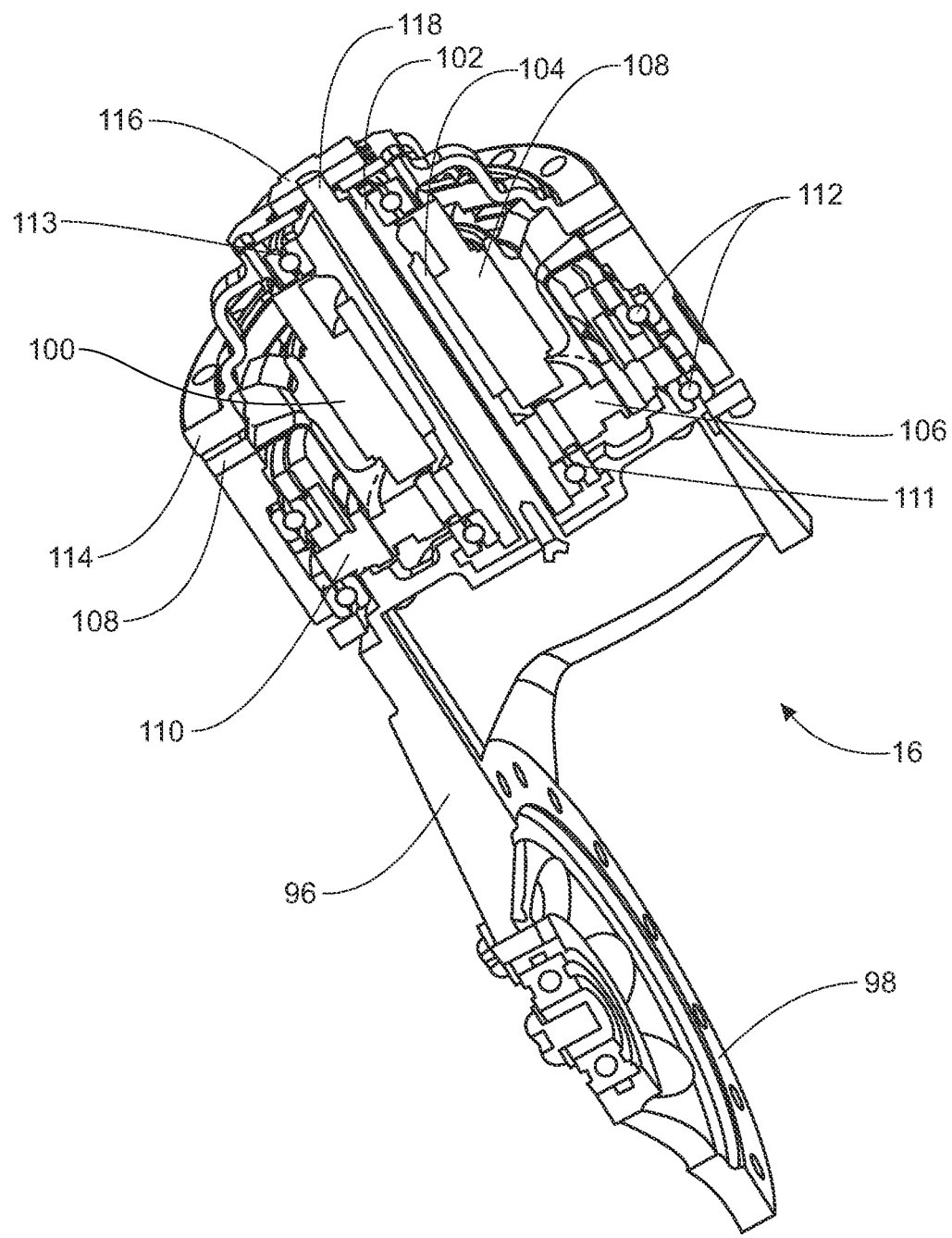
FIG. 17 is a cross-sectional perspective view of the humeral rotator of FIG. 16.

FIG. 17 shows a cross-sectional view of the humeral rotator 16. A humeral motor armature 100 drives a humeral motor rotor 102 having humeral magnets 104 disposed on its surface. The lower portion of the motor rotor 102 engages a humeral harmonic drive gearing system wave generator 106. A humeral harmonic drive gearing system flexspline 108 rotates with the humeral harmonic drive gearing system wave generator 106 against the humeral harmonic drive gearing system circular spline 110, resulting in a speed of rotation reduction as the humeral harmonic drive gearing system flexspline 108 causes the humeral mount 96 to move. Bearings 111 and 113 support the humeral motor rotor 102. Bearings 112 support the harmonic drive gearing system components 106, 108, 110. A bearing support 114 caps the outer bearing carrier 90 between the outer bearing carrier 90 and the first control housing 92.

Still referring to FIG. 17, the one embodiment, a humeral potentiometer 116 of the humeral rotator 16, measures the rotational displacement of a humeral potentiometer shaft 118 that rotates proportionately to the humeral mount 96.

Figure 18:
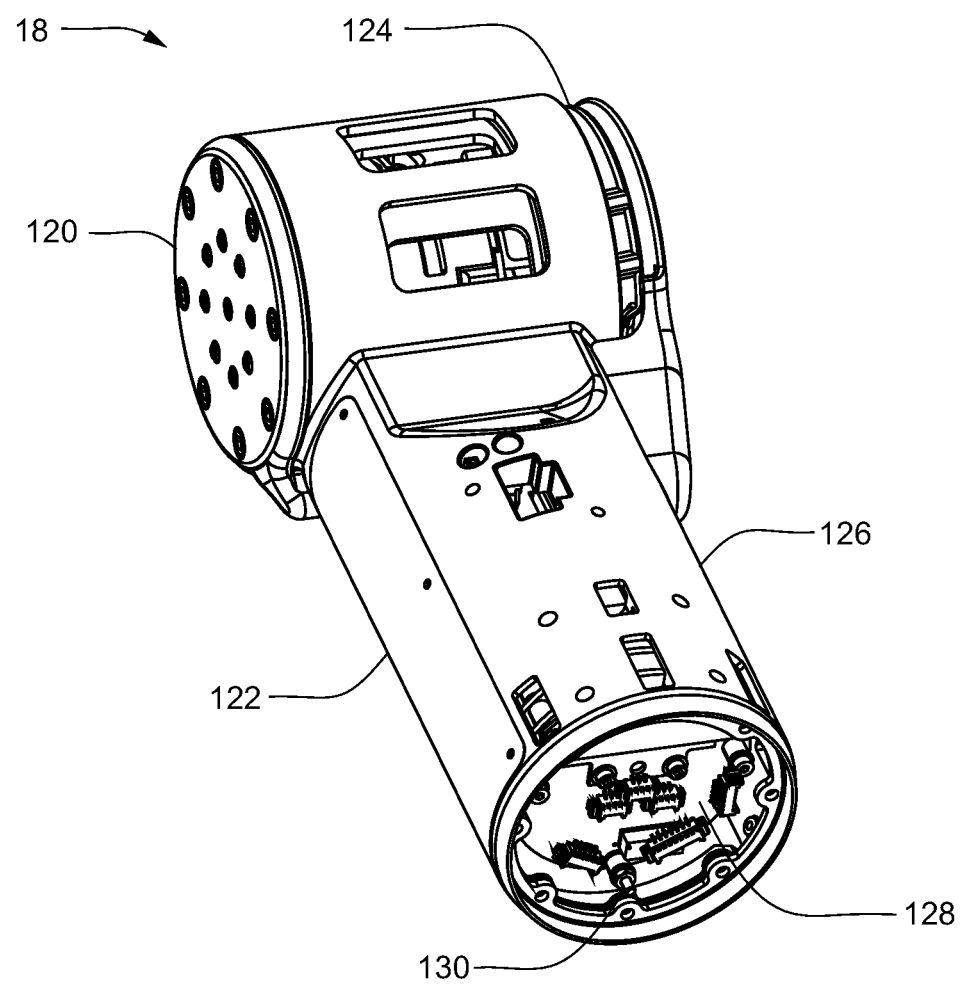
FIG. 18 is a perspective view of an elbow flexion assembly of the prosthetic arm apparatus of FIG. 1 according to the present invention.

Referring to FIG. 18, the elbow flexion assembly 18 includes an elbow joint 120 and a radial mount 122. The elbow joint 120 includes a slot 124 into which the elbow interface 98 of the humeral rotator is inserted to facilitate connection of the elbow flexion assembly 18 to the humeral rotator 16. The radial mount 122 provides a second electronics housing 126, in which an ACM stack 128 is located. "ACM" as used herein refers to Arm Control Module. The radial mount 122 includes a wrist interface 130, for attachment of the wrist rotator 20.

Figure 19:
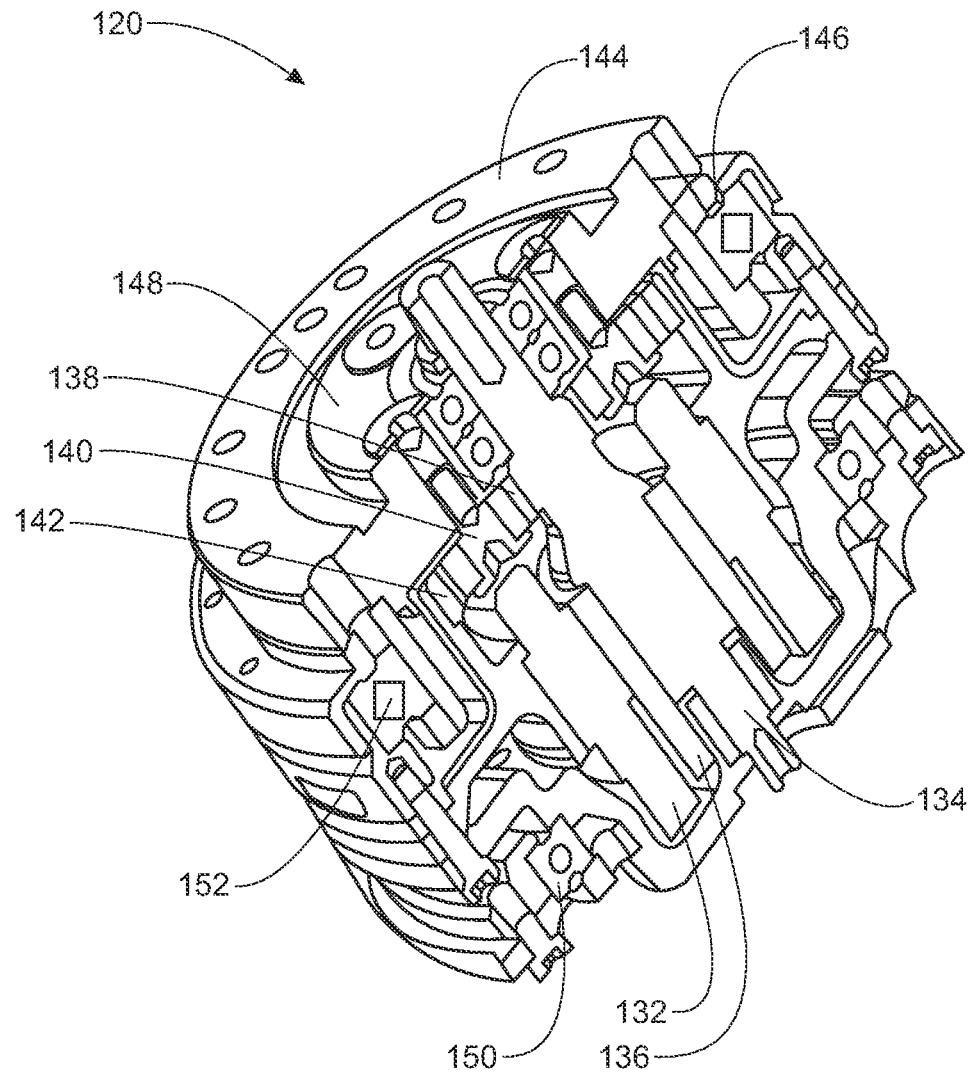
FIG. 19 is a cross-sectional perspective view of one embodiment of the elbow flexion 15 assembly shown without the radial mount.

Referring to FIG. 19, the elbow joint 120 includes an elbow motor armature 132 that drives an elbow motor rotor 134. Elbow magnets 136 are disposed at one end of the motor rotor 134, and the opposing end of the motor rotor 134 has a sun gear 138. As the motor armature 132 drives the sun gear 138, the sun gear 138 in turn drives four planetary gears 140 positioned equidistant from each other around the sun gear 138. The four planetary gears 140 in turn react against a ring gear 142, giving the elbow flexion assembly 18 a first stage of speed reduction through an elbow harmonic drive gearing system wave generator 148 which also acts as the planet carrier. The elbow harmonic drive gearing system wave generator 148 powers the elbow harmonic drive gearing system flexspline 146, which drives against the elbow harmonic drive gearing system circular spline 144, giving the elbow flexion assembly 18 a second stage of reduction. The elbow harmonic drive gearing system flexspline 146 then drives the motion of the elbow flexion assembly 18. Bearings 150 and crossed roller bearings 152 support the outer perimeter of the elbow flexion assembly 18. Although described with both a planetary gear system and an elbow harmonic drive gearing system, the elbow flexion assembly 18 could be controlled solely by a harmonic drive gearing system by changing the gear reduction ratio.

In various embodiments, it may be desirable to avoid having to perform additional measurement by using the measurement in the compliance process. One example includes, in various embodiments, where the planetary gears may be used for compliance and measurement of load.

Figure 20:
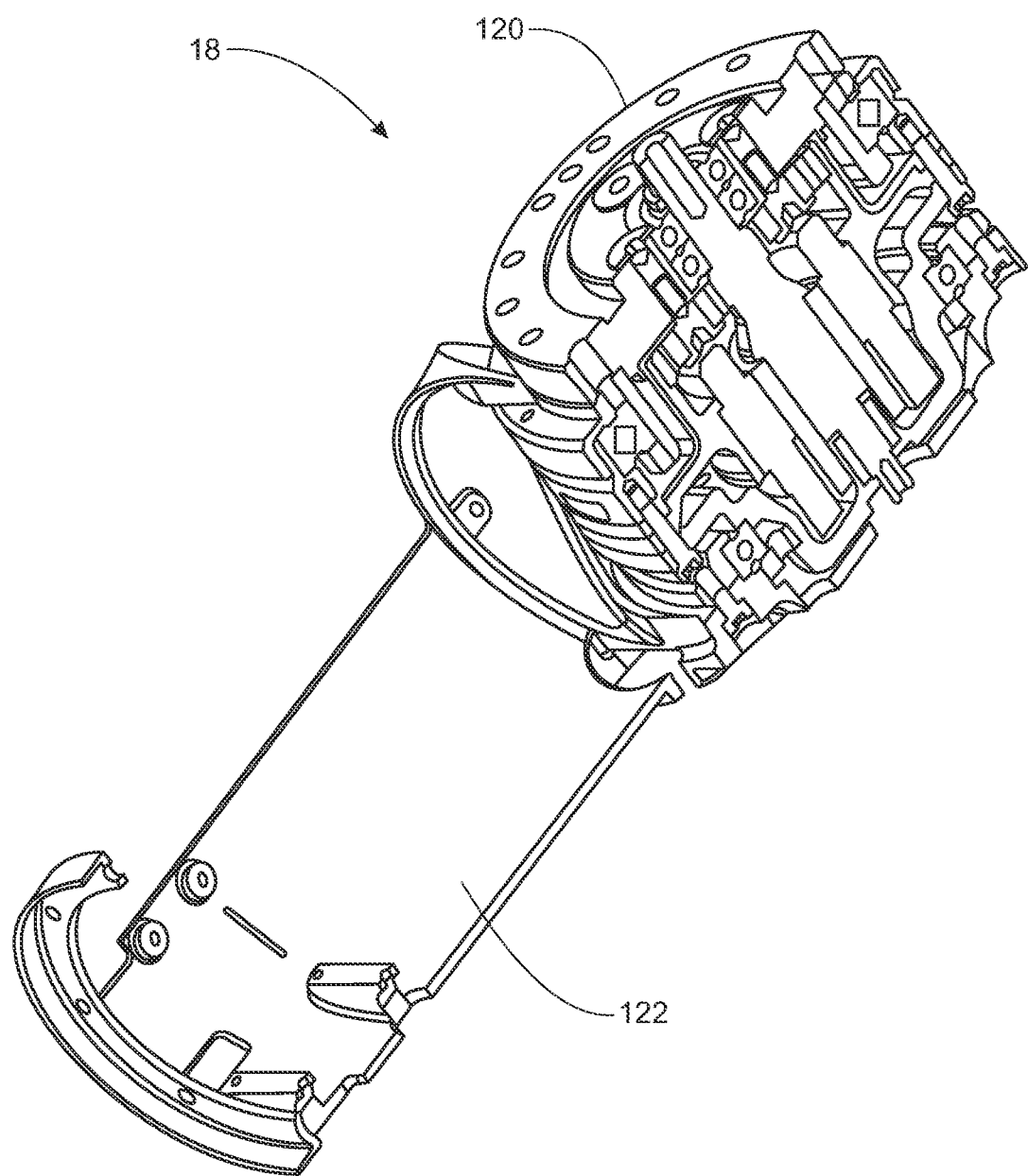
FIG. 20 is a cross-sectional perspective view of the elbow flexion assembly shown with the radial mount.

Referring to FIG. 20, in the embodiment shown, the radial mount 122 is structurally fixed to the elbow joint 120, such that when the elbow joint is actuated, the radial mount 122 moves.

Figure 21:
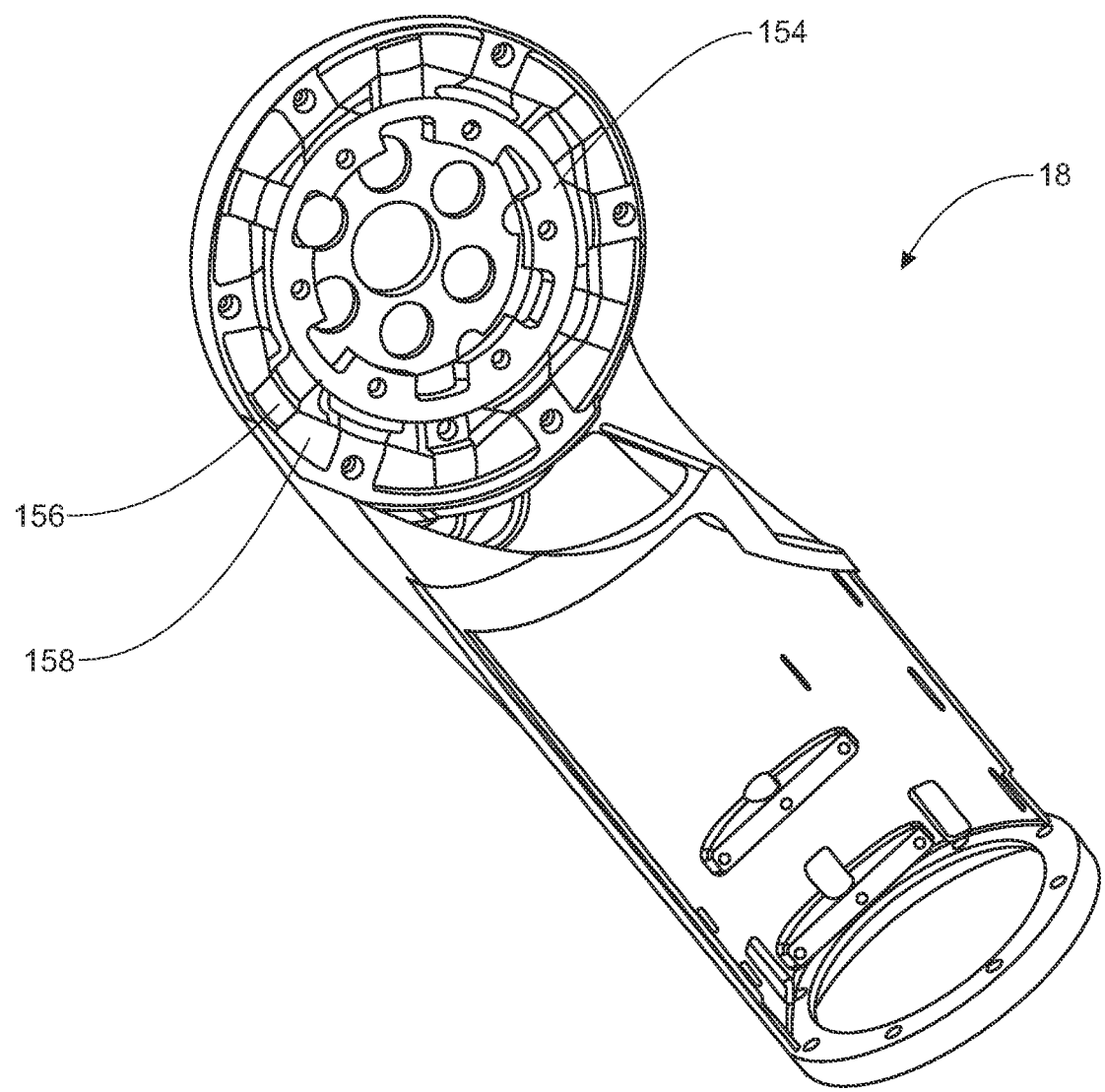
FIG. 21 is a perspective view showing the compliance subassembly of the elbow flexion assembly of FIG. 19.

Referring to FIG. 21, an elbow compliance subassembly 154 is incorporated into the elbow flexion assembly 18. A plurality of arms 156 extends from the center portion of the elbow compliance subassembly 154. Each arm 156 has an elbow series elastic element 158 disposed on either side of the am 156. Similar to the shoulder flexion assembly 14, if the elbow flexion assembly 18 is subject to a torque, the elbow compliance subassembly 154, with its series elastic elements 158, is capable of absorbing the shock attenuating the torque magnitude through the rest of the elbow flexion assembly 18.

Figure 22:
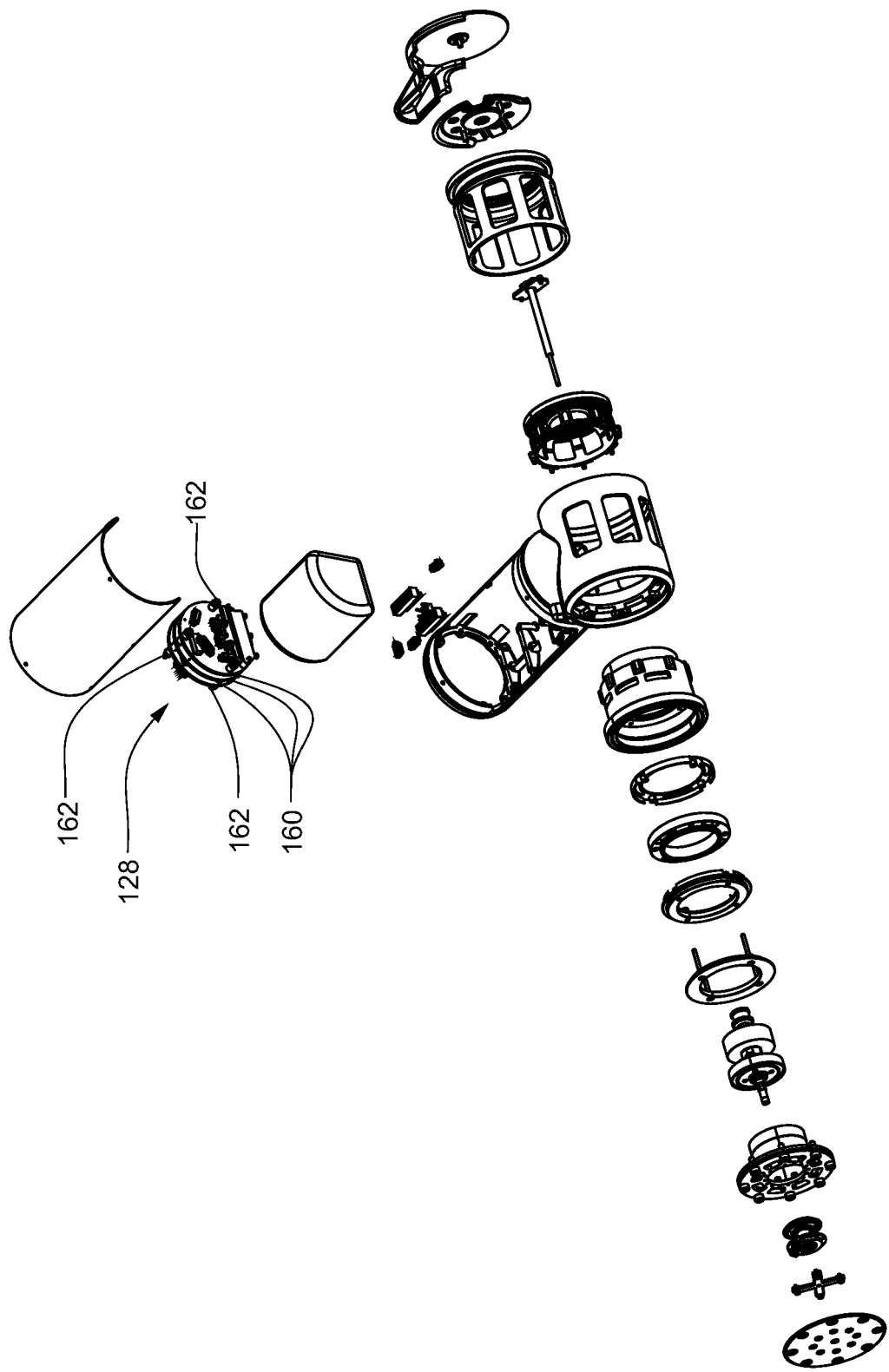
FIG. 22 is an exploded perspective view of the elbow flexion assembly of FIG. 18.

Referring to FIG. 22, the ACM stack 128, includes circuit boards 160 connected to one another by structural standoffs 162. The structural standoffs 162 are constructed of a conductive material, so that electrical power may be passed through the circuit boards 160. The structural standoffs allow power to be supplied to each circuit board 160 without conventional power connections.

Figure 23:
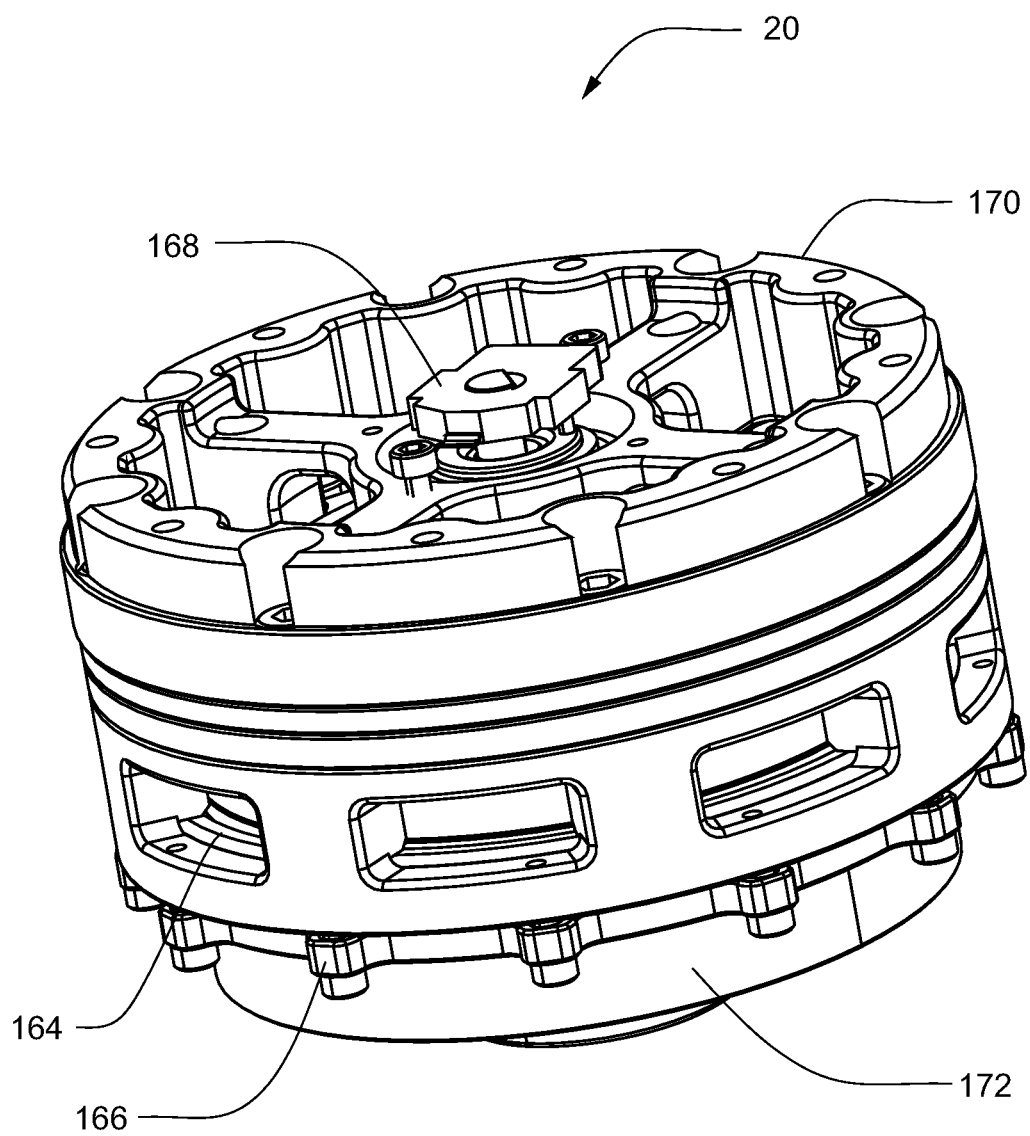
FIG. 23 is a perspective view of a wrist rotator of the prosthetic arm apparatus of FIG. 1 according to the present invention.

Referring to FIG. 23, the wrist rotator 20 includes a wrist outer bearing carrier 164, a wrist clamp 166, a wrist potentiometer 168, an elbow interface 170, and a wrist flexion assembly interface 172.

Figure 24:
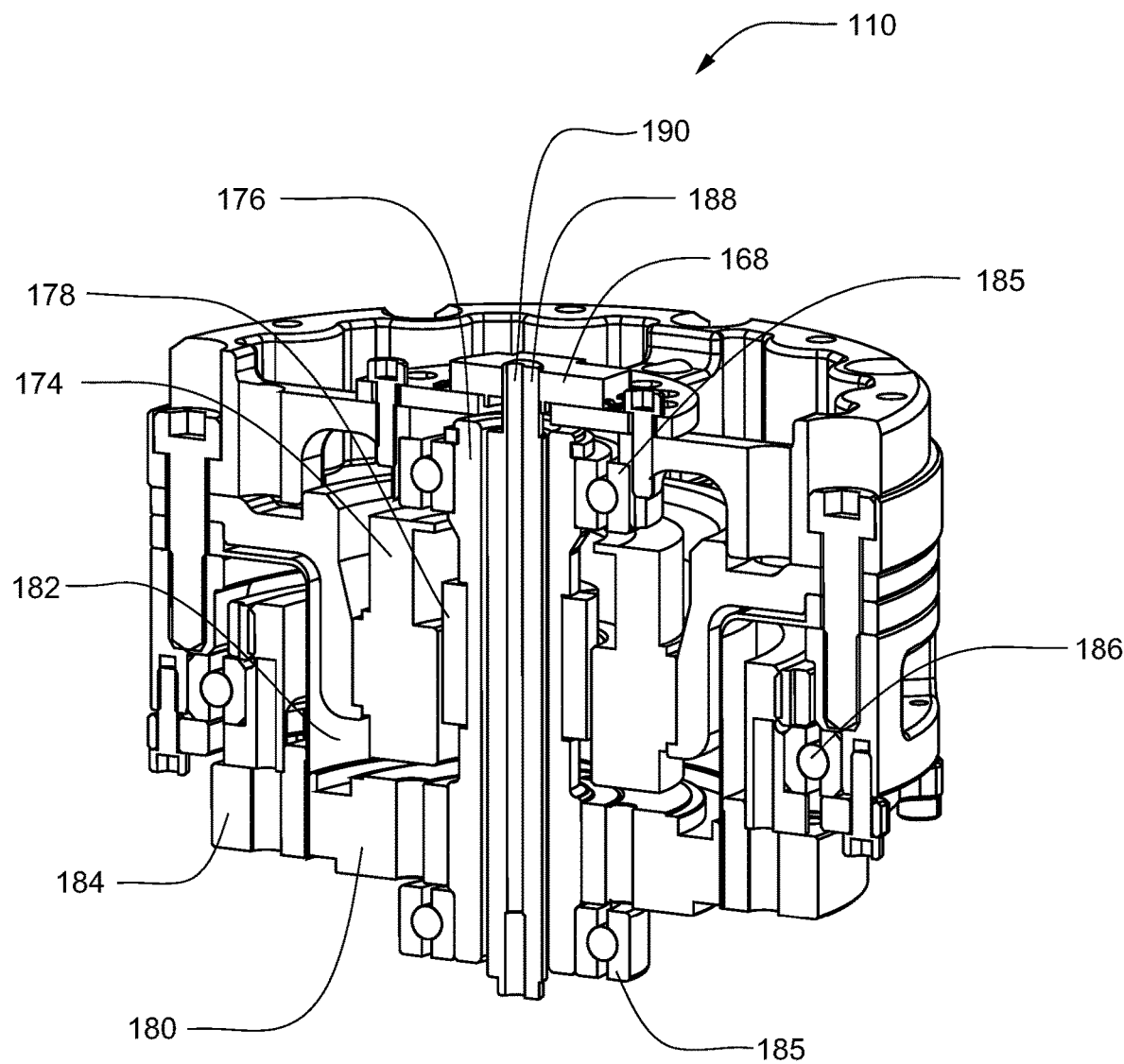
FIG. 24 is a cross-sectional perspective view of the wrist rotator of FIG. 23.

Referring to FIG. 24, movement of the wrist rotator 20 is controlled by a harmonic drive gearing system similar to that described for the humeral rotator. A wrist rotator motor armature 174 drives a wrist rotator motor rotor 176 having wrist rotator magnets 178 disposed to its surface. The lower portion of the wrist rotator motor rotor 176 integrates a wrist rotator harmonic drive gearing system wave generator 180. A wrist rotator harmonic drive gearing system flexspline 182 rotates with the wrist rotator harmonic drive gearing system wave generator 180 against a wrist rotator harmonic drive gearing system circular spline 184, resulting in reduction in the speed of rotation as the wrist rotator harmonic drive gearing system flexspline 182 causes the wrist flexion assembly interface 172 to move with respect to the rest of the wrist rotator 20. Bearings 185 support the wrist rotator motor rotor 176. Bearings 186 support the harmonic drive gearing system components 180,182, and 184.

Still referring to FIG. 24, the wrist potentiometer 168 of the wrist rotator 20 is disposed at one end of a wrist shaft 188 and measures the rotational displacement thereof. The wrist shaft 188 may be tubular, having an electronics channel 190 for passing electronic power and controls through the wrist rotator 20.

Figure 25:
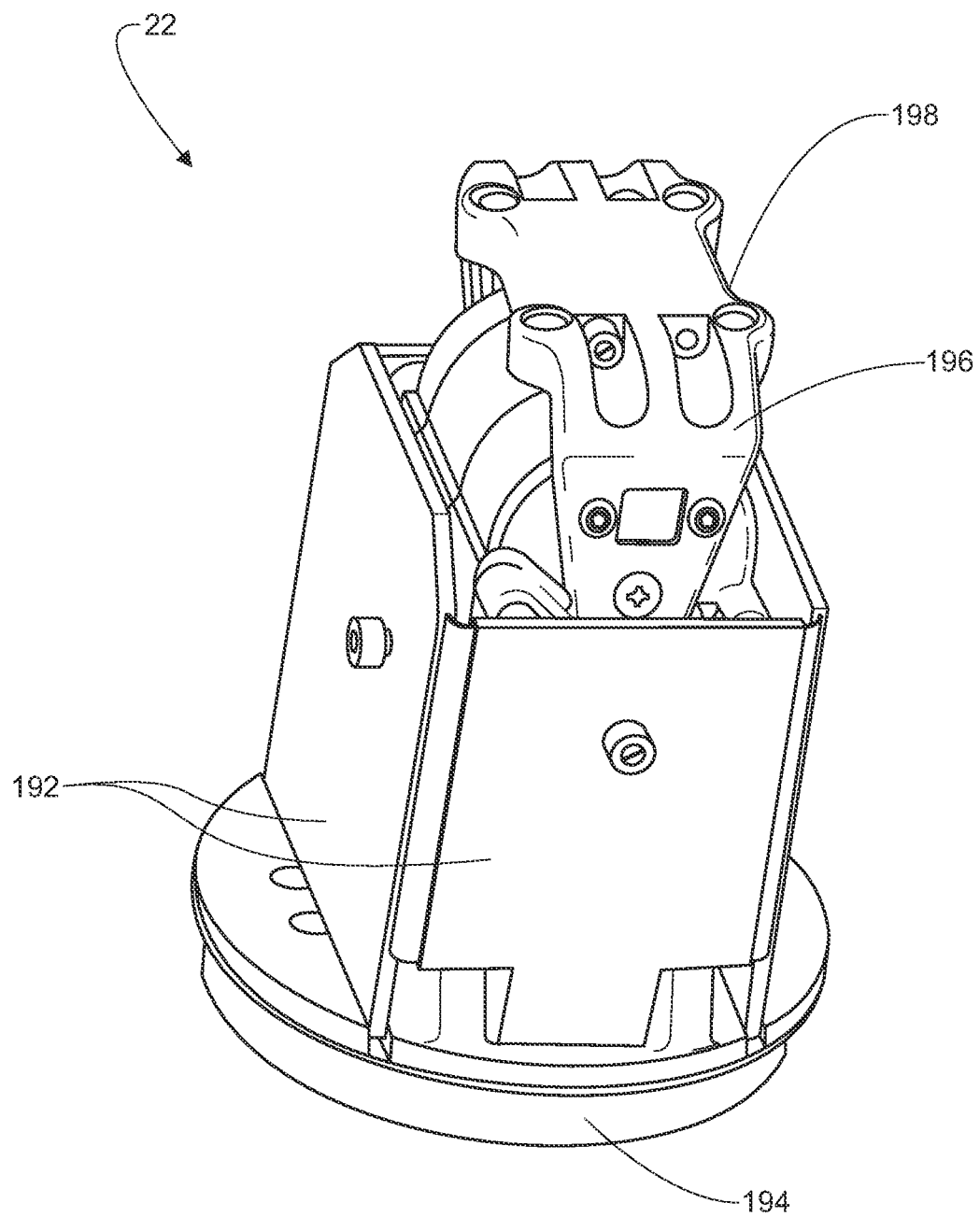
FIG. 25 is a perspective view of a wrist flexion assembly and a hand control module of the prosthetic arm apparatus of FIG. 1 according to the present invention.
Figure 26:
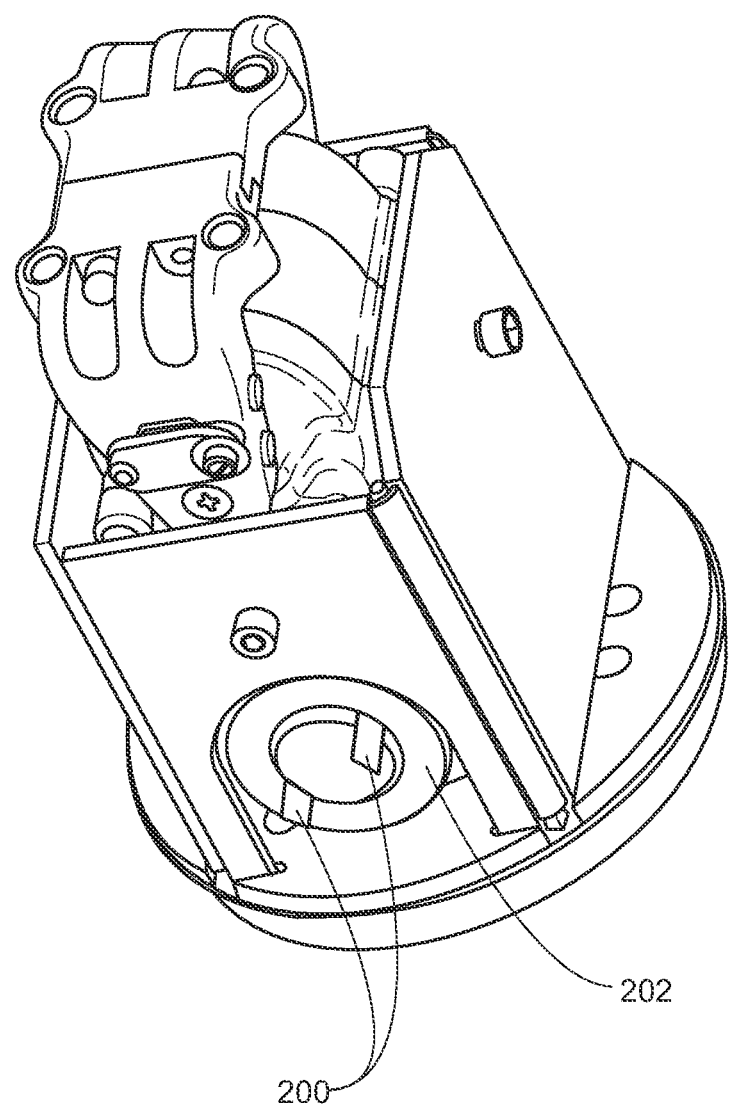
FIG. 26 is a rear perspective view of the wrist flexion assembly and hand control module of FIG. 25.

Referring to FIG. 25, the wrist flexion assembly 22 includes hand control module circuit boards 192, an input support structure 194, an output arm 196, and a hand interface 198. The input support structure 194 connects the wrist rotator 20 with the wrist flexion assembly 22. The output arm 196 has positive and negative flexion, such that the output arm 196 is able to move in two opposite directions in reference to the support structure 194. The hand interface 198 allows the hand assembly 24 to be connected to the wrist flexion assembly 22. Referring to FIG. 26, the wrist flexion assembly 22, has wrist electrical connections 200 for supplying power to a wrist flexion motor 202.

Figure 27:
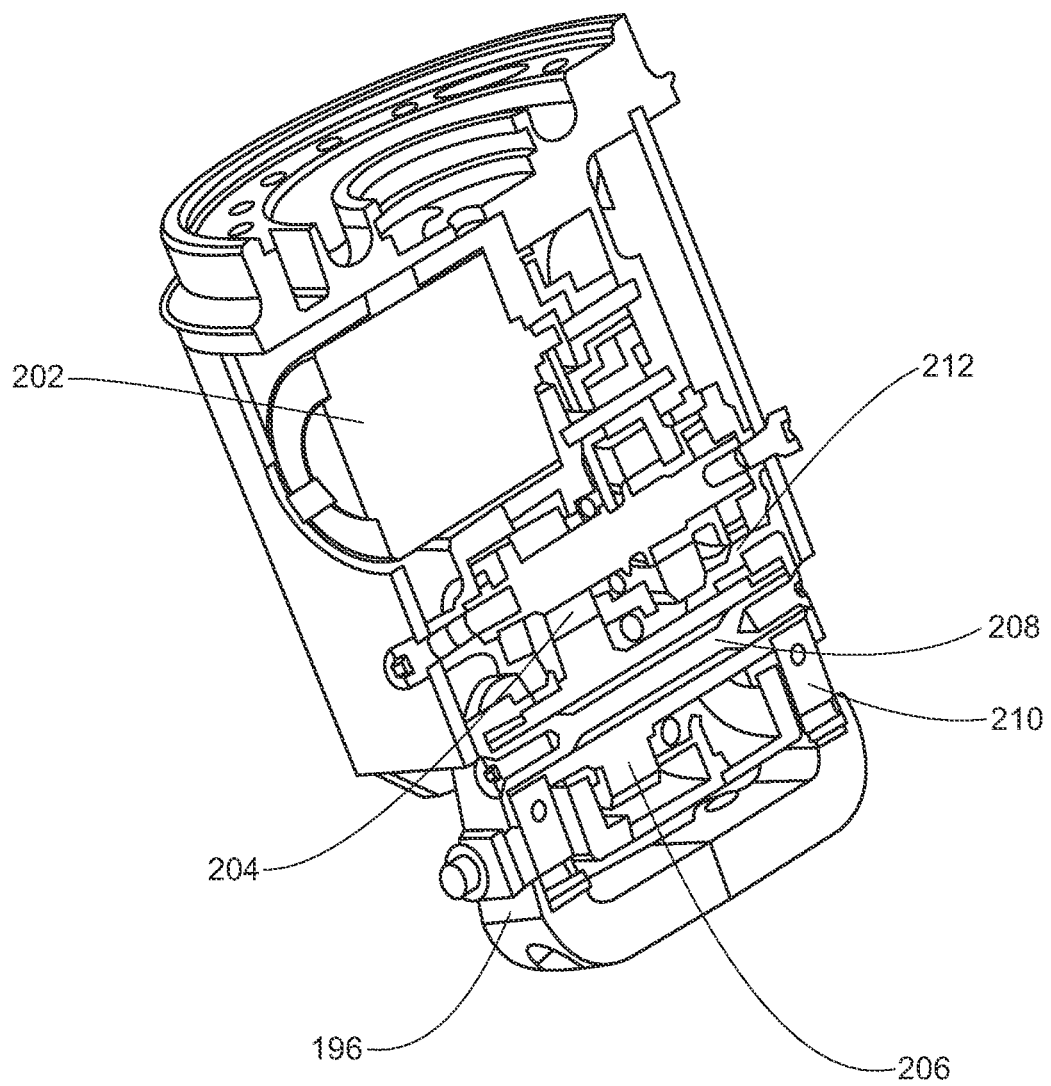
FIG. 27 is a cross-sectional perspective view of the wrist flexion assembly and hand control module of FIG. 25.

Referring to FIG. 27, in the embodiment shown, the wrist flexion motor 202 drives a wrist flexion output gear 204, which in turn drives a wrist flexion final stage-driven gear 206. A wrist flexion pivot axle 208 of the output arm 196 is axially disposed inside an opening defined by the interior of the wrist flexion final stage-driven gear 206. Wrist flexion series elastic elements 210 are disposed in the interior of the output arm 196. Movement of the wrist flexion final stage-driven gear 206 facilitates the positive and negative motion of the output arm 196. A non-backdriving clutch 212 is disposed at one end of the wrist flexion output gear 204.

Figure 28:
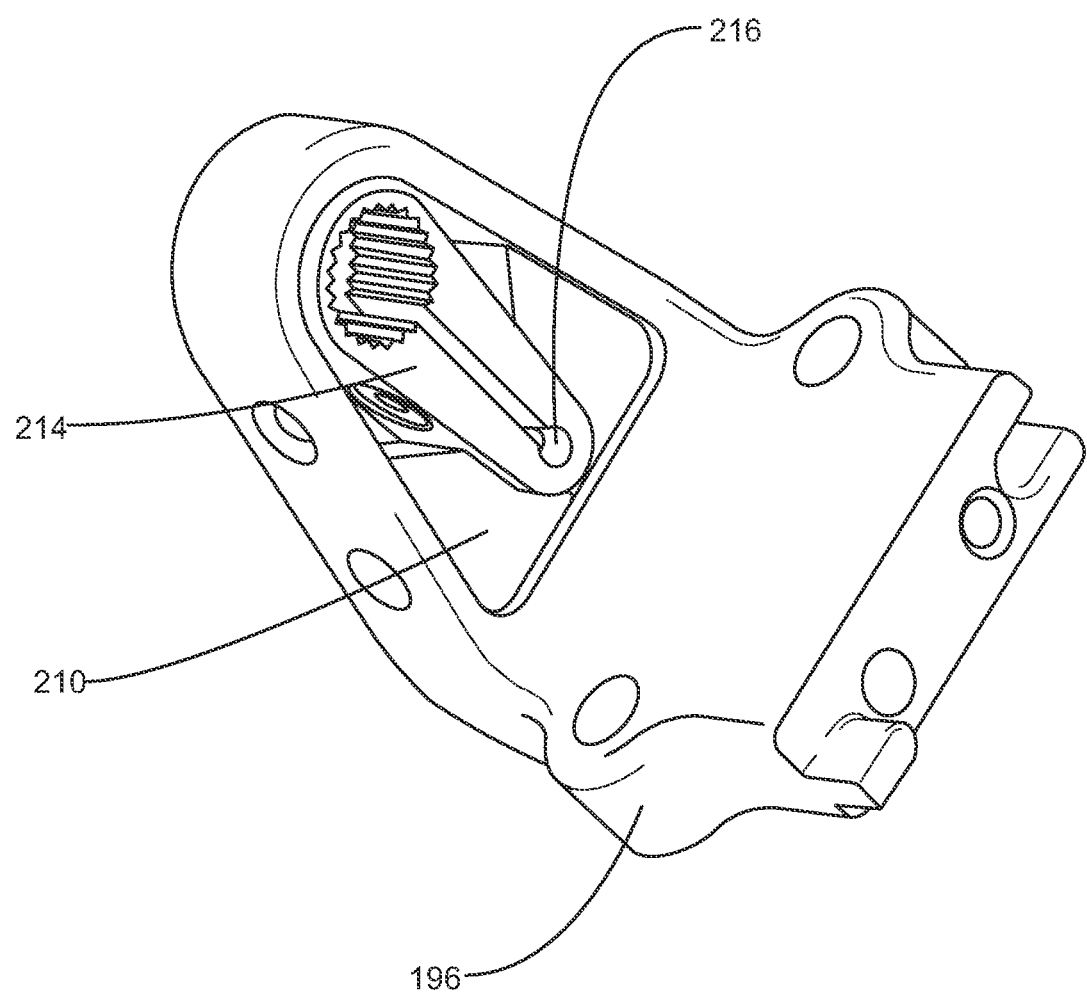
FIG. 28 is a perspective view of a wrist assembly output arm of FIG. 25.

Referring to FIG. 28, the output arm 196 has a wrist flexion drive arm 214, which is driven by the wrist flexion final stage-driven gear 206. The end of the wrist flexion drive arm 214 accommodates a wrist flexion compliance sensor magnet 216. The wrist flexion series elastic elements 210 are disposed on either side of the wrist flexion drive arm 214, and the wrist flexion series elastic elements 210 and the drive arm 214 are substantially enclosed within the output arm 196. Similar to the elbow flexion assembly 18 and the shoulder flexion assembly 14, if the wrist flexion assembly 22 is subjected to a force, the wrist flexion drive arm 214 compresses the wrist flexion series elastic elements 2 10 and attenuates the force or impact through the rest of the wrist flexion assembly 22.

Figure 29:
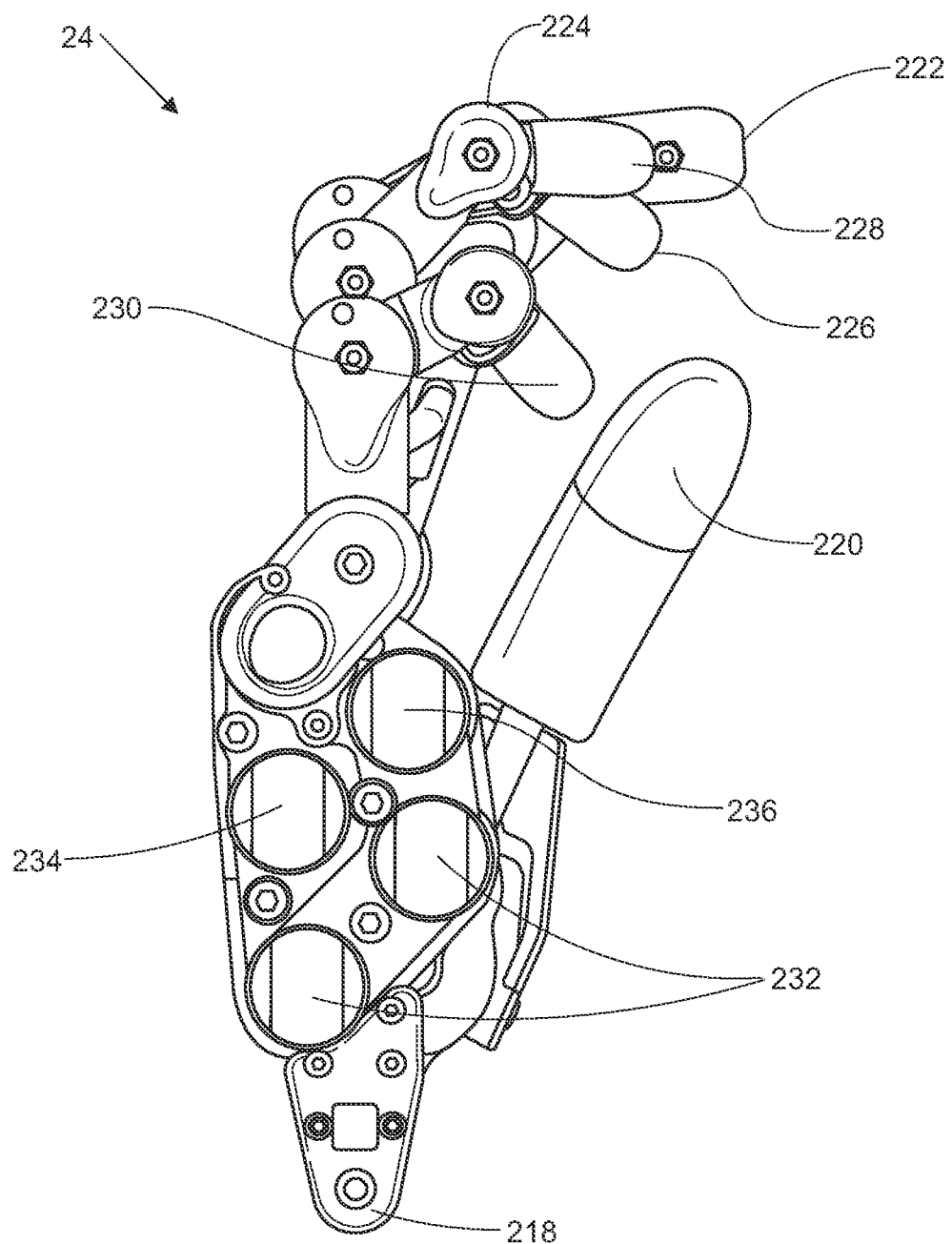
FIG. 29 is a side view of a hand assembly of the prosthetic arm apparatus of FIG. 1 according to one embodiment.
Figure 30:
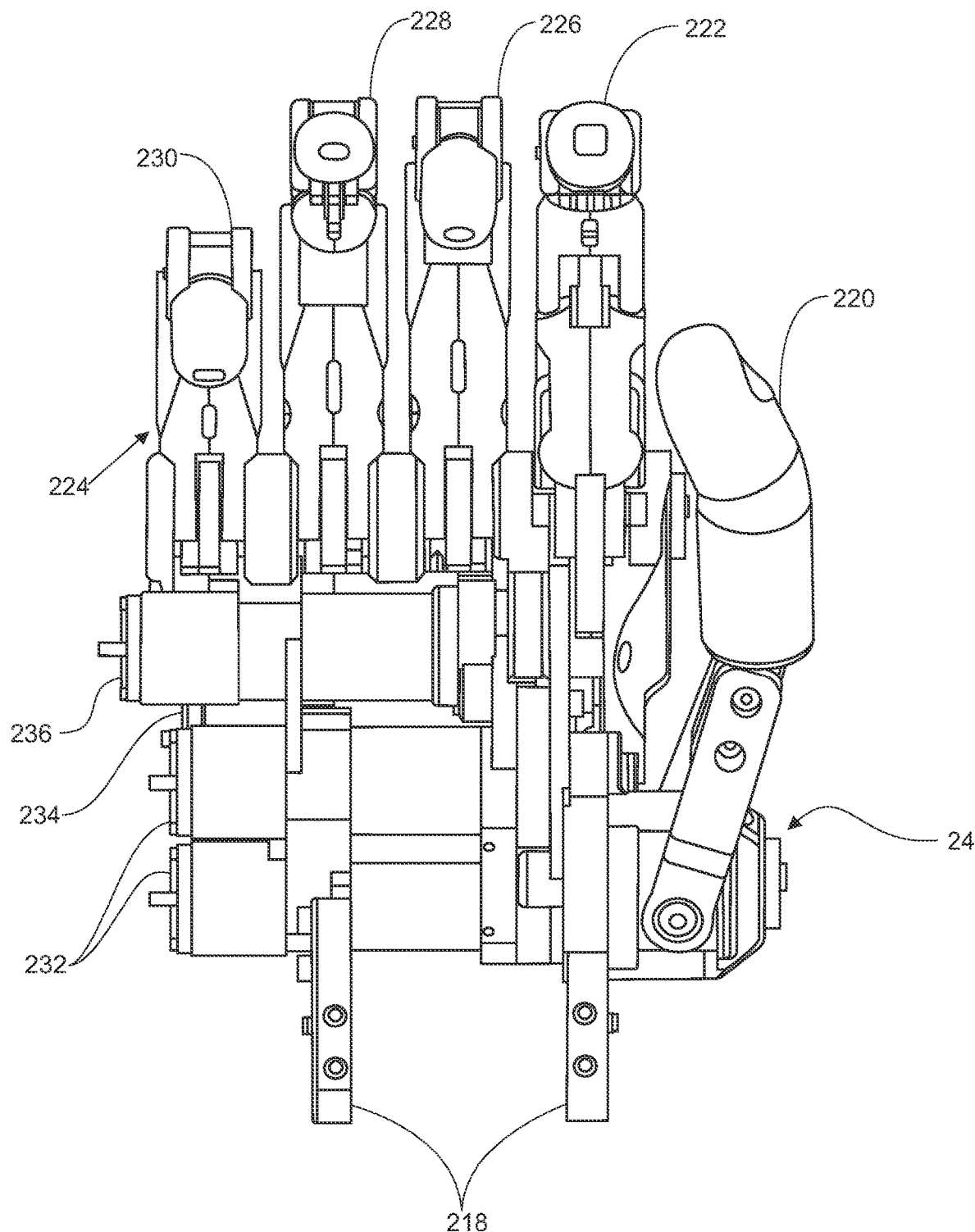
FIG. 30 is a front view of one embodiment of the hand assembly of FIG. 29.

The following is a description of one embodiment of the hand assembly. Other embodiments of the hand assembly are described and shown elsewhere in this specification. Referring to FIGS. 29 and 30 the hand assembly 24 includes a hand support 21 8 for providing an interface for connecting the hand assembly 24 to the wrist flexion output arm 196. The hand assembly 24 also includes a thumb structure 220, an index finger structure 222, and an MRP structure 224 replicating a middle finger 226, a ring finger 228, and a pinky finger 230. In various embodiments, the thumb structure 220 may be driven by two thumb drives 232 that feed into a single differential, giving the thumb structure 220 two degrees of freedom of movement. The index finger structure 222 may be driven by a single index drive 234 and the MRP structure 224 may be driven by a single MRP drive 236 that feeds a double differential. The MRP approach allows for an indeterminate versus determinate linkage.

Figure 31:
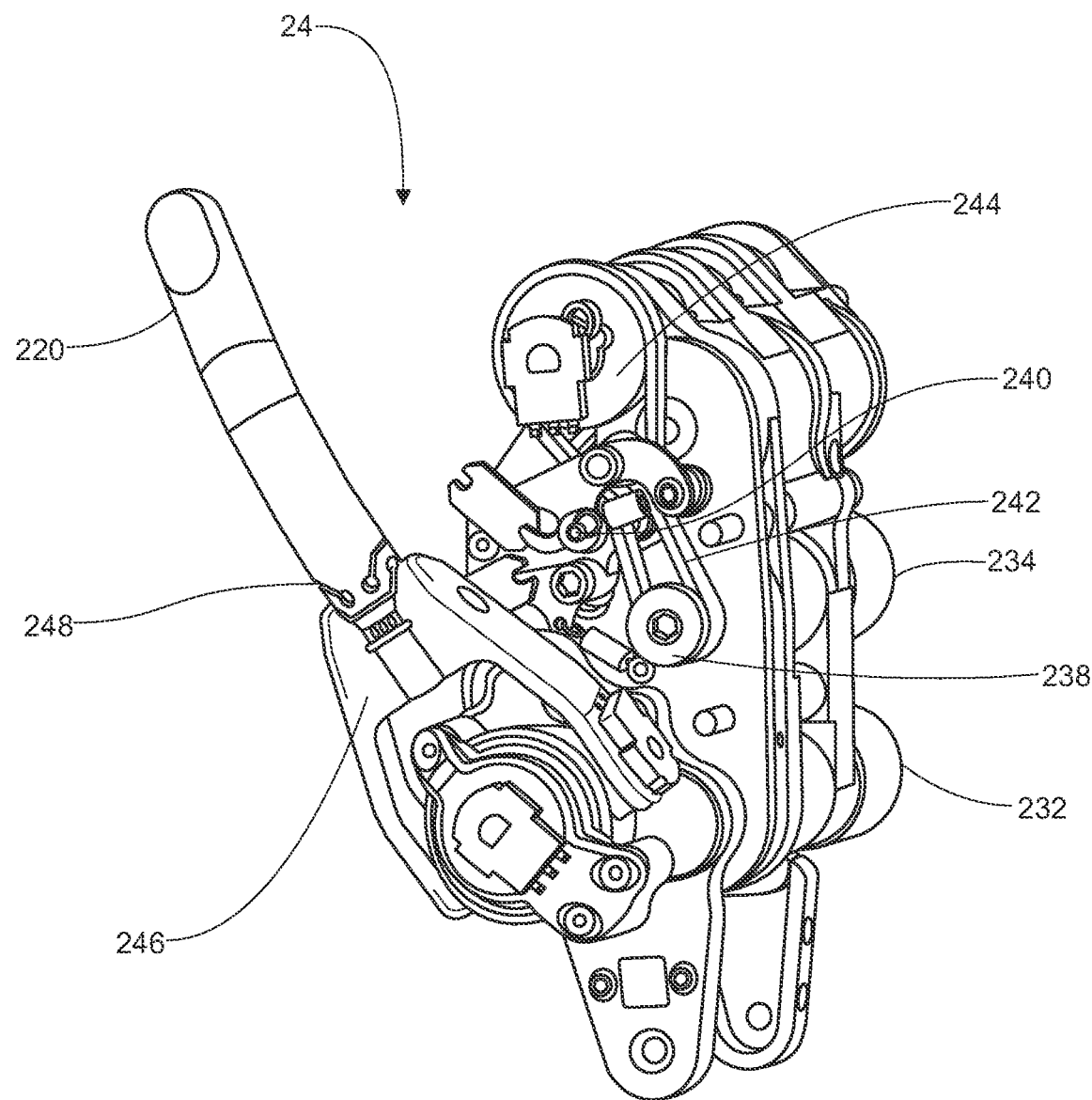
FIG. 31 is a perspective view of one embodiment of the hand assembly of FIG. 29 showing an index finger tensioner assembly.

Referring to FIG. 31, the index finger structure 222 (not shown) is driven by the index drive 234 through an index drive pulley 238, an index tensioner 240, an index tension belt 242, and an index finger pulley 244. The index drive pulley 238 is stage driven and transfers the torque to the index tension belt 242, which in turn rotates the index finger pulley 244, causing the index finger structure 222 to move. As the index tension belt 242 transfers the torque, one side of the index tension belt 242 tightens and the other side loosens, depending on which direction the index drive pulley 238 is rotated. The index tensioner 240 is located between the index drive pulley 238 and the index finger pulley 244 and the index tensioner 240 displaces in relation to the change in load to maintain the tension of the index tension belt 242. The index tensioner 240 has one side grounded and the other side capable of displacement upon the application of a load. The index tensioner 240 may instead ground the moveable side of the index tensioner 240 with a spring.

Figure 38:
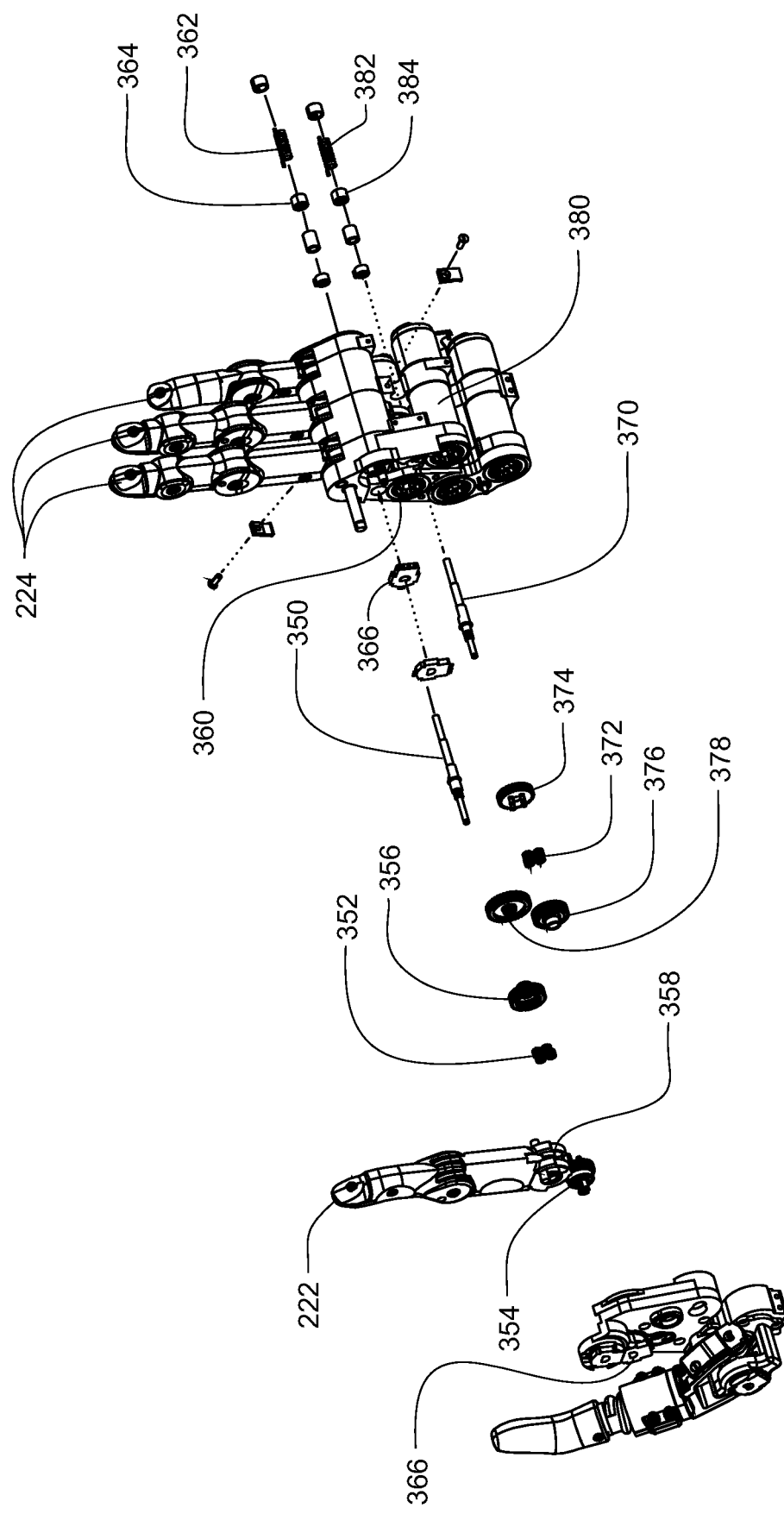
FIG. 38 is an exploded view of a portion of the hand showing another embodiment of the index and MRP fingers drives.
Figure 39:
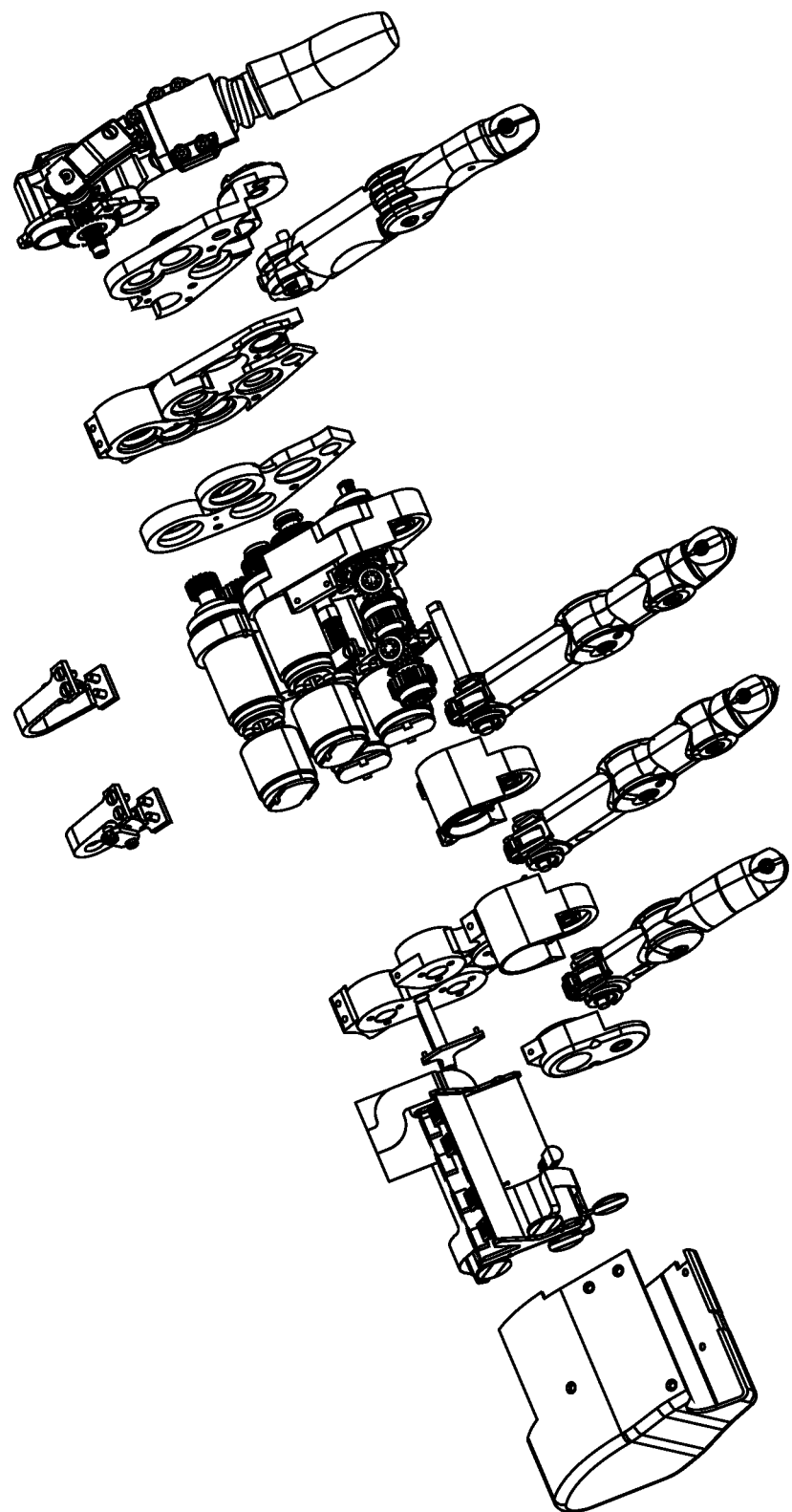
FIG. 39 is an exploded view of another embodiment of the hand.

Referring to FIG. 38, in another embodiment, the index finger structure 222 is driven through an index sun shaft 350, a set of index planets 352, an index planet carrier 354, an index ring gear 356, and an index drive gear 358. The index drive 360 drives the index ring gear 356, turning the index planets 352, the turning of which causes the index planet carrier 354 to rotate. The index drive gear 358 is driven by the external teeth of the index planet carrier 354, causing the index structure 222 to move. Any torque transmitted by the index planet carrier 354 will react against the index sun shaft 350 causing it to rotationally displace the index spring 362 through the index spring mount 364. This rotational displacement, sensed by an index potentiometer 366 can be used to infer the load on the index finger structure 222. This rotational displacement may be used to store elastic energy and to provide the index finger structure 222 with a measure of compliance that may aid in gripping and with load absorption.

Referring to FIG. 31, the thumb structure 220 is mounted on a thumb support 246, which is driven by the two thumb differential drives 232. The thumb structure 220 has flexural cuts 248 at its base allowing the compliant thumb structure 220 to move when a load is applied to it. This compliance in the thumb structure 220 may aid in gripping and with load absorption, which may prevent the hand assembly 24 from damaging objects (not shown) by closing around them too quickly and forcefully.

Figure 32:
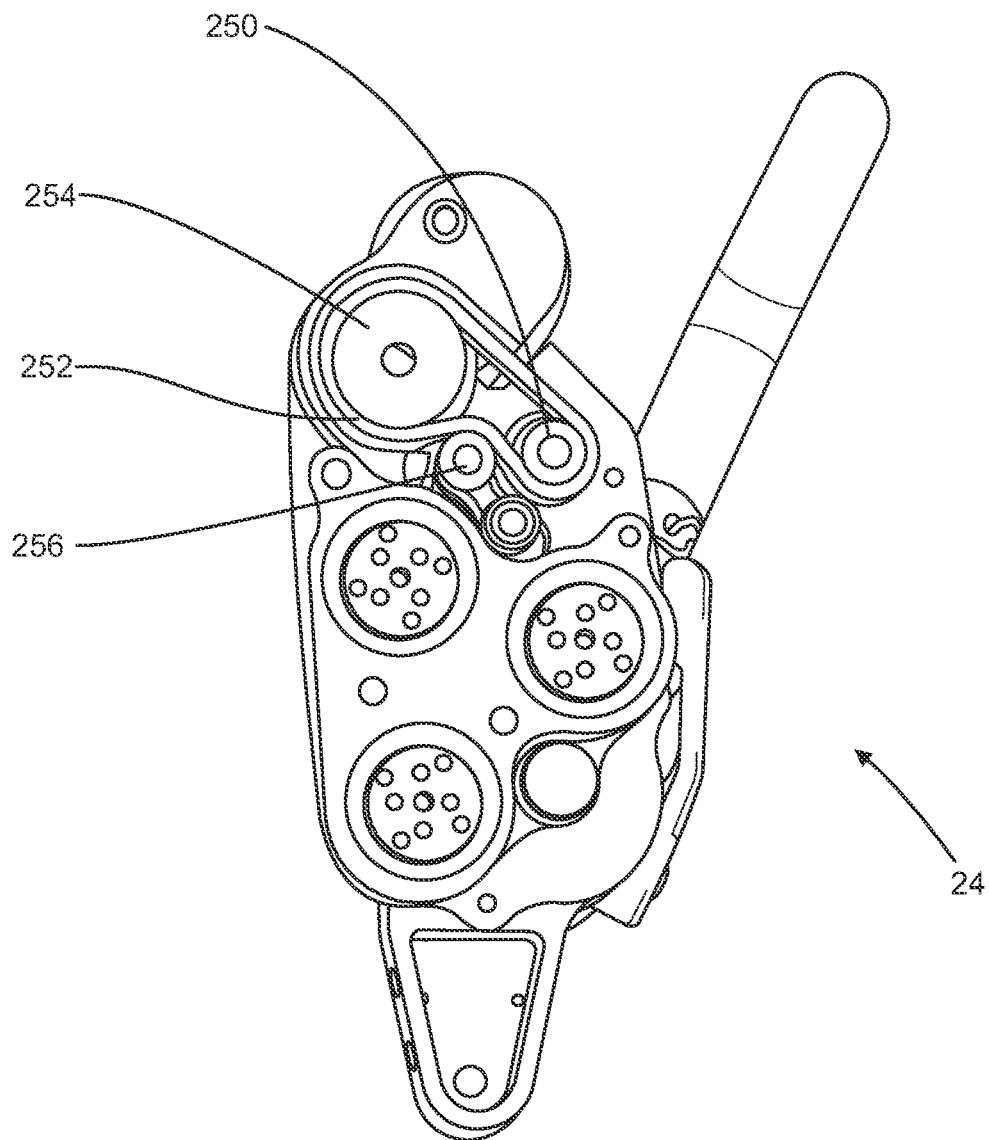
FIG. 32 is a cross-sectional view of one embodiment of the hand assembly of FIG. 29 showing an MRP tensioner assembly.

Referring to FIG. 32, the hand assembly 24 includes an MRP drive pulley 250 driven by the MRP drive 236 (not shown). The MRP drive pulley 250 is connected through an MRP tension belt 252 to the MRP pulley 254, enabling movement of the MRP structure 224. The MRP drive pulley 250 is stage driven and transfers the load to the MRP tension belt 252, which in turn rotates the linked MRP structure 224 via the MRP pulley 254. As the MRP tension belt 252 transfers torque, one side of the MRP tension belt 252 tightens as the other side loosens. An MRP tensioner 256 located at one side of the MRP tension belt 252 displaces in relation to the change in load to maintain the tension of the MRP tension belt 252. This also provides the MRP structure 224 with compliance to aid in gripping and with load absorption, which may prevent the hand assembly 24 from damaging object s (not shown) by closing around the objects (not shown) too quickly and forcefully.

Referring to FIG. 38, in another embodiment, the MRP finger structures 224 are driven through an MRP sun shaft 370, a set of MRP planets 372, an MRP planet carrier 374, an MRP ring gear 376, and an MRP drive gear 378. The MRP drive 380 drives the MRP ring gear 376, turning the MRP planets 372, the turning of which causes the MRP planet carrier 374 to rotate. The MRP drive gear 378 is driven by the external teeth of the MRP planet carrier 374, causing the MRP structures 224 to move. Any torque transmitted by the MRP planet carrier 374 will react against the MRP sun shaft 370 causing it to rotationally displace the MRP spring 382 through the MRP spring mount 384. This rotational displacement can be used to store elastic energy.

Figure 33:
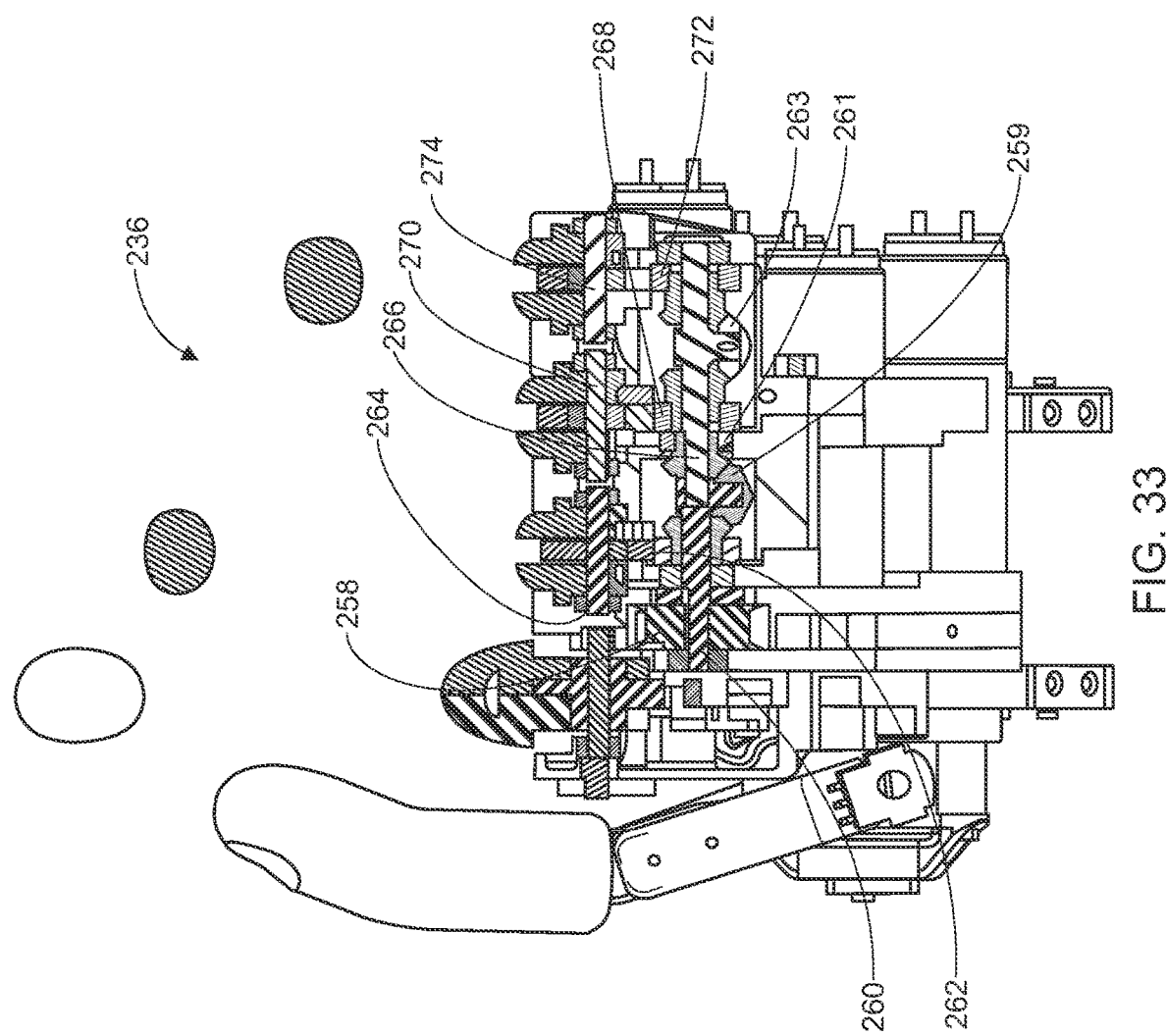
FIG. 33 is a front cross-sectional view of one embodiment of the MRP differential drive of FIG. 30.

Referring to FIG. 33 the MRP differential drive 236 includes a main MRP drive gear 258. The MRP drive gear 258 drives a first MRP input axle 260. The first MRP input axle 260 drives a first differential idler gear 259 which optionally drives a middle spur gear 262 or a differential interface gear 261. The middle spur gear 262 drives a middle pivot axle 264. The middle finger 226 is mounted on the middle pivot axle 264 and is thus actuated by the MRP differential drive 236. The differential interface gear 261 drives a second MRP input axle 266. The second MRP input axle 266 drives a second differential idler gear 263 which optionally drives a ring spur gear 268 or a pinky spur gear 272. The ring spur gear 268 drives a ring pivot axle 270. The ring finger 228 is mounted on the ring pivot axle 270 and is thus actuated by the MRP differential drive 236. The pinky spur gear 272 drives a pinky pivot axle 274. The pinky finger 230 is mounted on the pinky pivot axle 274 and is thus actuated by the MRP drive 236. While the MRP drive 236 drives the middle finger 226, the ring finger 228 and the pinky finger 230, the gear configuration of the first input axle 260 and the second input axle 266 allows independent movement for the under-actuated finger gear system of the MRP structures 224.

Figure 41:
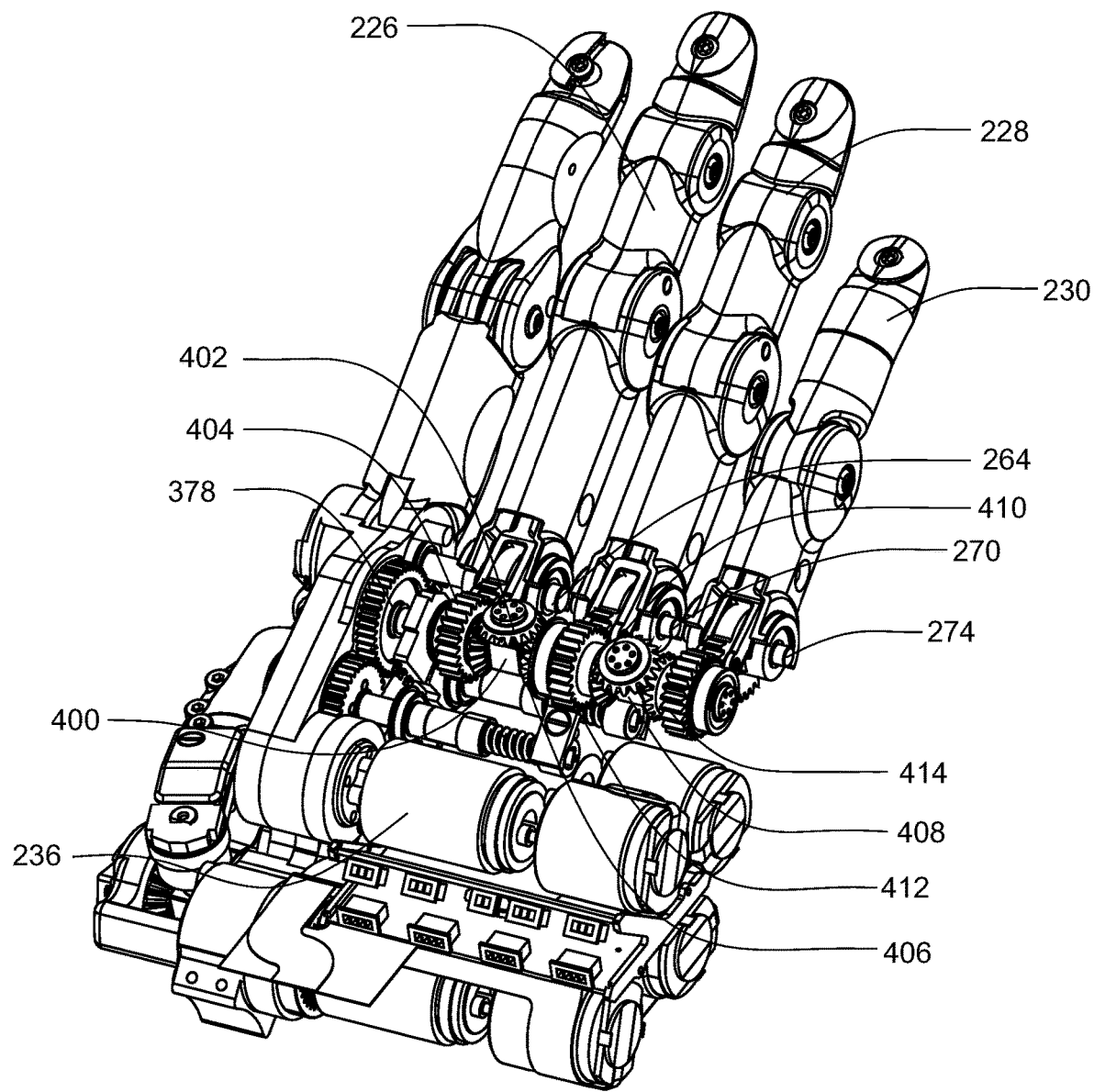
FIG. 41 is a perspective cutaway view of the hand.

Referring to FIG. 41, in another embodiment of the hand, the MRP differential drive includes an MRP drive gear 378 which drives a double differential allowing the MRP fingers to conformably wrap around an object. The MRP drive gear 378 drives a first MRP input axle 400. The first input axle 400 drives a first differential idler gear 402 which optionally drives a middle spur gear 404 or a differential interface gear 406. The middle spur gear 404 drives a middle pivot axle 264. The middle finger 226 is mounted on the middle pivot axle 264 and is thus actuated by the MRP drive 236. The differential interface gear 406 drives a second MRP input axle 408. The second MRP input axle 408 drives a second differential idler gear 410 which optionally drives a ring spur gear 412 or a pinky spur gear 414. The ring spur gear 412 drives a ring pivot axle 270. The ring finger 228 is mounted on the ring pivot axle 270 and is thus actuated by the MRP drive 236. The pinky spur gear 414 drives a pinky pivot axle 274. The pinky finger 230 is mounted on the pinky pivot axle 274 and is thus actuated by the MRP drive 236. While the MRP drive 236 drives the middle finger 226, the ring finger 228 and the pinky finger 230, the gear configuration of the first input axle 400 and the second input axle 408 allows independent movement for the under-actuated finger gear system of the MRP structures 224.

Figure 34:
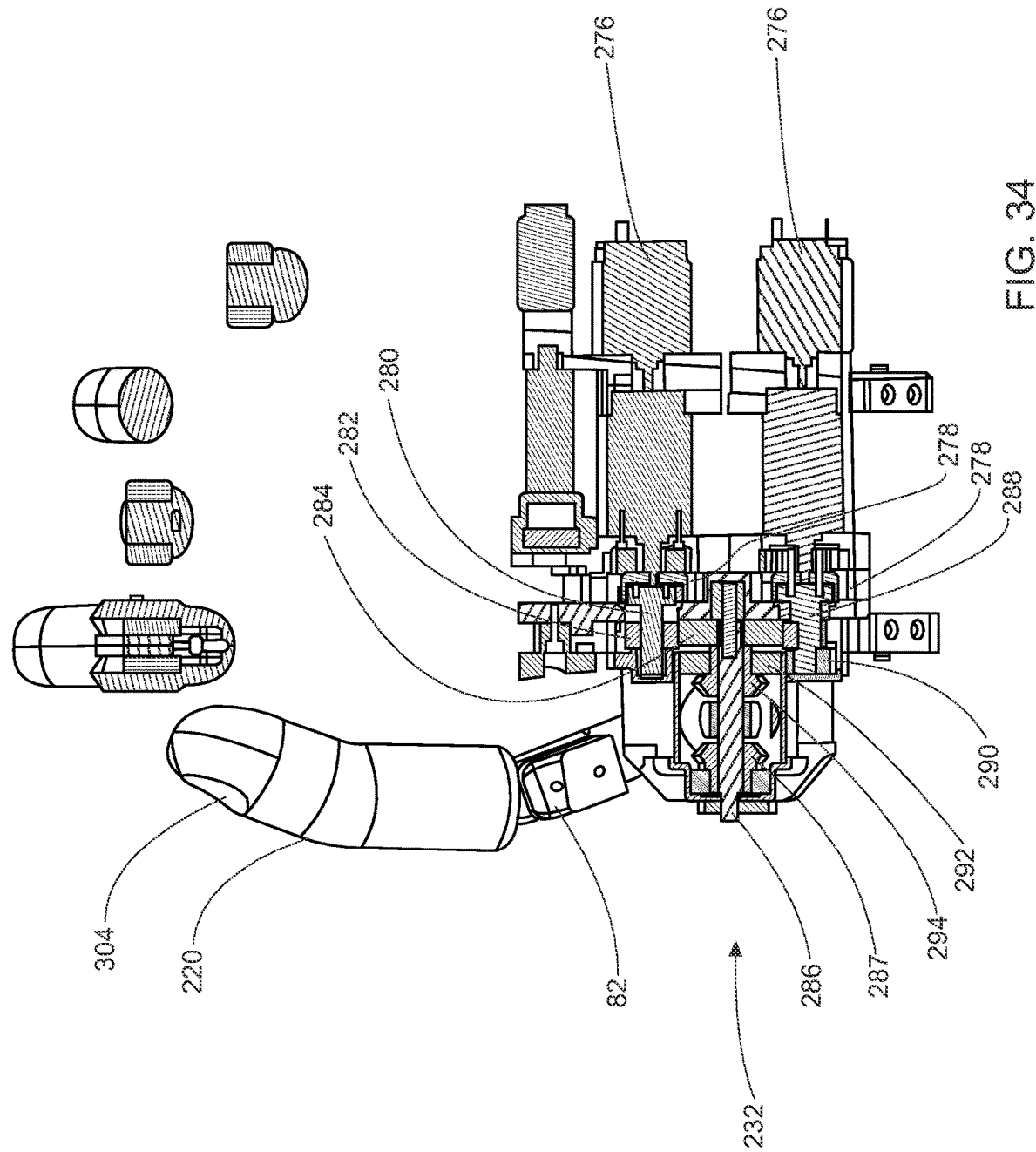
FIG. 34 is a front cross-sectional view of one embodiment of thumb differential drives of FIG. 30.

Referring to FIG. 34 the thumb differential drives 232 control the movement of the thumb structure 220 and are driven by thumb actuators 276. The thumb actuators 276 have nonbackdriving thumb clutches 278 to prevent output loads from reaching and backdriving the thumb actuators. One thumb actuator 276 drives a first thumb output drive 280 and a first thumb output gear 282. The first thumb output gear 282 in turn drives a first thumb transfer gear 284, which drives a fixed differential shaft 286. The fixed differential shaft 286 drives one thumb differential bevel gear 287. The second thumb actuator 276 drives a second thumb output drive 288 and a second thumb output gear 290. The second thumb output gear 290 drives a second thumb transfer gear 292, which drives a thumb differential bevel gear 294. The two thumb differential bevel gears 287 and 294 operate the thumb structure 220 in its two degrees of motion.

The thumb structure 220, the index finger structure 222, and MRP structure 224 in one embodiment are covered in silicone, which provides additional friction and aids in gripping objects. In some embodiments, the entire hand assembly 24 may also be covered in silicone to provide additional grip for holding objects. In other embodiments, the silicone material may be replaced by other compliant materials.

The hand assembly 24 is advantageous because the thumb structure 220, index finger structure 222 and MRP structure 224 provide various degrees of freedom that allow the formation of various grasps or grips. Additionally, the different drives for each of the thumb structure 220, index finger structure 222 and MRP structure 224 provide various beneficial characteristics to the hand assembly 24. For instance, the thumb structure 220 moves relatively slow, but with greater force than the index finger structure 222 and MRP structure 224. The index finger structure 222 moves quickly, but with less force and is non-backdrivable. This combination of thumb structure movement and index finger structure movement allow the quick formation of strong hand grips. Additionally, the combination allows for a smaller index finger actuator, which reduces size and weight of the hand assembly 24. Additionally, the index finger structure 222 and MRP structure 224 move similar to human fingers, which makes them look more natural and makes them more intuitive for the user to control. The MRP structure 224 provides only bulk control for gripping objects, without providing for individual finger manipulation, since fine control is not necessary for the MRP structure 224. Additionally, the MRP structure 224 advantageously moves each finger of the MRP structure 224 with a single actuator, eliminating excessive bulk in the hand assembly 24. Like the index finger structure, the MRP structure 224 moves quickly with low force but is also non-backdrivable. Additionally, the fingers of the MRP structure 224 are highly flexible, allowing them to grip objects of varying size and shape. The MRP structure 224 functionality allows the user to grasp an object with the MRP structure 224 and thumb structure 220, while allowing the user to move the index finger structure 222 separately, for example, to activate a button on the object.

The various parts of the prosthetic arm apparatus 10 are, in some embodiments, constructed from plastic or magnesium. However, where more strength is desired, the parts may be made of aluminum, titanium or steel. In other embodiments, the various parts of the prosthetic arm may be constructed of other metals or plastics, depending on the desired characteristics, including strength, weight, compliance or other similar performance characteristics of the various parts.

Figure 35:
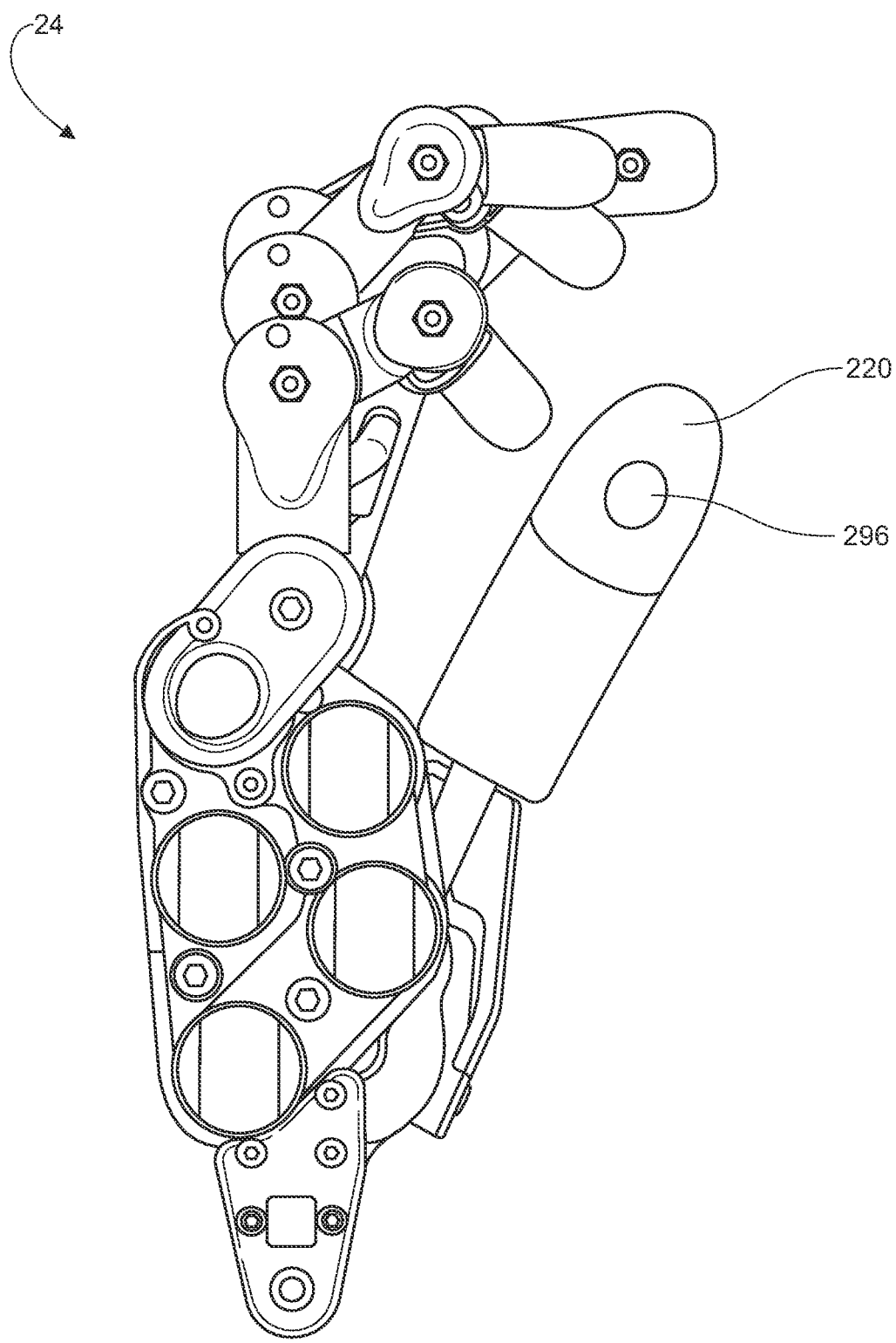
FIG. 35 is a side view of one embodiment of the hand assembly of FIG. 30 showing a tactile feedback sensor according to the present invention.
Figure 36:
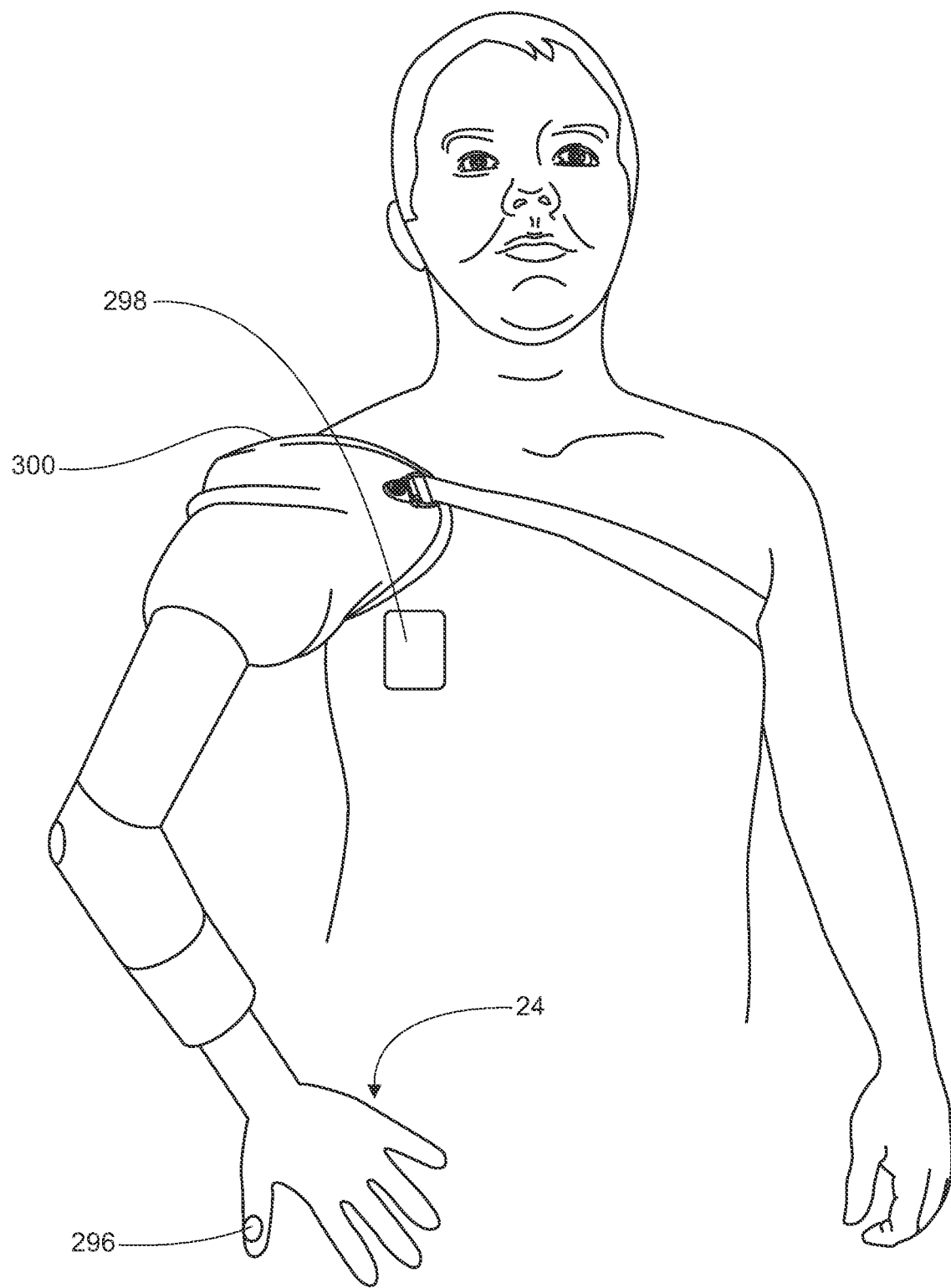
FIG. 36 is a perspective view of one embodiment of the tactile feedback sensor and a feedback actuator of the prosthetic arm apparatus of FIG. 1.
Figure 37:
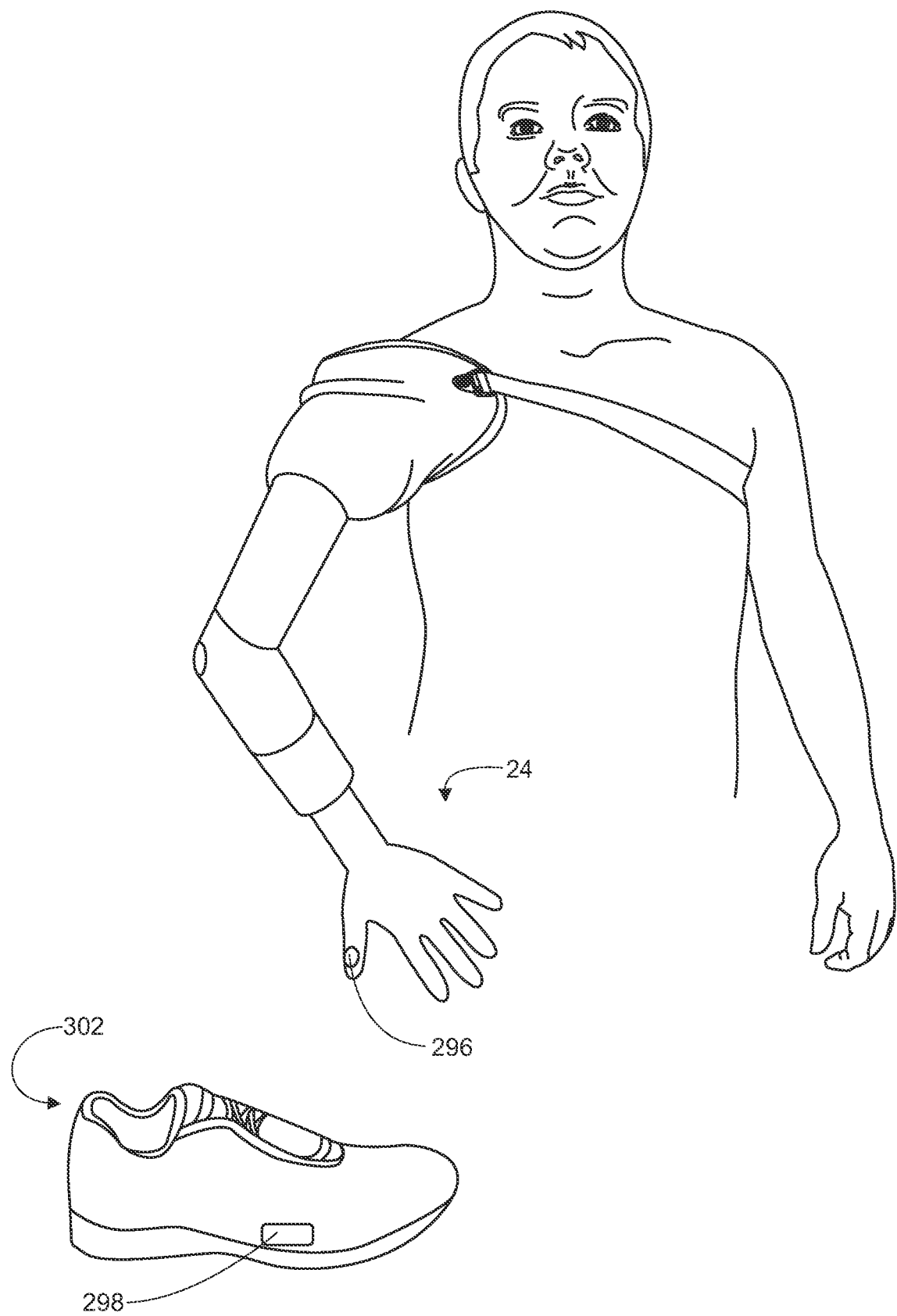
FIG. 37 is a perspective view of another embodiment of the tactile feedback sensor and feedback actuator of the prosthetic arm apparatus of FIG. 1 according to the present invention.

Referring to FIG. 35, a tactile feedback sensor 296 may be positioned on the inner side of the thumb structure 220. The tactile feedback sensor 296 may be a pressure sensor, force sensor, a displacement sensor, or other similar sensor capable of providing the user with feedback. Referring to FIG. 36, the tactile feedback sensor 296 is operatively connected to a feedback actuator 298. The tactile feedback sensor 296 may be connected to the feedback actuator 298 by either wires or wirelessly. In operation, as the user grips an object with the hand assembly 24, feedback sensor 296 reads the displacement of or the force exerted on the thumb structure 220. That reading is then sent to the feedback actuator 298, which gives the user tactile feedback that indicates the strength of the grip. Feedback actuator 298 may be placed on the chest of the user, located on a prosthetic support apparatus 299 in an area of tactile communication with the user, or in any other location capable of receiving tactile feedback, such as on a user's residuum 300. Referring to FIG. 37, the feedback actuator 298 may be located on a foot controller 302 that is used to control hand assembly 24.

Feedback actuator 298 may be a vibration motor, such as any vibration motor known in the art, placed against the skin of the user. As the user grips an object, feedback actuator 298 begins vibrating, notifying the user how strong the object is being gripped. As the force on or displacement of the tactile feedback sensor 296 changes, frequency and/or amplitude of vibration may also change, notifying the amputee of a changing grip. For example, if a vibrating actuator 298 is placed at the chest of the user as in FIG. 36, the user will feel the vibration at his chest.

The feedback actuator 298 may also be placed wherever the controller for the hand assembly 24 is located. For example, if a foot controller 302 controls the hand assembly 24, the feedback actuator 298 may be incorporated into the foot controller 302. The user will then receive tactile feedback of the strength of the prosthetic grip at the same location where the controller is located.

The actuator 298 may also be a pressure actuator that applies pressure against the user's skin. For example, the actuator 298 may have a rod that increases pressure against the amputee's skin as the hand assembly 24 increases its grip on an object.

Although described with a single tactile feedback sensor 296, additional tactile feedback sensors may be placed at other locations on the hand assembly 24. For example, additional tactile feedback sensors 296 may be placed on the index finger structure 222, the MRP structures 224, on the palm of the hand assembly 24, or on any combination of these positions or any other location. Each tactile feedback sensor 296 would then be operatively connected to an associated feedback actuator 298. Multiple tactile feedback sensors 296 and actuators 298 would provide more sophisticated tactile feedback of the strength of the grip, improving the control of the hand assembly 24.

In some embodiments, the tactile feedback sensor 296 may indicate a change in pressure or force, rather than an absolute pressure or force. For example, if the force detected by the tactile feedback sensor 296 is constant, the feedback actuator 298 does not actuate, but if that pressure or force increases or decreases, the actuator 298 would actuate to indicate the change in pressure or force. Additionally, although described in terms of grip strength, the tactile feedback sensors 296 and actuators 298 may provide a variety of other feedback in including temperature, an operational mode of the prosthetic arm 10, surface finish of a object, slip of an object within the hand assembly 24 or the like.

In operation, the prosthetic arm apparatus is able to move substantially similar to a human arm. Referring to FIGS. 29 and 30, starting with the hand assembly 24, the thumb structure 220, index finger structure 222, and MRP structure 224 are each driven independent of the others, and therefore, each may be actuated without actuating the other two structures. Both of the thumb actuators 276 control motion of the thumb structure 220 in a direction toward or away from the center of the palm of the hand assembly 24, as shown in FIG. 34, through the miter gear 294 and in a direction toward or away from the side of the palm of the hand assembly 24, as shown in FIG. 34, through the lateral rotation shaft, depending upon the direction and speed of rotation of each thumb actuator 276. Thus, the thumb actuators 276, shown in FIG. 34, provide the thumb structure 220 with two degrees of freedom in the thumb structure's movement. Coupling the two thumb actuators 276 through the differential described above to provide the two degrees of freedom to the thumb structure 220 is advantageous over providing a single degree of freedom with each actuator 276 because the torque of each actuator 276 through the differential is used for movement in both degrees of freedom, which effectively doubles the torque of the thumb in each direction as compared to single actuators. The index finger structure 222, driven by a single index differential drive 234, may be actuated with two degrees of freedom. Specifically, the index finger structure 222 may be actuated toward or away from the palm of the hand assembly 24, wherein the movement path is similar to that of a human index finger while making or releasing a fist. The middle finger 226, ring finger 228, and pinky finger 230 of the MRP structure 224 are actuated by the MRP differential drive 236. Additionally, the middle finger 226, ring finger 228, and pinky finger 230 are actuated toward or away from the palm of the hand assembly 24, similar to the index finger structure 222. However, the middle finger 226, ring finger 228, and pinky finger 230 are each geared separately, such that the rate of movement of each is different, simulating human finger movement and making the hand assembly 24 more similar to a human hand than conventional prior art prosthetic devices.

Referring to FIG. 1, the hand assembly 24 is mounted on the wrist flexion assembly 22 via the hand interface 198, as shown in FIG. 25. Referring to FIG. 25, as the output arm 196 of the wrist flexion assembly 22 is actuated, the hand assembly 24 is also caused to move. The output arm 196 of the wrist flexion assembly 22 may be actuated pivotally about wrist flexion pivot axle 208, as shown in FIG. 27, moving the hand interface 198 to the left or right, and thus pivoting the hand assembly 24 in relation to the input support structure 192.

Referring back to FIG. 1, the wrist flexion assembly 22 is attached to the wrist rotator 20 via wrist flexion assembly interface 172, shown in FIG. 23. Referring to FIGS. 23 and 24, when actuated, the wrist flexion assembly interface 172 is rotated about wrist shaft 188 in relation to 10 the wrist outer bearing carrier 164. Therefore, the wrist flexion assembly 22, and attached hand assembly 24 are also caused to rotate in reference to the wrist outer bearing carrier 164 by actuation of the wrist rotator 20. Therefore, the wrist rotator 20 allows the prosthetic arm apparatus 10 to move in rotation similar to a human wrist joint.

Referring back to FIG. 1, the wrist rotator 20 is attached to the elbow flexion assembly 18 via the wrist interface 130, shown in FIG. 18. Referring to FIG. 20, when the elbow flexion assembly 18 is actuated, the radial mount 122 is rotated about the axis of motor rotor 134. The wrist rotator 20, wrist flexion assembly 22, and hand assembly 24 are thus also caused to rotate about the axis of motor rotor 134 because they are attached at the wrist interface to the radial mount 122. Therefore, the elbow flexion joint 18 allows the prosthetic arm apparatus 10 to move similar to flexion extension of a human elbow joint.

Referring back to FIG. 1, the elbow flexion assembly 18 is attached to the humeral rotator 16 via the humeral mount 96, shown in FIG. 27. Referring to FIG. 16, actuation of the humeral rotator 16 causes the humeral mount 96 to rotate in relation to the outer bearing carrier 90 of the humeral rotator 16. Since the elbow flexion assembly 18, wrist rotator 20, wrist flexion 25 assembly 22, and hand assembly 24 are attached to the humeral mount 96, they are also caused to rotate in relation to the outer bearing carrier 90. This allows the prosthetic arm apparatus 10 to rotate to perform an arm wrestling motion.

Referring back to FIG. 1, the humeral rotator 16 is attached to the shoulder flexion assembly 14 through the humeral interface 46, shown in FIG. 9. Referring to FIG. 9, actuation of the shoulder flexion assembly 14 causes the main shoulder housing 42 to pivot about the center of the abductor interface 44. Since the humeral rotator 16, elbow flexion assembly 18, wrist rotator 20, wrist flexion assembly 22, and hand assembly 24 are attached to the main housing 42, they are also caused to rotate in relation to the abductor interface 44. Therefore, the shoulder flexion assembly 14 allows the prosthetic arm apparatus 10 to move along the torso simulating running motion.

Referring to FIG. 1, the shoulder flexion joint 14 is attached to the shoulder abductor 12 through the shoulder flexion assembly mount 30, shown in FIG. 5. Referring to FIG. 5, the shoulder abductor 12 is attached to a harness that is worn by the user via harness mount 26. When the shoulder abductor 12 is actuated in a positive direction, the shoulder flexion assembly mount 30 pivots away from the harness mount 26, and the user. Similarly, by actuating the shoulder abductor in a negative direction, the shoulder flexion assembly mount 30 is pivoted toward the harness mount 26 and the user. Since the shoulder flexion assembly 14, humeral rotator 16, elbow flexion assembly 18, wrist rotator 20, wrist flexion assembly 22, and hand assembly 24 are attached to shoulder abductor 12 at the flexion assembly mount 30, they are also caused to pivot with the shoulder flexion assembly mount 30.

One characteristic of the prosthetic arm apparatus described herein is that it provides the user with substantially the same movement capabilities and degrees of freedom of a human arm, including two degrees of freedom in shoulder functionality. Additionally, the modularity of each segment of the prosthetic arm apparatus 10 provides a significant advantage over conventional prosthetic devices. In particular, since each segment of the plurality of segments operates independently of each other segment of the plurality of segments, fewer segments may be used for less severe amputees. For example, a transhumeral amputee may have full shoulder functionality in the residuum, in which case the shoulder abductor 12 and shoulder flexion assembly 14 segments would be omitted from the prosthetic arm apparatus 10. The resulting prosthetic arm apparatus 10 would include the humeral rotator 16, the elbow flexion assembly 18, the wrist rotator 20, the wrist flexion assembly 22, and the hand assembly 24, wherein the humeral rotator 16 would be attached to the prosthetic harness. In some cases, the residuum of the transhumeral amputee may even have humeral rotation, in which case the prosthetic arm apparatus 10 may be further simplified to include only the elbow flexion assembly 18, the wrist rotator 20, the wrist flexion assembly 22 and the hand assembly 24, with the elbow flexion assembly 22 being attached to the prosthetic support apparatus. Similarly, for a transradial amputee, the prosthetic arm apparatus 10 may include only the wrist rotator 20, wrist flexion assembly 22 and the hand assembly 24, with the wrist rotator 20 being attached to the prosthetic support apparatus. Additionally, in some embodiments, the prosthetic arm apparatus 10 may be further simplified to include only the wrist flexion assembly 22 and the hand assembly 24 when the transradial amputee has wrist rotation in their residuum. In these embodiments, the wrist flexion assembly 22 may be attached to the prosthetic support apparatus. Thus, the modularity of each segment of the prosthetic arm apparatus 10 advantageously allows for customization of different prosthetic arm configurations for various users based on the differing degrees of amputation of each user.

A further advantage of the present invention is the use of non-backdriving clutches to preclude movement of the segments due to forces exerted on the prosthetic arm apparatus 10 when not in motion. These non-backdriving clutches may be particularly beneficial when the segments of the prosthetic arm apparatus 10 have different strength capacities so that the clutches for specific segments of the prosthetic arm apparatus 10 may lock those segments while other stronger segments are actuated to lift heavy objects. For instance, the non-backdriving clutch in the shoulder flexion assembly 14 may be used to lock out shoulder movement while the elbow flexion assembly 18 is actuated to lift a heavy object. The non-backdriving clutches may also advantageously conserve power since the non-backdriving clutches prevent motion without using power. Thus, the power to specific segments of the prosthetic arm apparatus 10 may be shut off, on a segment-by-segment basis, when not in use, since the non-backdriving clutches in those segments are locking out motion. Additionally, the non-backdriving clutches may also save power by allowing power to the entire prosthetic arm apparatus 10 to turned off whenever the arm is not in motion while maintaining the prosthetic arm apparatus 10 in a locked position.

An additional characteristic of the apparatus is that the hand assembly includes independently moving fingers and is capable of completing fine tasks such as pinching, grasping non-uniform objects, and lifting small objects off flat surfaces. Also, the tactile feedback sensor provides the user with feedback, during use of the prosthetic arm apparatus, such as the force of a grip. The apparatus also includes a cosmesis covering on the finger structures, which will be discussed in greater detail below, providing, amongst other things, grip for grasping objects. The rigid fingernail 304, which may be included on any of the finger structures, provides a backstop for the finger cover to enhance gripping capability. The rigid fingernail 304 also enhances gripping capability by anchoring the finger cover to the finger and allows the user to lift small objects from a surface with the prosthetic arm apparatus 10.

Referring to FIG. 42, wherein like numerals represent like elements, in some embodiments, the shoulder abductor 12 and the shoulder flexion assembly 14 shown in FIG. 2, may be integrated as a single shoulder unit 1416, providing both degrees of freedom provided by the shoulder abductor 12 and shoulder flexion assembly 14 of FIG. 2. The single shoulder unit 1416 includes a shoulder housing 1418 pivotally connected to the harness mount 1026, which allows the shoulder unit 1416 to be connected to a prosthetic harness (not shown) as discussed above. In some embodiments, the shoulder housing 1418 has a smooth outer surface 1419 to shape the shoulder unit 1416 to be similar to a human arm. The shoulder housing 1418 is divided into a flexor portion 1420 and an abductor portion 1422, which are movable relative to one another. The flexor portion 1420 of the shoulder housing 1418 includes the humeral interface 1046 for connecting the humeral rotator 16, shown in FIGS. 1 and 2, to the shoulder unit 1416. The abductor portion 1422 of the shoulder housing 1418 is pivotally connected to the harness mount 1026, which allows the shoulder unit 1416 to interface with a prosthetic harness (not shown) as discussed above.

Referring to FIGS. 43 and 44, within the housing 1418 is a shoulder flexion drive 1424 for causing flexion motion of the flexor portion 1420 about a shoulder flexion axis 1426 and an abduction drive 1428 for causing abduction motion of the shoulder housing 1418 about an abduction axis 1430. Additionally, the housing also defines an electronics compartment 1432 for housing control systems and circuits for the integrated shoulder unit 1416.

The shoulder flexion drive 1424, in one embodiment, includes a shoulder flexion motor 1434 having motor shaft 1058 for driving the shoulder flexion motor pulley 1056. The shoulder flexion motor pulley 1056 drives the shoulder flexion belt 1060, which, in turn, drives the shoulder flexion belt-driven pulley 1062. The shoulder flexion belt-driven pulley 1062 drives the wave generator 1064 of a shoulder flexion harmonic drive gearing system 1436, the output of which is fixedly interfaced with the abductor portion 1422. Thus, as power is transmitted through the shoulder flexion drive 1424 from the shoulder flexion motor 1434 to the output of the harmonic drive gearing system 1436, the flexor portion 1420 rotates relative to the abductor portion 1422 about the shoulder flexion axis 1426. In some embodiments, the motor shaft 1058 and the wave generator 1064 are both hollow shafts to allow passage of an abductor motor shaft 1438 and an abductor screw shaft 1440, respectively, as will be discussed in greater detail below.

In the exemplary embodiment, the abduction drive 1428 includes the abductor motor 1036 for driving the abductor motor shaft 1438. The abductor motor shaft 1438 is configured to drive the abductor belt 1038 about its distal end. The abductor belt 1038, in turn, drives the abductor screw shaft 1440, which has an abductor nut 1442 threadedly coupled thereto. The abductor nut 1442 is connected to the harness mount 1026 through a linkage 1444, which is, in some embodiments, a four bar linkage. As power is transmitted through the abductor drive 1426 from the abductor motor 1036 to the abductor screw shaft 1440, the screw shaft 1440 rotates. The rotation of the screw shaft 1440 causes the abductor nut 1442 to displace axially along the screw shaft 1440, which causes pivotal motion of the shoulder housing 1418 through the linkage 1444 about the abduction axis 1430.

The relative movement between the flexor portion 1420 and the abductor portion 1422 provides the shoulder unit 1416 with a first degree of freedom similar to that of the shoulder flexion joint 14 of FIG. 2. The abductor portion 1422 of the shoulder housing 1418 is pivotally connected to the harness mount 1026 at the abductor joint 1034, providing the shoulder unit with the second degree of freedom by allowing the shoulder housing 1418 to pivot relative to the harness mount 1026 in a similar manner to that discussed above in connection with the shoulder abductor 12 of FIG. 2. The integrated shoulder unit 1416 locates the shoulder flexion axis 1426 and the abduction axis 1430 relatively close to one another as compared to separate shoulder flexion and shoulder abduction assemblies, which provides for more intuitive motion that more closely simulates the movement of a human shoulder.

The shoulder flexion drive 1424 and the abduction drive 1428 discussed above include coaxial motors and coaxial shafts to minimize the size of the single shoulder unit 1416 and to reduce the weight thereof. Thus, these exemplary single shoulder unit 1416 is beneficial because its weight relative to the separate shoulder abductor 12 and shoulder flexion assembly 14, shown in FIG. 2. Additionally, the single shoulder unit 1416 provides more narrow housing 1418, which allows a more natural anatomical position of the shoulder for a broader range of users and may reduce bumping with the user's residuum during use. embodiments have an additional benefit of decreasing the weigh of the prosthetic. Additionally, as seen in FIGS. 43 and 44, both the abduction motor 1036 and the shoulder flexion motor 1434 may be located in the vicinity of the electronics compartment 1432, so the electronics for both the shoulder flexion drive 1424 and the abduction drive 1428 may be located in the same place, which eliminates any need to route wiring through the shoulder unit 1416. This is advantageous since running wires across joints is a failure mode in which the wires may crimp and break when moved. Thus, the shoulder unit 1416 eliminates this failure mode by eliminating wires running across the joints that could cause failure of the prosthetic arm 1010.

Figure 45:
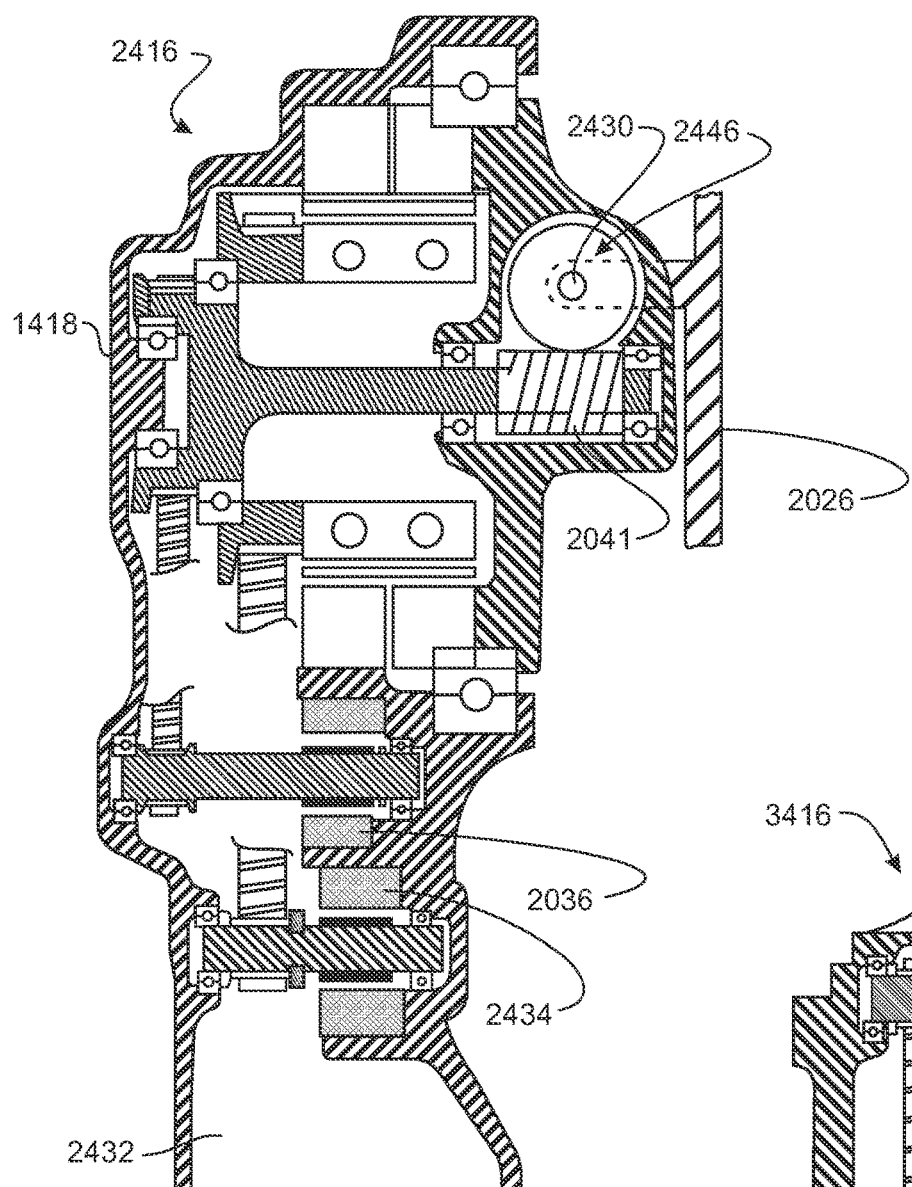
FIG. 45 is a cross sectional view of another embodiment of an integrated shoulder unit according to the present invention.

Although the shoulder flexion drive 1424 and the abduction drive 1428 have been shown in an exemplary configuration, it should be understood by those skilled in the art that other drive configurations may also be used to drive the single shoulder unit 1416 about the shoulder flexion axis 1426 and the abduction axis 1445. For instance, referring to FIG. 45, the shoulder flexion motor 2434 and the abduction motor 2036 do not need to be coaxial and they may still each be located in the vicinity of the electronics compartment 2432. Additionally, rather than driving the linkage 1444, shown in FIG. 43, the worm drive 2041 may instead threadably engage an abduction gear 2446 coupled to the harness mount 2026, shown in FIG. 43, to generate pivotal movement about the abduction axis 2430.

Figure 46:
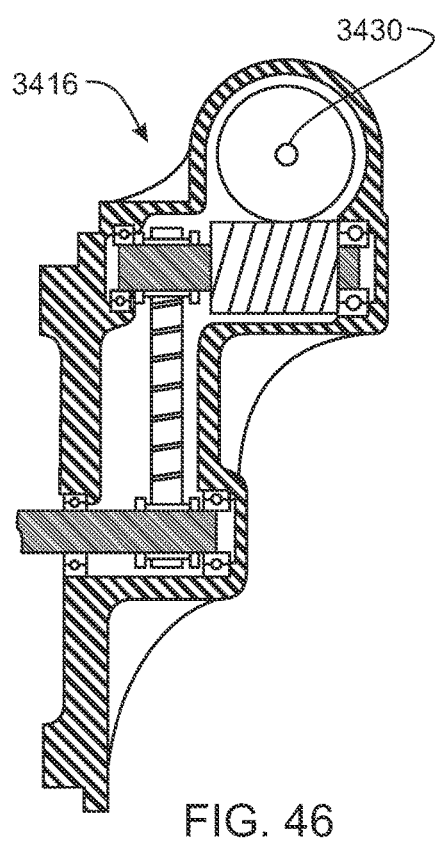
FIG. 46 is a cross sectional view of another embodiment of the integrated shoulder unit of FIG. 45.

Additionally, referring now to FIG. 46, in various embodiments, the integrated shoulder unit 3416 may shift the abduction output to change the location of the harness mount 3026 to improve mounting location and/or to allow for ninety degrees (90°) of abduction about the abduction axis 3430 without bumping with the residuum (not shown). For example, the location of the abduction output may be changed by extending the abduction drive 3428 with one or more additional shafts, gears, and/or belts.

Figure 47:
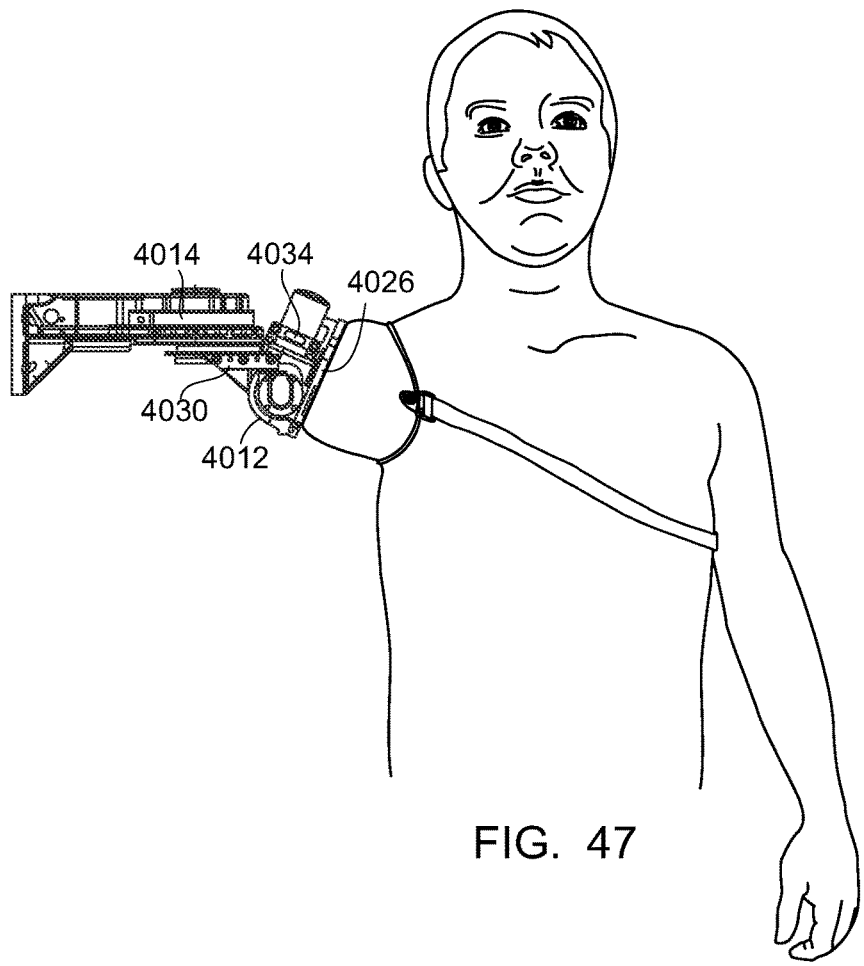
FIG. 47 is a top view of a shoulder abductor and shoulder flexion assembly according to another embodiment of the present invention.
Figure 48:
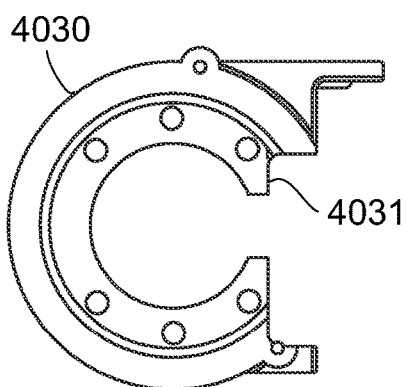
FIG. 48 is a side plane view of shoulder flexion assembly mount of the shoulder abductor of FIG. 47.

Referring to FIG. 47, the flexion assembly mount 4030 may also be shifted away from the harness mount 4026 in the non-integrated shoulder abductor 4012. Referring to FIG. 48, the flexion assembly mount 4030 may also include an accommodating slot 4031 adapted to accommodate portions of the abductor joint 4034, shown in FIG. 47. Referring back to FIG. 47, the shifted flexion assembly mount 4030 allows the user to orient the shoulder abductor 4012 on the prosthetic support apparatus (not shown) in different orientations while still allowing a range of motion of the shoulder abductor 4012 of at least approximately ninety degrees (90°). This may be particularly advantageous since the mounting orientation of the shoulder abductor 4012 may vary from user to user, which may limit the range of abduction motion with the non-shifted flexion assembly mount 30, shown in FIG. 6. Additionally, in some embodiments, the shifted flexion assembly mount 4030 may house a flex sensor plunger for detecting flexion motion of the shoulder flexion assembly 4014.

Figure 49:
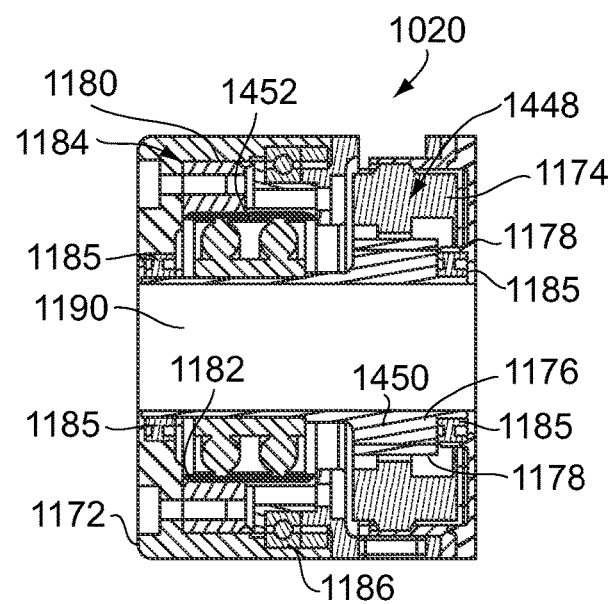
FIG. 49 is a cross-sectional view of one embodiment of a rotator according to the present invention.
Figure 50:
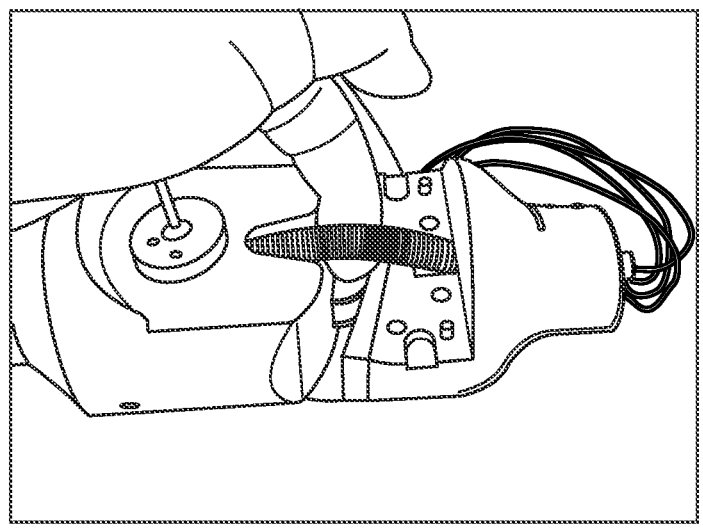
FIG. 50 is a side view of one embodiment of a flexion assembly according to the present invention.
Figure 51:
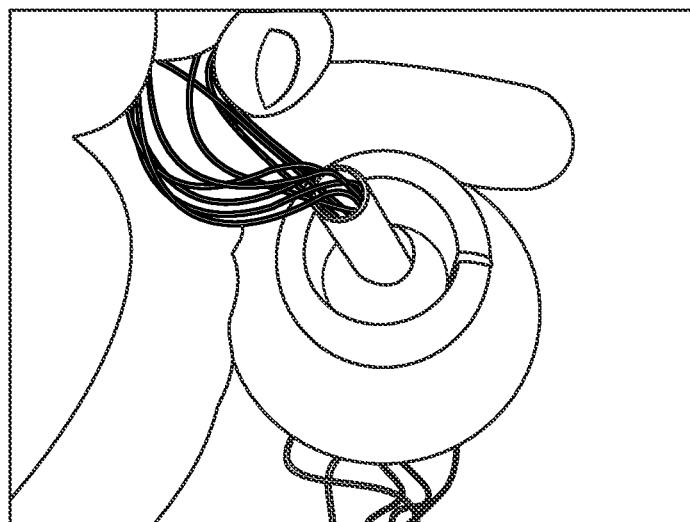
FIG. 51 is a front view of the flexion assembly of FIG. 50.

Referring now to FIG. 49, another embodiment of the wrist rotator 1020 is shown for providing improved electronic wiring capability to the prosthetic device. Although shown as the wrist rotator 1020, it should be understood by those skilled in the art that a similar configuration may be used for other rotating joints, such as the humeral rotator 16, shown in FIG. 1. In this embodiment of the wrist rotator 1020, the wrist rotator motor 1448, including the wrist rotator motor armature 1174 and a driven portion 1450 of the wrist rotator motor rotor 1176 having wrist rotator magnets 1178 disposed thereon, and the wrist harmonic drive gearing system 1452, including the wrist rotator harmonic drive gearing system wave generator 1180, the wrist rotator harmonic drive gearing system flexspline 1182 and the wrist rotator harmonic drive gearing system circular spline 1184, are separated into coaxial side-by-side units with the wrist rotator motor 1448 being proximate to the elbow interface 1170 and the harmonic drive gearing system 1452 being proximate to the wrist flexion assembly interface 1172. By arranging the wrist rotator motor 1448 and the wrist harmonic drive gearing system 1452 in the side-by-side configuration, the electronics channel 1190 passing through the center of the wrist rotator rotor 1176 may be formed large enough to allow electronic wiring to be run internally through the center of the wrist rotator 1020. Referring to FIGS. 50 and 51, the wiring through the prosthetic arm 10, shown in FIG. 1, in some embodiments, may run through one or more extension springs 1454, in particular around the flexion joints, such as the elbow flexion assembly 18 and the wrist flexion assembly 22, shown in FIG. 1, where internal wiring is difficult or impractical.

Routing the wiring through the center of the wrist rotator 1020 eliminates the need for external wiring, thereby minimizing any flexing movement experienced by the wiring, which can cause wire pinching, abrasions and failure. The internal wiring also eliminates the possibility that external wiring will become caught on something and break. Routing the wiring through the one or more extension springs 1454 where internal wiring is not practical, possible or desired allows for controlled loading of the external wiring and protects the wiring from pinching to reduce wire failure.

Figure 52:
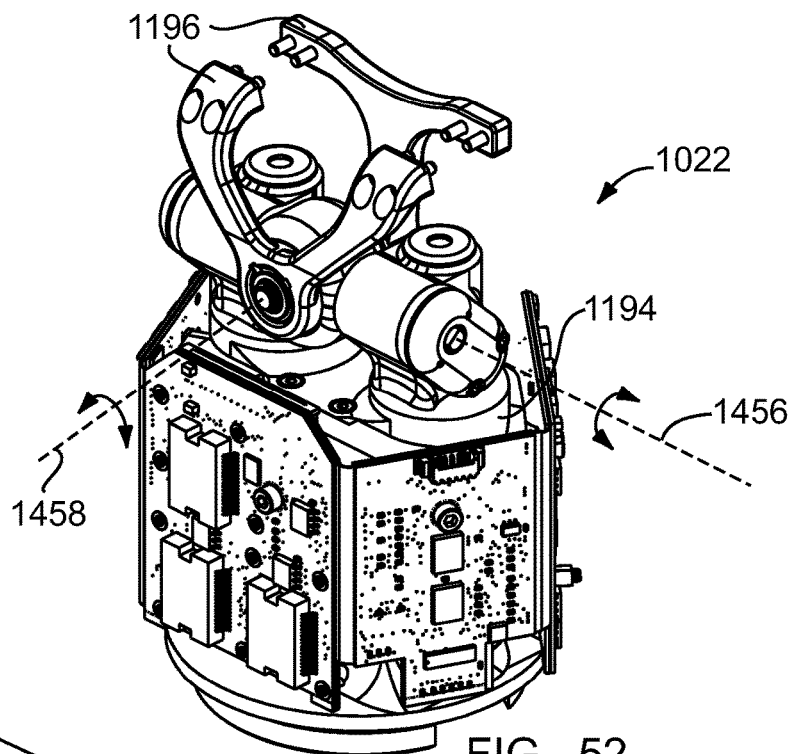
FIG. 52 is a perspective view of another embodiment of a wrist flexion assembly according to the present invention.

Referring to FIG. 52, in another embodiment of the wrist flexion assembly 1022, the output arm 1196 is able to move in flexion relative to the input support structure 1194 about a flexion axis 1456 and to move in ulnar-radial deviation relative to the input support structure 1194 about a deviation axis 1458. Thus, when the hand assembly 24, shown in FIG. 1, is attached to the output arm 1196 of the wrist flexion assembly 1022, the hand assembly 24, shown in FIG. 1, is able to move in both flexion and ulnar-radial deviation.

Figure 53:
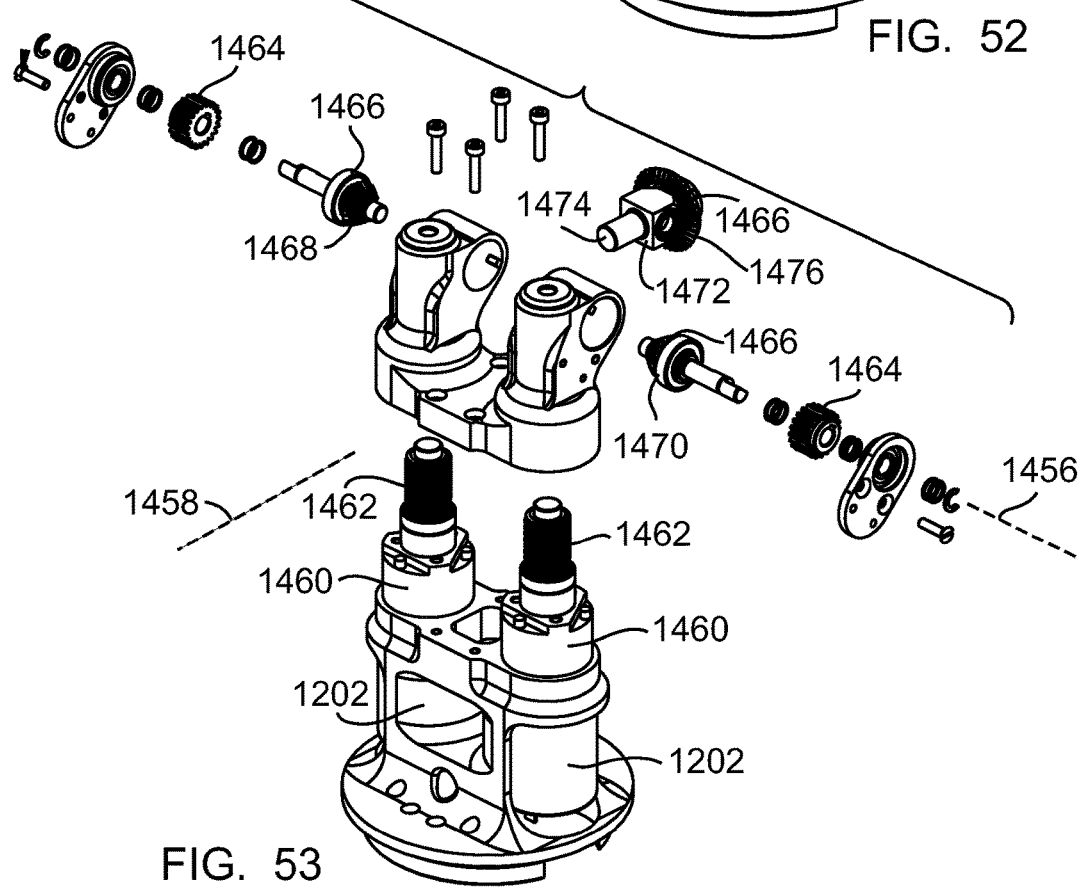
FIG. 53 is a partially exploded perspective view of the wrist flexion assembly of FIG. 52.

Referring to FIG. 53, the wrist flexion assembly 1022 includes two wrist motors 1202, for controlling the flexion and ulnar-radial deviation of the output arm 1196, shown in FIG. 52. Each wrist motor 1202 drives an input gear train 1460, which, in turn, drives a wrist worm gear 1462. Each worm gear 1462 drives an input gear 1464 of a wrist differential 1466. The wrist differential 1466 includes a first bevel gears 1468 and a second bevel gear 1470 that are rotatable about the flexion axis 1456. The first bevel gear 1468 and the second bevel gear 1470 may be driven by one of the input gears 1464. The wrist differential 1466 also includes a differential body 1472 rotatably attached about the flexion axis 1456 between the first and second bevel gears 1468 and 1470. An ulnar-radial axle 1474 extends from one side of the differential body 1472 along the ulnar-radial axis 1458 and a third bevel gear 1476 extends from the differential body 1472 on the opposite side thereof. The third bevel gear 1476 is rotatable about the ulnar-radial axis 1458 and meshes with and is driven by the first bevel gear 1468 and the second bevel gear 1470.

Figure 54:
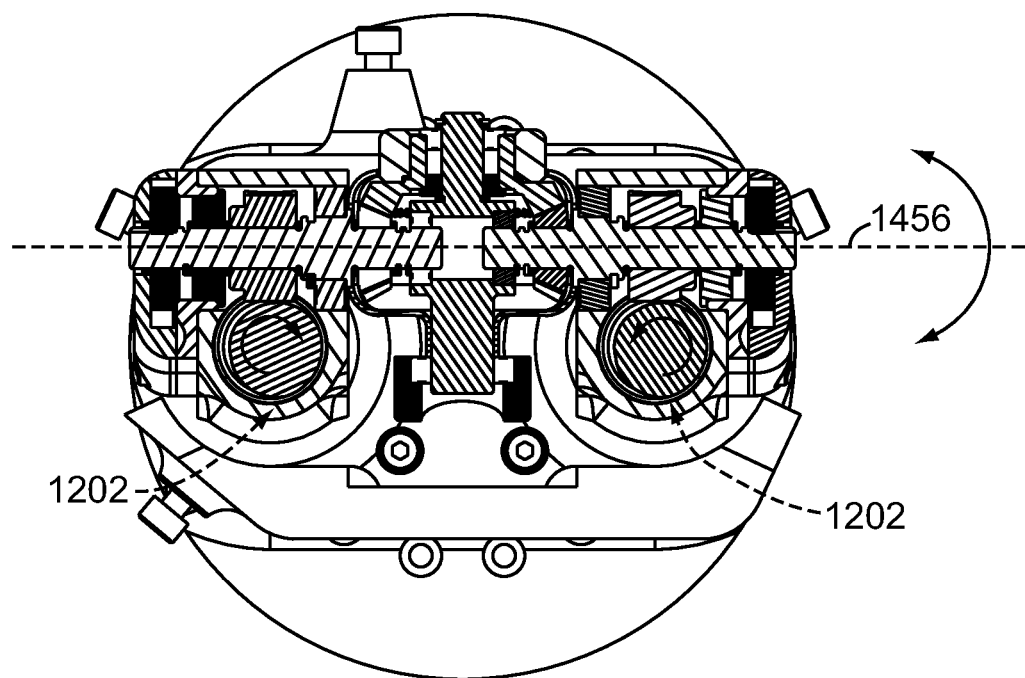
FIG. 54 is a top cross-sectional view of the wrist flexion assembly of FIG. 52.
Figure 55:
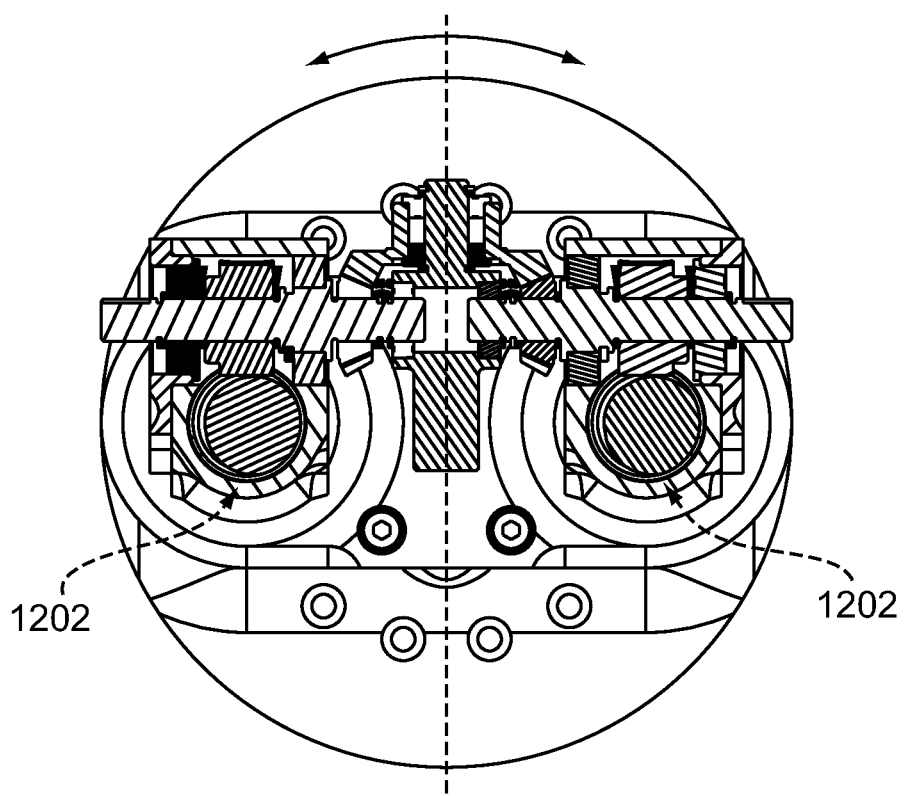
FIG. 55 is a top cross-sectional view of the wrist flexion assembly of FIG. 52.

In operation, the user is able to actuate wrist flexion, wrist ulnar-radial deviation and combinations thereof by actuating the motors 1202 in various ways. For example, referring to FIG. 54, if the motors 1202 are driven at the same speed in opposite directions, i.e. one is driven clockwise and the other counterclockwise, the output arm 1196, shown in FIG. 52 will move in flexion in one direction about the flexion axis 1456. If the direction of each motor is reversed, i.e. from spinning clockwise to counterclockwise and vice versa, the output arm 1196, shown in FIG. 52, will flex in the opposite direction. Similarly, referring to FIG. 55, if the motors 1202 are driven at the same speed in the same direction, i.e. both are driven clockwise, the output arm 1196, shown in FIG. 52, will move in ulnar-radial deviation in one direction about the deviation axis 1458. If the direction of each motor is reversed, i.e. from spinning clockwise to counterclockwise, the output arm 1196, shown in FIG. 52, will move in ulnar-radial deviation in the opposite direction about the deviation axis 1458. In addition to varying the direction of rotation of the motors 1202, varying the speed of one motor 1202 relative to the other will result in a combination of flexion and ulnar-radial deviation. Accordingly, in this embodiment, wrist flexion and ulnar-radial deviation may both be controlled simply by varying the direction and speed of the motors 1202.

Figure 56:
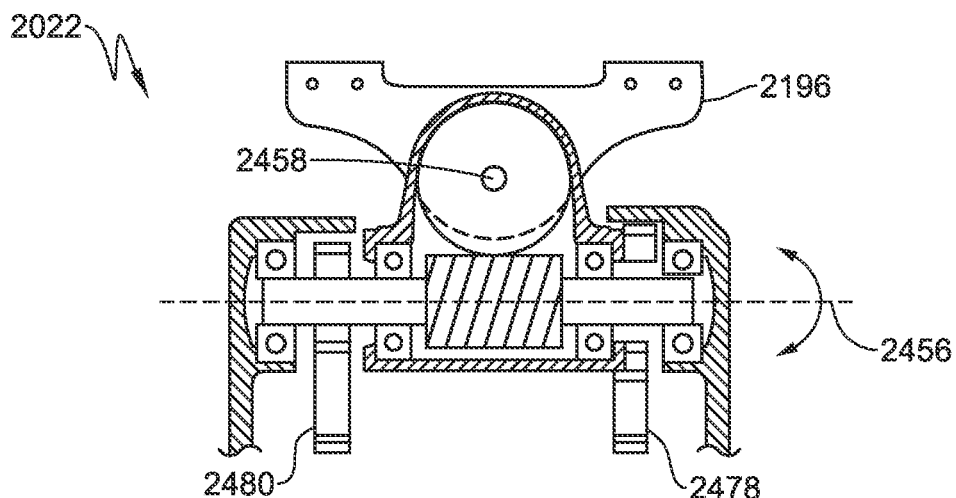
FIG. 56 is a cross-sectional view of another embodiment of a wrist flexion assembly according to the present invention.

Although the wrist flexion assembly 1022 is described as having a differential drive 1466 for imparting wrist flexion and wrist ulnar-radial deviation movement to the output arm 1196, it should be understood by those skilled in the art that other drives may be used to achieve similar capabilities. For instance, referring to FIG. 56, the wrist flexion assembly 2022 may include a separate wrist flexion gear train 2478 for imparting flexion motion to the output arm 2196 about the flexion axis 2456 and a separate ulnar-radial geartrain 2480 for imparting ulnar-radial deviation to the output arm 2196 about the deviation axis 1458.

Figure 76:
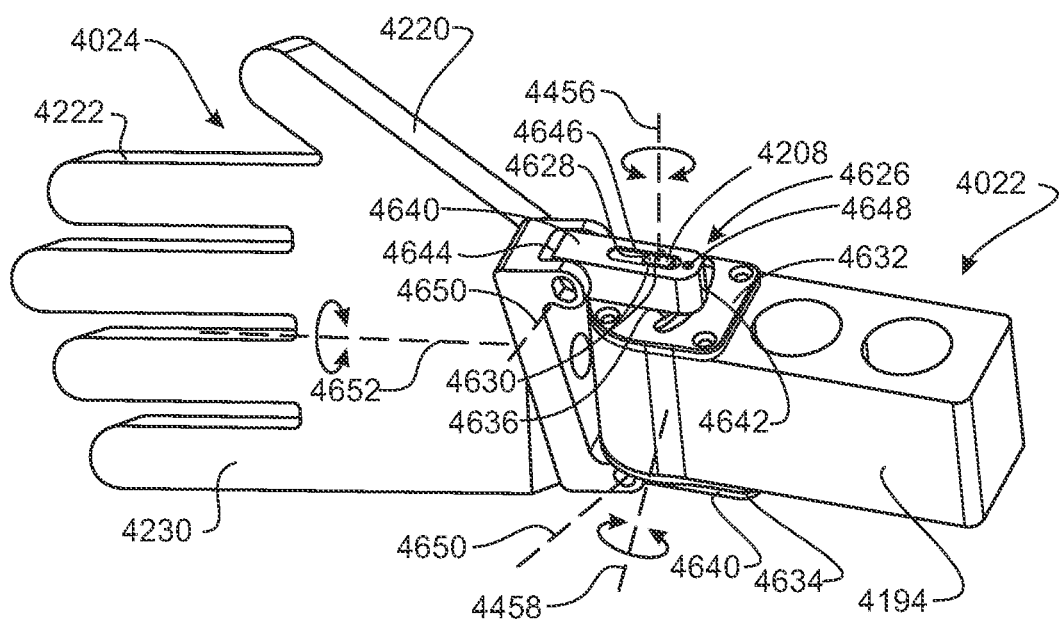
FIG. 76 is a perspective view of a wrist flexion assembly according to another embodiment of the present invention.
Figure 77:
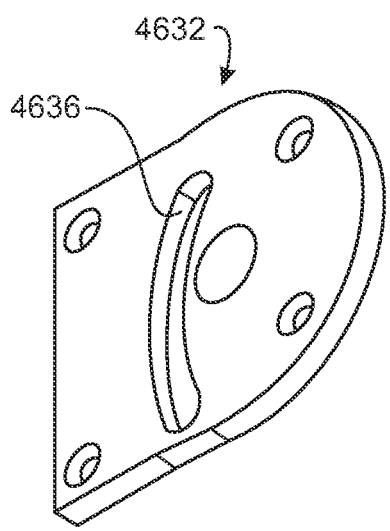
FIG. 77 is a perspective view of a first cam bearing of the wrist flexion assembly of FIG. 76.
Figure 78:
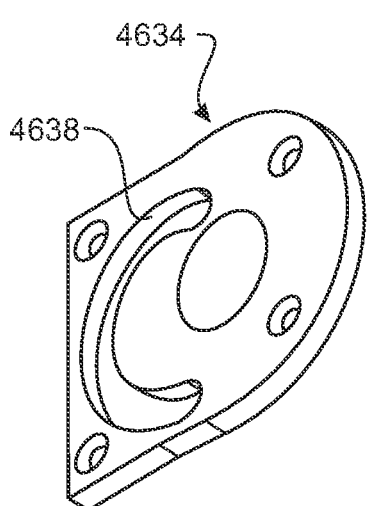
FIG. 78 is a perspective view of a second cam bearing of the wrist flexion assembly of FIG. 76.

Referring to FIG. 76, in another embodiment of the present invention, a wrist flexion assembly 4022 is provided for imparting a combination of both flexion about the flexion axis 4456 and ulnar-radial deviation about the deviation axis 4458 to the hand assembly 4024 in a single movement. The wrist flexion assembly 4022 includes the input support structure 4194 adapted to be connected to the wrist rotator 20, shown in FIG. 1, in the same manner as discussed above. The wrist support structure 4194 includes a hand interface 4626 proximate to the hand assembly 4024 for attaching the hand assembly 4024 to the wrist support structure 4194. The wrist support structure 4194 houses a wrist motor 202, shown in FIG. 26, which drives the wrist pivot axle 4208 in rotary motion about the wrist flexion axis 4456 through an appropriate gear train (not shown). The wrist pivot axle includes flattened end portions 4628 at each end thereof, extending outwardly from the wrist support structure 4194 and into the hand interface 4626. Each flattened end portion 4628 has two substantially parallel planar surface 4630 extending parallel to the wrist flexion axis 4456. The hand interface 4626 includes a first cam bearing 4632 fixedly secured to the wrist support structure 4194 about the flattened end portion 4628 of the wrist pivot axle 4208 proximate to the thumb structure 4220 of the hand assembly 4024. The hand interface also includes a second cam bearing 4634 fixedly secured to the wrist support structure 4194 about the flattened end portion 4628 of the wrist pivot axle 4208 proximate to the pinky finger 4230 of the hand assembly 4024. Referring to FIG. 77, the first cam bearing 4632 includes a first cam profile 4636 formed therein. Referring to FIG. 78, the second cam bearing 4634 includes a second cam profile 4638 formed therein. Referring back to FIG. 76, the hand interface 4626 also includes first and second slider blocks 4640 coupling the hand assembly 4024 to the wrist flexion assembly 4022. The first and second slider blocks 4640 each have a proximate end 4642 at the hand interface 4626 and a distal end 4644 near the hand assembly 4024. Each of the first and second slider blocks 4640 has a slot 4646 formed therein that slidably receives one of the flattened end portions 4628 of the wrist pivot axle 4208. The first and second slider blocks 4640 include cam followers 4648 at their proximate ends 4642 that are received within the first cam profile 4636 of the first cam bearing 4632 and the second cam profile 4638, shown in FIG. 78, of the second cam bearing 4634. The first and second slider blocks 4640 are pivotally coupled to the hand assembly 4024 at their distal ends 4644 about pivot axes 4650.

In this embodiment, the hand assembly 4024 may be angled away from the flexion axis 4456 about a wrist rotation axis 4652 to reduce the motion that the first cam profile 4636 and the second cam profile 4638 need to produce to achieve the desired combined flexion and ulnar-radial deviation movement of the hand assembly 4024. In some embodiments, the hand assembly 4024 is angled approximately thirty degrees clockwise (30° clockwise) assuming left hand user perspective from the flexion axis 4456.

Figure 79A:
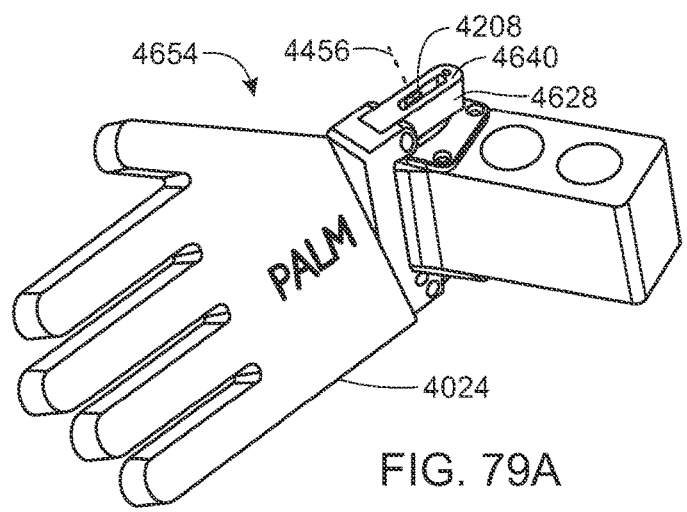
FIG. 79A is a perspective view of the wrist flexion assembly of FIG. 76 in a first position.
Figure 79B:
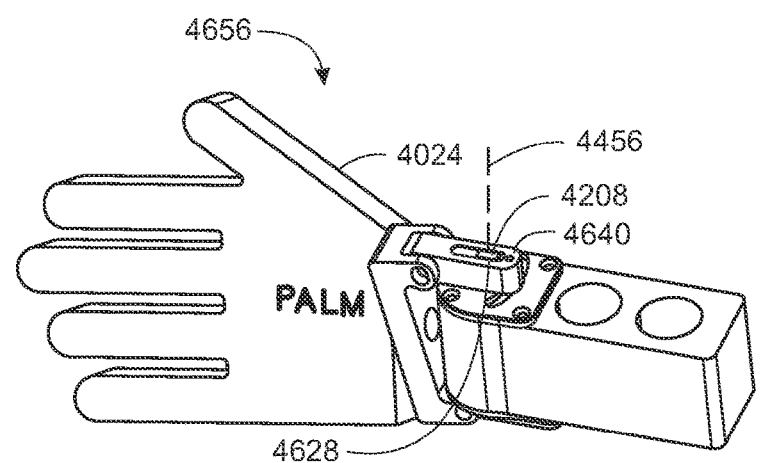
FIG. 79B is a perspective view of the wrist flexion assembly of FIG. 76 in a second position.
Figure 79C:
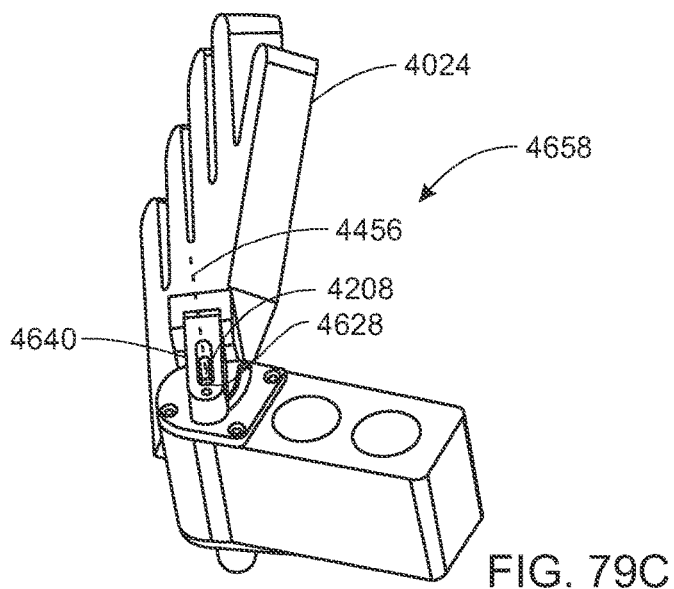
FIG. 79C is a perspective view of the wrist flexion assembly of FIG. 76 in a third position.

Referring to FIGS. 79A-79C, in operation, the wrist motor 202, shown in FIG. 26, drives the wrist pivot axle 4208 in rotation movement about the flexion axis 4456, which provides the hand assembly 4024 with flexion movement. Additionally, the sliding engagement between the flattened end portions 4628 of the wrist pivot axle 4208 and the first and second slider blocks 4640 causes the first and second slider blocks 4640 to pivot about the flexion axis 4456 as the wrist pivot axle 4208 rotates. As the first and second slider blocks 4640 pivot, the cam followers 4648, shown in FIG. 76, follow the first cam profile 4636, shown in FIG. 76, and the second cam profile 4638, shown in FIG. 76, which causes the first and second slider blocks 4640 to slide relative to the wrist pivot axle 4208. This sliding motion of each of the first and second slider blocks 4640 causes the hand assembly 4024 to pivot about the pivot axes 4650, shown in FIG. 76, which results in the ulnar-radial deviation movement of the hand assembly 4024. Thus, as the wrist motor drives the wrist pivot axle 4208, the hand assembly 4024 moves from a first position 4654, shown in FIG. 79A, in which the hand is fully flexed and deviated in the ulnar direction, to a second position 4656, shown in FIG. 79B, which is a neutral position with respect to flexion movement but includes some degree of ulnar deviation. Then, the hand assembly 4024 continues to move until it reaches a third position 4658, shown in FIG. 79C, in which the hand assembly 4024 is fully extended about the flexion axis 4456 and is also fully deviated in the radial direction.

Figure 80:
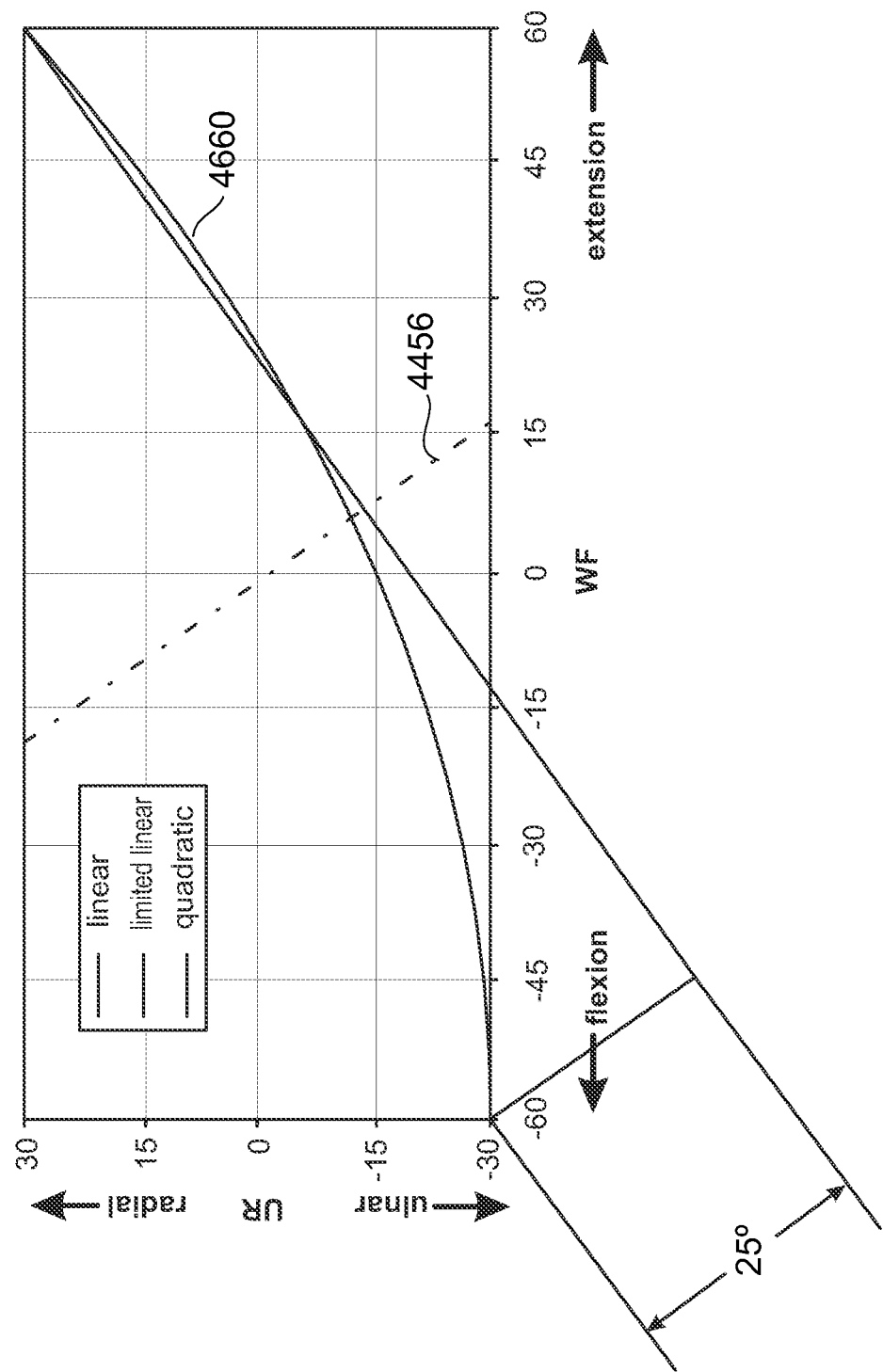
FIG. 80 is a line graph of a fixed movement path of the wrist flexion assembly of FIG. 76.

Referring to FIG. 80, the first cam profile 4636, shown in FIG. 77, and the second cam profile 4638, shown in FIG. 78, provide for movement of the hand assembly 4024, shown in FIG. 76, along a constrained flexion-deviation movement path 4660 that includes components of both flexion motion and ulnar-radial deviation motion. The constrained flexion-deviation movement path 4660 is advantageous because the user only needs to think about controlling a single degree of freedom, unlike the embodiments discussed above that provide independent wrist flexion movement and ulnar-deviation movement. Additionally, the constrained flexion-deviation movement path 4660 is beneficial because it provides for full flexion movement and also provides for nearly full ulnar deviation without requiring full wrist flexion. Thus, functionality is particularly beneficial when users use the prosthetic arm apparatus 10, shown in FIG. 1, to pick up an object (not shown) from overhead. The constrained flexion-deviation movement path 4660 also advantageously allows for some degree of flexion movement without significant ulnar deviation, which allows the user to move an object, such as a spoon, in flexion motion without spilling its contents. This range of flexion movement with minimal ulnar deviation provided by the constrained flexion-deviation movement path 4660 may also be beneficial to compensate for offset in situations where the prosthetic arm apparatus 10, shown in FIG. 1, is mounted at an offset, for example, to avoid the user's residuum. Additionally, since the hand assembly 4024, shown in FIG. 76, is angled in the neutral second position 4656, shown in FIG. 79B, pinching of the thumb structure 4220, shown in FIG. 76, and index finger structure 4222, shown in FIG. 76, are more in line with the wrist rotation axis 4652, which makes various tasks easier for the user, such as turning a door knob, turning a key or the like. Thus, the constrained flexion-deviation movement path 4660 provided by the wrist flexion assembly 4022, shown in FIG. 76, provides a variety of advantages over conventional prosthetic devices.

Although described in terms of constrained flexion-deviation movement path 4660, it should be understood by those skilled in the art that the first cam profile 4636, shown in FIG. 77, and the second cam profile, shown in FIG. 78, may be formed in various configurations to achieve a variety of different constrained movement paths. Additionally, although the constrained flexion-deviation movement path 4660 has been described in connection with the wrist flexion assembly 4022, the constrained flexion-deviation movement path 4660 may also be commanded using the flexion assembly 1022, shown in FIG. 52, by programming the prosthetic controller to actuate the motors 1202, shown in FIG. 53, to move the prosthetic hand assembly 24 along the same constrained flexion-deviation path 4660.

Figure 57:
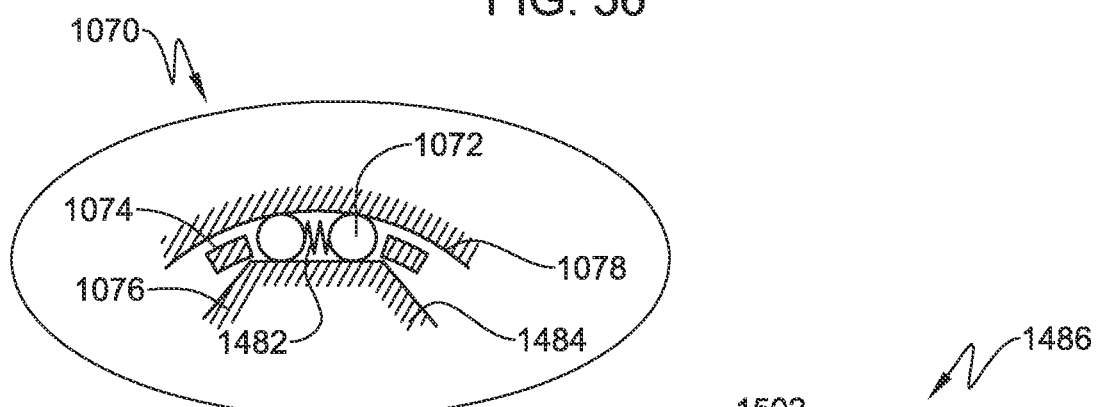
FIG. 57 is a partial cross sectional view of another embodiment of the non-backdriving clutch of FIG. 12.

Referring to FIG. 57, in various embodiments, the non-backdriving clutch 1070 may replace spacers of the input cage 1074 with springs 1482 between the rollers 1072. The springs 1482 push the rollers 1072 apart and into contact with both the race 1078 and the output polygon 1484, which may be an output hex 1076. Thus, when a backdriving torque (not shown) is applied to the output hex 1076 to friction lock the rollers 1072 between the output hex 1076 and the bearing race 1078, the rollers 1072 are already contacting both the race 1078 and the output hex 1076, thereby eliminating backlash, i.e. a slight rotation of the output polygon 1076, when the backdriving torque (not shown) is applied. Thus, the non-backdrivable clutch 1070 imparts a frictional lock, which additional backdriving torque (not shown) through the output hex 1076 will not overcome. Additionally, as discussed above in connection with FIG. 12, in various embodiments, the non-backdriving clutch 1070 may unlock itself through the application of an input load through the input cage 1074. Variations of this embodiment may include, but are not limited to, additional or fewer springs 1482, additional or fewer rollers 1072 or a differently shaped race 1078. For example, in various embodiments, the relative position of the output hex 1076 and the race 1078 may be shifted, i.e., rather than the hollow, circular race 1078 with the output polygon 1484 inside, in various embodiments, the clutch may include an outer hollow output polygon surrounding a circular race. Additionally, although shown as a coil spring, it should be understood by those skilled in the art that the springs 1482 may be formed in various configurations and/or from a variety of metal or elastomeric materials to provide the force for separating the rollers 1072.

Figure 58:
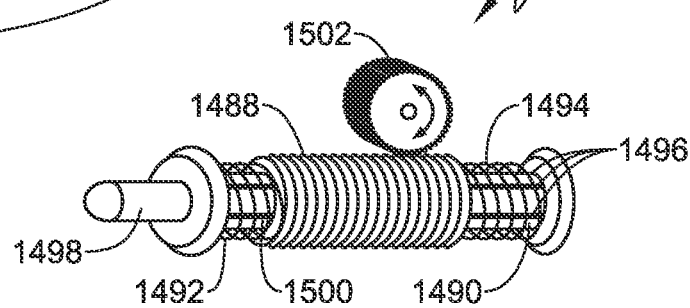
FIG. 58 is a perspective view of a compliance assembly according to an embodiment of the present invention.

Referring to FIG. 58, an embodiment for output load sensing through a drive 1486 having a worm gear 1488, such as the shoulder abduction drive 1428 of FIG. 46, is shown. Including one or more worm gears 1488 in the drive 1486 is beneficial because the worm gear 1488 may itself prevent backdriving. The worm gear 1488 may be arranged on a splined shaft 1490 between a first spring 1492 and a second spring 1494. The splined shaft includes a plurality of splines 1496 arranged axially around the surface of the splined shaft 1490 and a shaft input 1498 portion, which may be rotated directly by a motor (not shown) or through a gear train or the like. The worm gear 1494 is tubular and has an interior surface 1500 designed to slidably interface with the splines 1496 of the splined shaft 1490 such that the worm gear 1488 may slide axially along the surface of the splined shaft 1490. The worm gear 1488 meshes with an output gear 1502 such that when the splined shaft 1490 is caused to rotate through its shaft input portion 1498, the splined shaft 1490 rotatably drives the worm gear #1488 through the splines 1496 which, in turn, drives the output gear 1502. When a load (not shown) is applied to the drive through the output gear 1502, for example, if the user is lifting an object, the load will generate a torque T at the output gear 1502. Although the torque T will not cause the worm gear 1488 to rotate, the torque T may cause the worm gear 1488 to displace axially along the splined shaft 1490 compressing one of the first spring 1492 or the second spring 1494, depending upon the direction of displacement. Thus, by designing the drive system 1486 with the first spring 1492 and the second spring 1494 of known spring constants, the compliance, i.e. the displacement of the worm gear 1488, may be measured to estimate the output load (not shown). This drive system 1486 for output load sensing is particularly beneficial since the compliance is still present or active while the worm gear 1488 is not being rotated, but is instead acting as a non-backdriving element.

Figure 59:
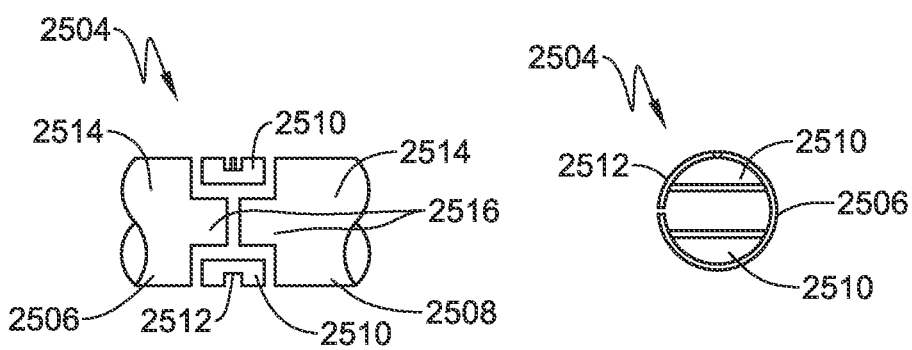
FIG. 59 is a side view of a breakaway mechanism according to an embodiment of the present invention.
Figure 60:
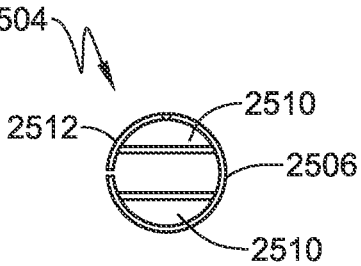
FIG. 60 is a front cross-sectional view of the breakaway mechanism of FIG. 59.

The prevention of backdriving with the various systems discussed above is beneficial because it allows the user to maintain a position of the prosthetic arm 10, shown in FIG. 1, while under a load (not shown). However, referring to FIGS. 59 and 60, in some embodiments, it may be desirable to provide the various arm segments with break-away mechanisms 2504 that will separate the drive output from the drive input to prevent damage to the drive system if the load becomes too large. The break-away mechanism 2504 may include an input shaft 2506, an output shaft 2508 and two break-away spacers 2510 that are held in contact with the input shaft 2506 and output shaft 2508 by a compression member 2512. The input shaft 2506 and the output shaft 2508 each include a shaft body 2514 and a torque transmission tab 2516 extending axially outward from the shaft body 2514 between the break-away spacers 2510. The compression element member 2512 surrounds the break-away spacers 2510 and sandwiches the torque transmission tabs 2516 therebetween. The compression member 2512 may be, for example, a snap ring, a round metal ring, an o-ring, multiple o-rings, a coil spring, or the like. The compression member 2512 applies a preset compressive force to the breakaway spacers 2510.

In operation, the input shaft 2506 of the break-away mechanism 2504 is rotated by a motor (not shown) or the like to generate a desired movement of the prosthetic arm 10, shown in FIG. 1. Thus, the torque transmission tab 2516 of the input shaft 2506 rotates and transmits the rotation through the break-away spacers 2510 to the torque transmission tab 2516 of the output shaft 2508 as long as the torque required to cause rotation of the torque transmission tab 2516 of the output shaft 2508 is not large enough to overcome the preset compressive force provided by the compression member 2510. If the torque is large enough to overcome the preset compressive force, the torque transmission tab 2515 will push the break-away spacers 2510 apart and the torque transmission tab 2516 will rotate between the break-away spacers 2510 without transmitting torque therethrough. Thus, the break-away mechanism 2504 may prevent torque above a preset level from being transmitted through the drive system, where it can damage the drive system components. Accordingly, the break-away mechanism 2504 may limit the amount of torque applied to sensitive parts of the various drive systems of the prosthetic arm 10, shown in FIG. 1, and may, therefore, impart a longer lifespan on the prosthetic arm.

Figure 61A:
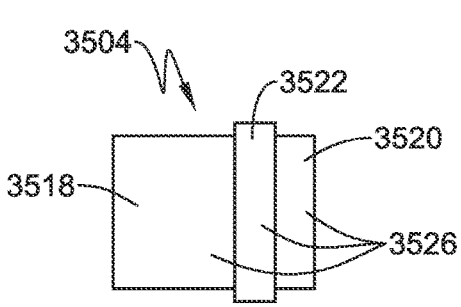
FIG. 61A-63B are various views of another embodiment of a breakaway mechanism according to the present invention.

Referring to FIG. 61A, another embodiment of a break-away mechanism 3504 includes an input ring 3518 and an output ring 3520 connected by a detent ring 3522. The breakaway mechanism 3504 may be connected between two prosthetic arm segments, for example, the input ring 3518 may be connected to the shoulder unit 1416, shown in FIG. 42, and the output ring 3520 may be connected to the humeral rotator 16, shown in FIG. 1. In some embodiments, the input ring 3518, output ring 3520 and the detent ring 3522 each includes an alignment marker 3524 on its outer surface 3526 to indicate proper positioning of the breakaway mechanism 3504.

Figure 61B:
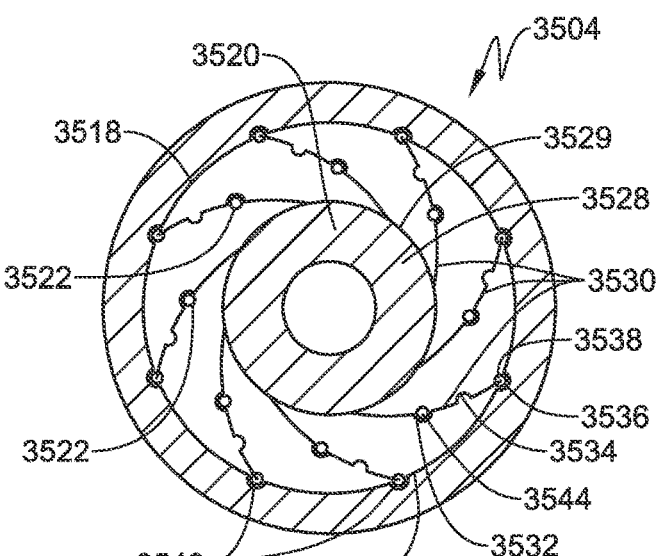

Referring to FIG. 61B, the output ring 3520 includes a central hub 3528 having an outer surface 3529 with a plurality of spring fingers 3530 radiating therefrom. Each spring finger 3530 has a first detent 3532 and a second detent 3534 along its length and a pin 3536 at its distal end 3538. The input ring 3518 includes a plurality of detents 3540 around the circumference of its inner surface 3542, within which the pins 3536 of the spring fingers 3530 may engage, as will be discussed in greater detail below. The detent ring 3522 includes a plurality of detent pins 3544 located partway between the inner surface 3542 of the input ring 3518 and the outer surface 3529 of the output ring 3520. The detent pins 3544 engage the first detents 3532 of the spring fingers 3530 during normal operation of the breakaway mechanism 3504, i.e. when torque is being transmitted through the breakaway mechanism 3504.

Figure 62A:
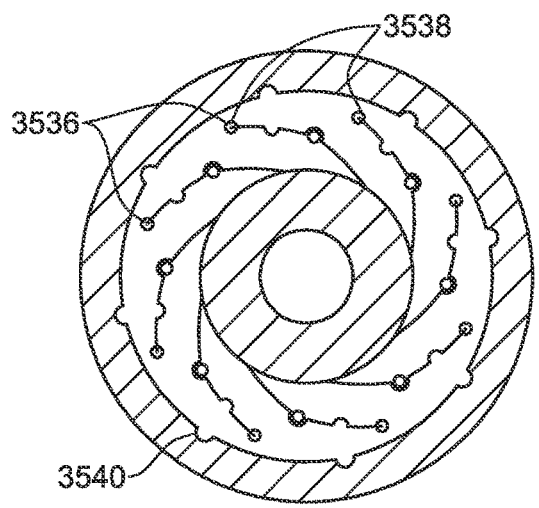
Figure 62B:
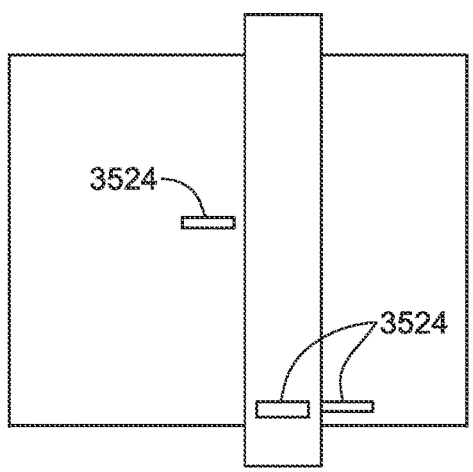

However, referring to FIG. 62A, if an overtorque situation occurs, the pins 3536 at the distal ends 3538 of the spring fingers 3530 will pop out of the ring detents 3540 so that the torque will not be transmitted back to the input ring 3504. Additionally, referring to FIG. 62B, the overtorque situation will also cause the alignment markers 3524 to move out of alignment. The user may then realign the alignment markers 3524 to transmit torque through the breakaway mechanism 3504.

Figure 63A:
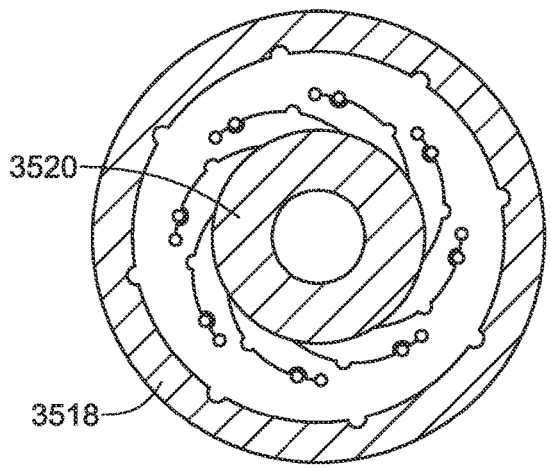
Figure 63B:
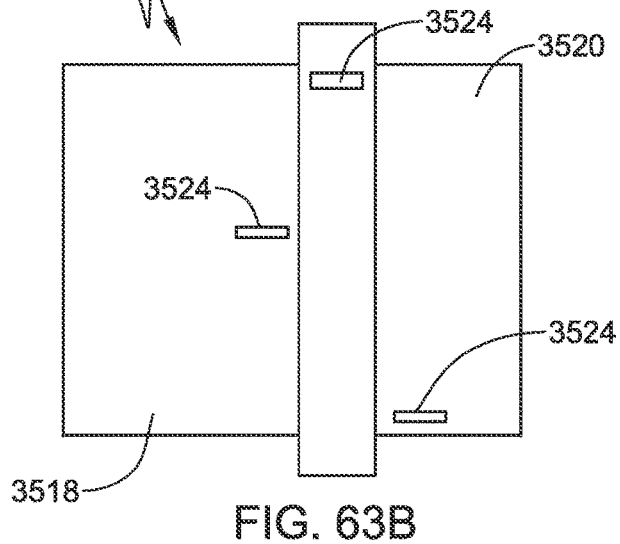

Referring to FIG. 63A, the user may also intentionally disengage the torque transmission by moving the alignment marker 3524 on the detent ring 3522 up to engage the breakaway mechanism 3504 in freeswing. As seen in FIG. 63B, this configuration entirely disengages the spring fingers 3530 from the input ring 3518, thereby allowing the output ring 3520 to rotate freely without driving the upstream components through the input ring 3518. Thus, this embodiment of the breakaway mechanism 3504 is advantageous because it also allows for the user to engage freeswing of the prosthetic arm 10, shown in FIG. 1.

These break-away mechanisms discussed above are beneficial because they prevent damage to the prosthetic arm apparatus 10 due to high loading situations. Additionally, the break-away mechanisms are advantageous in that once the break-away mechanisms break under high loading, they may be reset by the user without the need to see a prosthetic technician.

Figure 64:
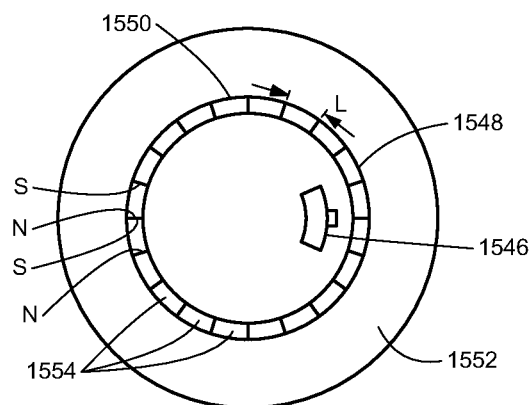
FIG. 64 is a front view of a magnetic sensor according to some embodiments of the present invention.

As discussed above, various embodiments of the prosthetic arm 10, shown in FIG. 1, include feedback mechanisms, such as potentiometers for position sensing. Referring now to FIG. 64, in some embodiments, the prosthetic arm 10, shown in FIG. 1, may include other feedback mechanisms, for example, a magnetic position sensor 1546. In these embodiments, at least one magnetic strip 1548 may be attached about the circumference of an inner surface 1550 of a rotatable drive component 1552. The magnetic strip 1548 includes a plurality of magnets 1554 of known length L1 arranged in series, each having a north pole N and a south pole S. Thus, the magnetic strip 1548 generates a magnetic field having a repeating pattern of alternating north poles N and south poles S. The magnetic position sensor 1546 is arranged to detect this magnetic field generated by the magnetic strip 1548. In operation, the rotatable drive component 1552 rotates, which causes the magnetic strip 1548 to rotate, thereby moving the portion of the magnetic strip 1548 being detected by the magnetic position sensor 1546. The magnetic position sensor 1546 detects this change in the magnetic field as the magnetic strip 1548 rotates from each north pole N to each south pole S and vice versa. Since the length L1 of each magnet 1554 is known, the detected changes in the magnetic field between each north pole N and/or each south pole S may be converted into the distance of rotational movement of the rotatable drive component 1552. Thus, the change in position of the rotatable drive component 1552 may be detected. The magnetic position sensor 1546 is also advantageous because it does not contact the rotating drive component 1552 and, therefore, will not experience contact wear due to the rotation of the rotatable drive component 1552.

Figure 65:
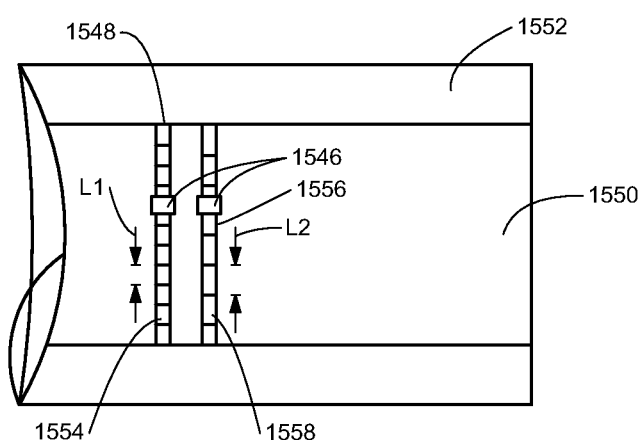
FIG. 65 is a side cross-sectional view of another embodiment of a magnetic sensor according to the present invention.

Referring to FIG. 65, in some embodiments, two magnetic position sensors 1546 may be used to detect the magnetic fields generated by the first magnetic strip 1548 and a second magnetic strip 1556 arranged next to each other around the circumference of the inner surface 1550 of a rotatable drive component 1552. A length L2 of each magnet 1558 of the second magnetic strip 1556 is, in some embodiments, different than the length L1 of the magnets of the first magnetic strip 1548. This difference in length allows for the magnetic position sensors 1546 to sense unique combinations of magnetic field values from the first magnetic strip 1548 and the second magnetic strip 1556 over the circumference of the inner surface 1550. Each unique magnetic field value may correspond to a position of the drive component 1552 and, therefore, absolute position of the drive component 1552 may be detected by the two magnetic position sensors 1546.

Figure 66:
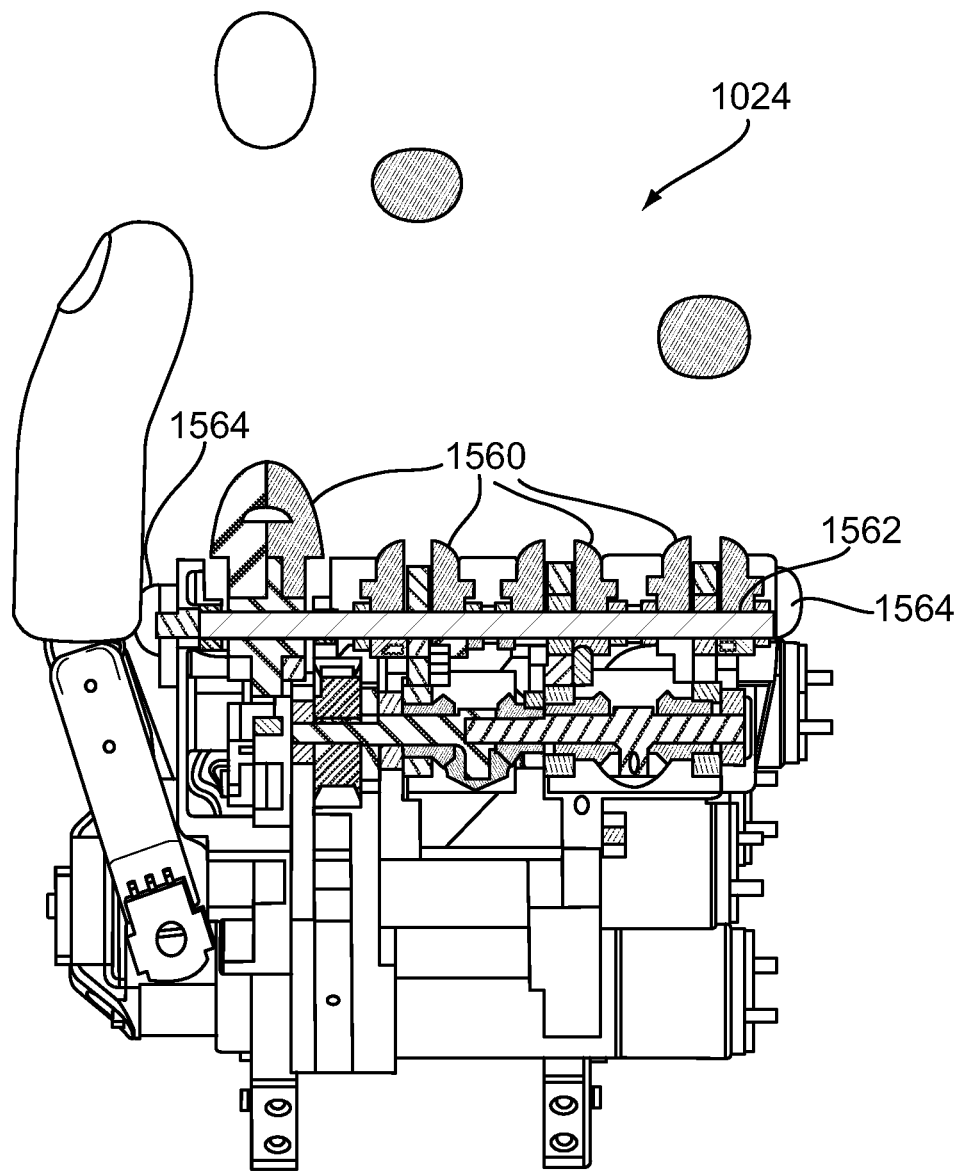
FIG. 66 is a cross-sectional view of a hand assembly according to an embodiment of the present invention.

In practice, the hand assembly 24, shown in FIG. 1, and particularly, the fingers of the hand assembly 24, i.e. the thumb structure 220, index finger structure 222, middle finger 226, ring finger 228 and pinky finger 230, all shown in FIG. 3, come into contact with objects frequently and, therefore, may be susceptible to wear and damage. Thus, referring to FIG. 66, it may be desirable for the prosthetic hand assembly 1024 to include removable fingers 1560. In this embodiment of the prosthetic hand assembly 1024, the removable fingers 1560 may be removed to allow for easier replacement of damaged fingers 1560 and also, to allow for easily customizable or tailored finger lengths for different user.

Each removable finger 1560 is driven in substantially the same manner as the fingers of the previously discussed embodiments. However, the removable fingers 1560 pivot about a common finger shaft 1562, rather than the individual pivot axles discussed in connection with FIG. 33. In some embodiments, end caps 1564 cover each end of the common finger shaft 1562 to prevent dirt or other contaminants from getting into the gear trains of the hand assembly 1024 and also to ensure that the common finger shaft 1562 does not become axially displaced unintentionally. In operation, either end cap 1564 may be removed from the hand assembly 1024 and the common finger shaft 1562 may be extracted to free the removable fingers 1560. Each finger 1560 may then be removed and replaced individually, as required.

Figure 67:
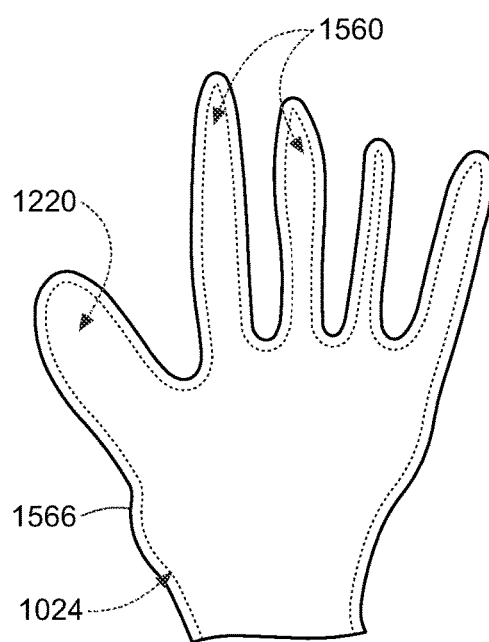
FIG. 67 is a front view of a hand assembly cosmesis according to an embodiment of the present invention.

As discussed above, the fingers 1560 of the hand assembly 1024 come into contact with objects frequently and are, therefore, susceptible to wear. Thus, referring to FIG. 67, some embodiments of the present invention may include a cosmesis 1566 for covering the hand assembly 1024 to reduce wear of the hand assembly 1024 and the fingers 1560, in particular. The cosmesis 1566 may be formed from silicone or a similar material, such as a urethane, to improve the grip capabilities of the hand assembly 1024 to assist with the various grasping and pinch functions of the hand, thereby, providing additional functionality.

Figure 68A:
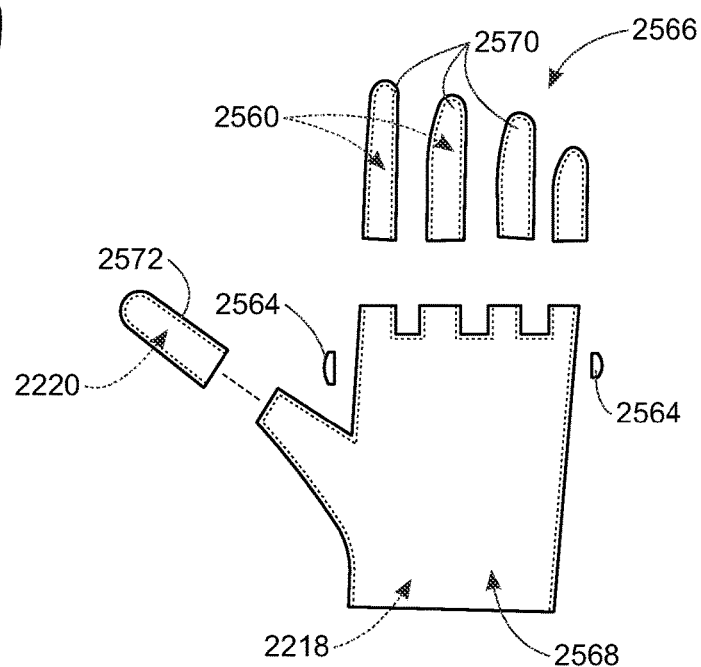
FIG. 68A is a front view of an embodiment of the cosmesis of FIG. 67 with removable finger portions.

In use, the cosmesis 1566 may wear more quickly around the fingers 1560 and the thumb structure 1220. Therefore, in some embodiments the cosmesis 1566 may separate into two or more sections to allow high wear areas to be replaced more frequently than low wear areas. For instance, referring to FIG. 68A, in some embodiments, the cosmesis 2566 includes a separate palm section 2568 covering the hand support 2218, finger sections 2570 covering each finger 2560 and a thumb section 2572 covering the thumb structure 2220. Thus, the finger sections 2570 and thumb section 2572 may each be replaced separately from the palm section 2568. Although shown as having separate finger sections 2570 and thumb section 2572, in various embodiments, the cosmesis 2566 may also include only two sections, for example, the finger sections 2570 and the thumb section 2572 may be combined into one section and the hand support 2218 may be covered by the separate palm section 2568.

Figure 40:
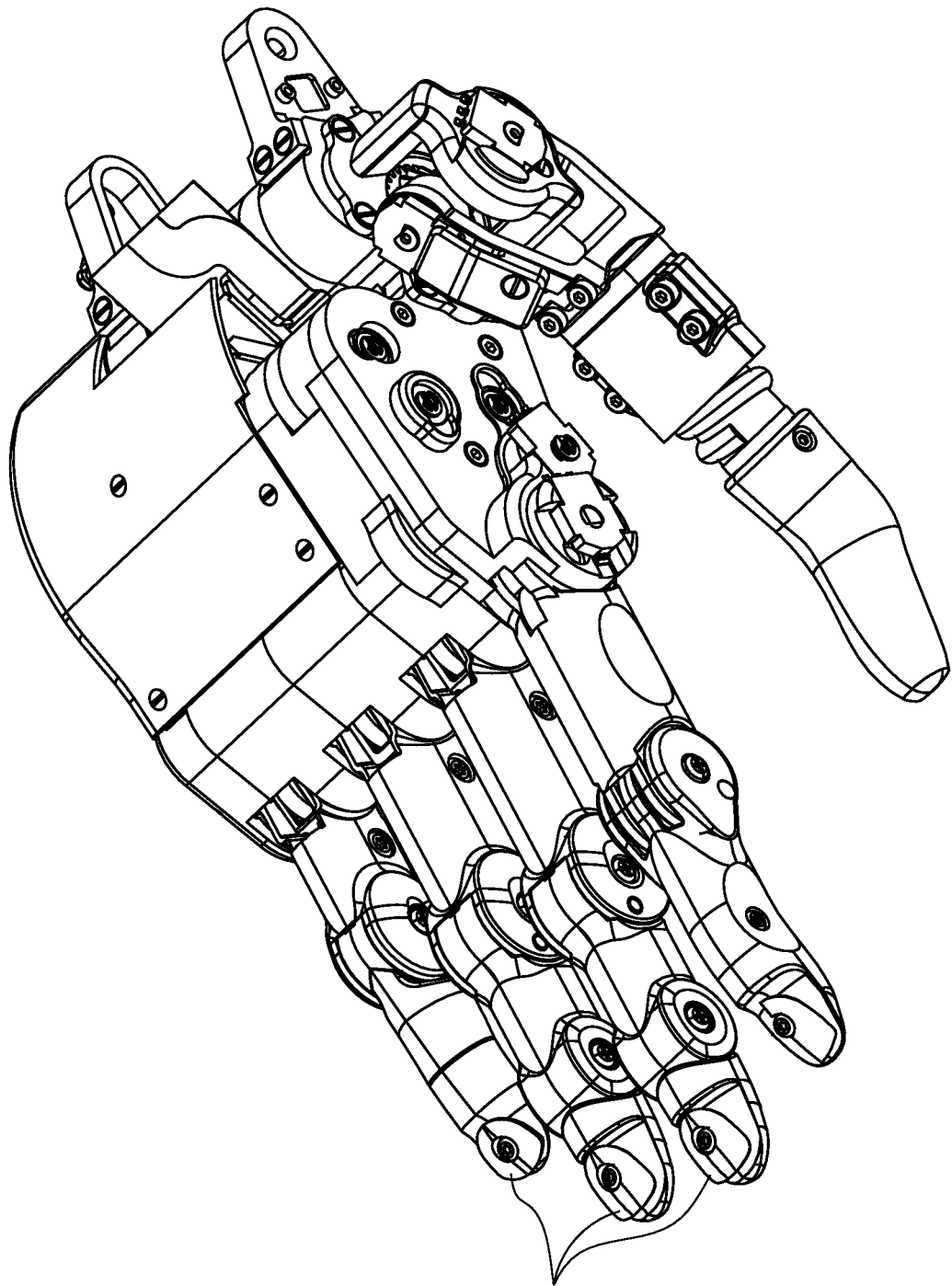
FIG. 40 is a perspective view of another embodiment of the hand.
Figure 68B:
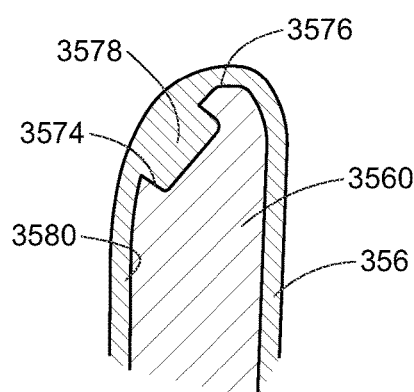
FIG. 68B is a cross-sectional view of an embodiment of a finger structure cosmesis of FIG. 68A.

Referring to FIG. 68B, in some embodiments of the present invention, the fingers 3560 may be provided with geometric features 3574, such as slots, in their outer surfaces 3576 that may accept corresponding geometric interlocks 3578 provided on the inner surface 3580 of the cosmesis 3566. This interlocking geometry may resist shear loads on the cosmesis 3566, thereby preventing the cosmesis 3566 from slipping off of the fingers 3560. Additionally, with respect to the hand cosmesis, fine pinch and other functions may require a structural backing at the tips of the fingers 3560 and thumb structure 3220. Therefore, in some embodiments, the geometric features 3574 of the fingers 3560 and thumb structure 3220 may each include a fingernail apparatus 579, shown in FIG. 40. The fingernail apparatus 579, shown in FIG. 40, interacts with the finger and thumb structure cosmesis 3566 to anchor the cosmesis 3566 of the fingers 3560 and thumb structure 3220, thereby mitigating and/or preventing the cosmesis 3566 from rolling over on the tips of the fingers 3560 and thumb structure 3220.

Figure 69:
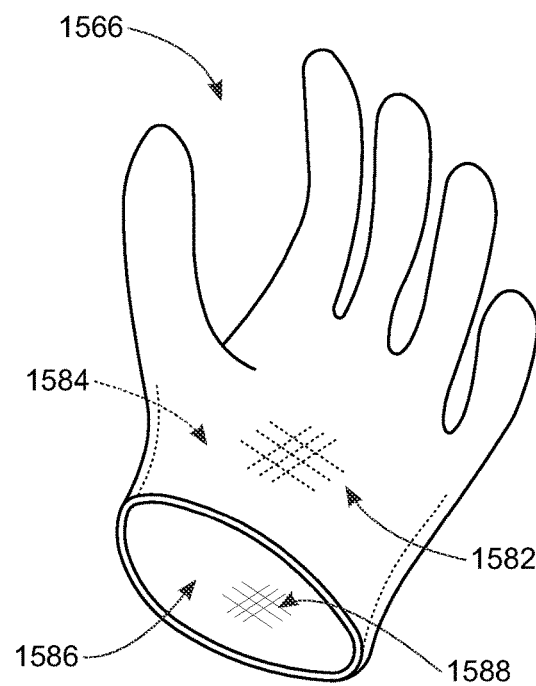
FIG. 69 is a perspective view of another embodiment of the cosmesis of FIG. 67.

Referring to FIG. 69, the palm section 1568 of the cosmesis 1566 may also be formed to resist slippage due to shear loads. For instance, a palm side 1582 of the cosmesis 1566 may be formed with a tacky inner surface 1584. In some embodiments, the material of the cosmesis 1566 itself will provide the tacky inner surface 1584, for example, silicon or a urethane material may be naturally tacky. In other embodiments, a tacky surface coating may be applied to the cosmesis to form the tacky inner surface 1584. Thus, as objects being held are pressed against the palm side 1582 of the cosmesis 1566, the tacky inner surface 1584 is pressed against the hand support 1218, shown in FIG. 29, thereby resisting slippage. In some embodiments, in this embodiment, a back side 1586 of the cosmesis 1566 is formed with a slippery inner surface 1588 to facilitate installation and removal of the cosmesis 1566. For example, the slippery inner surface 1588 may be formed by applying a surface modifying coating to the cosmesis, or applying a surface texture to the cosmesis 1566. For example, to install the cosmesis 1566 onto the hand support 1218, shown in FIG. 29, the cosmesis 1566 may be pulled down and away from the palm so that the slippery inner surface 1588 of the back side 1586 slides along the hand support 1218, while the tacky inner surface 1584 of the palm side 1582 is pulled away from the hand support 1218. Thus, the cosmesis 1566 may be easily slid onto the hand support 1218. To remove the cosmesis 1566, the palm side 1582 may again be pulled away from the hand support 1218 while the cosmesis 1566 is pulled toward the fingers 1560, thereby allowing the cosmesis 1566 to slide easily off the hand support 1218.

Figure 70:
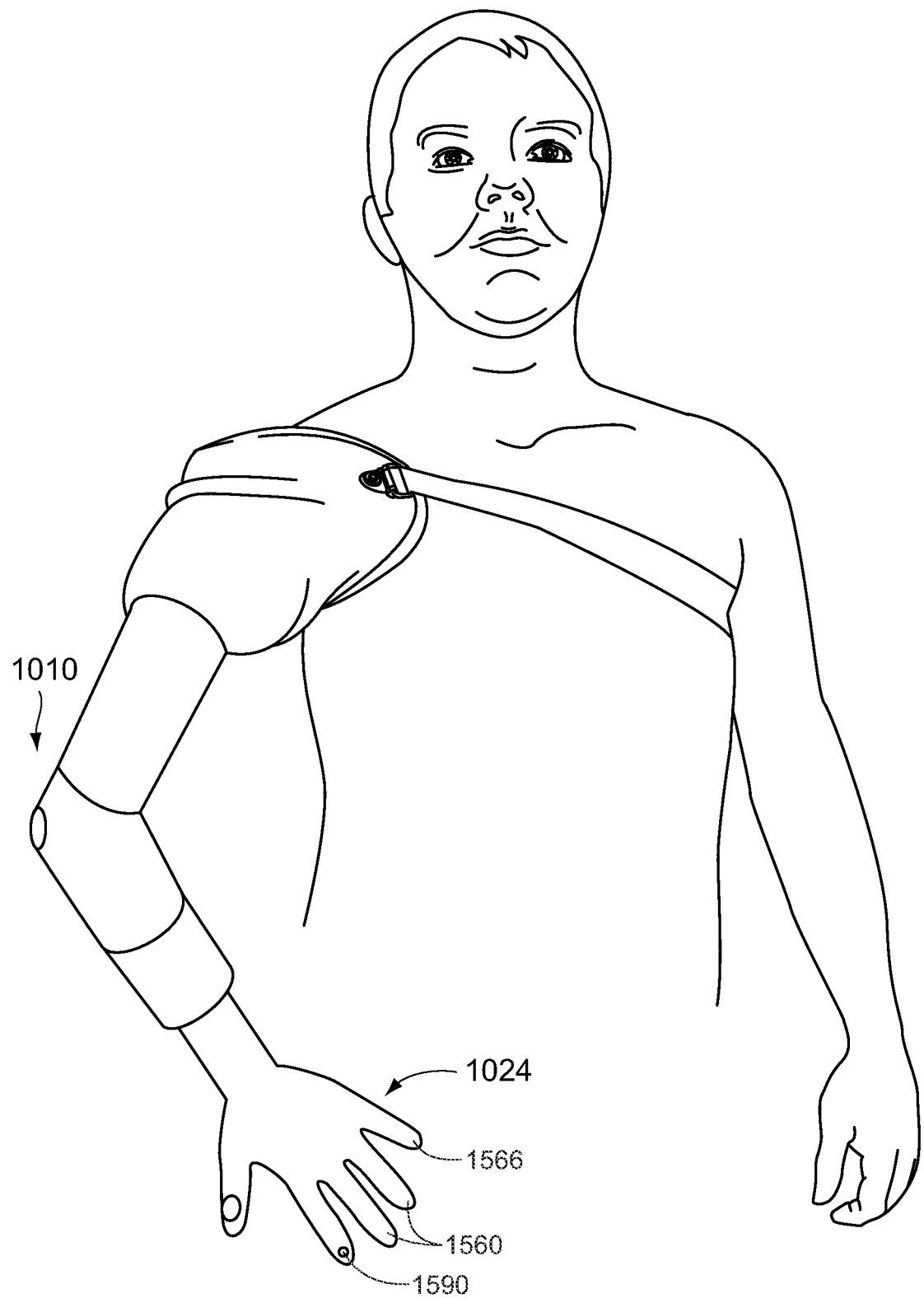
FIG. 70 is a perspective view of a prosthetic arm apparatus having a temperature sensor according to an embodiment of the present invention.

Additionally, in some embodiments, the fingers 1560 may include one or more additional functions. For example, referring to FIG. 70, one or more fingers 1560 may include a thermal sensor 1590 disposed thereon to determine the temperature of an object (not shown) brought into contact with the finger 1560. The signal from the sensor 1590 may be transmitted to a controller (not shown) for the prosthetic arm 1010 and displayed to the user as will be discussed in greater detail below. In some embodiments, temperature detection may be provided by forming the cosmesis 1560, or a portion thereof, from a temperature sensitive polymer, such as a polymer with a thermochromic color changing additive therein or thermochromic liquid crystal that allows a variety of colors to be shown as temperature changes, which will change color depending upon the temperature of the cosmesis 1566. For example, the cosmesis 1566 may change from one color to another if a present temperature is exceeded. This temperature sensing functionality may be used to determine the temperature of an object (not shown) in the hand 1024 and to warn the user of a high temperature or low temperature condition to mitigate the threat of burns or other harm.

Figure 71:
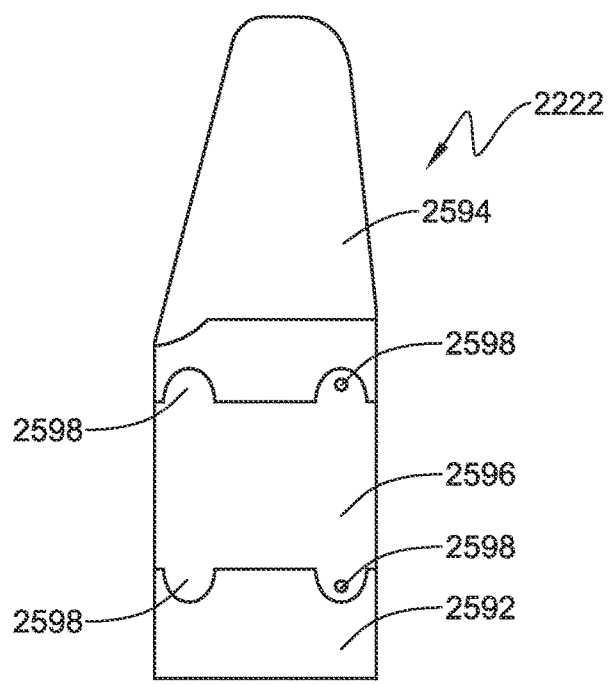
FIG. 71 is a side view of a thumb structure according to an embodiment of the present invention.

Referring to FIG. 71, another embodiment of the thumb structure 2222 is shown for providing thumb compliance detection. The thumb structure includes a thumb base 2592 and a thumb tip 2594, which are each substantially rigid and are joined together by an elastomeric spring 2596. In some embodiments, the interface between the thumb tip 2594 and the elastomeric spring 2596 includes one or more alignment features 2598 to ensure proper alignment of the thumb tip 2594 with the elastomeric spring 2596. Similarly, the interface between the thumb base 2592 and the elastomeric spring 2596 also includes one or more alignment features 2598 to ensure proper alignment of the thumb base 2592 and the elastomeric spring 2596.

Figures 72, 73:
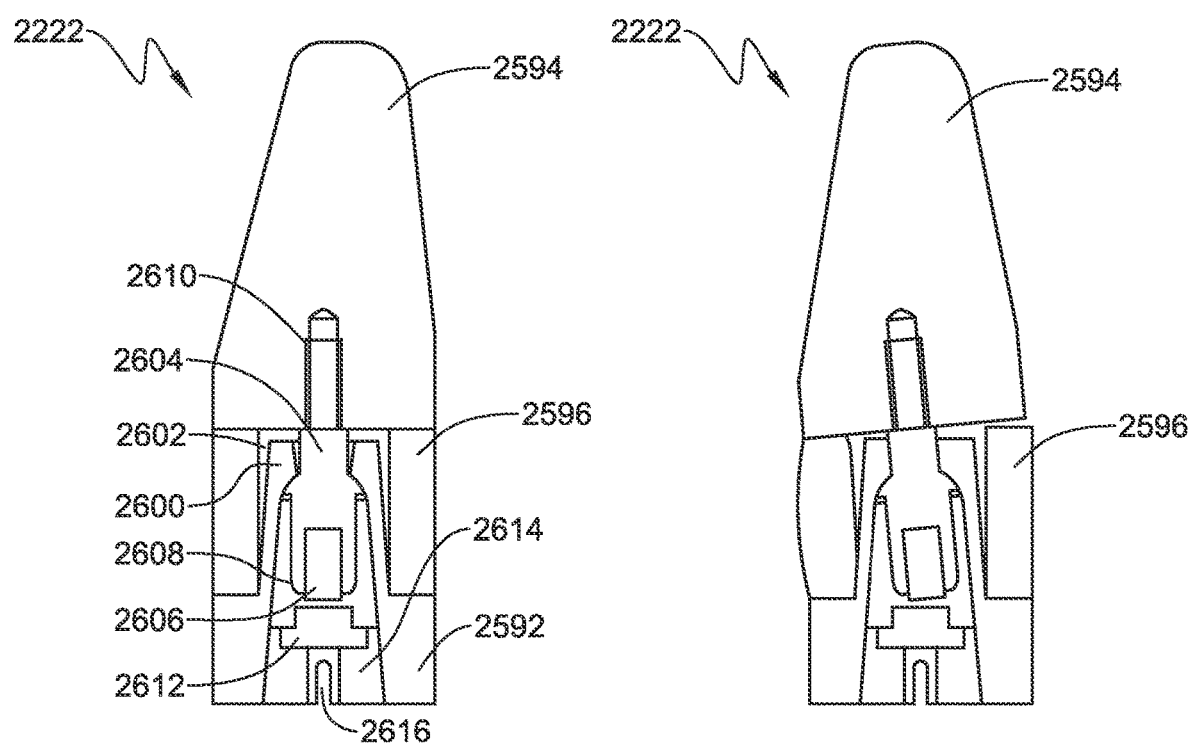
FIG. 72 is a side cross-sectional view of the thumb structure of FIG. 71.
FIG. 73 is a side cross-sectional view of the thumb structure of FIG. 71 under a load.

Referring to FIG. 72, within the thumb structure 2222, the thumb base 2592 includes a pivotal interface tube 2600 extending upward into a central bore 2602 of the elastomeric spring 2596. A pivot shaft 2604, having a magnet 2606 disposed at its lower end 2608, is arranged with the pivotal interface tube 2600 and extends upwardly therefrom into a central bore 2610 in the thumb tip 2594 of substantially the same diameter as the pivot shaft 2604. Below the pivot shaft 2604 within the thumb base 2592 is arranged a Hall effect sensor 2612 on a sensor bracket 2614. The sensor bracket 2614 includes a wire channel 2616 to facilitate wiring the Hall effect sensor 2612 to the prosthetic control circuits (not shown). Referring to FIG. 73, in operation, when a load L is applied to the thumb tip 2594 the elastomeric spring 2596 compresses on the side of the thumb structure 2222 opposite the applied load L, allowing the thumb tip 2594 to tilt. The tilt of the thumb tip 2594 causes a corresponding tilt of the pivot shaft 2604 within the pivotal interface tube 2600, thereby displacing the magnet 2606 disposed on the lower end 2608 of the pivot shaft 2604. The Hall effect sensor 2612 detects this displacement of the magnet 2606, which can be correlated to the applied load L on the thumb tip 2594. By detecting the various loads on the thumb structure 2222, the user may ensure that objects are not gripped so hard that they could break and that the thumb is not subjected to loads that could cause failure of the thumb structure 2222.

Figure 74:
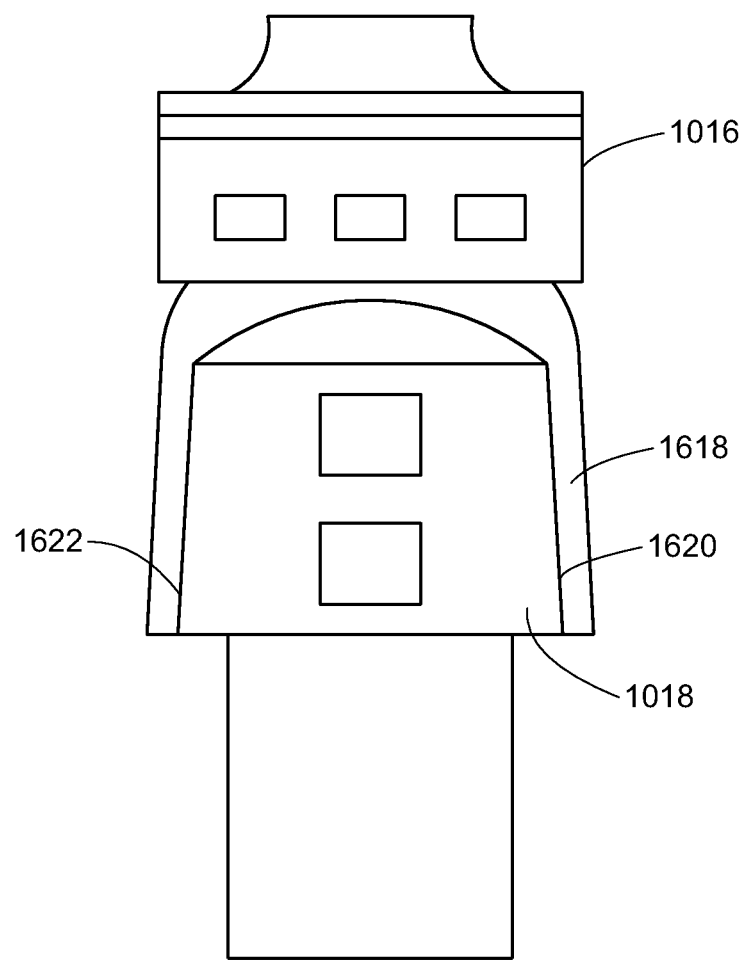
FIG. 74 is a top view of a humeral rotator and an elbow flexion assembly according to another embodiment of the present invention.

Referring to FIG. 74, in some embodiments, the humeral rotator 1016 may include a yolk 1618, rather than the cantilever mounting interface shown in FIG. 16, for interfacing with the elbow flexion assembly 1018. The yolk 1618, interfaces with a first side 1620 and a second side 1622 of the elbow flexion assembly 1018 to provide increased strength to the interface when compared to the cantilever mounting interface shown in FIG. 16, which only interfaces with one side of the elbow flexion assembly 1018.

Figure 75A:
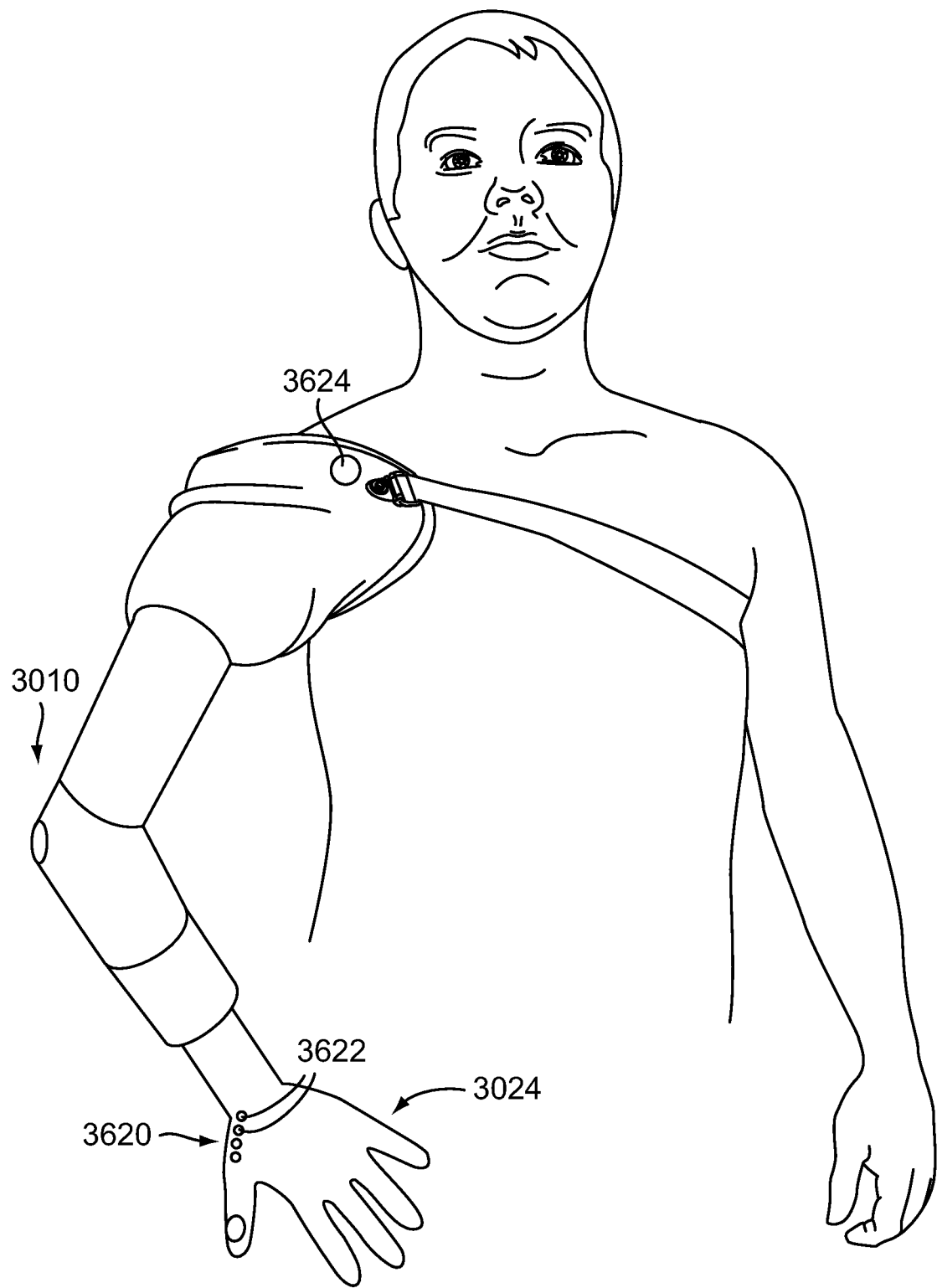
FIG. 75A is a perspective view of a prosthetic arm apparatus having an emergency switch according to an embodiment of the present invention.
Figure 75B:
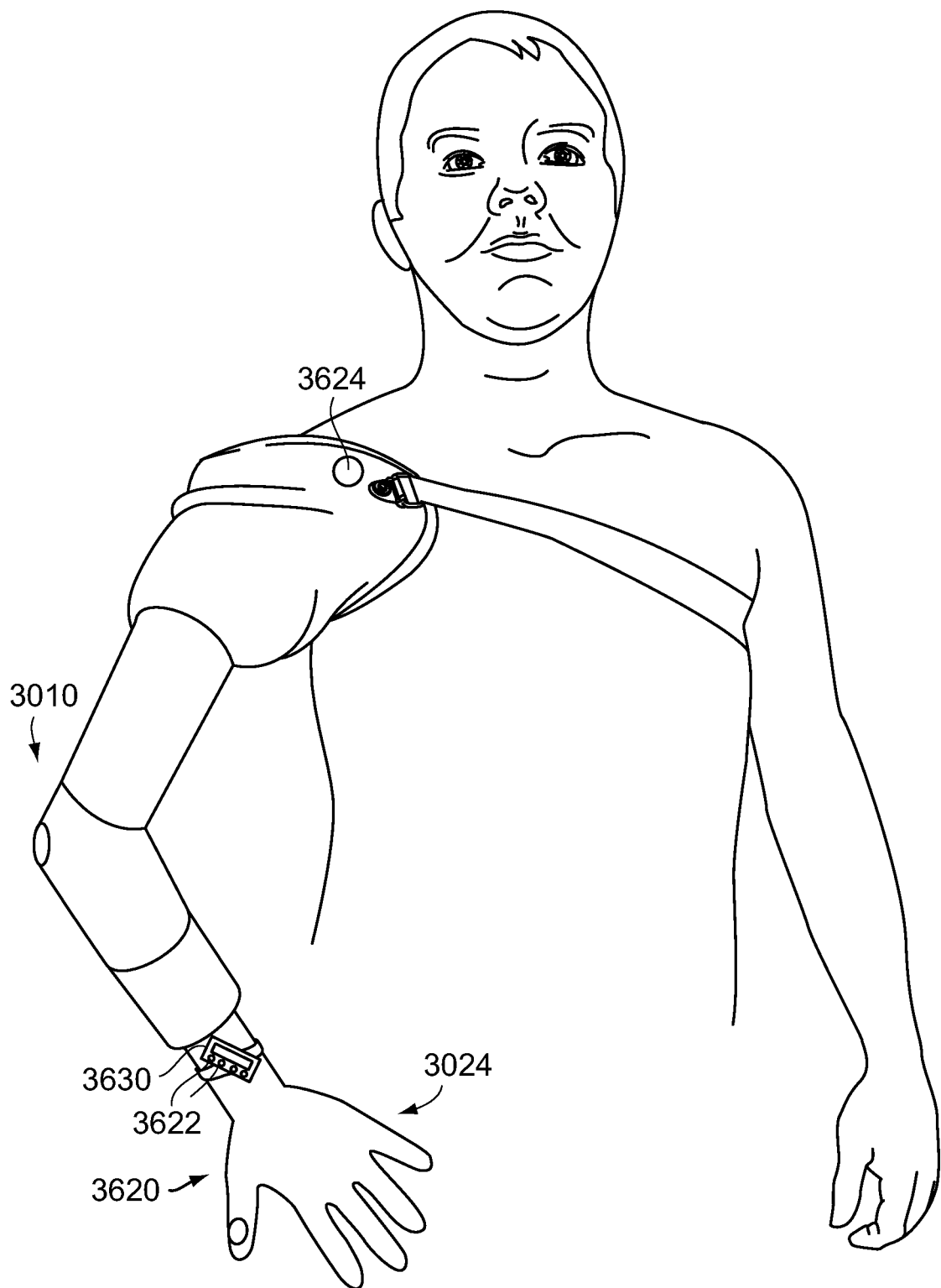
FIG. 75B is a perspective view of a prosthetic arm apparatus having an emergency switch according to an embodiment of the present invention.

Referring to FIG. 75A, in some embodiments of the present invention, the prosthetic arm 3010 may be provided with a status indicator 3620. In some embodiments the status indicator 3620 may include, but is not limited to, one or more LEDs 3622 arranged on the hand assembly 3024. However, in other embodiments, the one or more LEDs 3622 may be located in various locations. The one or more LEDs 3622 may be configured to communicate a variety of information to the user, including, but not limited to, one or more of the following, battery power level, an operational mode of the prosthetic device, faults, alarms, alerts, messages, and/or the like. Additionally, although shown as one or more LEDs 3622 the status indicator 3620 may, in other embodiments, include a digital display and/or user interface, which may be arranged on the prosthetic device 3010, built into the prosthetic device 3010 and/or may be a separate display unit (for example, as shown in FIG. 75B as 3630), and in some embodiments, may be a unit worn similarly to a wrist watch or bracelet as shown in FIG. 75B as 3630. However, in other embodiments, the unit 3630 may be a portable unit that may be worn or carried near the user, for example, but not limited to, clipped on clothing, belt and/or attached to the user, and/or carried in a pocket either in the user's clothing and/or in a separate bag and/or pack. In some embodiments, the unit 3630 may be a PDA (personal data assistant), smart phone or other electronic device configured to communicate with the prosthetic device 3010 by way of a wireless communications protocol, including, but not limited to, RF and Bluetooth®.

Thus, in some embodiments, it may be desirable to include both a separate display unit and one or more LEDs 3622, where, for example, but not limited to, the one or more LEDs 3622 may be used to display one or more critical piece of information to the user, while the separate display unit, 3630 may provide a greater variety of information in more detail.

Still referring to FIG. 75, in some embodiments of the present invention, the prosthetic arm 3010 may be provided with an emergency switch 3624 which may turn off power to the system and thus engage the various brakes and/or clutches in the prosthetic arm 3010. In some embodiments, the emergency switch 3624 is a chin switch that the user may activate with their chin.

The prosthetic arm apparatus of the present invention has a variety of benefits over conventional prosthetic devices, such as the modularity of each segment of the prosthetic arm apparatus as discussed above, which allows the formation of customized prosthetic devices for different users. In particular, each segment of the prosthetic arm apparatus 10 contains all of the actuators for that segment so that it may be removed as a separate unit. For instance, the hand assembly includes all of the finger actuators therein, allowing it to be connected and/or removed as a separate unit. Additionally, various degrees of freedom of the hand assembly are particularly beneficial because they allow the formation of various grasps or grips.

Exoskeleton System and Apparatus for Robotic Device

Figure 81:
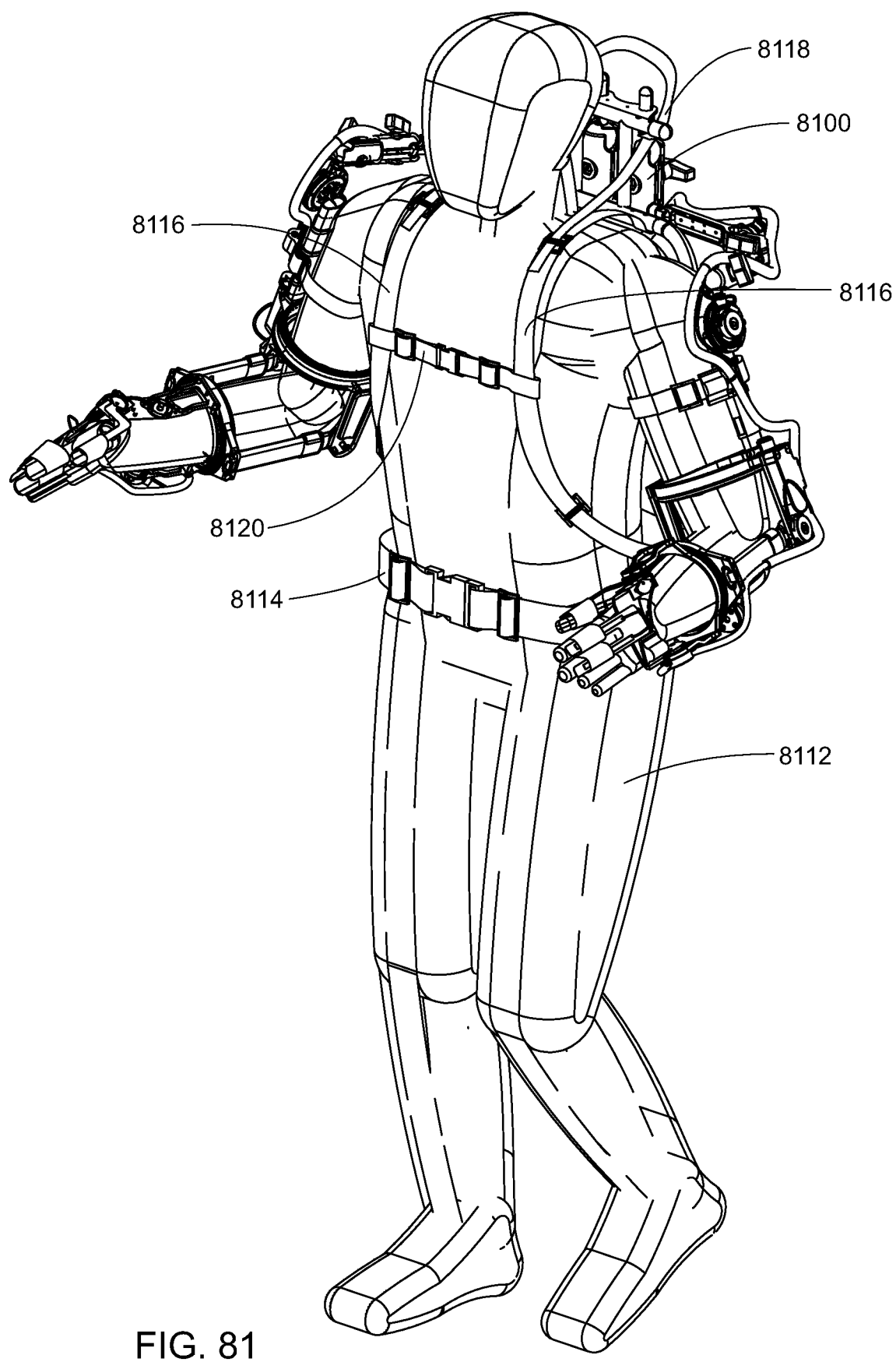
FIG. 81 is a view of one embodiment of the exoskeleton worn by a user.
Figure 82:
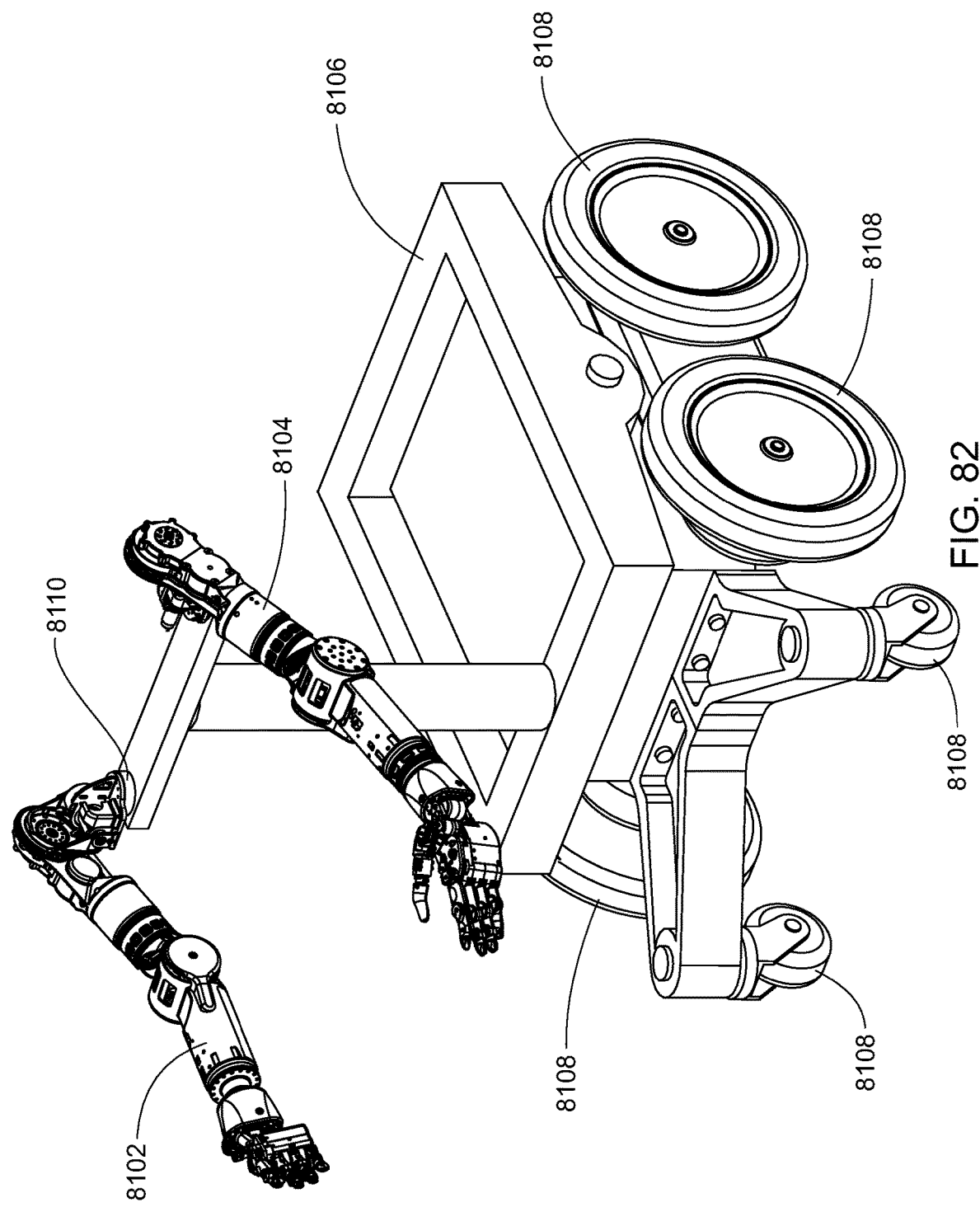
FIG. 82 is a view of one embodiment of the mobile platform.

Referring now to FIGS. 81 and 82, an exemplary embodiment of the exoskeleton system may include an exoskeleton apparatus 8100, at least one robotic device 8102, 8104, which, in the embodiment shown, may be robotic arms 8102, 8104. In some embodiments, the system may include a structure 8106 for attaching the one or more robotic devices 8102, 8104. In the exemplary embodiment shown, the structure 8106 may be a mobile platform/mobile structure 8106 which may include one or more wheels 8108. In some embodiments, the mobile platform/mobile structure may include the a device, apparatus and/or control scheme as described in U.S. Pat. No. 5,971,091 issued Oct. 26, 1999 and entitled TRANSPORTATION VEHICLES AND METHODS; U.S. Pat. No. 6,223,104, issued Apr. 24, 2001 and entitled "FAULT-TOLERANT ARCHITECTURE FOR PERSONAL VEHICLE", both of which are hereby incorporated herein by reference in their entireties. Although an exemplary embodiment is referred to herein, this is merely for illustrative purposes only. Additional embodiments are contemplated and discussed and the devices, system and apparatus are not limited to the embodiments shown as the exemplary embodiments.

Figure 83:
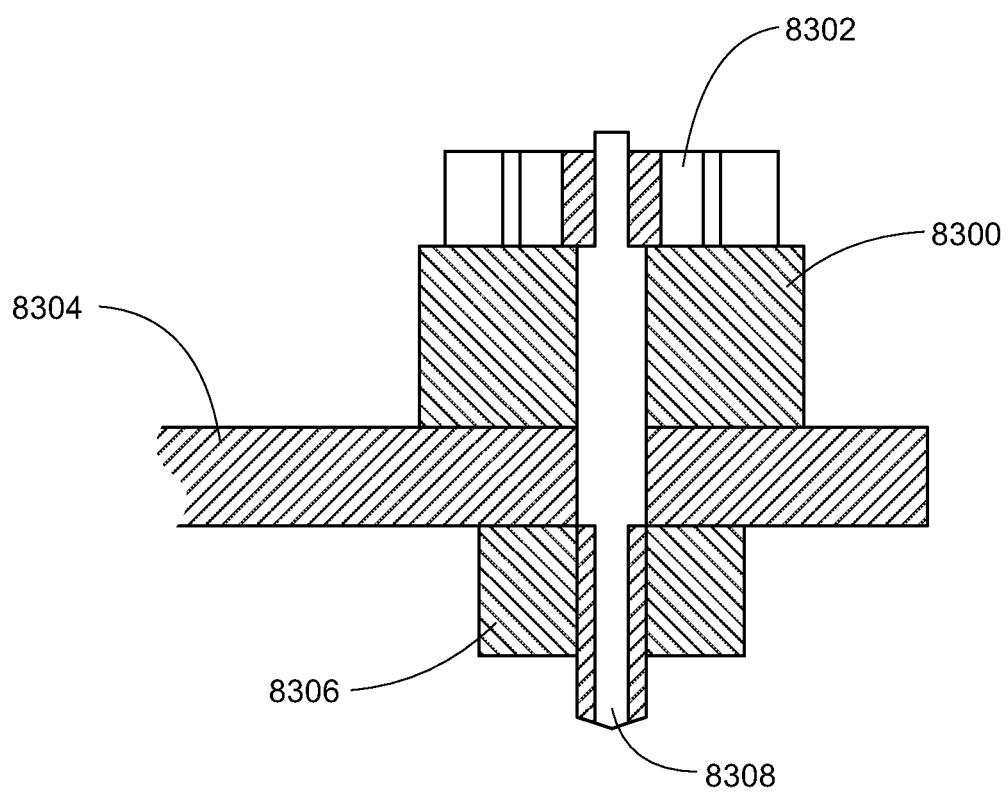
FIG. 83 is an illustrative cross sectional view of one embodiment of the attachment point to the mobile platform.
Figure 84A:
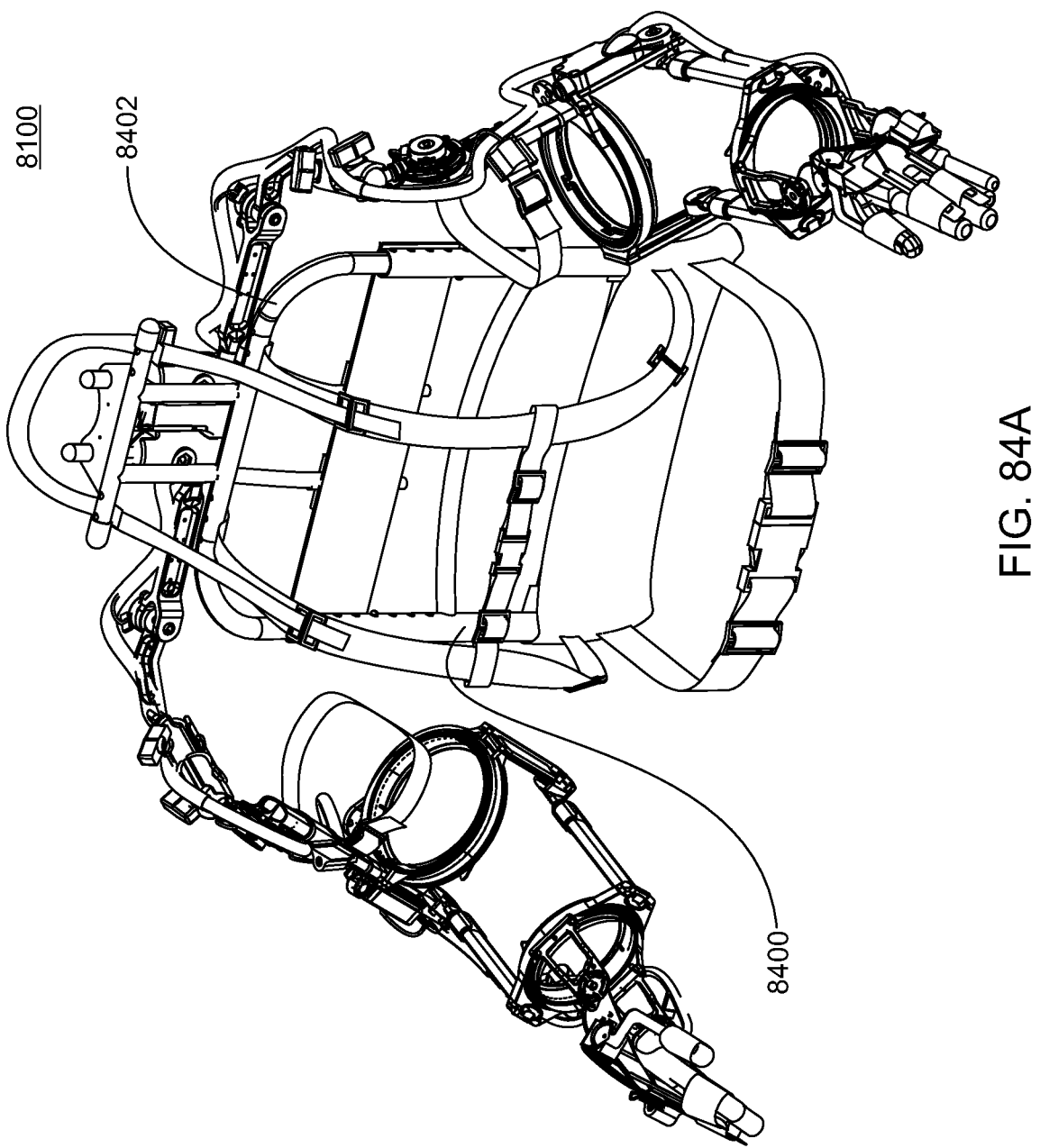
FIG. 84A is an isometric view of one embodiments of the exoskeleton.
Figure 84B:
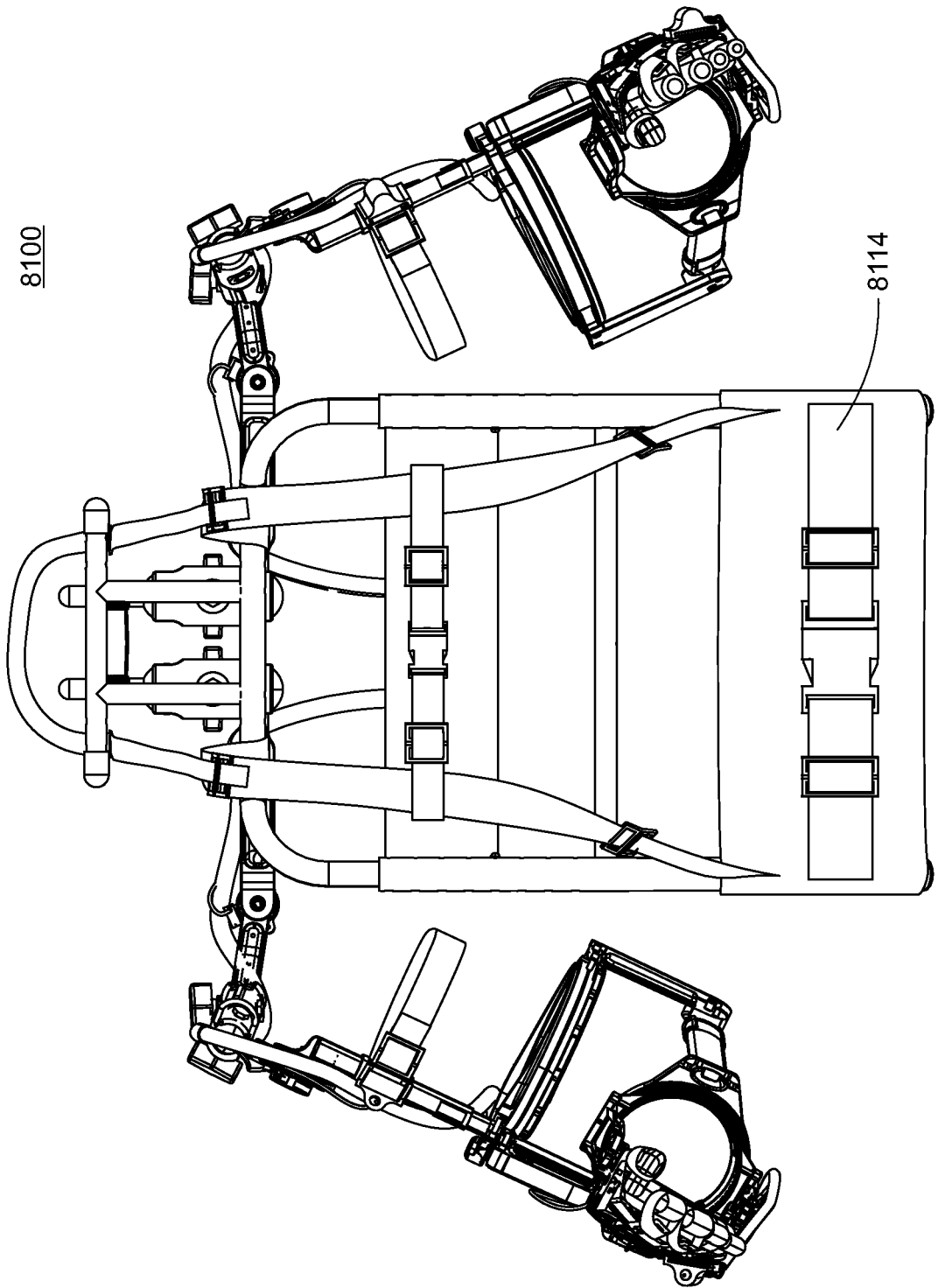
FIG. 84B is a front view of one embodiments of the exoskeleton.
Figure 84C:
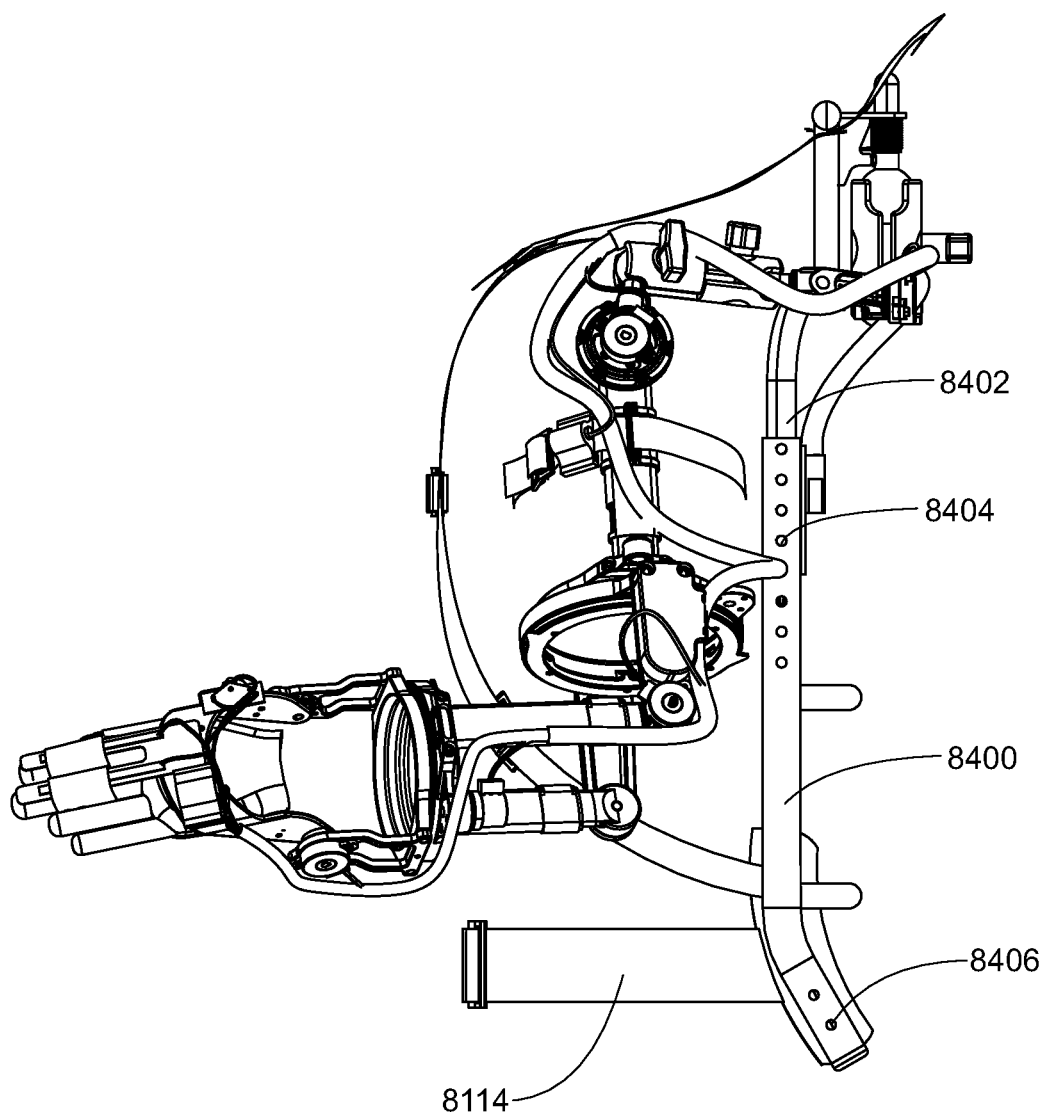
FIG. 84C is a side view of one embodiments of the exoskeleton.
Figure 84D:
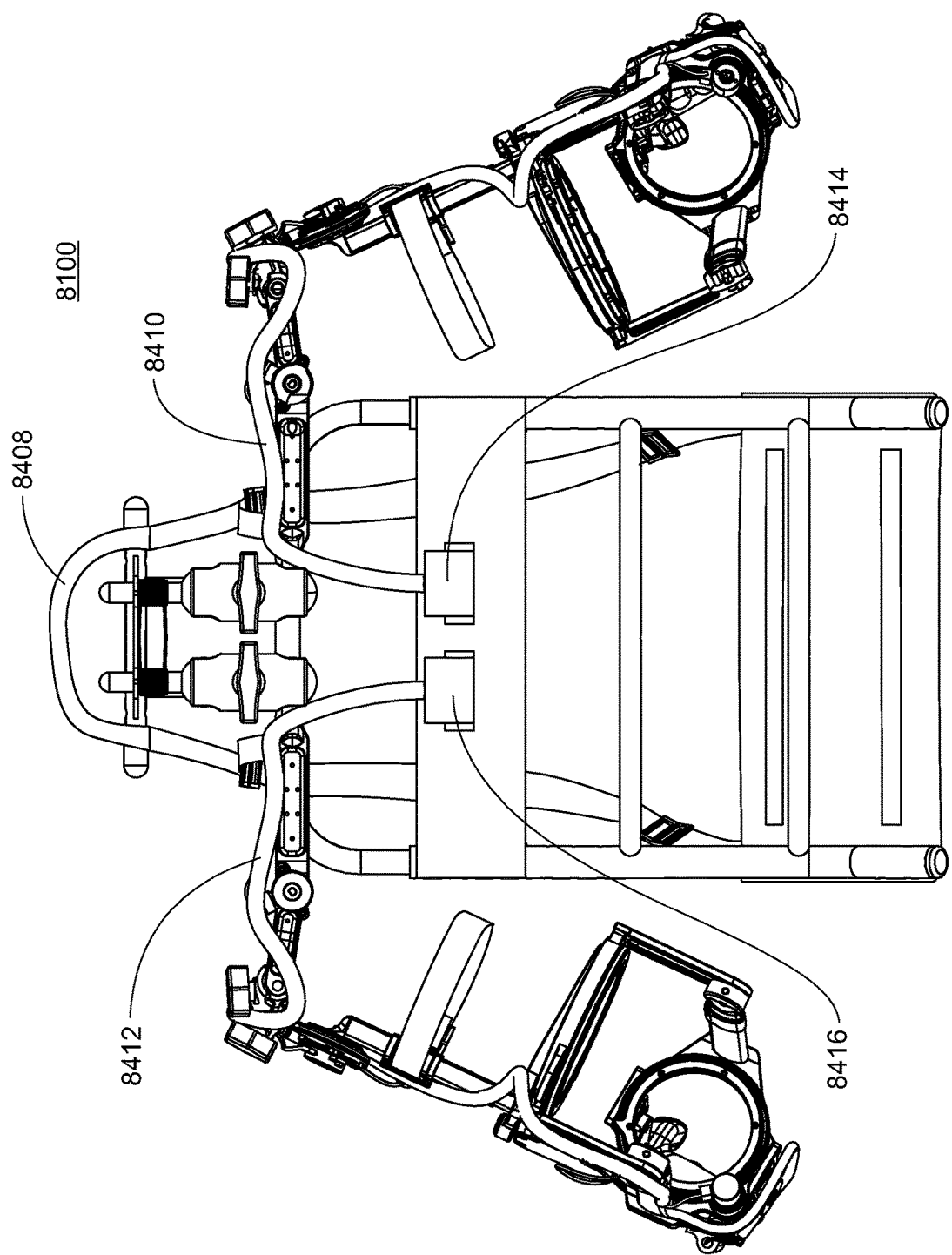
FIG. 84D is a back view of one embodiments of the exoskeleton.

In the exemplary embodiments, the robotic arms 8102, 8104 are attached to the mobile platform 8106 by attachment via a compliant member 8110. In some embodiments, the compliant member 8110 may be made from a compliant materials, e.g., polyurethane, which may be desirable for polyurethane includes compliance in all directions, i.e., "3D compliance", as well, polyurethane has damping properties which may be desirable in some applications. However, in other embodiments, the compliant member 8110 may be another member, for example, but not limited to, one or more of the following: a metal spring or other compliant material, means, assembly and/or device. Referring to FIG. 83, one embodiment of the attachment is shown. In this embodiment, the robotic assembly 8302 attaches to the complaint member 8300 and the compliant member 8300 attaches to the platform 8304. A bolt 8308 may be used as an attachment point for the robotic assembly 8302, the compliant member 8300 and the platform 8304. A nut 8306 may be used, in some embodiments, to stabilize/maintain the bolt 8308.

Referring to FIG. 81, in some embodiments, including the embodiment shown in FIG. 81, the exoskeleton may be worn by a human 8112 by way of an attachment system which may include a series of straps 8114, 8116, 8118. In some embodiments, the straps 8114, 8116, 8118 may be adjustable (as shown in FIG. 81), however, in other embodiments, one or more straps 8114, 8116, 8118 may not be adjustable. In some embodiments, the attachment system may be customized to the user and thus, adjustability may not be necessary. However, in some embodiments of the customizable embodiments, one or more straps may be adjustable. With respect to adjustable straps 8114, 8116, 8118, these may be adjusted along the hips of the user using a hip strap 8114, the torso of the user using shoulder straps 8118 and chest strap 8114 and the distance between the back of the user and the top of the exoskeleton may be adjusted using the upper torso straps 8118. In some embodiments, the attachment system may be similar to one found on an ergonomic backpack for example, in the exemplary embodiment, the backpack strap system from Trekker 3950 backpack made by KELTY®, Boulder Co., USA, may be used as the attachment system. In some embodiments, the exoskeleton 8100 is removable. In various embodiments, the exoskeleton attachment system may include fewer straps than shown and described herein with respect to the exemplary embodiments and/or in some embodiments, the exoskeleton may include additional straps than shown and described herein with respect to the exemplary embodiments. For example, in some embodiments, the exoskeleton may include a lower body component and thus, may include different and/or additional straps adapted to removably or nonremovably attach to the user's lower body. For example, to attach to their hip, upper leg, knee, lower leg, ankle and/or foot. In some embodiments, the exoskeleton may be a lower body exoskeleton and may not include an upper body portion.

Referring now to FIGS. 84A-84D, isometric, front, back and side views of one exemplary embodiment of the exoskeleton are shown. In addition to the straps discussed above, the exoskeleton, in some embodiments, may include an exoskeleton frame which may include a lower portion 8400 and an upper portion 8402. In some embodiments, the upper portion 8402 may be telescopingly connecting to the lower portion 8400 such that the frame is adjustable. As shown in 84C, in some embodiments, the adjustability may be in the form of a ball detent mechanism 8404 and may include one or more adjustable sizes. As shown in one embodiment, the adjustablility may include seven sizes. As discussed above, in some embodiments, the frame may be a backpack frame, for example, a Trekker 3950 backpack made by KELTY®, Boulder Co., USA. In various embodiments, the adjustability mechanism may vary and, in some embodiments, the frame may not include adjustability and may be customzably sized and/or may be made based on the size of the intended user. In some embodiments, the frame may be made to average sizes of intended users.

In some embodiments, the frame may be made from aluminum. However, in some embodiments, the frame may be made from one or more plastic materials, stainless steel, magnesium or any other material that may be used to make a frame such as one of the embodiments discussed herein.

Still referring to FIGS. 84A-84D, in some embodiments, the hip strap 8114 may be adjustable with respect to the distance from the top of the frame to the hip strap 8114 as well as adjustable with respect to the circumference of the strap. In some embodiments, the adjustability feature with respect to height may be a ball detent mechanism 8406.

In some embodiments, the exoskeleton may include a support structure 8408 which may also serve as a handle for carrying the exoskeleton and/or for user mounting the exoskeleton either alone or with assistance.

Described herein are various sensors and feedback mechanisms which may be used to both control at least one robotic assembly and also, in some embodiments, to provide feedback regarding the at least one robotic assembly to the user. In some embodiments, where at least one sensor is used, the at least one sensor and, in embodiments including at least one feedback mechanism, the at least one feedback mechanism, may communicate via electronic wiring, i.e., they may be hardwired. However, in other embodiments, at least one of the at least one sensor and/or the at least one feedback mechanism may be wirelessly connected, i.e., via at least one form of wireless communication.

With respect to the exemplary embodiment shown in the various figures, the system includes a hard wired embodiment. In the exoskeleton, the wires are contained within a wiring housing 8410, 8412 to organize the wires. This embodiment may be desirable to prevent accidental/unintentional catching of the wires on an object and or to protect the wires from breakage and tangling. In some embodiments, as shown in the various figures, there may be one or more wiring housing 8410, 8412, and, in some embodiments, there may be more than two wiring housings. In some embodiments, the wiring housing 8410, 8412 may be made from any material desired, however, in the exemplary embodiments, is made from a flexible plastic. However, in other embodiments, may be made from other materials, including, but not limited to, rigid or flexible materials.

The wiring housing 8410, 8412 is connected to the exoskeleton through a wire connection 8414, 8416. In some embodiments, there may be one wire connection, however, in other embodiments; there may be more than one wire connection, as shown in the exemplary embodiment. The wire connection 8414, 8416, is, in some embodiments, a housing for the wires that run through the wiring housing 8410, 8412, to connect to a point on the exoskeleton. The wire connection 8414, 8416 may be made from any material desired, but in some embodiments, may be made from a metal, e.g., aluminum or stainless steel, or a plastic.

Figure 85A:
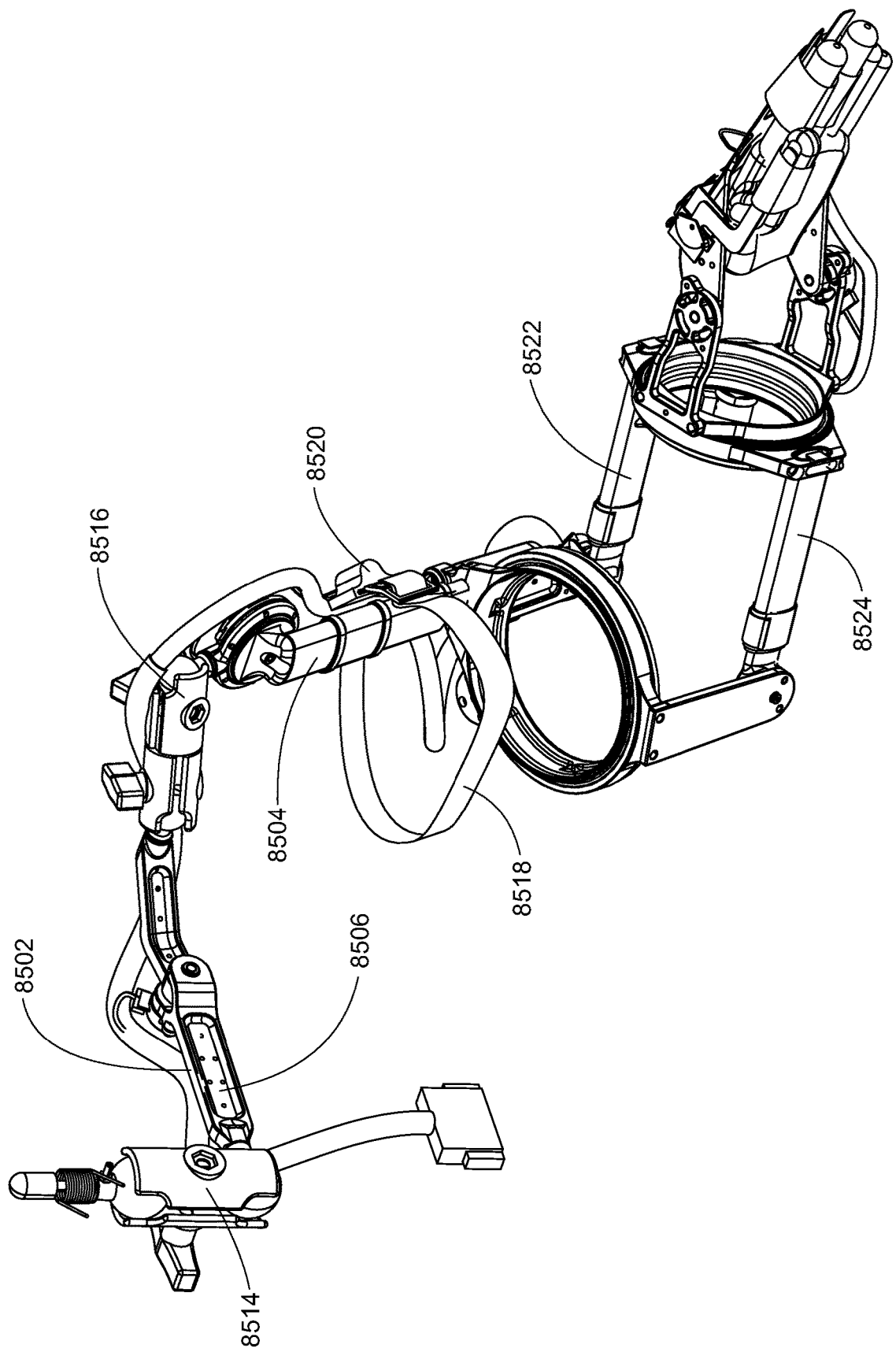
FIG. 85A is a view of one embodiment of an arm of the exoskeleton detached from an exoskeleton.
Figure 85B:
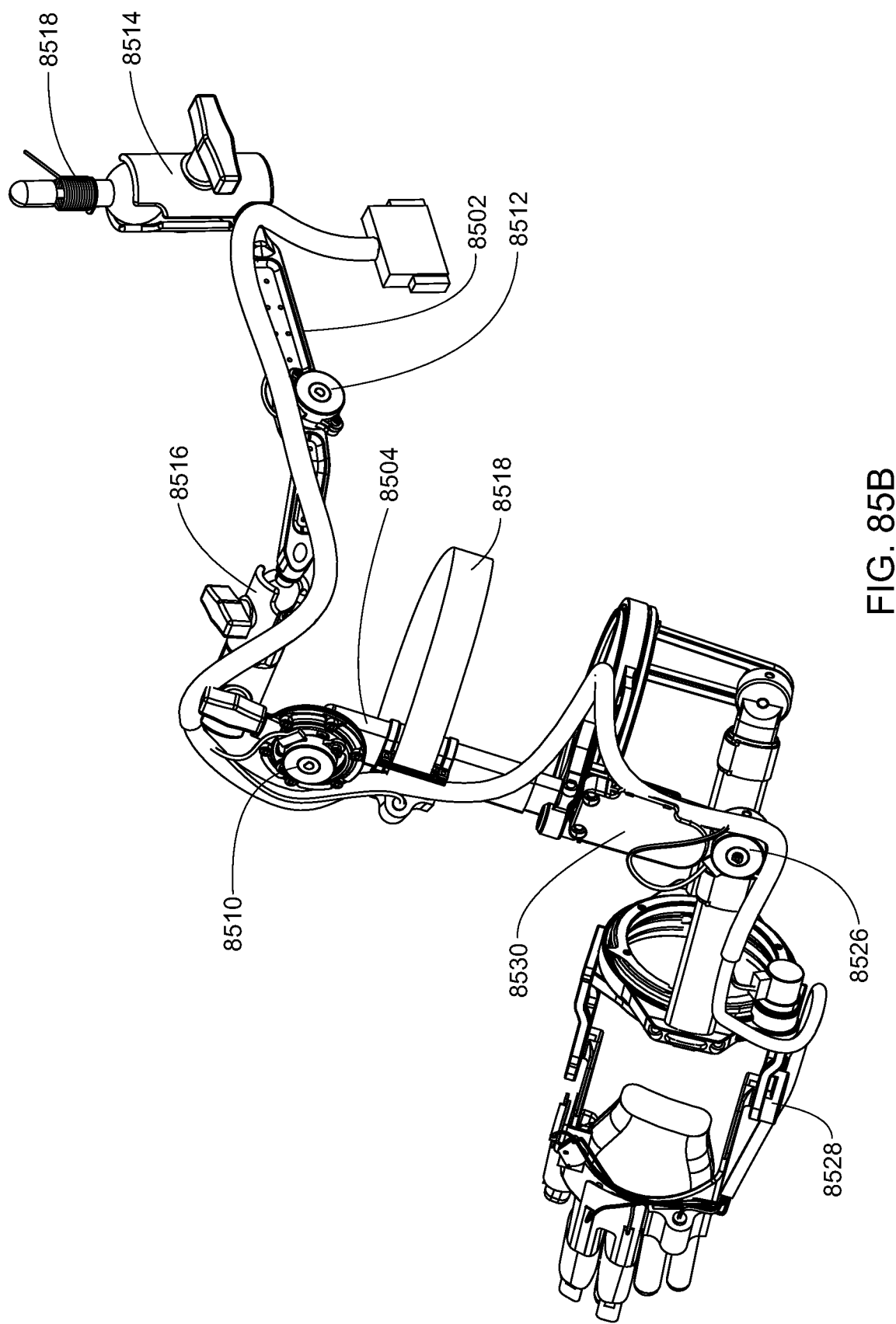
FIG. 85B is a view of one embodiment of an arm of the exoskeleton detached from an exoskeleton.

Referring also to FIGS. 85A-85B where isometric views of a shoulder, arm and hand portion of one embodiment of the exoskeleton are shown. In these views, the shoulder, arm and hand portion has been broken away from the exoskeleton apparatus shown in previous figures. Together with the previous figures, exemplary embodiments of the arm and hand portions are described below.

Various embodiments of the exoskeleton rely on mapping movement by the user to movement by the at least one robotic assembly. Thus, it is critical that the movement of the user be sensed appropriately to map the movement to the at least one robotic assembly. For purposes of the description of the exemplary embodiments, the description will refer to the at least one robotic assembly as "robotic assemblies". However, it should be understood that in various embodiments, one robotic assembly may be used.

In some embodiments, gross movements by the user may be translated by the shoulder. Thus, the rotation points of the shoulder of the user are critical to map correctly in these embodiments. To do so, it may be necessary to determine the center point of the shoulder thus determining the center point of rotation of the shoulder. However, finding the center of rotation of a shoulder of a user may be difficult. Also, users may have different centers of rotation of the shoulder. Thus, adjustability of the exoskeleton is critical to mapping the center of rotation of the shoulders correctly to thus translate to true mapping of the gross movements of the user to the robotic assemblies.

Still also referring to FIGS. 85A-85B, in the exemplary embodiment, the exoskeleton shoulder and arm portions are essentially located on two planes. In the exemplary embodiment, through various adjustability features, the lengths of the exoskeleton from the spine area of the user to the shoulder as well as the length of the exoskeleton from the shoulder to the elbow, the elbow to the wrist, are adjustable.

In the exemplary embodiment, the exoskeleton shoulder portion includes at least two sensors 8510, 8512, which, in some embodiments, are potentiometers. The type of potentiometer may be any potentiometer, including but not limited to, a linear potentiometer. In various embodiments, at least one potentiometer is used to measure/sense shoulder abduction and at least one potentiometer is used to measure/sense shoulder flexion. In some embodiments, the system may use two different potentiometers to measure the shoulder abduction and shoulder flexion, and in some embodiments, the system may use the same potentiometers to measure both motions. In the exemplary embodiment, each joint of the user's arm/shoulder includes at least one potentiometer to measure the amount of rotation. The signal data from the potentiometers is used by the control system (described below) to map movement to the robotic assemblies.

In the various embodiments, to fit the exoskeleton to a user, one goal is to adjust and/or design the exoskeleton for a particular user such that the center axis of rotation of each shoulder potentiometer meets in the center of the ball joint of the user's shoulder.

In various embodiments, to assist in adjusting the exoskeleton such that the center axis of the potentiometers meets in the center of the shoulder ball joint of the user, ball joints 8514, 8516 are included in the exoskeleton. It should be understood that in the exemplary embodiments of the exoskeleton, there are two ball joints for each arm (shoulder, hand), thus, in the exemplary embodiments, there are four ball joints on the exoskeleton. However, in various embodiments, there may be more than four or less than four ball joints. Also, in various embodiments, components accomplishing the same functionality as described with respect to the ball joints may be used.

In the exemplary embodiment, the ball joint used is a RAM® mount such as one made by National Products Incorporated, Seattle, Wash., USA. Using these ball joints 8514, 8516, the exoskeleton may be adjusted such that the length and orientation/angle of the back portion 8502 and the side portion 8504 of the exoskeleton may be adjusted. Thus, the exoskeleton may be adjusted to fit a user such that the axis of rotation of the potentiometers 8510, 8512 meet in the center of the user's shoulder ball joint.

With respect to the ball joint located on the back of the frame 8514, in some embodiments, including the exemplary embodiment, a compliance section 8518 may be included to allow for sternoclavicular motion by the user. Thus, with the compliance section 8518, the user may move their arms forward and having compliance in the joint. The compliance section 8518, in the exemplary embodiment, may be a torsion spring which springs back the user stops movement in the forward direction. This allows articulation and the torsion spring 8518 automatically pulls the exoskeleton back. The torsion spring 8518, in some embodiments, may be set such that the user may overcome the spring when forward movement is desired and the spring pulls the exoskeleton back in a light fashion such that the user may not notice. In the exemplary embodiment, the spring constant of the torsion spring 8518 may be 0.014 inch pounds per degree. Also, in the exemplary embodiment, the torsion spring 8518 may produce a torque of 5.15 inch pounds at 360 degrees of rotation with a preload of approximately 2.5 inch pounds. Additionally, in some embodiments, the torsion spring 8518 may be preloaded with a hard stop. The hard stop may be adjustable to the user such that the torsion spring 8518 is limited in how far it may pull the exoskeleton back. In some embodiments, this adjustment may be made at the time of initially using the exoskeleton. In some embodiments, this may be accomplished where the user rolls their shoulder back and the hard stop is adjusted to that position. In some embodiments, the adjustment may be made using a knob, however, in other embodiments; the adjustment may be made using anything that may adjust the hard stop. In the exemplary embodiments, the hard stop may be desirable to maintain the flexion joint in the correct place where the shoulder ball joint may be accurately tracked.

Still referring to FIGS. 85A-85B, in the exemplary embodiment, the exoskeleton includes at least one tactor motor to provide feedback regarding the robotic assemblies to the user. In some embodiments, the at least one tactor may be connected to the exoskeleton by a strap which may be strapped to the user using a tactor strap 8518 such that the tactor motor 8520 may be in close proximity to the user such that the user may feel signals from the tactor motor 8520. In the exemplary embodiment, the tactor strap 8518 may be an adjustable strap which may, in some embodiment, attach to itself by way of a hook and loop fastening system. However, in other embodiments, a buckle system, clip system or any other attachment or fastening mechanisms may be used. In some embodiments, the strap may not be adjustable, however, in the exemplary embodiment, the strap is adjustable.

In the exemplary embodiment, the at least one tactor motor 8520 may be a vibration motor or other motor that may provide a signal to the user. In the exemplary embodiments, at least one or the at least one tactor motor 8520 provides feedback to the user related to the torque of the shoulder and elbow joint of the robotic assembly. In the exemplary embodiment, the user may wear two tactor motors 8520, one on each arm, each providing feedback from one robotic assembly.

Thus, the at least one tactor motor 8520 receives input from at least one joint on the at least one robotic assembly. For example, in the exemplary embodiments, the at least one tactor motor 8520 receives input from the compliance measurements on the robotic arm. In some embodiments, however, the at least one tactor motor 8520 may receive input from one or more compliance sensors which may be in the compliant member 8110. In some embodiments, four or more compliance sensors may be on the compliant member 8110 and thus provide directional feedback, via at least one tactor motor 8520, regarding the direction of force being imparted on to the robotic arms/assembly. In various embodiments of this embodiment, the user may wear four tactor motors to receive input in four directions. Thus, in some embodiments, where the user may not be able to see the robotic assembly, this may be desirable to determine the direction where there may be an object or wall and thus, navigate away from a problematic area.

In some embodiments, the feedback is proportional to the average of the two, and in other embodiments, may be the sum of the two, etc. However, in the various embodiments, the feedback relates to gross overall arm motion and whether or not the robot assembly may have hit anything or is jammed up against a structure/wall or other. Thus, in some embodiments, this feedback may indicate to the user if one or more of the robotic assemblies are jammed, stuck, etc. The tactor motor 8520 may also provide feedback related to how hard the robotic assembly is pushing on something which may be useful in controlling the robotic assemblies and completing one or more tasks. In some embodiments where a vibration motor is used, the intensity of the vibration may be proportional to the torque. In some embodiments, however, an auditory feedback may be used, which may include, but is not limited to, feedback where a single tone is given, the higher the tone, for example, the higher the torque. In other embodiments, one or more lights, for example, one or more LEDs, may be used, and this may include variations including, but not limited to, one or more of the following: using blinking/on/off patterns and/or color to indicate feedback to the user.

Still referring to FIGS. 85A-85B, the exoskeleton between the shoulder and the elbow and between the elbow and the wrist may, in some embodiments, be adjustable. In the exemplary embodiment, a telescoping feature may be used for adjustment of the upper arm 8504 and lower arm portions 8522, 8524. In some embodiments, a mechanism similar to a camera tripod adjustability feature may be used. In some embodiments, the tripod-like mechanism may be desirable for its ability to lock in place easily and include a strong locking mechanism as well as its ability to open and close easily. However, in various other embodiments, any mechanism allowing for adjustability may be used. By using the various adjustability features, the location of the wrist joint and elbow joint of the exoskeleton may be adjusted to be proximate to the location of these joints on the user. Similarly as with the shoulder joint, the accuracy of the control of the robotic assemblies using the exoskeleton will depend partly on the exoskeleton's ability to map the movement of the user's joints, which may be improved with the one or more sensors being located proximate to the user's joints. The movement of the user may be mapped using at least one sensor for each user joint. In addition to the ones discussed above with respect to the shoulder joints, in the exemplary embodiments, the exoskeleton includes at least one potentiometer 8526 on the elbow joint and at least one potentiometer 8528 on the wrist joint which may sense wrist rotation and may be referred to as the wrist rotation sensor 8528. It should be understood that although in some embodiments, potentiometers are used, in other embodiments, various other sensors may be used to track the movement of the joints. These sensors may include, but are not limited to, IMUs (inertial measurement units), which, in some embodiments, may be one of the IMUs described in International Publication No. WO 2010/120403 A2 to Van der Merwe et al. on Oct. 21, 2010 and entitled "System, Method and Apparatus for Control of a Prosthetic Device". However, in other embodiments, the sensor may be any sensor, including but not limited to, bend sensors.

The elbow joint and wrist joints are formed from a series of rings. These are referred to as the humeral and wrist rotators. In the exemplary embodiments, the humeral and wrist rotators rotate with the user's humeral and wrist rotation. Additionally, in some embodiments, where there may be limitations of movement inherent in the one or more robotic assemblies being controlled using the exoskeleton, those limitations may be built into and/or reflected in the movement of the exoskeleton. In this way, the user may be limited in motion in the exoskeleton, however, this may lead to more accurate control of the one or more robotic assemblies as the user will not expect or intend for the robotic assembly to move in a way that the user can not move while using the exoskeleton. Thus, in some embodiments, there may be one or more stops built into the joints at particular/predetermined locations which prevent the user from commanding the robotic assembly to move in a way it is not able to move. In some embodiments, the stops may also prevent the exoskeleton from being tangled.

In the exemplary embodiment, the humeral and wrist rotators may be similar. In the exemplary embodiments, the rotators include large thin ring bearings, which, in some embodiments, may be KAYDON bearings, or another similar bearing. These large thin ring bearings allow a cantilever mode to account for moment loads. Also, the rotators include a ring spur gear that go to a pinion gear attached to the sensor/potentiometer. However, as discussed above, in other embodiments, the sensor may a sensor other than a potentiometer and in some embodiments; the joint may include more than one potentiometer.

In some embodiments, such as the ones shown in the exemplary embodiment, the stops may be a plate with protrusions that protrudes from the plate that act as stops so that the user may not command the robotic assembly to go past where the robotic assembly can move. In some embodiments, the stops may be adjustable such that the exoskeleton may be used with different robotic assemblies. However, in some embodiments, the stops are nonadjustable and are designed to be used with specific robotic assemblies.

In some embodiments, as in the exemplary embodiment, the exoskeleton may include a feature such the area between the humeral and wrist rotators may rotate. This may be desirable for when a user extends their arm in the exoskeleton, their arm rotates. Thus, the exoskeleton, in some embodiments, also rotates to a second position to map the user's arm. However, in some embodiments, when the exoskeleton rotates, there is a return mechanism 8530 to rotate the area between the humeral and wrist rotator back to its original/starting/first position. In some embodiments, the return mechanism 8530 includes a pulley and a bungee wrapped about the pulley inside a housing. The bungee may be anchored to the humeral joint. Thus, in these embodiments, when the user rotates the humeral and wrist joint, this loads the bungee and the pulley/bungee system pull the joints back from the second position such that the joints rotate to the starting/original/first position.

In the exemplary embodiment, the wrist rotator is constructed in a similar fashion as the humeral rotator. However, in the exemplary embodiments, the wrist rotator has a smaller diameter and does not include a return mechanism. However, in various embodiments, the diameter of the wrist rotator may be the same as the humeral rotator. Also, in some embodiments, a return mechanism may be included on the wrist rotator.

Figure 86A:
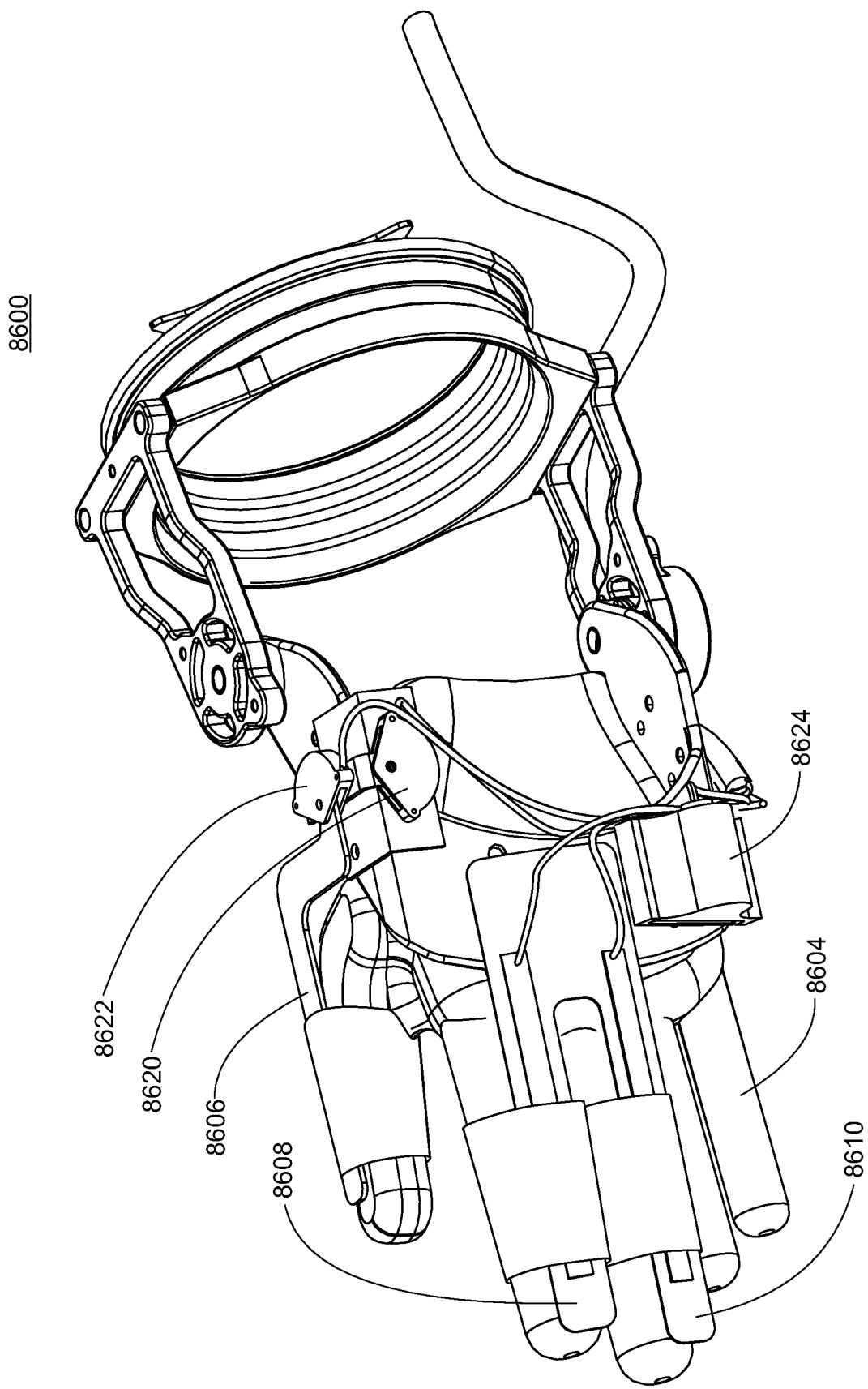
FIG. 86A is a view of one embodiment of a hand of the exoskeleton detached from an exoskeleton.
Figure 86B:
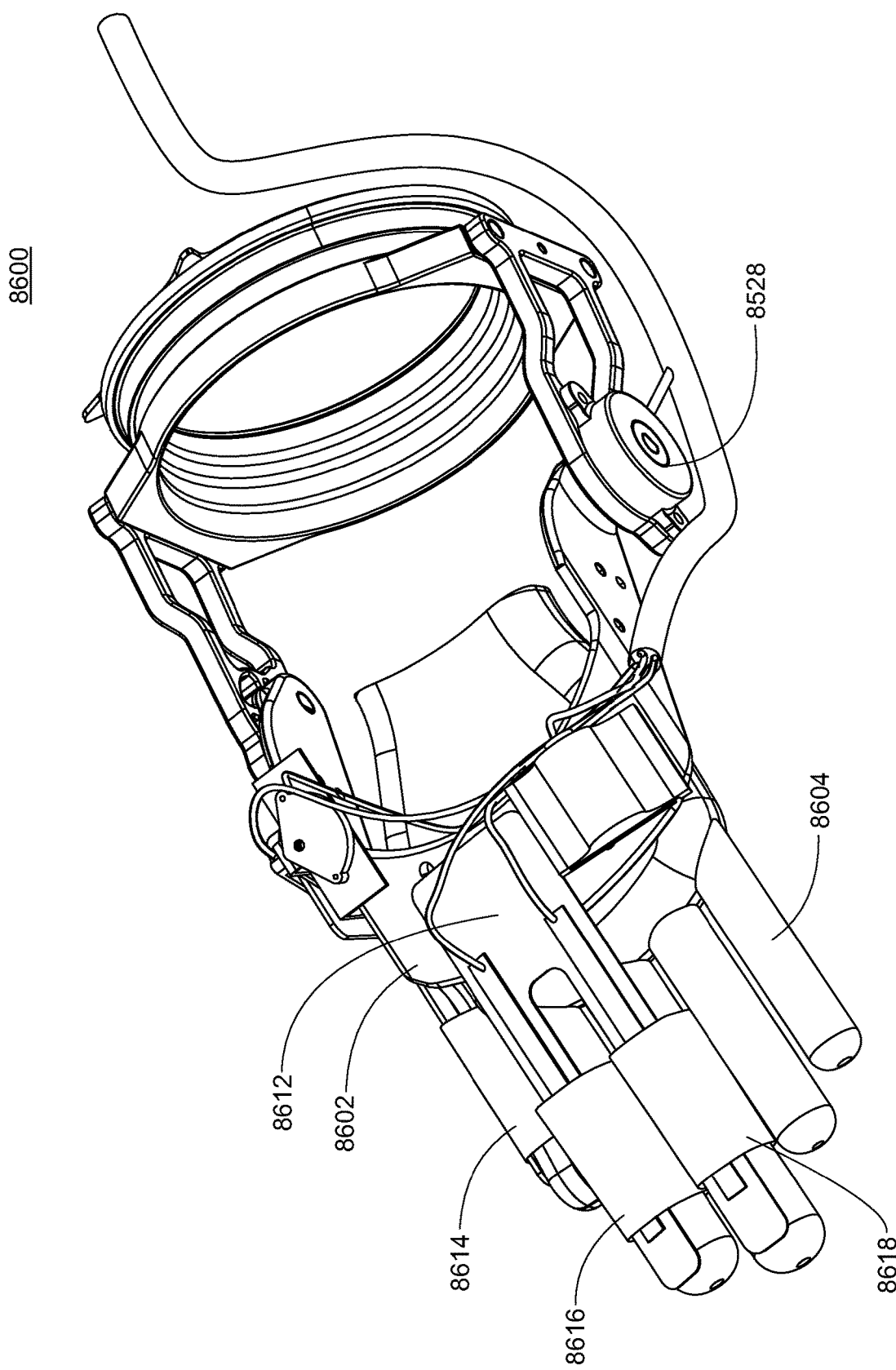
FIG. 86B is a view of one embodiment of a hand of the exoskeleton detached from an exoskeleton.
Figure 86C:
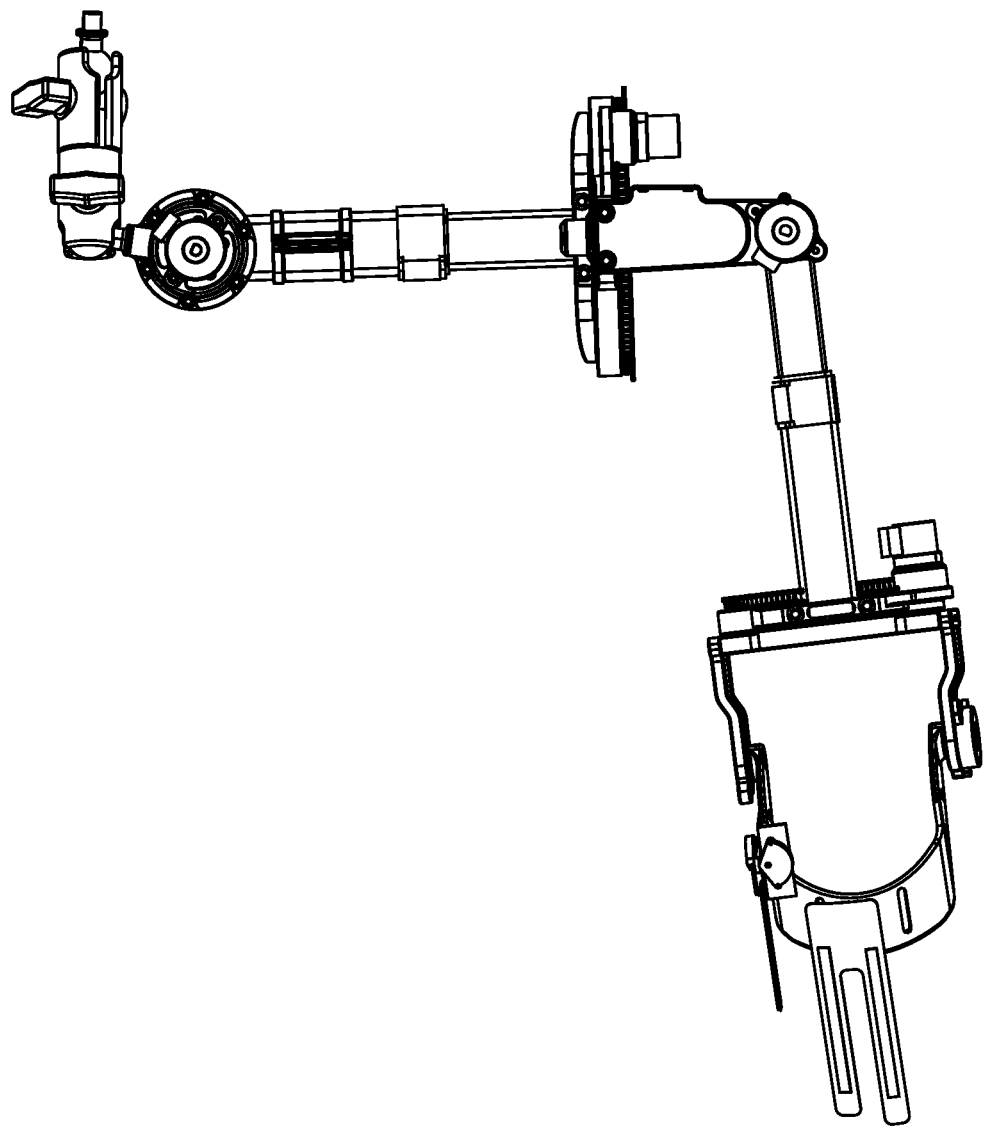
FIG. 86C is a view of one embodiment of an arm of the exoskeleton detached from an exoskeleton.
Figure 86D:
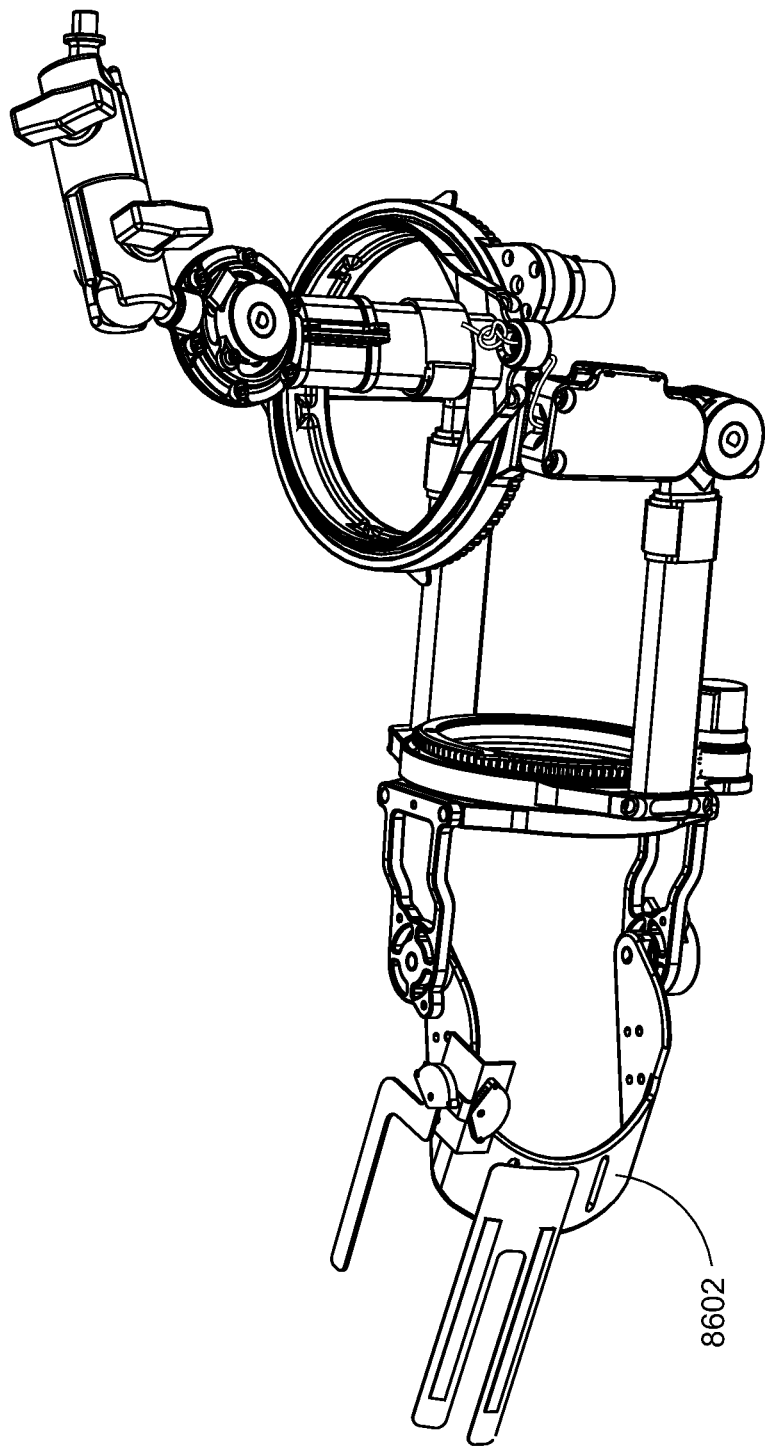
FIG. 86D is a view of one embodiment of an arm of the exoskeleton detached from an exoskeleton.
Figure 86E:
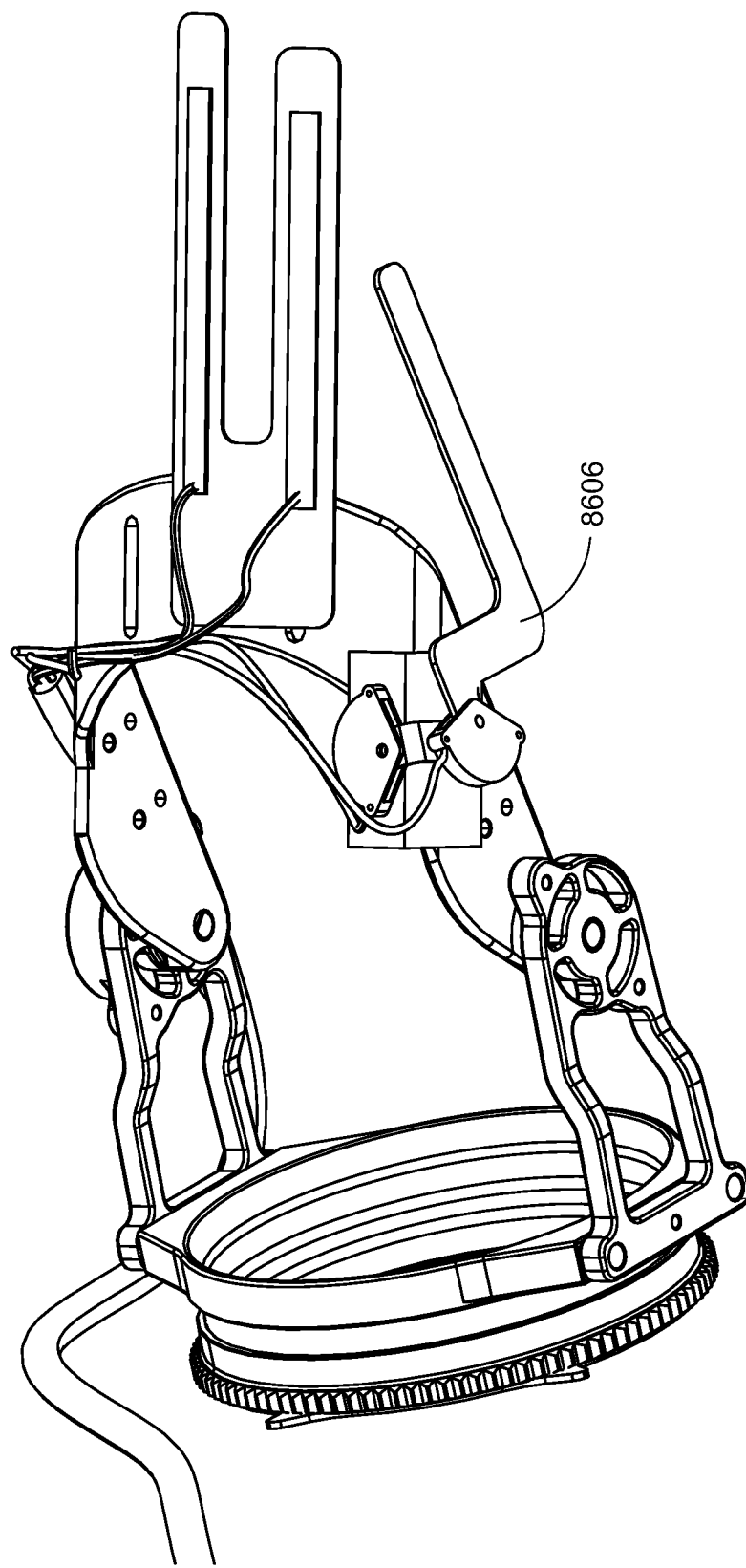
FIG. 86E is a view of one embodiment of an arm of the exoskeleton detached from an exoskeleton.
Figure 86F:
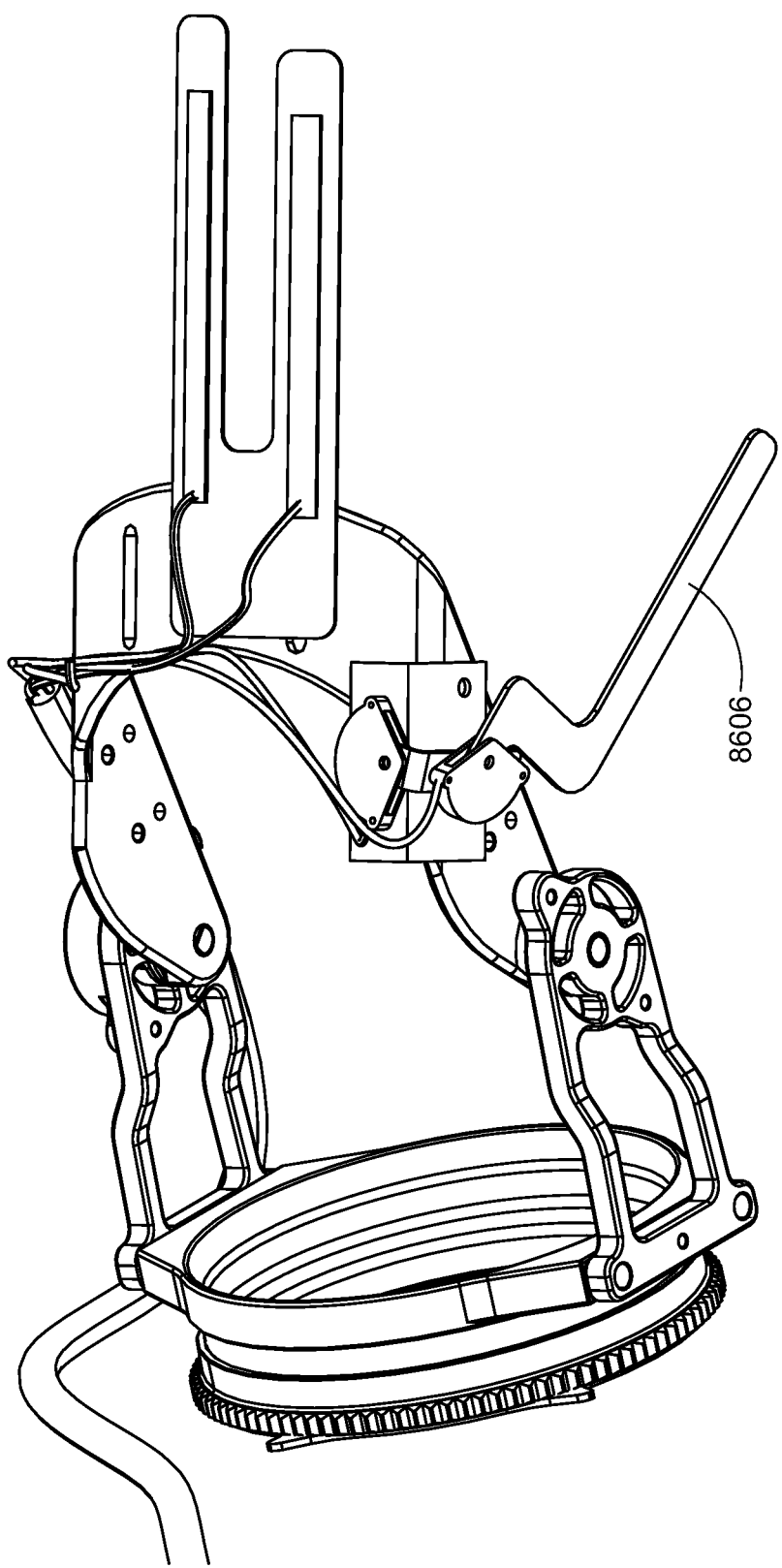
FIG. 86F is a view of one embodiment of an arm of the exoskeleton detached from an exoskeleton.
Figure 86G:
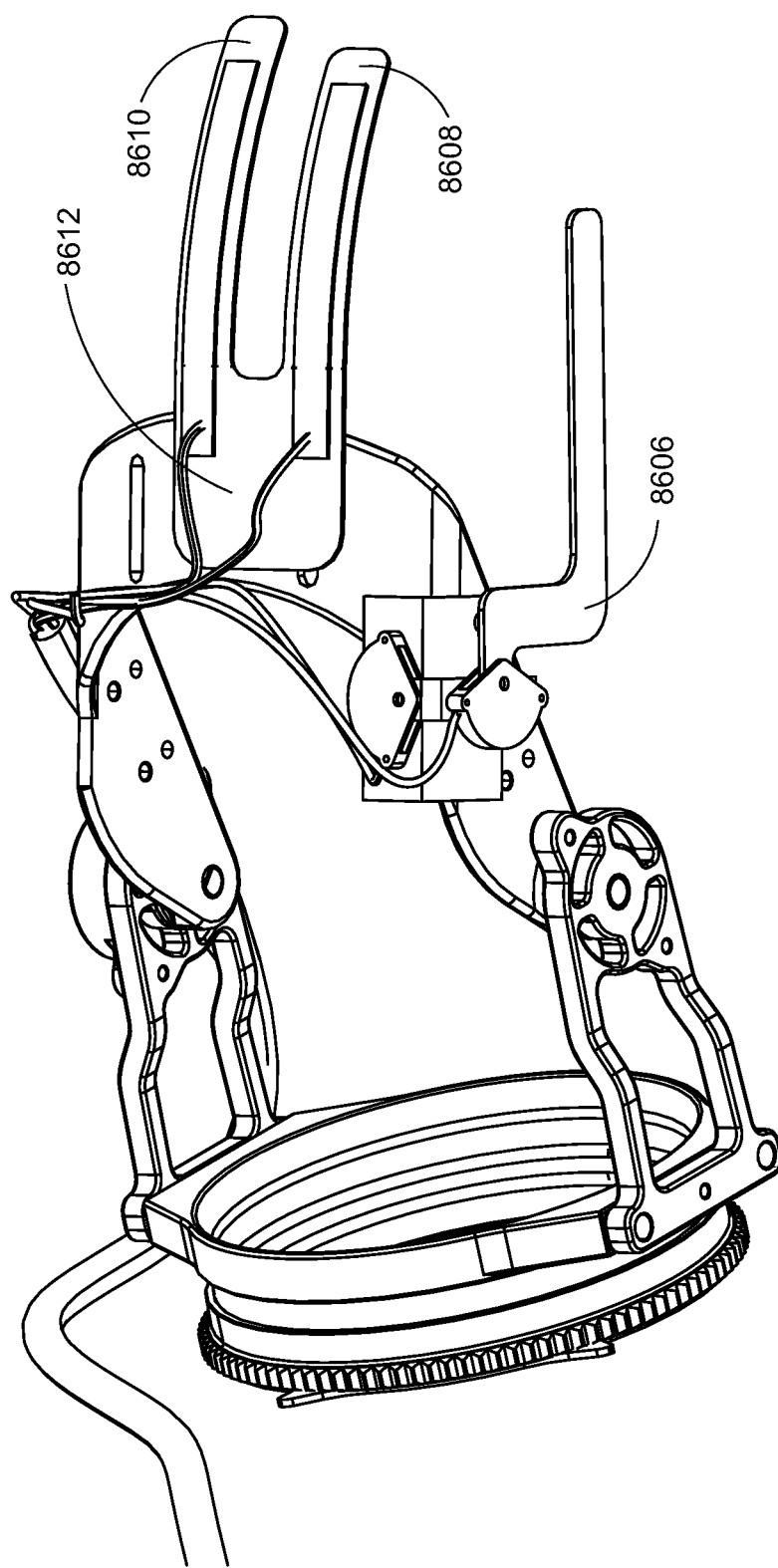
FIG. 86G is a view of one embodiment of an arm of the exoskeleton detached from an exoskeleton.

Referring now to FIGS. 86A-86B, as well as FIGS. 86C-86G, the exoskeleton, in some embodiments, may include a hand portion 8600 which includes the wrist rotation portion including the wrist rotation sensor 8528. In the exemplary embodiments, the hand portion 8600 may include a glove plate 8602. In the exemplary embodiments, the user may place their hands in a glove 8604. The glove 8604, in the exemplary embodiment, includes a thumb splint 8606, an index finger sensor 8608 and a middle finger sensor 8610. In some embodiments, and as shown in FIGS. 86A-86B, the index finger sensor 8608 and a middle finger sensor 8610 may be included on the same body 8612. In some embodiments, any glove may be used and attached to the glove plate 8602. In the exemplary embodiment, the glove plate 8602 may include various holes for attachment of the glove 8604 (the hole features may also be seen in FIGS. 86C-86G). The various holes allow for attachment of various sized gloves to accommodate different sized users. However, in some embodiments, the glove plate 8602 may not include adjustability features.

In some embodiments, the sensors 8612 and thumb splint 8606 are connected to the exoskeleton and may fit into pockets 8614, 8616, 8618 on the glove 8604. In the exemplary embodiments, the thumb splint 8606 includes at least two sensors 8620, 8622, which, in some embodiments, may be potentiometers. In the exemplary embodiments, the sensors 8616, 8618 are flexible bend sensors such that the sensors detect when the user bends their index or middle fingers. The bend sensors 8616, 8618 send signals, through an electrical connection, to a control system (described below). In various embodiments, the bend sensor may detect bend using resistance change data. Thus, in some embodiments, the further the user bends their finger, the more the resistance changes, thus indicating movement. In various other embodiments, additional sensors may be included on the middle, ring and pinky fingers. However, in the exemplary embodiment, these sensors may not be necessary as the control system works to control a robotic hand/arm and that robotic hand arm includes a hand in which the middle, ring and pinky move together. However, in other embodiments, where various robotic assemblies may be controlled using the exoskeleton, different sensors may be used and selected based on the robotic assembly functionality and the control system thereof.

As discussed above, the exemplary embodiment includes a thumb splint 8606. In the exemplary embodiments, the thumb splint 8606 limits the movement of the user's thumb. It may be desirable, as discussed with respect to the stops discussed in the joint rotators above, to limit movement of the user where the robotic assembly the exoskeleton controls includes limited movements. Thus, in the exemplary embodiment, the exoskeleton controls two robotic arms/hands/shoulders (collectively referred to as a "robotic arm"). In some embodiments of the robotic arm, the robotic thumb includes specifically programmed movements. Thus, the exoskeleton includes a thumb splint 8606 to limit the user's thumb movements to those that are included in the robotic thumb's programmed movements. Although herein are some examples of limited movements in the exoskeleton to mimic the limited movement of the robotic assembly, these are not an exhaustive list. In various embodiments of the exoskeleton, mechanical features may be added to the exoskeleton to limit the movements of the user to match and/or mimic the allowed/possible movements of the robotic assembly. However, in some embodiments, as discussed in more detail below, the robotic assembly may include additional capabilities that the user may not accomplish. Thus, in some embodiments, although stops may be used to limit the movement of the user, the control system may allow for additional and expanded/continued movement of the robotic assembly.

With respect to the robotic arm controlled by the exoskeleton in the exemplary embodiment, the thumb includes two degrees of freedom, yaw and pitch. Thus, the exoskeleton includes two potentiometers 8620, 8622, one to sense yaw, one to sense pitch, which sense the movement of the thumb splint 8606 and provide signals to the control system map the movement of the robotic arm's thumb. In other embodiments, additional sensors or different sensors may be used. In some embodiments, a single sensor may be used.

In some embodiments, the exoskeleton hand or the glove may include a tactor motor 8624. In some embodiments, the tactor motor on the glove or the exoskeleton hand is located such that the user may see, feel or hear the tactor. In some embodiments, the tactor motor is a vibratory motor. However, in some embodiments, the tactor may be an auditory tactor. In other embodiments, the tactor is a visual tactor and may include one or more lights, e.g., LEDs, which may indicate/signal to the user via blinking, on/off, and/or colors, to indicate various feedback to the user. In the exemplary embodiment, the tactor motor is a vibratory motor and provides feedback to the user with respect to the thumb grip strength of the robotic arm. Although in the exemplary embodiment, the thumb tactor is located on the glove or hand portion of the exoskeleton, in some embodiments, the tactor may be located elsewhere on the exoskeleton. In some embodiments, the tactor may be located on a strap and/or on a separate device containing one or more feedback indicators to the user. For example, in some embodiments, the tactor may be an indicator as described in WO 2010/120403 A2.

In some embodiments, the exoskeleton may include an inertial measurement device and/or potentiometer and/or sensor to indicate the movement of the users's torso and/or feet and/or head, etc. These one or more sensors may be used to control the platform/mobile platform/robotic assembly in one or more ways. For example, where the user's torso movement may be sensed, torso forward movement by the user may send a signal to the control system that the mobile platform should move forward. One or more sensors worn on the user's feet, which may include, but is not limited to, those described in WO 2010/120403 A2, may send control signals to the robotic assembly and/or the mobile platform.

Control System

Figure 87:
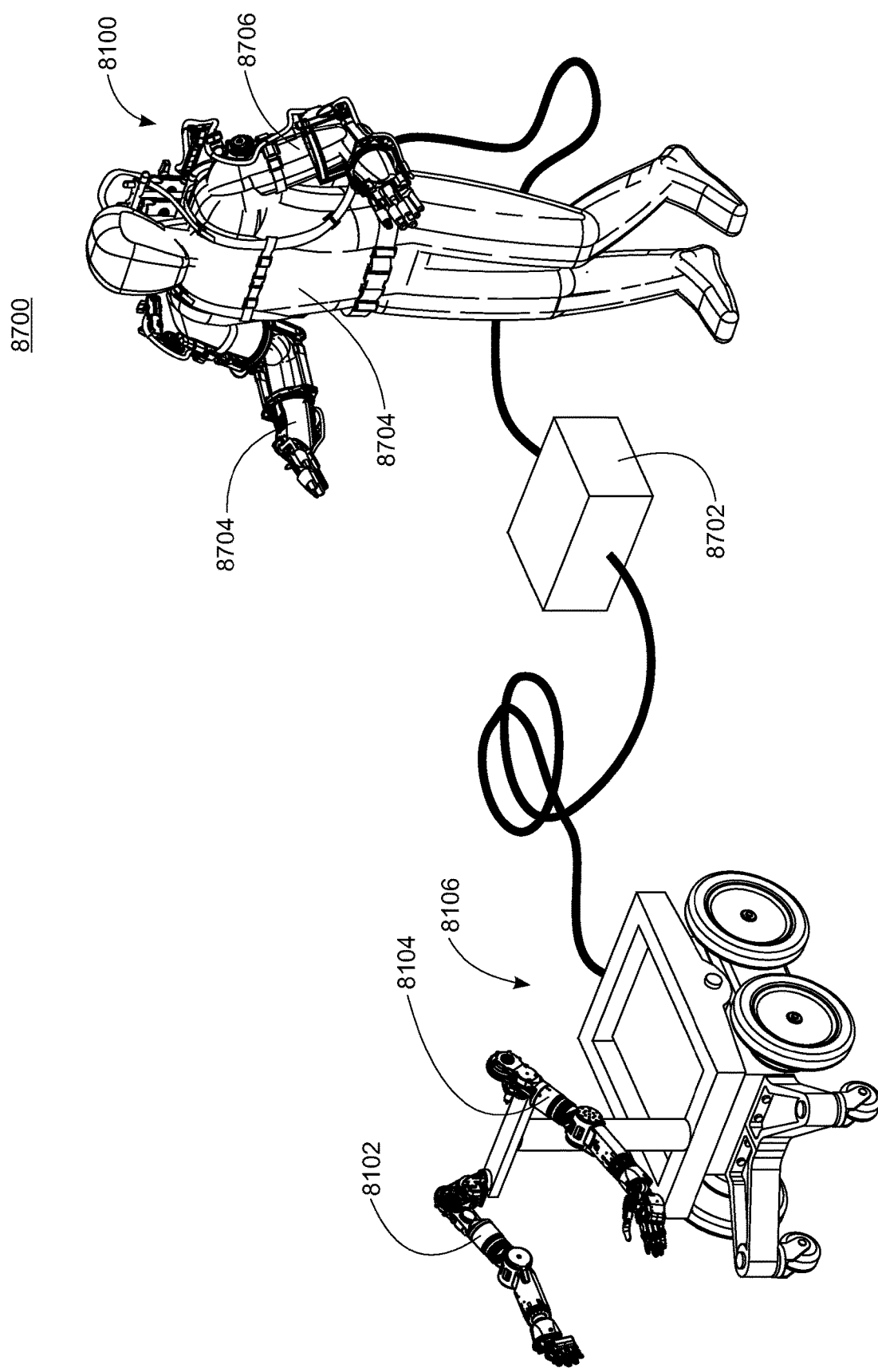
FIG. 87 is an illustrative view of one embodiment of the system.

WO 2010/120403 A2 includes description of various control systems and methods for a robotic arm or another robotic assembly. At least part of the description may be applicable to the exoskeleton control system. Referring to FIG. 87, in the exemplary embodiment, and used for illustration purposes, the system 8700 includes an exoskeleton 8100 which controls at least one robotic arm 8102, 8104. The system 8700 may be powered by a power source located in a housing 8702. However, in other embodiments, the exoskeleton 8100 may be powered by one power source and the mobile platform by another power source (not shown). This embodiment may be used where the mobile platform 8106 and the exoskeleton 8100 are remote one from another. Thus, in various embodiments, the user 8704 may be located in a location remote from the robotic assemblies 8102, 8104. However, in some embodiments, the user 8704 and the robotic assemblies 8102, 8104 may be located in the same area.

As discussed above, the various joints of the exoskeleton include sensors such that the movement of the user may be captured by the sensors. The sensors, in the exemplary embodiment, send signals to a control system. In various other embodiments, a camera may be used to capture the movement of the user and send the signals to the control system. In some embodiments if these embodiments of the system, the user may use a hand portion, which, in some embodiments, may include one or more of the various sensors described herein, such that the camera may determine the gross movements of the user and the hand portion may send signals regarding the movement of the hand and/or fine movements. However, for description purposes, the exoskeleton embodiment is described below, although it should be understood that the system may include one or more devices, apparatus and/or systems to capture the user movements (both gross and fine) and send signals to the control system indicating the movements such that the control system may map the movement to the one or more robotic assemblies. Thus, in the various embodiments, the control system maps the movement of the exoskeleton to the movement of the robotic assemblies. For purposes of illustration, the exemplary embodiment will be used to describe the controls.

In the exemplary embodiment, the control system is a many to one or many to few mapping system. The movement of the user is captured by the one or more sensors of the exoskeleton. The movement data is sent to the control system which maps the movement and sends commands for movement to the at least one robotic assembly. Various embodiments may include preprogrammed gestures and/or preprogrammed signals that may be made by the user and automatically translated to a particular movement and/or movements of the robotic assembly. In this way, the user may easily, efficiently and with little to no training, control the at least one robotic assembly.

Further, as the exoskeleton allows the user to move in a natural way, and translate these natural movements to movements by the at least one robotic assembly, control of the at least one robotic assembly is easy and efficient and, as well, does not require extensive training. With respect to the exemplary embodiment, where the exoskeleton controls two robotic arms, the robotic arms move in a natural/human manner. Thus, where the user moves in a natural/human manner, and this movement is translated to robotic arms which move in natural/human manner, the system allows for easy and efficient use of the robotic arms and easy and efficient control, but the user, of the robotic arms, to perform natural/human-like tasks.

In the exemplary embodiment, the control system is calibrated to a user. This calibration, once completed, in some embodiments, may be "saved" or "stored" and recalled by the control system such that multiple users may use a single exoskeleton at different times. To do so, they may calibrate at each use, or, in some embodiments, may upload/load a previously configured calibration at time of use.

In various embodiments, calibration may be performed either manually or automatically. For example, in some embodiments, there may be a software system which takes the user through the calibration process by prompting the user, wearing the exoskeleton, to position their arms/torso in specific orientations, one after the next. The system thus may record the at least one sensor position/signal at a particular position of the arm. Thus, completing a series of calibration steps, the control system may then map movement of the exoskeleton/user to movement by the robotic arm/at least one robotic assembly.

With respect to the exemplary embodiment, where two robotic arms may be controlled by the exoskeleton, calibration may be particularly important with respect to positions where the hands/arms of the robotic arms are touching/meet/make contact in free space. Thus, it is critical to map the joints of the exoskeleton at these points to ensure that the robotic arms will touch when commanded by the user. Thus, in the exemplary embodiment, it may be critical that the robotic arms are capable of interacting with items of interest.

In the exemplary embodiment, after calibration, when the user moves while in the exoskeleton, the robotic arms will move in the same manner, i.e., will map to the user/exoskeleton.

Thus, in the exemplary embodiment, the exoskeleton collects data/signals from sensors on two arms of the user. The controls then maps these positions, thus, the controls map the joint positions of each of the two arms of the user directly to the arm positions of each of the respective robotic arms 8102, 8104. Thus, the movement of the right arm 8704 of the user is mapped to move/control the right robotic arm 8102 and so on and so forth with respect to the left arm of the user 8706 and the left robotic arm 8104.

With respect to the hands of the user and the robotic arms 8102, 8104, as discussed herein and in WO 2010/120403 A2, the robotic arms include hands which include a plurality of grips. Although as discussed in WO 2010/120403 A2, mode switching may be used to control the hands, in the embodiment described herein with respect to the exoskeleton system, mode switching may not be used. Thus, when the user, wearing the exoskeleton, moves their hands, this movement may be mapped to the robotic arms.

However, in some embodiments, for ease or use and also, to ensure the user's intended grip is mapped to the robotic arms, gestures may be preprogrammed to the system as part of a calibration movement. Thus, where, for example, the user is intending to command a pinch grip, but in their hand movement, fails to correctly place their index finger with respect to their thumb, the robotic arms, without a gesture program, may mimic exactly the movement of the user. Thus, in this case, the robotic arm(s) would move in a user unintended, although commanded, manner. However, in some embodiments where gesture programming is used, while the user may not have completed the pinch grip movement correctly, the system may interpret the movement as a gesture, and signal to the robotic arm(s) to move to pinch grip. Although "pinch grip" is discussed, this is merely an illustrative example, all of the various grips and intermediate grips may be commanded by the user via a gesture that is preprogrammed into the control system.

Additionally, with respect to some embodiments of the hand mapping, where the human hand/fingers may be able to move in various ways, in some embodiments, the robotic arm/hand may not be able to move in all of the same ways. Thus, in some embodiments, the control system may be preprogrammed to interpret the movements by the human hand to specific movements by the robotic arm/hand, i.e., those movements that the robotic arm/hand are capable of performing. Thus, in some embodiments, the hand mapping may be a many to one or many to few mapping.

For example, in some embodiments, with respect the hand mapping, and specifically with respect to the index finger, although a user may close their index finger in a number of different ways, the control system may map the user closing their index finger (whichever way the user closes it) to a single way of closing the robotic hand/arm index finger. Thus, in some embodiments, the mapping may be a many to one mapping. Similarly, with respect to the middle, ring and pinky finger, as discussed above, the middle finger includes a sensor and, in some embodiments, the ring and pinky do not. Thus, when the user closes their middle finger, in some embodiments, this may translate to a specific closing of the ring and pinky fingers as well.

Another example is the thumb movements. In some embodiments, although the human thumb may close in a number of different ways, the control system may map these ways to a preprogrammed 2 degrees of freedom.

In some embodiments of the control system, the system is position based rather than orientation based. Thus, the position of the hand, for example, rather than the orientation of the hand, commands the robotic arm/hand. This may be desirable for wherever, with respect to orientation, the user's hand is; the user may command movement by the hand without respect to the orientation of the user's hand, rather, only with respect to the position of the user's hand. However, in other embodiments, the system may be orientation and position based.

In various embodiments, the control system need not include endpoint control, as discussed in WO 2010/120403 A2. Thus, the user may be mechanically constrained by the exoskeleton and their body to limit the movements commanded to the robotic arms. However, in some embodiments, endpoint control, similar to the embodiments described in WO 2010/120403 A2, may be used in the control system for the exoskeleton system.

Figure 93:
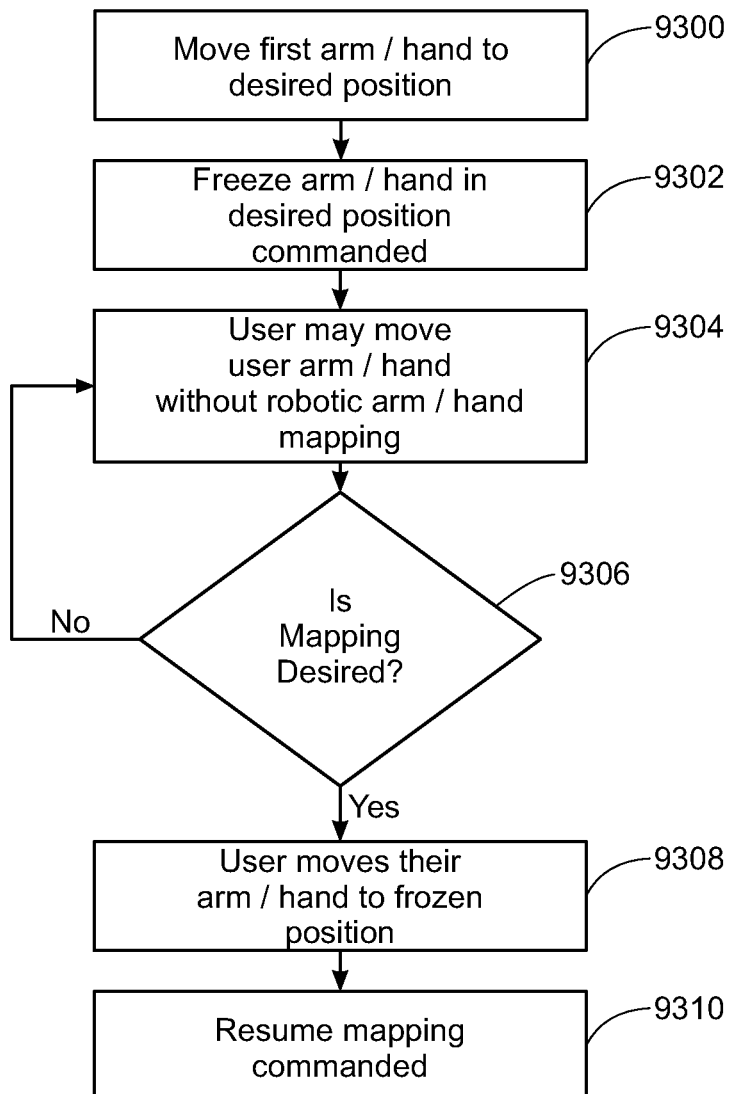
FIG. 93 is a flow chart of one embodiments of a control method.

In some embodiments, a method for freezing the robotic arm and/or hand in a particular position may be desired. For example, circumstances where an object may be grasped by one robotic hand while being worked upon by the second robotic hand, it may be desirable that the first robotic arm/hand remain in the same position. In some embodiments, in addition, a user may wish to maintain the robotic arm/hand in a frozen position for an extended amount of time and "rest" or "free" their arm simultaneously. Therefore, and referring now to FIG. 93, in some embodiments, a method for freezing a robotic arm/hand in a position in shown. The user first moves the first robotic arm/hand to the desired position 9300. The user commands the control system to freeze that particular robotic arm 9302, which, in some embodiments, may be commanded using voice commands, IMU commands and/or other inputs to the control system. The user then may move their arm/hand without the control system mapping the user movement to the frozen robotic arm/hand 9304. When mapping becomes desired

9306, for example, once the second robotic arm has finished working on an object controlled by the first robotic arm, the user moves their arm/hand to the frozen position 9308 and commands the mapping resume 9310. Thus, in some embodiments, the mapping will resume seamlessly from the frozen position.

In some embodiments, the robotic arm, in some embodiments, and/or other robotic assemblies in various embodiments, may have capabilities beyond that of the user. For example, the robotic arm may be capable of a longer "wing span" and may be capable of 360 degree rotation. However, the user, for which the control system maps their movement onto the robotic arm, for example, may be unable to command the robotic arm to its full expansion and capability. Thus, in some embodiments, a method for extended control may be used. In this method, various locations/points in the user movement path may be preprogrammed to trigger a mapping ratio of movement between the user and the movement to the robotic assembly. For example, at a preprogrammed location, the ratio may switch from "one-to-one" to "one-to-two", and further, at a second location, the ratio may switch from "one-to-two" to "one-to-three", etc. In this way, by increasing the mapping ratio, the user may command the robotic assembly to move in such a way as they can not. During user calibration, which is discussed in more detail above, the potential paths of the user may be preprogrammed into the systems and the trigger or switch locations as well as the mapping ratio associated with the "path" between two locations will be preprogrammed.

As discussed herein, in various embodiments, the robotic hand assembly may include preprogrammed grip trajectories. These embodiments may increase the accuracy of the remotely controlled robotic hand for without a preprogrammed trajectory, and where visibility of the fingers of the hand may be obscured on a video feed, the desired grip may be difficult to achieve. Thus, with preprogrammed trajectories, the user may instruct (for example, using an IMU) the robotic hand to move to a particular trajectory and therefore, the trajectory will be achieved regardless of the quality of visualization at the time.

In some embodiments, although each arm of the exoskeleton may weight about 3 pounds, it may be desirable for an assistance mechanism to alleviate the weight of the arms for the user may become tired over time. Thus, in some embodiments, the exoskeleton system may include supporting apparatus/mechanism/means, which, in some embodiments, may be wires that attach to both the arm and a ceiling or other structure, to aid in supporting the arms. In various embodiments, the supporting mechanism may allow for freedom of movement by the user, and, in some embodiments, the supporting mechanism may maintain the arms of the exoskeleton in a fixed position. In some embodiments, the exoskeleton may include motors and drives inside the joints of the exoskeleton to provide for less weight experienced by the user.

In various embodiments of the system, the user may wear one or more IMU or other type of sensor, to send additional control signals to the system. These additional control signals may be used to control one or more mobile platforms 8106, one or more sensors, including, but not limited to, one or more cameras. Referring to FIG. 87, in some embodiments, the exoskeleton 8100 and the mobile platform 8106 and robotic arms 8102, 8104 are hard wired, however, as discussed above, in various embodiments, they may communicate by way of wireless communications. These wireless communications may be any wireless communications.

In some embodiments, the one of more IMU may be used to control the hand grips, as is described in WO 2010/120403 A2.

In some embodiments where the user controls the mobile platform using one or more IMUs, the user may wear, for example, one IMU on their foot to control the forward, backward, right and left movement of the mobile platform. However, in some embodiments, the user may wear an IMU on both their right foot and left foot. In these embodiments, one of the IMUs (either right or left) may be used to control the forward, backward, right and left movement of the mobile platform. The other IMU may be used to select grips on the hand.

Although in some embodiments, the power supply 8702 may be provided in a housing and hard wired to one or more components of the system, in other embodiments, one or more power supplies may be worn by the user and/or integrated with the exoskeleton and/or integrated in the robotic arms 8102, 8104 and/or integrated in the mobile platform 8106.

Figure 88:
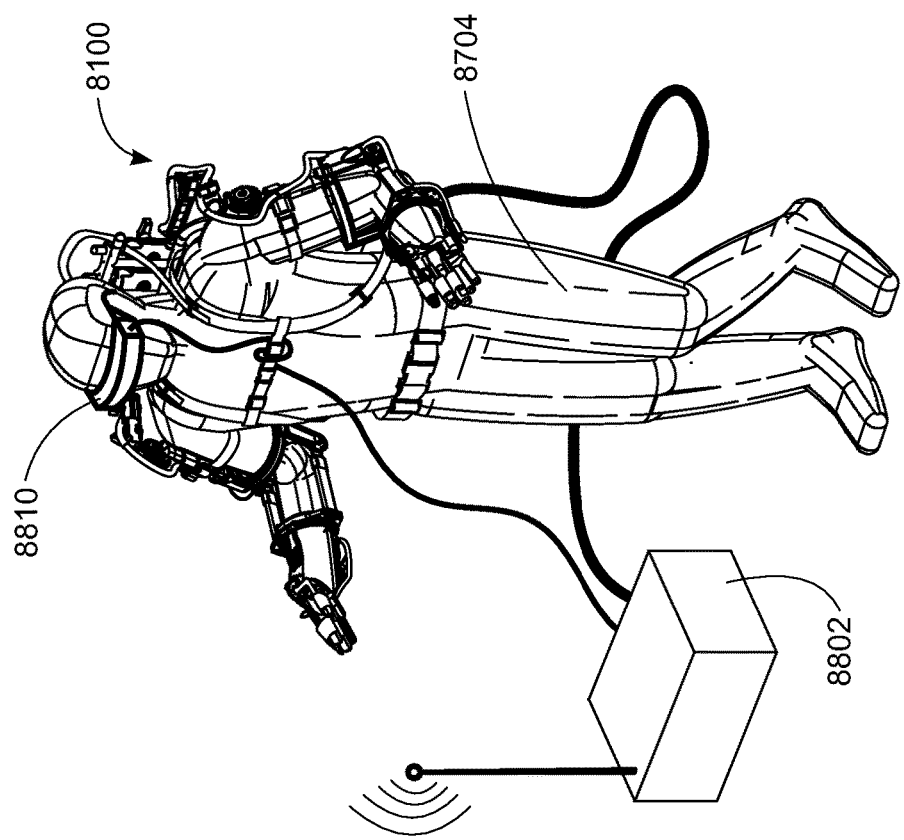
FIG. 88 is an illustrative view of one embodiment of the system.
Figure 88:
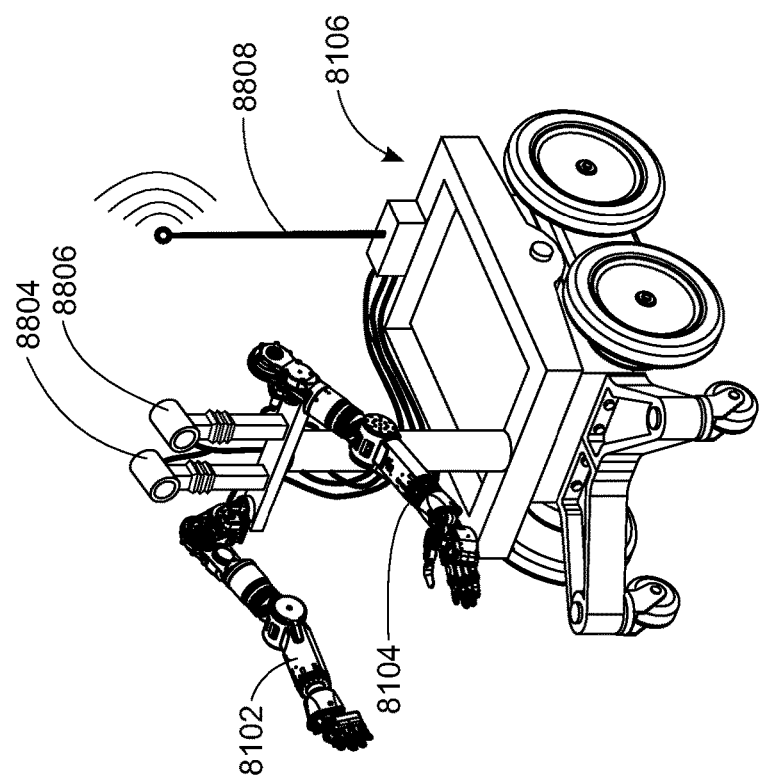

Referring now to FIG. 88, in some embodiments, the user 8704 may be located remotely from the mobile platform 8106 and thus, remotely from the robotic arms and/or one or more robotic assemblies 8102, 8104 (hereinafter "robotic arms"). In these embodiments, the exoskeleton 8100 commands the mobile platform 8106 and/or robotic arms 8102, 8104 by way of wireless communications 8802, 8808. Additionally, in some embodiments, the system may include one or more sensors, which, may include, but are not limited to, one or more cameras 8804, 8806, Ultraviolet ("UV") sensors, thermal sensors and/or Infrared ("IR") sensors. In various embodiments, additional sensors of any kind may be used and in some embodiments, may be selected based on factors, including, but not limited to, the task in which the robotic assemblies are being used to accomplish. The one or more sensors may be desirable to assist the user 8704 in decision making regarding the task being performed.

Figure 89:
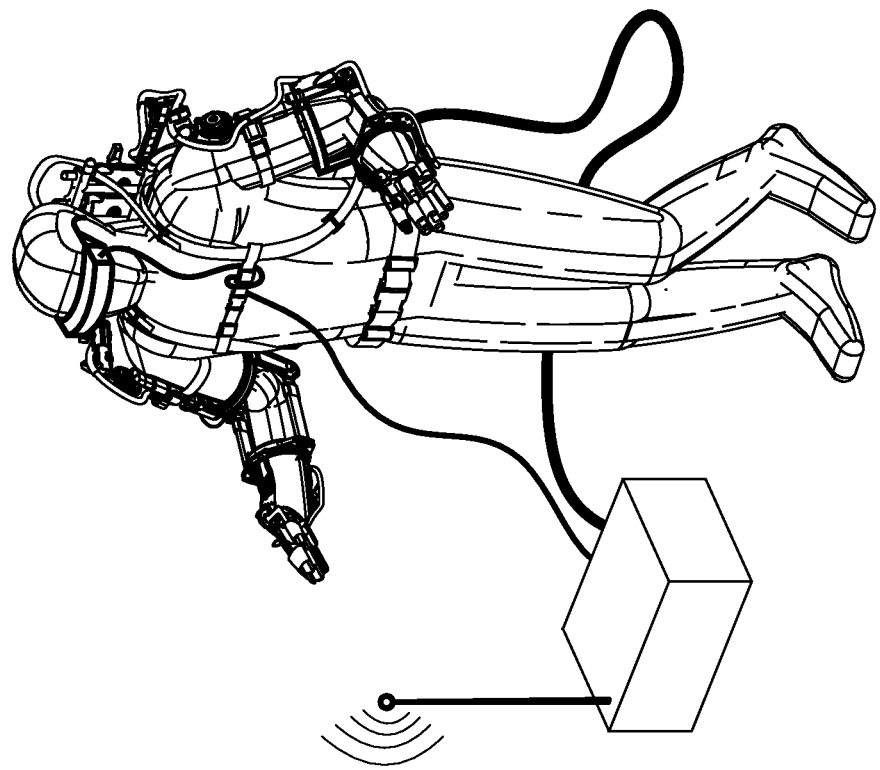
FIG. 89 is an illustrative view of one embodiment of the system.
Figure 89:
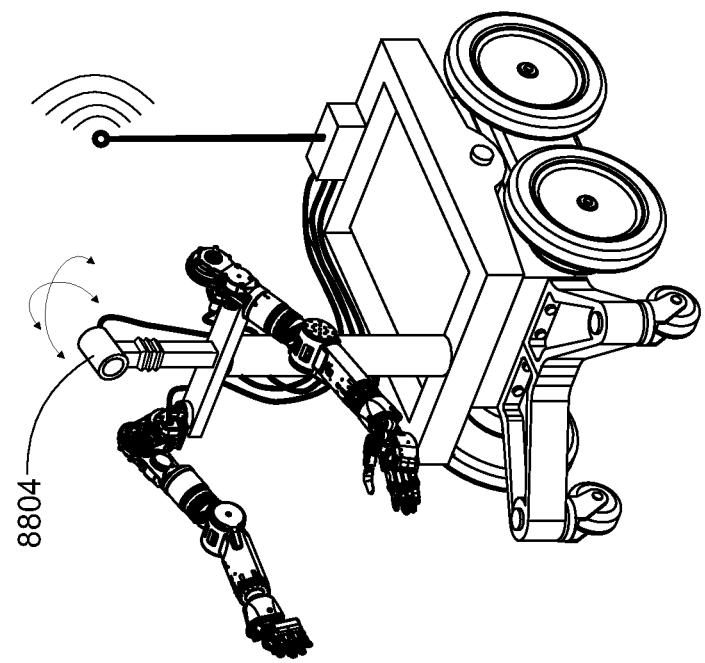
Figure 90:
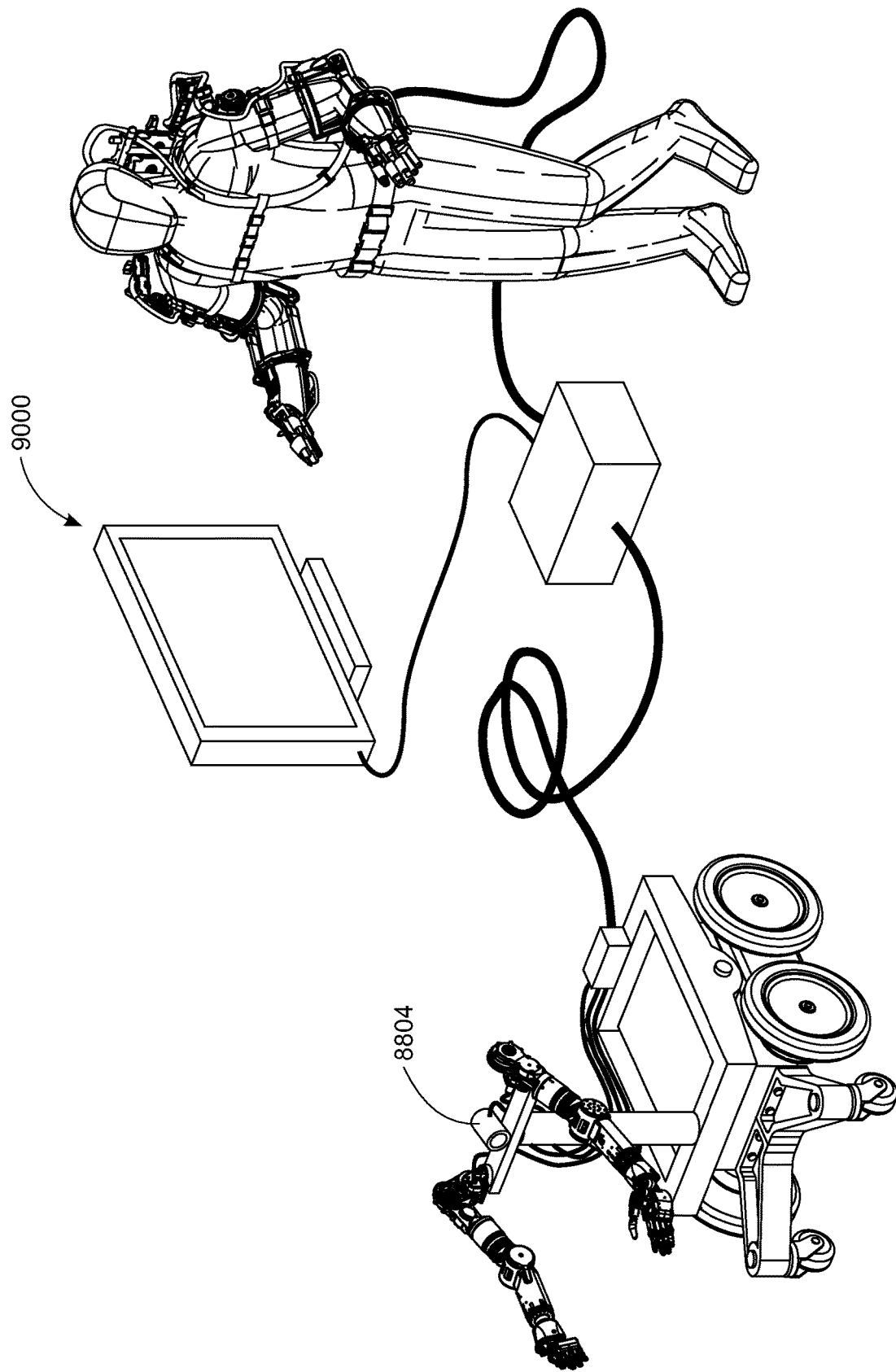
FIG. 90 is an illustrative view of one embodiment of the system.

The cameras 8804, 8806 (which may be any type of camera including, but not limited to, night vision cameras and underwater cameras) may be located anywhere desired, including but not limited to, distributed about the mobile platform 8106 such that they may collect images of the surroundings of the mobile platform 8106. In some embodiments, there may be a plurality of cameras such that a 360 degree view may be communicated to the user 8704. Referring to FIGS. 88-90, in some embodiments, a camera 8804 may be used which may be capable of pivoting and collecting images where the user 8704 desires. In some embodiments, the camera 8804 may be controlled by an IMU or other sensor worn by the user and/or part of the exoskeleton. In some embodiments, the IMU may be one described in WO 2010/120403 A2. In some embodiments, the camera 8804 may be controlled by way of IMU sensors which may be worn on the user's feet. In some embodiments, as shown in FIG. 90, the camera 8804 may be mounted anywhere on the mobile platform 8106.

In some embodiments, the one or more cameras 8804, 8806 may transmit images to the user 8704. The user 8704 may, in some embodiments, view the images using LED glasses 8810 and/or at least one monitor/viewing apparatus 9000. In some embodiments, multiple monitors/viewing apparatus 9000 are used. Although in FIG. 90, the various system components are shown wired together, it should be understood that in the various embodiments, one or more components may wirelessly communicate with one or more components.

In some embodiments, the mobile platform 8106 may include one or more IMUs and transmit yaw, pitch and roll data to the user by way of one or more tactors. In some embodiments, the user 8704 may stand on a platform which may mimic movement of the mobile platform 8106 thus provided feedback to the user 8704 regarding terrain, etc. This may be desirable to communicate perspective to the user 8704 for the user 8704 to determine control strategy.

In some embodiments, as discussed above, the user 8704 may wear one or more sensors to control the mobile platform 8106. These sensors may include, but are not limited to, one or more of the following: accelerometers, joysticks, IMUs. Thus, in these embodiments, the user 8704 may control the mobile platform 8106 using body English to move the platform.

In practice, the system may be used in any environment and the system may be distributed in any way, i.e., the user may be in any location and the mobile platform/robotic assembly may be in any location. Thus, the system may be used to accomplish any type of task including but not limited to, tasks related to the mining industry. For example, in some embodiments, the user may control two robotic arms to move about a mine, place explosives in the wall of the mine and attach detonation devices. In some embodiments, this task may be accomplished by a user in a remote location, far from any danger or harm related to the mine and/or the explosives. Using one or more sensors, which, in some embodiments, may be one or more cameras, are used such that the user may follow the progress of the robotic arms and the explosives. Also, in some embodiments, because the robotic arm moves naturally, the user may perform the task using "dummy" explosives and walls, while the mobile platform and robotic arms mimic the user and complete the actual task at hand. Many other uses are contemplated for the system described herein, including, but not limited to, Explosive Ordinance Disposal (sometimes commonly referred to as "EOD").

Figure 91:
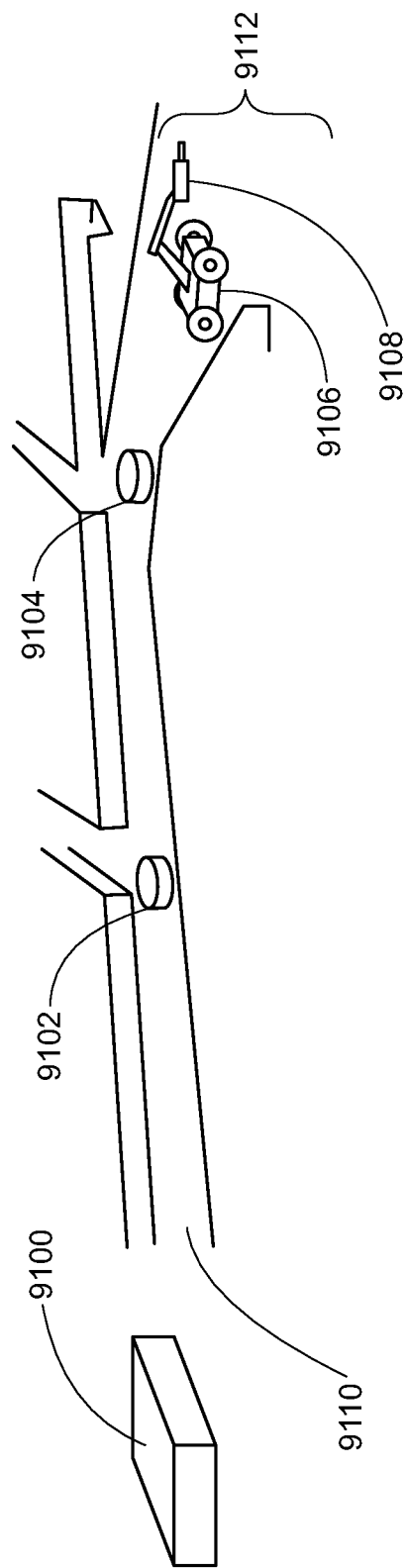
FIG. 91 is an illustration of one embodiment of a communication system and method.

Referring now to FIG. 91, in some embodiments, a base station 9100 may be used for wireless communication between the user/exoskeleton and the robotic assembly 9112. When navigating, communication with the robotic assembly 9112 may become interrupted due to the environment, for example, due to reflection on hard surfaces. Thus, in some embodiments, small, low power radio communication modules 9102, 9104 that act as relays may be used. Thus, as the robotic assembly 9112 moves about the area 9110, it will maintain communication with the base station 9100 and, in some embodiments, measure the signal strength of the communications. In some embodiments, when the signal strength reduces to, or below, a minimum threshold strength (which, threshold may be predetermined based on the signal strength needed to continue communication between the base station 9100 and robotic assembly 9112, the robot may place a small, low power base relay radio 9102, 9104 onto the area 9110. As shown in FIG. 91, for illustration purposes, the robotic assembly 9112, including a mobile platform 9106 and a robotic arm 9108, determined that the radio strength is at or below the predetermined minimum threshold strength, a placed a first low power base relay radio 9102, then a second low power base relay radio 9104 onto the area 9110. In some embodiments, the low power base relay radios 9102, 9104 may be approximately 1 inch in diameter. FIG. 91 and the description thereto is an example of one embodiment. In various embodiments, multiple low power base relay radios may be used.

Figure 92A:
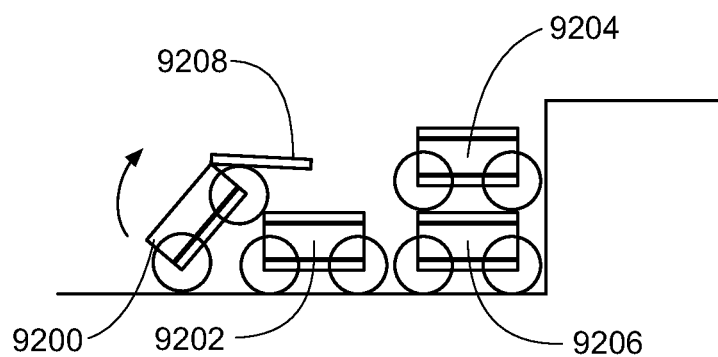
FIGS. 92A-92C are illustrations of various embodiments of the system.
Figure 92B:
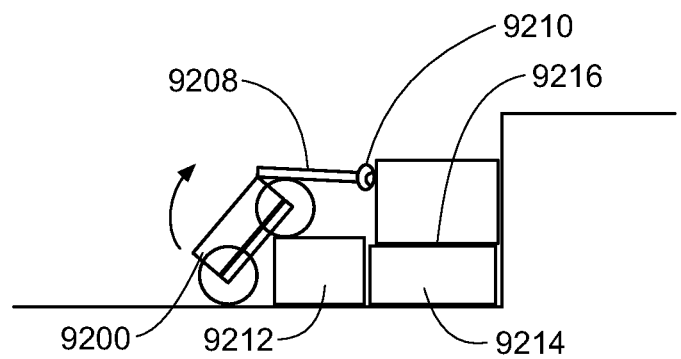
Figure 92C:
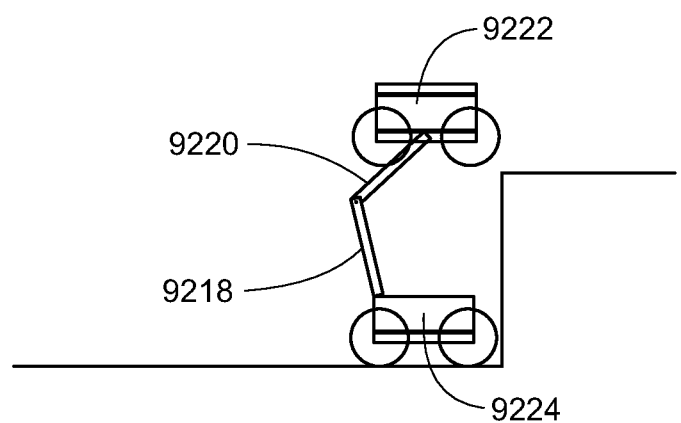

Referring now to FIG. 92A-92C, in some embodiments, where a mobile platform is used, maneuvering in small, confined areas with or without uneven topography including, but not limited to, inclines, declines, deep trenches and steep vertical faces, may be improved using a system including a mobile platform configuration that may be stacked (see FIG. 92A) to allow subsequent mobile platforms 9200 to use the stack of mobile platforms 9202, 9204, 9206 as a ladder or step configuration. In some embodiments, the mobile platforms 9202, 9204, 9206 in the stacked configuration may either move a robotic assembly attached thereto prior to stacking, or, in some embodiments, the mobile platforms 9202, 9204, 9206 may be used to assist the mobile platform 9200 that includes the robotic arm 9208. In some embodiments, the robotic arm 9208 on the mobile platform 9200 may be extended so as to position the center of gravity onto the front wheel of the mobile platform 9200.

Referring now to FIG. 92B, in some embodiments, the stacked mobile platforms may be replaced by moveable stacking blocks 9212, 9214, 9216. In some embodiments, and as shown in FIG. 92B, the robotic arm 9208, including a hand assembly 9210, may use a hand grip for climbing assist for example, for heavier payloads. In some embodiments, the stacking blocks 9212, 9214, 9216 may include hand holds for the hand assembly 9210 to grip for assistance.

Referring now to FIG. 92C, in some embodiments, for example, to overcome obstacles of some sizes, a second robotic arm 9218 on a second mobile platform 9224 may lift a first mobile platform 9222 by holding onto the first robotic arm 9220 on the first mobile platform 9222. When the first mobile platform 9222 is resting on a surface, the first robotic arm 9220 of the first mobile platform 9222 may then lift the second mobile platform 9224 by pulling up on the second robotic arm 9218.

In the exemplary embodiment where two robotic arms such as those described here are used, any task that requires a tool and/or machinery and/or device that is used by humans may be used by the robotic arms. In some embodiments, the hand of the robotic arm may be removable by the other robotic arm, and replaced with an end effecter.

Although the invention has been described in the context of a prosthetic arm, an apparatus according to the elements of this invention could be used in other robotic tools, such as those used in manufacturing and/or teleoperations, where an operator is not connected directly to the controlled device. For example the prosthetic arm apparatus may be used for teleoperation in hazardous environments and/or hazardous activities, for the detonation of explosive devices or the like. In these environments, the prosthetic arm apparatus may provide a more intuitive interface for the user since the user will already be familiar with the natural movements of the arm, which may make control translation of the prosthetic arm apparatus easier.

While the principles of the invention have been described herein, it is to be understood by those skilled in the art that this description is made only by way of example and not as a limitation as to the scope of the invention. Other embodiments are contemplated within the scope of the present invention in addition to the exemplary embodiments shown and described herein. Modifications and substitutions by one of ordinary skill in the art are considered to be within the scope of the present invention.

What is claimed is:

1. A robotic assembly control system comprising:
   an exoskeleton apparatus adapted to be worn by a user comprising at least one tactor motor;
   at least one robotic assembly, separate from the exoskeleton, the at least one robotic assembly controlled by the user by way of the exoskeleton;

at least one mobile platform controlled by the user and separate from the exoskeleton and wherein the at least one robotic assembly is attached to the at least one mobile platform;

wherein the at least one robotic assembly and the at least one mobile platform are in wireless communication with the exoskeleton; and wherein the at least one tactor motor provides feedback related to torque of the shoulder joint on the at least one robotic assembly.

2. The robotic assembly control system of claim 1, the exoskeleton further comprising:

an attachment system comprising a plurality of straps, the attachment system for attaching to a user; and a frame comprising a lower portion and an upper portion wherein the upper portion telescopingly connects to the lower portion wherein the frame is adjustable.

3. The robotic assembly control system of claim 2, the frame further comprising a ball detent mechanism for adjusting the frame.

4. The robotic assembly control system of claim 1, further comprising at least one potentiometer.

5. The robotic assembly control system of claim 1, further comprising at least two ball joints.

6. The robotic assembly control system of claim 1, further comprising a compliance section wherein the compliance section senses sternoclavicular motion by a user.

7. The robotic assembly control system of claim 6, wherein the compliance section is a torsion spring.

8. The robotic assembly control system of claim 7, wherein the torsion spring is preloaded with a hard stop, wherein the hard stop is adjustable.

9. The robotic assembly control system of claim 1, further comprising a tactor strap for each tactor motor wherein the tactor strap attaches to a user.

10. The robotic assembly control system of claim 9, wherein the at least one tactor motor is a vibration motor.

11. The robotic assembly of claim 1, further comprising a hand assembly.

12. The robotic assembly control system of claim 11, the hand portion comprising at least one tactor motor wherein the tactor motor provides feedback of the robotic assembly thumb force sensor to the user.

13. The robotic assembly of claim 11, wherein the hand assembly comprising:

a thumb structure comprising a thumb force sensor;
an index finger structure; and
a middle finger structure.

14. The robotic assembly control system of claim 13, the thumb force sensor further comprising at least one potentiometer.

15. A method for controlling a robotic assembly comprising:

providing an exoskeleton apparatus adapted to be worn by a user comprising at least one tactor motor;

providing at least one robotic assembly, separate from the exoskeleton, the at least one robotic assembly controlled by the user by way of the exoskeleton;

providing at least one mobile platform controlled by the user and separate from the exoskeleton and wherein the at least one robotic assembly is attached to the at least one mobile platform, wherein the at least one robotic assembly and the at least one mobile platform are in wireless communication with the exoskeleton; and the at least one tactor motor providing feedback related to torque of the shoulder joint on the at least one robotic assembly.

16. The method of claim 15, further comprising providing at least one potentiometer.

17. The method of claim 15, further comprising providing a compliance section and sensing the sternoclavicular motion by a user.

18. The method of claim 15, wherein the at least one tactor motor is a vibration motor.

19. The method of claim 15, further comprising a hand assembly, wherein the hand assembly comprising:

a thumb force sensor;
an index finger sensor; and
a middle finger sensor.

20. The method of claim 19, further comprising providing at least one tactor motor in the hand assembly, the tactor motor providing feedback of the robotic assembly thumb force sensor to the user.

* * * * *